United States Patent
Gibson et al.

(10) Patent No.: US 8,410,134 B2
(45) Date of Patent: Apr. 2, 2013

(54) 8-OXY-QUINOLINE DERIVATIVES AS BRADYKININ B2 RECEPTOR MODULATORS

(75) Inventors: Christoph Gibson, Berlin (DE); Thomas Tradler, Berlin (DE); Karsten Schnatbaum, Berlin (DE); Jochen Pfeifer, Berlin (DE); Elsa Locardi, Berlin (DE); Dirk Scharn, Berlin (DE); Matthias Paschke, Berlin (DE); Ulf Reimer, Berlin (DE); Uwe Richter, Berlin (DE); Gerd Hummel, Berlin (DE); Ulrich Reineke, Berlin (DE)

(73) Assignee: Shire Orphan Therapies GmbH, Berlin (DE)

( * ) Notice: Subject to any disclaimer, the term of this patent is extended or adjusted under 35 U.S.C. 154(b) by 542 days.

(21) Appl. No.: 12/532,703

(22) PCT Filed: Mar. 22, 2008

(86) PCT No.: PCT/EP2008/002316
§ 371 (c)(1),
(2), (4) Date: Apr. 1, 2010

(87) PCT Pub. No.: WO2008/116620
PCT Pub. Date: Oct. 2, 2008

(65) Prior Publication Data
US 2010/0234344 A1 Sep. 16, 2010

(30) Foreign Application Priority Data

Mar. 23, 2007 (EP) .................................... 07006089

(51) Int. Cl.
*A61K 31/04* (2006.01)
*C07D 215/38* (2006.01)
(52) U.S. Cl. ........................................ 514/312; 546/159
(58) Field of Classification Search ................. 546/159; 514/312
See application file for complete search history.

(56) References Cited

U.S. PATENT DOCUMENTS

| | | | |
|---|---|---|---|
| 6,008,229 A | 12/1999 | Oku et al. | |
| 6,083,959 A | 7/2000 | Oku et al. | |
| 6,100,284 A | 8/2000 | Oku et al. | |

FOREIGN PATENT DOCUMENTS

| | | |
|---|---|---|
| WO | 97/11069 A1 | 3/1997 |
| WO | 97/41104 A1 | 11/1997 |

OTHER PUBLICATIONS

Voegtle et al., "4-(Dimethylamino)-8-hydroxyquinoline as a new chelating ligand and as a donor-reinforced end group in podands", Chemische Berichte, Verlag Chemie GmbH, vol. 118, No. 4, Jan. 1, 1985, pp. 1556-1563.
Chemical Encyclopedic Dictionary, Soviet Encyclopedia; 130-131(1983).
International Search Report for International Application PCT/EP2008/002316, mailed Jun. 20, 2008.
Ch, et al., The kinin system—bradykinin: biological effects and clinical implications. Multiple role of the kinin system—bradykinin. Hippokratia 11(3): 124-128 (2007).
Cicardi, et al., Icatibant, a New Bradykinin-Receptor Antagonist, in Hereditary Angioedema. The New England Journal of Medicine. 363:6 Aug. 5, 2010.
Landgraft, et al., Differential modulation of murine lung inflammation of bradyinin B1 and B2 selective receptor antagonists. European Journal of Pharmacology 460: 75-83 (2003).
Uknis, et al., Bradykinin receptor antagonists type 2 attenuate the inflammatory changes in peptidoglycan-induced acute arthritis in the Lewis rat. Inflammation Research 50: 149-155 (2001).

*Primary Examiner* — D M Seaman
(74) *Attorney, Agent, or Firm* — Morse, Barnes-Brown & Pendleton, P.C.; Lisa M. Treannie, Esq.

(57) ABSTRACT

The present invention is related to compound of the formula (I): or a pharmacologically acceptable salt, solvate, or hydrate thereof, wherein A is a 6-membered heteroaryl having from 1 to 3 heteroatoms, each independently selected from N or O and the other substituents are defined as in the claims.

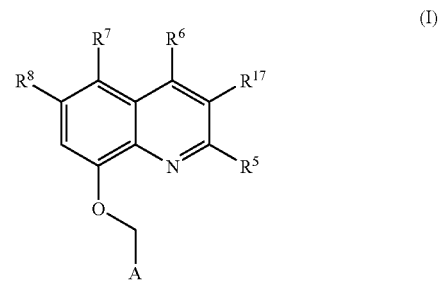

(I)

36 Claims, No Drawings

8-OXY-QUINOLINE DERIVATIVES AS BRADYKININ B2 RECEPTOR MODULATORS

CROSS REFERENCE TO RELATED APPLICATION

This application is a 35 U.S.C. 371 National Phase Entry Application from PCT/EP2008/002316, filed Mar. 22, 2008, which claims the benefit of European Patent Application No. 07006089.2 filed on Mar. 23, 2007, the disclosure of which is incorporated herein in its entirety by reference.

This invention relates to novel 8-(heteroarylmethoxy) quinoline compounds, compositions containing the same and the use of said compounds. These compounds act as selective modulators of bradykinin (BK) B2 receptors and can therefore be used in pharmaceutical compositions for the treatment of conditions responsive to BK B2 receptor modulation. Compounds of the invention are also useful as probes for the localization of BK B2 receptors and as standards in assays for BK B2 receptor binding.

Bradykinin (BK) is a vasoactive nonapeptide, H-Arg-Pro-Pro-Gly-Phe-Ser-Pro-Phe-Arg-OH, formed by the action of various plasma enzymes such as kallikrein on kininogens. In some aspects, it has some similar actions to that of histamine, and like histamine is released from venules rather than arterioles.

Two types of BK receptors are recognized in mammals, B1 and B2 (Leeb-Lundberg, et al *Pharmacol. Rev.* 2005, 57, 27-77). The actions of BK mediated by the B2 receptor are important physiological functions, such as increases in vascular permeability, modulation of inflammatory responses and pain as well as vasoactive effects (vasodilatation, vasoconstriction). These effects at the B2 receptor are responsible for BK's role in numerous diseases, such as inflammation, cardiovascular disease, and pain. Hence agents that block the binding of BK to its B2 receptor can inhibit or at least alleviate the pathogenic events.

Numerous peptide and non-peptide antagonists of BK B2 receptor have been described in the prior art. For instance, WO 2006/40004, WO 03/103671, WO 03/87090, WO00/23439, WO 00/50418, WO 99/64039, WO 97/41104, WO 97/28153, WO 97/07115, WO 96/13485, EP 0 795 547, EP 0 796 848, EP 0 867 432, and EP 1 213 289 disclose quinoline compounds that are BK B2 receptor antagonists.

In view of the severe conditions associated with a pathophysiological level of bradykinin, both acute and chronic, there is still a need for highly selective B2 receptor modulators having improved properties.

Therefore, the problem underlying the present invention is to provide highly selective B2 receptor modulators, preferably having improved properties.

The problem underlying the present invention is solved by the subject matter of the attached claims.

In a first aspect the problem underlying the instant application is solved by a sompound of the formula (I):

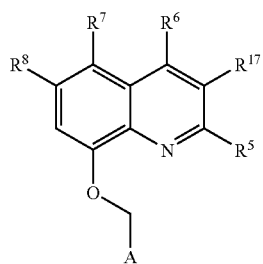

(I)

or a pharmacologically acceptable salt, solvate, or hydrate thereof, wherein

A is a 6-membered heteroaryl having from 1 to 3 heteroatoms each independently selected from N or O, wherein said 6-membered heteroaryl is substituted with from 2 to 4 substituents each independently selected from halogen atom, oxygen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl;

$R^5$ is halogen atom, hydroxy, cyano, nitro, mercapto, alkyl, alkenyl, alkynyl, or heteroalkyl;

$R^6$ is optionally substituted alkyl; optionally substituted alkenyl; 5-membered heterocycloalkyl having from 1 to 3 heteroatoms each independently selected from N, O or S, or cycloalkyl, wherein said 5-membered heterocycloalkyl or cycloalkyl is substituted with from 0 to 3 substituents each independently selected from halogen atom, oxygen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl; 5-membered heteroaryl having from 1 to 4 heteroatoms each independently selected from N, O or S, wherein said 5-membered heteroaryl is substituted with from 0 to 3 substituents each independently selected from halogen atom, oxygen atom, hydroxy, cyano, amino, nitro, mercapto, alkyl, alkenyl, alkynyl, heteroalkyl, optionally substituted aryl or optionally substituted heteroaryl; or —S—$R^{10}$;

$R^{10}$ is 5-membered heterocycloalkyl having from 1 to 3 heteroatoms each independently selected from N, O or S, or cycloalkyl, wherein said 5-membered heterocycloalkyl or cycloalkyl is substituted with from 0 to 4 substituents each independently selected from halogen atom, oxygen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl; or 5-membered heteroaryl having from 1 to 4 heteroatoms each independently selected from N, O or S, wherein said 5-membered heteroaryl is substituted with from 0 to 4 substituents each independently selected from halogen atom, oxygen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl;

$R^7$ is hydrogen atom, halogen atom, hydroxy, cyano, amino, nitro, alkyl, or heteroalkyl;

$R^8$ is hydrogen atom or halogen atom; and $R^{17}$ is hydrogen atom or halogen atom.

In an embodiment of the first aspect of the present invention the compound the heteroaryl A comprises 1 to 3 nitrogen atoms.

In an embodiment of the first aspect of the present invention A is

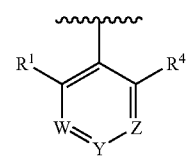

wherein
W is N, NO or $CR^9$;
Y is N, NO or $CR^2$;

Z is N, NO or $CR^3$;
with the proviso that at least one of W, Y or Z is N or NO;
$R^1$ is halogen atom, hydroxy, cyano, amino, nitro, mercapto, alkyl, alkenyl, alkynyl, heteroalkyl, or heteroalkylcycloalkyl;
$R^2$ is hydrogen atom, hydroxyl, halogen atom, cyano, nitro, mercapto, alkyl, alkenyl, alkynyl, or heteroalkyl;
$R^3$ is hydrogen atom, halogen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl;
$R^4$ is halogen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl; and
$R^9$ is hydrogen atom, halogen atom, or $C_1$-$C_6$alkyl.

In an embodiment of the first aspect of the present invention $R^6$ is

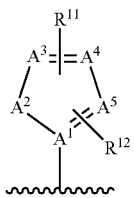

wherein
$A^1$, $A^2$, $A^3$, $A^4$, and $A^5$ are each independently selected from O, S, N, N—H, NO, C, or C—H; and
$R^{11}$ and $R^{12}$ are each independently selected from hydrogen atom, halogen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl.

In an embodiment of the first aspect of the present invention $R^6$ is

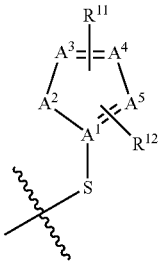

wherein
$A^1$, $A^2$, $A^3$, $A^4$, and $A^5$ are each independently selected from O, S, N, N—H, NO, C, or C—H; and
$R^{11}$ and $R^{12}$ are each independently selected from hydrogen atom, halogen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl.

In an embodiment of the first aspect of the present invention $R^4$ is selected from heteroalkyl, heterocycloalkyl, heteroalkylcykloalkyl, aralkyl or heteroaralkyl;
W is $CR^9$;
Y is N, NO or $CR^2$;
Z is N, NO or $CR^3$;
with the proviso that at least one of Y or Z is N or NO;
$R^1$ is halogen atom, hydroxy, cyano, —O—$C_1$-$C_6$alkyl or $C_1$-$C_6$alkyl;
$R^2$ is hydrogen atom, halogen atom, hydroxy, cyano, —O—$C_1$-$C_6$alkyl or $C_1$-$C_6$alkyl; and
$R^3$ is hydrogen atom, halogen atom, hydroxy, cyano, amino, nitro, —O-alkyl or alkyl.

In an embodiment of the first aspect of the present invention $R^4$ is selected from the groups —S—$Y^a$-L, —S—$Y^a$—CO—$NR^aR^b$, —$Y^a$—$NR^c$—CO—$NR^aR^b$, —$Y^a$—$NR^c$—CO—O—$R^e$, —$Y^a$—$NR^c$—CO—$R^e$, —$Y^a$—O—CO—$NR^aR^b$, —$Y^a$—CO—$NR^aR^b$, —$Y^a$—CO—$NR^cL$, —O—$Y^a$—CO—$NR^aR^b$, —$Y^a$—$NR^c$—CO-L, —$Y^a$-L, —$Y^a$—O—CO—O—$R^e$, —$Y^a$—O—CO—$R^e$, —$Y^a$—$NR^c$—$SO_2$—$NR^aR^b$, —$Y^a$—$SO_2$—$NR^aR^b$, or —$Y^a$—$NR^c$—$SO_2$—$R^e$,
wherein
$Y^a$ is a bond, a $C_1$-$C_6$alkylene, a $C_2$-$C_6$alkenylene or a $C_2$-$C_6$alkynylene;
$R^a$ is hydrogen atom, $C_1$-$C_6$alkyl, $C_2$-$C_6$alkenyl, $C_2$-$C_6$alkynyl or is joined to $R^b$ to form a 4- to 10-membered cycloalkyl or heterocycloalkyl;
$R^b$ is hydrogen atom, $C_1$-$C_6$alkyl, $C_2$-$C_6$alkenyl, $C_2$-$C_6$alkynyl, or taken together with $R^a$ to form a 4- to 10-membered cycloalkyl or heterocycloalkyl;
$R^c$ and $R^e$ are each independently selected from hydrogen atom, an optionally substituted $C_1$-$C_6$alkyl, an optionally substituted $C_2$-$C_6$alkenyl, or an optionally substituted $C_2$-$C_6$alkynyl; and
L is a cycloalkyl, heterocycloalkyl, alkylcycloalkyl, heteroalkylcycloalkyl, aryl, optionally substituted heteroaryl, aralkyl, or heteroaralkyl.

In an embodiment of the first aspect of the present invention $R^4$ is

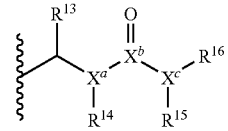

wherein
$X^a$ is N, O or CH;
$X^b$ is C, S or S=O;
$X^c$ is N, O or CH;
$R^{13}$, if present, is $C_1$-$C_6$alkyl;
$R^{14}$, if present, is $C_1$-$C_6$alkyl, $C_2$-$C_6$alkenyl or joined to $R^{15}$ to form
(i) a 5- to 10-membered cycloalkyl;
(ii) a 5- to 10-membered heterocycloalkyl;
(iii) a 5- to 10-membered heteroaryl; or
(iv) a 6- to 10-membered aryl;
$R^{15}$ is alkyl, alkenyl, or joined to $R^{14}$ to form
(i) a 5- to 10-membered cycloalkyl;
(ii) a 5- to 10-membered heterocycloalkyl;
(iii) a 5- to 10-membered heteroaryl; or
(iv) a 6- to 10-membered aryl; and/or
if $R^{15}$ is taken together with $R^{16}$ to form
(i) a 4- to 10-membered cycloalkyl;
(ii) a 4- to 10-membered heterocycloalkyl;

(iii) a 5- to 10-membered heteroaryl; or (iv) a 6- to 10-membered aryl; and

R$^{16}$ is hydrogen, alkyl, alkenyl, aryl, heteroaryl or taken together with R$^{15}$ to form (i) a 4- to 10-membered cycloalkyl;

(ii) a 4- to 10-membered heterocycloalkyl;

(iii) a 5- to 10-membered heteroaryl; or (iv) a 6- to 10-membered aryl.

In an embodiment of the first aspect of the present invention R$^4$ is

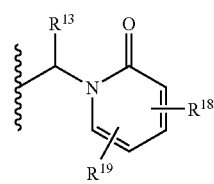

wherein

R$^{13}$ is hydrogen atom or C$_1$-C$_6$alkyl;

R$^{18}$ and R$^{19}$ are each independently selected from hydrogen atom, halogen atom, hydroxy, cyano, amino, nitro, C$_1$-C$_6$alkyl, —O—C$_1$-C$_6$alkyl, —CO—NR$^a$R$^b$, or —SO$_2$—NR$^a$R$^b$, wherein R$^a$ and R$^b$ are each independently selected from hydrogen atom, or C1-C6alkyl.

In an embodiment of the first aspect of the present invention R$^5$ is halogen atom, cyano, or C$_1$-C$_6$alkyl.

In an embodiment of the first aspect of the present invention R$^7$, R$^8$, and R$^{17}$ are each independently selected from H or F.

In an embodiment of the first aspect of the present invention R$^5$ is methyl or ethyl.

In an embodiment of the first aspect of the present invention R$^6$ is selected from the groups:

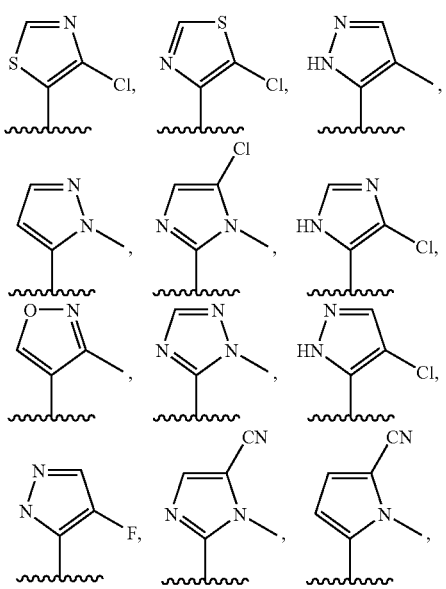

-continued

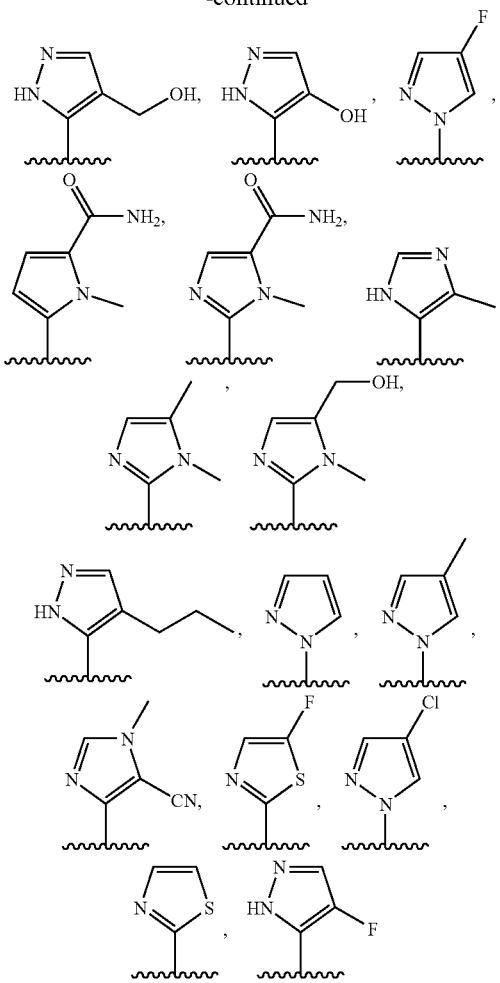

In an embodiment of the first aspect of the present invention

R$^1$ is methyl, Cl, F, CN, or O—CH$_3$;

W is CH;

Y is N, NO, CH, C—CH$_3$, C—OH, or C—OCH$_3$;

Z is N, NO, CH, C—CH$_3$, C—OH, or C—OCH$_3$; and with the proviso that at least one of Y or Z is N or NO.

In an embodiment of the first aspect of the present invention R$^4$ is

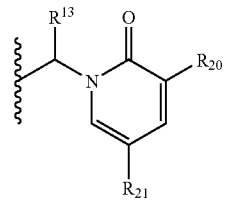

wherein

R$^{13}$ is hydrogen atom or methyl;

R$^{20}$ is Cl, F, cyano, or CF$_3$; and

R$^{21}$ is hydrogen atom or F

In an embodiment of the first aspect of the present invention wherein R$^7$, R$^8$ and R$^{17}$ are H.

In an embodiment of the first aspect of the present invention the compound according to the present invention, or a salt or solvate thereof, exhibits an $IC_{50}$ of 500 nM or less in a standard in vitro BK B2 receptor-mediated assay.

In a second aspect the problem underlying the present invention is solved by a compound, whereby such compound is preferably a compound according to the first aspect of the present invention, which is:

1-{3-[4-(5-Chloro-thiazol-4-yl)-2-methyl-quinolin-8-yloxymethyl]-4-methyl-pyridin-2-ylmethyl}-3-trifluoromethyl-1H-pyridin-2-one,
1-{4-Chloro-3-[4-(5-chloro-thiazol-4-yl)-2-methyl-quinolin-8-yloxymethyl]-6-methyl-pyridin-2-ylmethyl}-3-trifluoromethyl-1H-pyridin-2-one,
1-{4-Chloro-3-[4-(5-chloro-thiazol-4-yl)-2-methyl-quinolin-8-yloxymethyl]-6-methyl-pyridin-2-ylmethyl}-2-oxo-1,2-dihydro-pyridine-3-carbonitrile,
1-{4-Methyl-3-[2-methyl-4-(4-methyl-2H-pyrazol-3-yl)-quinolin-8-yloxymethyl]-pyridin-2-ylmethyl}-3-trifluoromethyl-1H-pyridin-2-one,
1-{4-Chloro-3-[4-(5-chloro-1-methyl-1H-imidazol-2-yl)-2-methyl-quinolin-8-yloxymethyl]-pyridin-2-ylmethyl}-3-trifluoromethyl-1H-pyridin-2-one,
1-{5-Chloro-2-methoxy-4-[2-methyl-4-(2-methyl-2H-[1,2,4]triazol-3-yl)-quinolin-8-yloxymethyl]-pyridin-3-ylmethyl}-3-trifluoromethyl-1H-pyridin-2-one,
1-(3-{4-[4-(2-Amino-ethoxy)-1H-pyrazol-3-yl]-2-methyl-quinolin-8-yloxymethyl}-4-methyl-pyridin-2-ylmethyl)-3-trifluoromethyl-1H-pyridin-2-one,
1-{4-Chloro-3-[4-(1,5-dimethyl-1H-imidazol-2-yl)-2-methyl-quinolin-8-yloxymethyl]-pyridin-2-ylmethyl}-3-trifluoromethyl-1H-pyridin-2-one,
1-{3-[4-(4-Hydroxymethyl-2H-pyrazol-3-yl)-2-methyl-quinolin-8-yloxymethyl]-4-methyl-pyridin-2-ylmethyl}-3-trifluoromethyl-1H-pyridin-2-one,
N-(3-{2-Methyl-8-[4-methyl-2-(2-oxo-3-trifluoromethyl-2H-pyridin-1-ylmethyl)-pyridin-3-ylmethoxy]-quinolin-4-yl}-1H-pyrazol-4-ylmethyl)-acetamide,
1-{3-[4-(4-Aminomethyl-1H-pyrazol-3-yl)-2-methyl-quinolin-8-yloxymethyl]-4-methyl-pyridin-2-ylmethyl}-3-trifluoromethyl-1H-pyridin-2-one,
N-(5-{8-[4-Chloro-2-(2-oxo-3-trifluoromethyl-2H-pyridin-1-ylmethyl)-pyridin-3-ylmethoxy]-2-methyl-quinolin-4-yl}-1H-pyrazol-4-ylmethyl)-acetamide,
2-{8-[4-Chloro-6-methyl-2-(2-oxo-3-trifluoromethyl-2H-pyridin-1-ylmethyl)-pyridin-3-ylmethoxy]-2-methyl-quinolin-4-yl}-3-methyl-3H-imidazole-4-carbonitrile,
1-{4-Chloro-6-methyl-3-[2-methyl-4-(4-methyl-2H-pyrazol-3-yl)-quinolin-8-yloxymethyl]-pyridin-2-ylmethyl}-2-oxo-1,2-dihydro-pyridine-3-carbonitrile,
1-{4-Chloro-6-methyl-3-[2-methyl-4-(4-methyl-1H-pyrazol-3-yl)-quinolin-8-yloxymethyl]-pyridin-2-ylmethyl}-3-trifluoromethyl-1H-pyridin-2-one,
5-{8-[4-Chloro-2-(2-oxo-3-trifluoromethyl-2H-pyridin-1-ylmethyl)-pyridin-3-ylmethoxy]-2-methyl-quinolin-4-yl}-3-methyl-3H-imidazole-4-carbonitrile,
1-{4-Chloro-3-[4-(4-chloro-thiazol-5-yl)-2-methyl-quinolin-8-yloxymethyl]-6-methyl-pyridin-2-ylmethyl}-2-oxo-1,2-dihydro-pyridine-3-carbonitrile,
1-{4-Chloro-3-[4-(5-cyano-1-methyl-1H-pyrrol-2-yl)-2-methyl-quinolin-8-yloxymethyl]-6-methyl-pyridin-2-ylmethyl}-2-oxo-1,2-dihydro-pyridine-3-carbonitrile,
1-{3-[4-(5-Chloro-thiazol-4-yl)-2-methyl-quinolin-8-yloxymethyl]-4-methoxy-pyridin-2-ylmethyl}-3-trifluoromethyl-1H-pyridin-2-one,
1-{4-Chloro-3-[4-(5-cyano-1-methyl-1H-pyrrol-2-yl)-2-methyl-quinolin-8-yloxymethyl]-pyridin-2-ylmethyl}-2-oxo-1,2-dihydro-pyridine-3-carbonitrile,
5-{8-[4-Chloro-6-methyl-2-(2-oxo-3-trifluoromethyl-2H-pyridin-1-ylmethyl)-pyridin-3-ylmethoxy]-2-methyl-quinolin-4-yl}-1-methyl-1H-pyrrole-2-carboxylic acid amide,
5-{8-[4-Chloro-2-(3-cyano-2-oxo-2H-pyridin-1-ylmethyl)-6-methyl-pyridin-3-ylmethoxy]-2-methyl-quinolin-4-yl}-1-methyl-1H-pyrrole-2-carboxylic acid amide,
1-{4-Chloro-3-[4-(4-hydroxymethyl-2H-pyrazol-3-yl)-2-methyl-quinolin-8-yloxymethyl]-pyridin-2-ylmethyl}-3-trifluoromethyl-1H-pyridin-2-one,
1-{4-Chloro-3-[4-(4-hydroxy-1H-pyrazol-3-yl)-2-methyl-quinolin-8-yloxymethyl]-6-methyl-pyridin-2-ylmethyl}-2-oxo-1,2-dihydro-pyridine-3-carbonitrile,
1-{4-Chloro-3-[4-(4-hydroxy-1H-pyrazol-3-yl)-2-methyl-quinolin-8-yloxymethyl]-6-methyl-pyridin-2-ylmethyl}-3-trifluoromethyl-1H-pyridin-2-one,
1-{4-Chloro-3-[4-(4-fluoro-pyrazol-1-yl)-2-methyl-quinolin-8-yloxymethyl]-6-methyl-pyridin-2-ylmethyl}-2-oxo-1,2-dihydro-pyridine-3-carbonitrile,
1-{3-[4-(5-Chloro-thiazol-4-yl)-2-methyl-quinolin-8-yloxymethyl]-4-methoxy-pyridin-2-ylmethyl}-2-oxo-1,2-dihydro-pyridine-3-carbonitrile,
2-{8-[5-Fluoro-2-methoxy-3-(2-oxo-3-trifluoromethyl-2H-pyridin-1-ylmethyl)-pyridin-4-ylmethoxy]-2-methyl-quinolin-4-yl}-3-methyl-3H-imidazole-4-carbonitrile,
1-{4-Chloro-6-methyl-3-[2-methyl-4-(5-methyl-1H-imidazol-4-yl)quinolin-8-yloxymethyl]-pridin-2-ylmethyl}-2-oxo-1,2-dihydro-pyridine-3-carbonitrile,
1-(1-{4-Chloro-3-[2-methyl-4-(4-methyl-1H-pyrazol-3-yl)-quinolin-8-yloxymethyl]-pyridin-2-yl}-ethyl)-2-oxo-1,2-dihydro-pyridine-3-carbonitrile,
1-(1-{4-Chloro-3-[4-(4-hydroxy-1H-pyrazol-3-yl)-2-methyl-quinolin-8-yloxymethyl]-pyridin-2-yl}-ethyl)-2-oxo-1,2-dihydro-pyridine-3-carbonitrile,
5-{8-[4-Chloro-2-(3-cyano-2-oxo-2H-pyridin-1-ylmethyl)-pyridin-3-ylmethoxy]-2-methyl-quinolin-4-yl}-1-methyl-1H-pyrrole-2-carboxylic acid amide,
1-{4-Chloro-3-[4-(4-fluoro-pyrazol-1-yl)-2-methyl-quinolin-8-yloxymethyl]-pyridin-2-ylmethyl}-2-oxo-1,2-dihydro-pyridine-3-carbonitrile,
1-(1-{4-Chloro-3-[4-(4-hydroxy-1H-pyrazol-3-yl)-2-methyl-quinolin-8-yloxymethyl]-6-methyl-pyridin-2-yl}-ethyl)-2-oxo-1,2-dihydro-pyridine-3-carbonitrile,
1-{4-Chloro-6-methyl-3-[2-methyl-4-(3-methyl-isoxazol-4-yl)-quinolin-8-yloxymethyl]-pyridin-2-ylmethyl}-2-oxo-1,2-dihydro-pyridine-3-carbonitrile,
1-{5-Chloro-4-[4-(5-cyano-1-methyl-1H-pyrrol-2-yl)-2-methyl-quinolin-8-yloxymethyl]-2-hydroxy-pyridin-3-ylmethyl}-2-oxo-1,2-dihydro-pyridine-3-carbonitrile,
1-{4-Methoxy-6-methyl-3-[2-methyl-4-(4-methyl-1H-pyrazol-3-yl)-quinolin-8-yloxymethyl]-pyridin-2-ylmethyl}-3-trifluoromethyl-1H-pyridin-2-one,
1-{4-Chloro-3-[4-(4-hydroxymethyl-1H-pyrazol-3-yl)-2-methyl-quinolin-8-yloxymethyl]-6-methyl-pyridin-2-ylmethyl}-2-oxo-1,2-dihydro-pyridine-3-carbonitrile,
1-{4-Chloro-3-[4-(5-fluoro-thiazol-2-yl)-2-methyl-quinolin-8-yloxymethyl]-6-methyl-pyridin-2-ylmethyl}-2-oxo-1,2-dihydro-pyridine-3-carbonitrile In a third aspect the problem underlying the present invention is solved by a pharmaceutical composition that comprises one or more compounds according to the first and/or second aspect of the present invention and, optionally, at least one carrier substance, excipient and/or adjuvant.

In an embodiment of the third aspect the pharmaceutical composition is formulated as an aerosol, a cream, a gel, a pill, a capsule, a syrup, a solution, a transdermal patch or a pharmaceutical delivery device.

In a fourth aspect the problem underlying the present invention is solved by a method of inhibiting binding of BK to a BK B2 receptor in vitro, the method comprising contacting the BK B2 receptor with at least one compound according to the first and/or second aspect of the present invention or a salt thereof, under conditions and in an amount sufficient to detectably inhibit binding of BK or any other substance to the BK B2 receptor.

In a fifth aspect the problem underlying the present invention is solved by a method for localizing or detecting a BK B2 receptor in a tissue, preferably a tissue section, in vitro, comprising:
(a) contacting a tissue sample containing the BK B2 receptor with a detectably labeled compound according to the first and/or second aspect of the present invention under conditions that permit binding of the compound to the BK B2 receptor; and
(b) detecting the bound compound.

In an embodiment of the fifth aspect the compound is radiolabeled, fluorescence-labeled or luminescence-labeled, or labeled with an antibody.

In a sixth aspect the problem underlying the present invention is solved by the use of a compound according to the first and/or second aspect of the present invention or of a pharmaceutical composition according to the third aspect of the present invention for the manufacture of a medicament for the treatment and/or prevention of a disease or a condition.

In an embodiment of the sixth aspect of the present invention the condition or disease is responsive to BK B2 receptor modulation.

In an embodiment of the sixth aspect the condition is skin disorders; eye diseases; ear diseases; mouth, throat and respiratory diseases; gastrointestinal diseases; liver, gallbladder and pancreatic diseases; urinary tract and kidney diseases; diseases of male genitale organs and female genitale organs; diseases of the hormone system; metabolic diseases; cardiovascular diseases; blood diseases; lymphatic diseases; disorders of the central nervous system; brain disorders; musculoskeletal system diseases; allergy disorders; pain; infectious diseases; inflammatory disorders; injuries; immunology disorders; cancers; hereditary diseases; or edema.

In a seventh aspect the problem underlying the present invention is solved by a method for the treatment of a subject which is in need of such treatment, comprising the administration of a compound according to the first and/or second aspect of the present invention of of a pharmaceutical composition according to the third aspect.

BK B2 receptor modulators provided herein exhibit high activity on human BK B2 receptor (i.e., an inhibition constant ($IC_{50}$) for competition with binding of labelled BK to human BK B2 receptor of less than 5 micromolar) or very high activity on human BK B2 receptor (i.e., an $IC_{50}$ for competition with the binding of labelled BK to human BK B2 receptor of preferably less than 50 nanomolar). In certain embodiments, such modulators exhibit a high activity on BK B2 receptors of species other than human, e.g. rat, mouse, gerbil, guinea pig, rabbit, dog, cat, pig, or cynomolgus monkey.

The activity and more specifically pharmacological activity of the B2 receptor modulators according to the present invention can be assessed using appropriate in vitro assays. For instance, the $IC_{50}$ values of the modulators according to the present invention for B2 receptor may be determined via a radioligand binding assay, such as the assay provided in Example 754, which is thus an embodiment of a standard in vitro BK B2 receptor-mediated assay. Inhibitory effects of the B2 receptor modulators provided herein for B2 receptor may be determined, for example, via calcium mobilization assay, such as the assay provided in Example 755.

Preferred compounds of the invention have an $IC_{50}$ (half-maximal inhibitory concentration) of about 5 micromolar or less, still more preferably an $IC_{50}$ of about 500 nM or less, or even 50 nM or less, even more preferably an $IC_{50}$ of about 10 nM or less, or even 1 nanomolar or less in the assays mentioned above.

The present invention further provides, within other aspects, pharmaceutical compositions comprising at least one BK B2 receptor modulator as described herein, in combination with a physiologically acceptable carrier or excipient. Processes for preparing such pharmaceutical compositions are also provided. Such compositions are particularly useful in the treatment of B2 receptor-mediated diseases as described below.

These and other aspects of the present invention will become apparent upon reference to the following detailed description.

Compounds are generally described herein using standard nomenclature. For compounds having asymmetric centers, it should be understood that (unless otherwise specified) all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope (i.e., an atom having the same atomic number but a different mass number). By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic centers, have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

Certain compounds are described herein using a general formula that includes variables (e.g., A, $R^1$-$R^{12}$, W, Y, Z). Unless otherwise specified, each variable within such a formula is defined independently of any other variable, and any variable that occurs more than one time in a formula is defined independently at each occurrence. Thus, for example, if a group is shown to be substituted with 0-2R*, the group may be unsubstituted or substituted with up to two R* groups and R* at each occurrence is selected independently from the definition of R*. Also, combinations of substituents and/or variables are permissible only if such combinations result in stable compounds (i.e., compounds that can be isolated, characterized and tested for biological activity).

The term "8-(heteroarylmethoxy)quinoline", as used herein, refers to compounds of formula (I) provided herein, as well as salts and preferably pharmaceutically acceptable salts thereof. It will be apparent that such compounds may be further substituted as indicated.

A "pharmaceutically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, $HOOC-(CH_2)_n-COOH$ where n is any integer from 0 to –4 (i.e., 0, 1, 2, 3, or 4) and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

It will be apparent that each compound of formula I may, but need not, be present as a hydrate, solvate or non-covalent complex. In addition, the various crystal forms and polymorphs are within the scope of the present invention, as are prodrugs of the compounds of formula (I) provided herein.

A "prodrug" is a compound that may not fully satisfy the structural requirements of the compounds provided herein, but is modified in vivo, following administration to a subject or patient, to produce a compound of formula I provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent," as used herein, refers to a molecular moiety that is covalently bonded to an atom within a molecule of interest. For example, a "ring substituent" may be a moiety such as a halogen, alkyl group, haloalkyl group, hydroxy, cyano, amino, nitro, mercapto, or other substituent described herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e., =O), then 2 hydrogens on the atom are replaced. An oxo group that is a substituent of an aromatic carbon atom results in a conversion of —CH— to —C(=O)— and a loss of aromaticity. For example a pyridyl group substituted by oxo is a pyridone.

The expression alkyl refers to a saturated, straight-chain or branched hydrocarbon group that contains from 1 to 20 carbon atoms, preferably from 1 to 12 carbon atoms, more preferably from 1 to 6 carbon atoms, for example a methyl, ethyl, propyl, iso-propyl, n-butyl, iso-butyl, sec-butyl, tert-butyl, n-pentyl, n-hexyl, 2,2-dimethylbutyl or n-octyl group.

The expressions alkenyl and alkynyl refer to at least partially unsaturated, straight-chain or branched hydrocarbon groups that contain from 2 to 20 carbon atoms, preferably from 2 to 12 carbon atoms, more preferably from 2 to 6 carbon atoms, for example an ethenyl, allyl, acetylenyl, propargyl, isoprenyl or hex-2-enyl group. Preferably, alkenyl groups have one or two (more preferred one) double bond(s) and alkynyl groups have one or two (more preferred one) triple bond(s).

Furthermore, the terms alkyl, alkenyl and alkynyl refer to groups in which one or more hydrogen atoms have been replaced each independently of the others by a halogen atom (preferably F or Cl) such as, for example, a 2,2,2-trichloroethyl or a trifluoromethyl group.

The expression heteroalkyl refers to an alkyl, alkenyl or alkynyl group (for example heteroalkenyl, heteroalkynyl) in which one or more (preferably 1, 2 or 3) carbon atoms have been replaced each independently of the others by an oxygen, nitrogen, phosphorus, boron, selenium, silicon or sulphur atom (preferably oxygen, sulphur or nitrogen). The expression heteroalkyl furthermore refers to a carboxylic acid or to a group derived from a carboxylic acid such as, for example, acyl, acylalkyl, alkoxycarbonyl, acyloxy, acyloxyalkyl, carboxyalkylamide, alkylcarbamoylalkyl, alkylcarbamoyloxyalkyl, alkylureidoalkyl, or alkoxycarbonyloxy.

Examples of heteroalkyl groups are groups of formulae $—S—Y^a$-L, $—S—Y^a—CO—NR^aR^b$, $—Y^a—NR^c—CO—NR^aR^b$, $—Y^a—NR^c—CO—O—R^c$, $—Y^a—NR^c—CO—R^c$, $—Y^a—O—CO—NR^aR^b$, $—Y^a—CO—NR^aR^b$, $—O—Y^a—CO—NR^aR^b$, $—Y^a—NR^c—CO$-L, $—Y^a$-L, $—Y^a—O—CO—O—R^c$, $—Y^a—O—CO—R^c$, $R^c—O—Y^a—$, $R^c—S—Y^a$, $R^a—N(R^b)—Y^a—$, $R^c—CO—Y^a—$, $R^c—O—CO—Y^a—$, $R^c—CO—O—Y^a—$, $R^c—CO—N(R^b)—Y^a—$, $R^a—N(R^b)—CO—Y^a—$, $R^c—SO—Y^a—$, $R^c—SO_2—Y^a—$, $—Y^a—NR^c—SO_2—NR^aR^b$, $—Y^a—SO_2—NR^aR^b$, $—Y^a—NR^c—SO_2—R^c$, $R^a—O—CO—N(R^b)—Y^a—$, $R^a—N(R^b)—C(=NR^d)—N(R^c)—Y^a—$, $R^c—S—CO—Y^a—$, $R^c—CO—S—Y^a—$, $R^c—S—CO—N(R^b)—Y^a—$, $R^a—N(R^b)—CO—S—Y^a—$, $R^c—S—CO—O—Y^a—$, $R^c—O—CO—S—Y^a—$, $R^c—S—CO—S—Y^a—$; $R^a$ being a hydrogen atom, a $C_1$-$C_6$alkyl, a $C_2$-$C_6$alkenyl, a $C_2$-$C_6$alkynyl, or is joined to $R^b$ to form a 4- to 10-membered cycloalkyl or heterocycloalkyl; $R^b$ being a hydrogen atom, a $C_1$-$C_6$alkyl, a $C_2$-$C_6$alkenyl or a $C_2$-$C_6$alkynyl, or taken together with $R^a$ to form a 4- to 10-membered cycloalkyl or heterocycloalkyl; $R^c$ being a hydrogen atom, an optionally substituted $C_1$-$C_6$alkyl, an optionally substituted $C_2$-$C_6$alkenyl or an optionally substituted $C_2$-$C_6$alkynyl; $R^d$ being a hydrogen atom, a $C_1$-$C_6$alkyl, a $C_2$-$C_6$alkenyl or a $C_2$-$C_6$alkynyl; L being a cycloalkyl, heterocycloalkyl, alkylcycloalkyl, heteroalkylcycloalkyl, aryl, optionally substituted heteroaryl, aralkyl, or heteroaralkyl; and $Y^a$ being a bond, a $C_1$-$C_6$alkylene, a $C_2$-$C_6$alkenylene or a $C_2$-$C_6$alkynylene group; each heteroalkyl group containing at least one carbon atom and it being possible for one or more hydrogen atoms to have been replaced by fluorine or chlorine atoms. Specific examples of heteroalkyl groups are methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, iso-propylethylamino, methylaminomethyl, ethylaminomethyl, diisopropylaminoethyl, enol ether, dimethylaminomethyl, dimethylaminoethyl, acetyl, propionyl, butyryloxy, acetyloxy, methoxycarbonyl, ethoxycarbonyl, isobutyrylamino-methyl, N-ethyl-N-methylcarbamoyl and N-methylcarbamoyl. Further examples of heteroalkyl groups are nitrile, isonitrile, cyanate, thiocyanate, isocyanate, isothiocyanate and alkylnitrile groups. An example of a hetero-alkylene group is a group of formula —$CH_2CH(OH)$— or —CONH—.

The expression cycloalkyl refers to a saturated or partially unsaturated cyclic group that contains one or more rings (preferably 1 or 2), containing from 3 to 14 ring carbon atoms, preferably from 3 to 10 (more preferably 3, 4, 5, 6 or 7) ring carbon atoms. In an embodiment a partially unsaturated cyclic group has one, two or more double bonds, such as a cycloalkenyl group. The expression cycloalkyl refers furthermore to groups in which one or more hydrogen atoms have been replaced each independently of the others by fluorine, chlorine, bromine or iodine atoms or by OH, $=$O, SH, $=$S, $NH_2$, $=$NH, CN or $NO_2$ groups, thus, for example, cyclic ketones such as, for example, cyclohexanone, 2-cyclohexenone or cyclopentanone. Further specific examples of a cycloalkyl group is a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetralin, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced each independently of the others by an oxygen, nitrogen, silicon, selenium, phosphorus or sulphur atom (preferably oxygen, sulphur or nitrogen). A heterocycloalkyl group has preferably 1 or 2 ring(s) containing from 3 to 10 (more preferably 3, 4, 5, 6 or 7) ring atoms. The expression heterocycloalkyl refers furthermore to groups in which one or more hydrogen atoms have been replaced each independently of the others by fluorine, chlorine, bromine or iodine atoms or by OH, $=$O, SH, $=$S, $NH_2$, $=$NH, CN or $NO_2$ groups. Examples are a piperidyl, piperazinyl, morpholinyl, urotropinyl, pyrrolidinyl, tetrahydrothiophenyl, tetrahydropyranyl, tetrahydrofuryl or 2-pyrazolinyl group and also a lactam, a lactone, a cyclic imide and a cyclic anhydride.

The expression alkylcycloalkyl refers to a group containing both cycloalkyl and also an alkyl, alkenyl or alkynyl group in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (preferably 3, 4, 5, 6 or 7) carbon atoms, and one or two alkyl, alkenyl or alkynyl groups having 1 or 2 to 6 carbon atoms, the cyclic groups being optionally substituted.

The expression heteroalkylcycloalkyl refers to alkylcycloalkyl groups as defined above in which one or more (preferably 1, 2 or 3) carbon atoms have been replaced each independently of the others by an oxygen, nitrogen, silicon, selenium, phosphorus or sulphur atom (preferably oxygen, sulphur or nitrogen). A heteroalkylcycloalkyl group preferably contains 1 or 2 ring systems having from 3 to 10 (preferably 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being optionally substituted and saturated or mono-, di- or tri-unsaturated.

The expression aryl or Ar refers to an aromatic group that contains one or more rings containing from 6 to 14 ring carbon atoms, preferably from 6 to 10 (more preferably 6) ring carbon atoms. The expression aryl (or Ar) refers furthermore to groups in which one or more hydrogen atoms have been replaced each independently of the others by fluorine, chlorine, bromine or iodine atoms or by OH, SH, $NH_2$, CN or $NO_2$ groups. Examples are a phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (more preferably 5 or 6) ring atoms, and contains one or more (preferably 1, 2, 3 or 4) oxygen, nitrogen, phosphorus or sulphur ring atoms (preferably O, S or N). The expression heteroaryl refers furthermore to groups in which one or more hydrogen atoms have been replaced each independently of the others by fluorine, chlorine, bromine or iodine atoms or by OH, $=$O, SH, $NH_2$, $=$NH, CN or $NO_2$ groups. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl.

The expression aralkyl refers to a group containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetralin, dihydronaphthalene, indanone, phenylcyclopentyl, cumene, cyclohexylphenyl, fluorene and indan. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms have been replaced each independently of the others by an oxygen, nitrogen, silicon, selenium, phosphorus, boron or sulphur atom (preferably oxygen, sulphur or nitrogen), that is to say to groups containing both aryl or heteroaryl and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, 1, 2, 3 or 4 of those carbon atoms having been replaced each independently of the others by oxygen, sulphur or nitrogen atoms.

Examples of heteroaralkyl groups are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl, heteroalkylheteroarylalkyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The expressions cycloalkyl, heterocycloalkyl, alkylcycloalkyl, heteroalkylcycloalkyl, aryl, heteroaryl, aralkyl and heteroaralkyl refer to groups in which one or more hydrogen atoms of such groups have been replaced each independently of the others by fluorine, chlorine, bromine or iodine atoms or by OH, =O, SH, =S, $NH_2$, =NH, CN or $NO_2$ groups.

The expression "optionally substituted" refers to groups in which one or more hydrogen atoms have been replaced each independently of the others by hydrogen, fluorine, chlorine, bromine or iodine atoms or by OH, =O, SH, =S, $NH_2$, =NH, CN or $NO_2$ groups. This expression refers furthermore to groups in which one or more hydrogen atoms have been replaced each independently of the others by unsubstituted $C_1$-$C_6$alkyl, unsubstituted $C_2$-$C_6$alkenyl, unsubstituted $C_2$-$C_6$alkynyl, unsubstituted $C_1$-$C_6$heteroalkyl, unsubstituted $C_3$-$C_{10}$cycloalkyl, unsubstituted $C_2$-$C_9$heterocycloalkyl, unsubstituted $C_6$-$C_{10}$aryl, unsubstituted $C_1$-$C_9$heteroaryl, unsubstituted $C_7$-$C_{12}$aralkyl or unsubstituted $C_2$-$C_{11}$heteroaralkyl groups.

As used herein a wording defining the limits of a range of length such as, e.g., "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

The present invention also comprises all isotopes of atoms of the described compounds. Isotopes are atoms having the same atomic number but different mass numbers. For example, tritium and deuterium are isotopes of hydrogen. Examples for carbon isotopes are $^{11}C$, $^{13}C$ and $^{14}C$.

The therapeutic use of compounds of formula (I), their pharmacologically acceptable salts, solvates or hydrates and also formulations and pharmaceutical compositions containing the same are within the scope of the present invention. The present invention also relates to the use of those compounds of formula (I) as active ingredients in the preparation or manufacture of a medicament.

The pharmaceutical compositions according to the present invention comprise at least one compound of formula (I) and, optionally, one or more carrier substances, excipients and/or adjuvants. Pharmaceutical compositions may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Furthermore, one or more other active ingredients may (but need not) be included in the pharmaceutical compositions provided herein. For instance, the compounds of the invention may advantageously be employed in combination with an antibiotic, anti-fungal, or anti-viral agent, an anti histamine, a non-steroidal anti-inflammatory drug, a disease modifying anti-rheumatic drug, a cytostatic drug, a drug with smooth muscle activity modulatory activity or mixtures of the aforementioned.

Pharmaceutical compositions may be formulated for any appropriate manner of administration, including, for example, topical (e.g., transdermal or ocular), oral, buccal, nasal, vaginal, rectal or parenteral administration. The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions (e.g., in the treatment of skin conditions such as burns or itch).

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active ingredient(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin) or a mixture thereof Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Compounds may be formulated for local or topical administration, such as for topical application to the skin or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included in a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing. Controlled release vehicles can also be used, and compositions may be formulated for transdermal administration as a transdermal patch.

A pharmaceutical composition may be formulated as inhaled formulations, including sprays, mists, or aerosols. Such formulations are particularly useful for the treatment of asthma or other respiratory conditions. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations or compositions suitable for nasal administration, wherein the carrier is a solid, include a coarse powder having a particle size, for example, in the range of 20 to 500 microns which is administered in the manner in which snuff is administered by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Pharmaceutical compositions may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

For the prevention and/or treatment of diseases mediated by BK or analogues thereof, the dose of the biologically active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day (about 0.5 mg to about 7 g per patient per day). The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient) and the severity of the particular disease undergoing therapy.

Preferred compounds of the invention will have certain pharmacological properties. Such properties include, but are not limited to oral bioavailability, such that the preferred oral dosage forms discussed above can provide therapeutically effective levels of the compound in vivo.

8-(heteroarylmethoxy)quinolines provided herein may be used as agonists or (preferably) antagonists of BK B2 receptors in a variety of applications, both in vitro and in vivo. B2 receptor antagonists according to the present invention may be used to inhibit the binding of BK B2 receptor ligands (e.g., BK) to BK B2 receptor in vitro or in vivo. BK B2 receptor modulator(s) provided herein are preferably administered to a patient (e.g., a human) orally or topically, and are present within at least one body fluid or tissue of the patient while modulating BK B2 receptor activity.

BK B2 receptor modulators according to the present invention are particularly useful for the treatment and/or prevention and/or prophylaxis of conditions or diseases that are responsive to BK B2 receptor modulation including skin disorders; eye diseases; ear diseases; mouth, throat and respiratory diseases; gastrointestinal diseases; liver, gallbladder and pancreatic diseases; urinary tract and kidney diseases; diseases of male genitale organs and female genitale organs; diseases of the hormone system; metabolic diseases; cardiovascular diseases; blood diseases; lymphatic diseases; disorders of the central nervous system; brain disorders; musculoskeletal system diseases; allergy disorders; pain; infectious diseases; inflammatory disorders; injuries; immunology disorders; cancers; hereditary diseases, edema or capillary leak syndrome(s), and for the use in specific methodology. It is within the present invention that the compounds according to the invention are used as or for the manufacture of a diagnostic agent, whereby such diagnostic agent is for the diagnosis of the diseases and conditions which can be addressed by the compounds of the present invention for therapeutic purposes as disclosed herein.

In the following the various diseases and conditions that are responsive to BK B2 receptor modulation and the use of the compounds according to the present invention in specific methodology and diagnostics are further specified.

Skin Disorders:

Within the present application the term "skin disorders" encompasses, but is not limited to, disorders such as skin aging, skin efflorescences including pressure sores, decubital ulcers, irritated, sensitive and dysaesthetic skin, erythema, rash, skin edema, psoriasis, eczema, lichen, bacterial, viral, fungal and parasites induced skin infections including furuncle, abscess, phlegmon, erysipelas, folliculitis and impetigo, lice, scabies and herpes simplex, acne, exanthema, dermatitis including atopic dermatitis, allergic contact dermatitis (Scholzen, T. E.; Luger, T. A. Exp Dermatol. 2004; 13 Suppl 4:22-6) neurodermatitis, radiation damage, sunburn, pruritus, itching, urticaria (EP0622361; Frigas, E.; Park, M. Immunol. Allergy Clin. North Am. 2006, 26, 739-51; Luquin, E.; Kaplan, A. P.; Ferrer, M. Clin. Exp. Allergy 2005, 35, 456-60; Kaplan, A. P.; Greaves, M. W. J. Am. Acad. Dermatol. 2005, 53, 373-88; quiz 389-92), psoriasis, mycosis, tissue ulceration, epidermolysis bullosa, wounds including abnormal wound healing, burns (Nwariaku, F. E.; Sikes, P. J.; Lightfoot, E.; Mileski, W. J.; Baxter, C. Burns 1996, 22, 324-7; Neely, A. N.; Imwalle, A. R.; Holder, I. A. Burns 1996, 22, 520-3), frostbite, skin inflammation and edema caused by venoms, alopecia, hair squama, corn, wart and panaris.

Eye Diseases:

Within the present application the term "eye diseases" encompasses, but is not limited to, inflammatory disorders such as scleritis, conjunctivitis, chemosis, iritis, iridocyclitis, uveitis, chorioretinitis, as well as disorders such as retinochoroidal circulatory disorders, bacterial eye infections, unspecific conjunctivitis and eye irritations, retinopathy of prematurity, proliferative vitreoretinopathy, macular degeneration (including age related macular degeneration and including both wet and dry forms), corneal diseases including corneal graft rejection, corneal injury, corneal scarring, corneal ulceration, corneal haze, keratoconus, glaucoma (preferably open angle glaucoma), myopia, ocular hypertension, ocular vessel damage, angiogenesis, eye fibrosis (e.g. anterior subcapsular fibrosis, posterior subcapsular opacities, posterior capsular opacities, corneal haze after laser surgery, subconjunctival scarring after glaucoma surgery), proliferative vitreoretinopathy (PVR), bacterial ocular infections including hordeolum and ptilosis.

Ear Diseases:

Within the present application the term "ear diseases" encompasses, but is not limited to, disorders such as Meniere's disease, inflammation of the middle ear, inflammation of the external auditory canal and acute hearing loss.

Mouth, Throat and Respiratory Diseases:

Within the present application the term "mouth, throat and respiratory diseases" encompasses, but is not limited to, disorders such as inflammation of the oral mucosa and gums including aphta and stomatitis, parodontitis, epiglottitis, pharyngitis, laryngotracheitis, tonsillitis, common cold, angina, rhinitis including seasonal allergic rhinitis or perennial allergic rhinitis, rhinorrea, sinusitis of whatever type, etiology or pathogenesis or sinusitis that is a member selected from the group consisting of purulent or nonpurulent sinusitis, acute and chronic sinusitis and ethmoid, frontal, maxillary or sphenoid sinusitis, expectoration, pneumoconiosis of whatever type or genesis, including for example aluminosis, anthracosis, asbestosis, chalicosis, siderosis, silicosis, tabacosis and, in particular, byssinosis, bronchitis, cough, trachitis, congestion, pneumonia, eosinophilc lung infiltrate, chronic eosinophilic pneumonia, idiopathic pulmonary fibrosis and other fibrotic lung diseases, treatment related fibrotic lung disease e.g. related to radiation, methotrexate, chemotherapy, amiodarone or nitrofurantoin, sarcoidosis, acute respiratory distress syndrome (ARDS), asthma of whatever type (Akbary, A. M.; Wirth, K. J.; Scholkens, B. A. Immunopharmacology 1996, 33, 238-42; WO 00/75107 A2), etiology, or pathogenesis, or asthma that is a member selected from the group of atopic asthma, non-atopic asthma, allergic and non-allergic asthma, extrinsic asthma caused by environmental factors, intrinsic asthma caused by pathophysiologic disturbances, bronchial asthma, IgE-mediated asthma, essential asthma and essential asthma of unknown or inapparent cause, true asthma, emphysematous asthma, exercise-induced asthma, occupational asthma, infective asthma caused by bacterial, fungal, protozoal or viral infection, incipient asthma, wheezy infant syndrome, bronchial hyperreactivity, chronic obstructive pulmonary disease (COPD), COPD that is characterized by irreversible, progressive airways obstruction, acute respiratory distress syndrome (ARDS) and exacerbation of airways hyperreactivity consequent to other drug therapy, dyspnea, hyperoxic alveolar injury, pulmonary emphysema, pleurisy, tuberculosis, exposure to high altitude i.e. acute mountain sickness and preferably high altitude pulmonary edema (HAPE).

Gastrointestinal Diseases:

Within the present application the term "gastrointestinal diseases" encompasses, but is not limited to, disorders including esophagitis, gastritis, irritable stomach, gastric and duodenal ulcer, ileus, colon irritable, inflammatory bowel diseases including Crohn's disease and ulcerative colitis, enteritis, hypertensive gastro- and colopathy, colitis, peritonitis, appendicitis, rectitis, gastrointestinal hemorrhage caused by a portal hypertension, collateral circulation or hyperemia, postgastrectomy dumping-syndrome, digestion discomfort, diarrhea, hemorrhoids, worm diseases, abdominal colic and colic of parts of the gastrointestinal system.

Liver, Gallbladder and Pancreatic Diseases (Cugno, M.; Salerno, F.; Nussberger, J.; Bottasso, B.; Lorenzano, E.; Agostoni, A. Clin. Sci. (Loud) 2001, 101, 651-7; WO 01/56995 A1; EP0797997 B1; Wirth, K. J.; Bickel, M.; Hropot, M.; Gunzler, V.; Heitsch, H.; Ruppert, D.; Scholkens, B. A. Eur. J. Pharmacol. 1997, 337, 45-53):

Within the present application the term "liver and gallbladder diseases" encompasses, but is not limited to, disorders such as hepatitis, cirrhosis of the liver, liver fibrosis (e.g. due to viral (HBV/HCV) infections, toxins (alcohol), fatty liver, bile stasis, hypoxia), portal hypertension, hepatorenal syndrome, hepatogenic edema, cholangitis, cholecystitis, acute and chronic pancreatitis, and biliary colic.

Urinary Tract and Kidney Diseases:

Within the present application the term "Urinary tract and kidney diseases" encompasses, but is not limited to, urinary tract infections such as acute and chronic cystitis, interstitial cystitis (Campbell, D. J. Clin. Exp. Pharmacol. Physiol. 2001, 28, 1060-5; Meini, S.; Patacchini, R.; Giuliani, S.; Lazzeri, M.; Turini, D.; Maggi, C. A.; Lecci, A. Eur. J. Pharmacol. 2000, 388, 177-82; Zuraw, B. L.; Sugimoto, S.; Parsons, C. L.; Hugh, T.; Lotz, M.; Koziol, J. J. Urol. 1994, 152, 874-8; Rosamilia, A.; Clements, J. A.; Dwyer, P. L.; Kende, M.; Campbell, D. J. J. Urol. 1999, 162, 129-34), irritable bladder, overactive bladder (WO 2007003411 A2), incontinence including but not limited to stress-, urge and reflex incontinence, benign prostate hyperplasia (Srinivasan, D.;

Kosaka, A. H.; Daniels, D. V.; Ford, A. P.; Bhattacharya, A. *Eur J Pharmacol.* 2004, 504(3):155-67), urethritis, inflammatory kidney diseases including glomerulonephritis, glomerular disease of the kidney, interstitial nephritis, pyelonephritis, diuresis, proteinuria, natriuresis, calciuresis, disorders of water balance, disorders of electrolyte balance, disorders of acid-base balance and renal colic, renal fibrosis, and chronic renal allograft dysfunction.

Diseases of Male Genitale Organs and Female Genitale Organs:

Within the present application the term "diseases of male genitale organs and female genitale organs" encompasses, but is not limited, to altered sperm mobility, male infertility, orchitis, prostatitis, prostate enhancement, mastitis, inflammatory pelvis diseases, vaginal infections and pain, adnexitis, colpitis, soft ulcus, syphilis, clap and ovarian hyperstimulation syndrome (Ujioka, T.; Matsuura, K.; Tanaka, N.; Okamura, H. *Hum Reprod.* 1998 November; 13(11):3009-15.).

Diseases of the Hormone System:

Within the present application the term "diseases of the hormone system" encompasses, but is not limited to, menstrual disorders and pain, climacteric disturbance, emesis, premature uterine contractions, premature labor, endometriosis, endometritis, myoma.

Metabolic Diseases:

Within the present application the term "metabolic diseases" encompasses, but is not limited to, disorders such as diabetes, including non-insulin dependent diabetes mellitus, diabetic retinopathy, diabetic macular edema (Speicher, M. A.; Danis, R. P.; Criswell, M.; Pratt, L. *Expert Opin. Emerg. Drugs* 2003, 8, 239-50; Gao, B. B.; Clermont, A.; Rook, S.; Fonda, S. J.; Srinivasan, V. J.; Wojtkowski, M.; Fujimoto, J. G.; Avery, R. L.; Arrigg, P. G.; Bursell, S. E.; Aiello, L. P.; Feener, E. P. *Nat. Med.* 2007, 13, 181-8; Tranos, P. G.; Wickremasinghe, S. S.; Stangos, N. T.; Topouzis, F.; Tsinopoulos, I.; Pavesio, C. E. *Surv. Ophthalmol* 2004, 49, 470-90), diabetic nephropathy and diabetic neuropathy, insulin resistance and diabetic ulceration, diseases of the proteo- and purine metabolism such as gout and disorder of lipometabolism.

Cardiovascular Diseases:

Within the present application the term "cardiovascular diseases" encompasses, but is not limited to, disorders including vascular permeability, vasodilation, peripheral circulatory disorders, arterial circulatory disorders including aortic aneurysm, abdominal aortic aneurysm, brain aortic aneurysm, hypertension and hypotension associated with sepsis, restenosis after percutaneous transluminal coronary angioplasty, atherosclerosis including atherosclerotic plaque rupture (Fernando, A. N.; Fernando, L. P.; Fukuda, Y.; Kaplan, A. P. *Am J Physiol Heart Circ Physiol.* 2005 July; 289(1):H251-7) hemangioma, angiofibroma, venous disorders such as thrombosis, varicosity, phlebitis, thrombophlebitis, phlebothrombosis, cardiopathy, congestive heart failure, carcinoid syndrome, angina pectoris, cardiac dysrhythmias, inflammatory heart diseases including endocarditis, pericarditis and constrictive pericarditis, myocarditis, myocardial infarct, postmyocardial infarction syndrome, left ventricular dilation, post ischemic reperfusion injury, shock and collapse including septic, allergic, post traumatic and hemodynamic shock, amniotic fluid embolism (Robillard, J.; Gauvin, F.; Molinaro, G.; Leduc, L.; Adam, A.; Rivard, G. E. *Am J Obstet Gynecol.* 2005 October; 193(4):1508-12.). Systemic inflammatory response syndrome (SIRS) including SIRS caused by heartlung bypass during surgery, sepsis and internal and external complications during cardiopulmonal bypass surgery (including but not limited to adverse hemodynamic effects following protamine sulfate reversal of heparin (Pretorius, M.; Scholl, F. G.; McFarlane, J. A.; Murphey, L. J.; Brown, N. J. *Clin Pharmacol Ther.* 2005 November; 78(5): 477-85).

Blood Diseases:

Within the present application the term "blood diseases" encompasses, but is not limited to, disorders such as coagulation, disseminated intravascular coagulopathy, hemorrhage, hemorrhagic diathesis, hypercholesterolemia and hyperlipemia.

Lymphatic Diseases:

Within the present application the term "Lymphatic diseases" as used herein encompasses, but is not limited to, splenomegaly, lymphangitis, lymphadenitis and hyperplastic adenoids.

Disorders of the Central Nervous System:

Within the present application the term "disorders of the central nervous system" encompasses, but is not limited to, disorders such as inflammatory diseases of the central nervous system including encephalitis, meningitis, encephalomyelitis, meningoencephalitis; hydrocephalus, amyotrophic lateral sclerosis, spinal cord trauma, spinal cord edema, demyelinating diseases of the nervous system, multiple sclerosis, acute and chronic neuro-degenerative disorders including Alzheimer's disease and Parkinson's disease, neuritis and peripheral neuropathy, depressions, anorexia, anxiety and schizophrenia.

Brain Disorders:

Within the present application the term "brain disorders" encompasses, but is not limited to, disorders including nootropic or cognition enhancement, cerebral amyloid angiopathy, stroke, head and brain trauma, traumatic brain injury (Marmarou, A.; Guy, M.; Murphey, L.; Roy, F.; Layani, L.; Combal, J. P.; Marquer, C.; American Brain Injury Consortium *J Neurotrauma* 2005 December; 22(12):1444-55) cerebral heat damage, cerebral ischemia, cerebral hemorrhage, post traumatic and post ischemic cerebral edema, general brain edema, acute mountain sickness and preferably high altitude cerebral edema (HACE), cytotoxic brain edema, vasogenic brain edema, post-surgical brain edema, brain edema associated with metabolic diseases, increase of permeability of blood-brain barrier or blood-brain tumor barrier.

Musculoskeletal System Diseases:

Within the present application the term "musculoskeletal system diseases" encompasses, but is not limited to, disorders such as inflammatory musculo skeletal disorders, arthrosis, osteoarthrosis, osteoarthritis, chondroporosis after joint trauma or relatively long immobilization of a joint after meniscus or patella injuries or torn ligaments, rheumatoid arthritis of whatever type, etiology, or pathogenesis including acute arthritis, acute gouty arthritis, chronic inflammatory arthritis, degenerative arthritis, infectious arthritis, Lyme arthritis, proliferative arthritis, vertebral arthritis, septic arthritis, psoriatic arthritis, chronic polyarthritis, rheumatism, Sjogren's syndrome, lumbago, spondylitis, spondylarthritis, ankylosing spondylitis, osteomyelitis, sprain, tenosynovitis, inflammation-induced bone resorption, fracture or the like, osteoporosis, musculoskeletal pain and hardening, spinal disk syndrome.

Allergy Disorders:

Within the present application the term "allergy disorders" encompasses, but is not limited to, disorders such as general allergic reactions, food allergy, anaphylactic shock, allergic contact hypersensitivity, allergic skin reactions, allergic asthma, vernal conjunctivitis and seasonal or perennial allergic rhinitis (Summers, C. W.; Pumphrey, R. S.; Woods, C. N.; McDowell, G.; Pemberton, P. W.; Arkwright, P. D. *J Allergy Clin Immunol.* 2008)

Pain:

Within the present application the term "pain" encompasses, but is not limited to, centrally and peripherally mediated pain, vascular pain, visceral pain, inflammatory mediated pain, neuralgic pain, referred pain, nociceptive pain, reflectory pain, psychosomatic pain, acute pain such as caused by acute injury, trauma or surgery of bones, muscle, tissue, soft tissue, organs, pain after insectbites, post-stroke pain syndrome, post-surgery pain, progressive disease related pain, chronic pain such as caused by neuropathic pain conditions (including but not limited to complex regional pain syndrome (WO00/75107 A2; Yamaguchi-Sase, S.; Hayashi, I.; Okamoto, H.; Nara, Y.; Matsuzaki, S.; Hoka, S.; Majima, M. *Inflamm. Res.* 2003, 52, 164-9; Petersen, M.; Eckert, A. S.; Segond von Banchet, G.; Heppelmann, B.; Klusch, A.; Kniffki, K. D. *Neuroscience* 1998, 83, 949-59; Birklein, F.; Schmelz, M.; Schifter, S.; Weber, M. *Neurology* 2001, 57, 2179-84; Weber, M.; Birklein, F.; Neundorfer, B.; Schmelz, M. *Pain* 2001, 91, 251-7), causalgia, morbus sudeck, reflex sympathetic dystrophy), diabetic peripheral neuropathy, post-herpetic neuralgia, trigeminal neuralgia, cancer-related pain, pain associated with rheumatoid arthritis, osteoarthritis (Bond, A. P.; Lemon, M.; Dieppe, P. A.; Bhoola, K. D. *Immunopharmacology* 1997, 36, 209-16; Cassim, B.; Naidoo, S.; Ramsaroop, R.; Bhoola, K. D. *Immunopharmacology* 1997, 36, 121-5; Calixto, J. B.; Cabrini, D. A.; Ferreira, J.; Campos, M. M. *Pain* 2000, 87, 1-5; Kaneyama, K.; Segami, N.; Sato, J.; Fujimura, K.; Nagao, T.; Yoshimura, H. *J. Oral. Maxillofac. Surg.* 2007, 65, 242-7), teno-synovitis, gout, menstruation and angina, fibromyalgia, ocular pain, back pain, headache, cluster headache, migraine (Ebersberger, A.; Ringkamp, M.; Reeh, P. W.; Handwerker, H. O. *J Neurophysiol.* 1997 June; 77(6):3122-33.), hyperalgesia, and fever. Furthermore, compounds of the invention are useful as analgesic agent for use during general and monitored anesthesia.

Infectious Diseases:

Within the present application the term "infectious diseases" encompasses, but is not limited to, diseases including those mediated by bacteria, viruses, fungi, parasites, protozoa, prions or mycobacterial infections. Particularly, the present invention is useful for the treatment of bacterial infections caused by *Streptococcus, Escherichia, Salmonella, Staphylococcus, Klebsiella, Moracella, Haemophilus* and *Yersinia*. Examples of bacterial infections intended to be within the scope of the present invention include, but are not limited to diseases such as pestis, sepsis, epidemic typhus, food poisoning, tetanus, scarlet red, whooping cough, diphtheria. Examples of viral infections intended to be within the scope of the present invention include, but are not limited to diseases such chickenpox and herpes zoster, AIDS, influenza, small pox, and children diseases such as measles, rubella, mumps, acute anterior poliomyelitis. The present invention is useful for the treatment of protozoa and parasites infections caused by *Schistosoma mansoni, Dermatofagoides farinae* and *Plasmodium* inducing Malaria. Examples of prion infections intended to be within the scope of the present invention include, but are not limited to diseases such bovine spongiform encephalopathy (BSE), Creutzfeldt Jacob disease and kuru.

Inflammatory Disorders:

Within the present application the term "inflammatory disorders" encompasses, but is not limited to, disorders such as acute-phase reaction, local and systemic inflammation and inflammation caused by other diseases whatever type, etiology or pathogenesis and caused by those inflammatory diseases specified within this application.

Injuries:

Within the present application the term "injuries" encompasses, but is not limited to, multiple trauma, head trauma, lung injuries, external, internal and surgery wounds.

Immunology Disorders:

Within the present application the term "immunology disorders" encompasses, but is not limited to, disorders such as hyperesthesia, autoimmune disorders, graft rejection in transplantation, transplant toxicity, granulomatous inflammation/tissue remodelling, myasthenia gravis, immunosuppression, immune-complex diseases, over- and underproduction of antibodies, vasculitis.

Cancers:

Within the present application the term "cancers" encompasses, but is not limited to, disorders such as solid tumor cancer including breast cancer, lung cancer (non-small-cell lung cancer and small-cell lung cancer), prostate cancer, cancers of the oral cavity and pharynx (lip, tongue, mouth, pharynx), esophagus, stomach, small intestine, large intestine, colon, rectum, gallbladder and biliary passages, pancreas, larynx, lung, bone, osteosarcoma, connective tissue, skin cancer including Kaposi's syndrome, melanoma and skin metastasis, epidermoid cancer, basal cell carcinoma, cervix uteri, corpus endometrium, cancer of ovary, testis, bladder, ureter and urethra, kidney, eye, brain and central nervous system, pseudotumor cerebri, sarcoma, sarcoid, thyroid and other endocrine glands (including but not limited to carcinoid tumors), Hodgkin's disease, non-Hodkin's lymphomas, multiple myeloma, hematopoetic malignancies including leukemias and lymphomas including lymphocytic, granulocytic and monocytic lymphomas, tumor invasion, metastasis, ascites, tumor growth and angiogenesis.

Hereditary Diseases:

Within the present application the term "hereditary diseases" encompasses, but is not limited to, disorders such as hereditary angioedema (Davis, A. E. et al., 3rd *Transfus. Apher. Sci.* 2003, 29, 195-203; Zuraw, B. L. *Immunol. Allergy Clin. North Am.* 2006, 26, 691-708; Bas, M. et al. *Allergy* 2006, 61, 1490-2) and angioneurotic edema, chondrocalcinosis, Huntington's disease, mucoviscidosis.

Edema:

Within the present application the term "edema" encompasses, but is not limited to, general edema and edema caused by inflammation, other drugs, e.g. drug induced angioedema (Mathelier-Fusade, P. *Clin. Rev. Allergy Immunol.* 2006, 30, 19-23; Finley, C. J. et al. *Am. J. Emerg. Med* 1992, 10, 550-2; Bielory, L. et al. *Allergy Proc.* 1992, 13, 85-7), infection, burns, injuries, trauma, frostbite, surgery, distorsions, fractures, exposure to high altitude (e.g. high altitude pulmonary edema (HAPE) and high altitude cerebral edema (HACE)), hereditary, autoimmune and other diseases and disorders, particularly but not limited to those disorders specified in this application.

Capillary Leak Syndrome(s):

Within the present application the term "capillary leak syndrome(s)" encompasses, but is not limited to, systemic capillary leak syndrome in sepsis (Marx, G. *Eur J Anaesthesia* 2003 20(6):429-42; Traber, D. L. *Crit Care Med.* 2000, 28(3):882-3), burn (Jonkam, C. C.; Enkhbaatar, P.; Nakano, Y.; Boehm, T.; Wang, J.; Nussberger, J. Esechie, A.; Traber, L. D.; Herndon, D.; Traber, D. L., *Shock.* 2007 December; 28(6): 704-9), allergy, drug/toxin-induced conditions, organ transplantation and IL-2 cytokine therapy.

Methodology and Diagnostics:

Compounds of the invention can be labelled by isotopes, fluorescence or luminescence markers, antibodies or antibody fragments, any other affinity label like nanobodies, aptamers, peptides etc., enzymes or enzyme substrates. These labelled compounds of this invention are useful for mapping the location of bradykinin receptors in vivo, ex vivo, in vitro and in situ (e.g. in tissue sections via autoradiography) and as radiotracers for positron emission tomography (PET) imaging, single photon emission computerized tomography (SPECT) and the like to characterize those receptors in living subjects or other materials.

The present invention also pertains to methods for altering the signal-transducing activity of bradykinin receptors in vitro and in vivo. For instance, compounds of the present invention and labelled derivatives thereof can be used as standard and reagent in determining the ability of a potential pharmaceutical to bind to the BK B2 receptor.

The present invention also provides methods for localizing or detecting a BK B2 receptor in a tissue, preferably a tissue section, which methods involve contacting the tissue sample containing BK B2 receptor with a detectably labelled compound according to the present invention under conditions that permit binding of the compound to the BK B2 receptor and detecting the bound compound. Such methods and their respective conditions are known to those skilled in the art and include, for example, the radioligand binding assay disclosed in example 754.

The present invention also provides methods of inhibiting the binding of BK or any other B2 receptor ligand to a BK B2 receptor which methods involve contacting a solution containing a BK B2 receptor antagonist compound disclosed herein with cells expressing BK B2 receptor under conditions and in an amount sufficient to detectably inhibit binding of BK or any other substance to BK B2 receptor. Such methods and their respective conditions are known to those skilled in the art and include, for example, the calcium mobilization assay disclosed in example 755.

The present invention further provides methods for treating patients suffering from conditions responsive to BK B2 receptor modulation as mentioned above. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to BK B2 receptor modulation" if modulation of BK B2 receptor activity results in alleviation of the condition or a symptom thereof. Patients may include but are not limited to primates (especially humans), domesticated companion animals (such as dogs, cats, horses) and livestock (such as cattle, pigs, sheep), with dosages as described herein.

It is also within the present invention that the compounds according to the invention are used as or for the manufacture of a diagnostic agent, whereby such diagnostic agent is for the diagnosis of the diseases and conditions which can be addressed by the compounds of the present invention for therapeutic purposes as disclosed herein.

The compounds of formula (I) according to the present invention have improved properties when compared to BK B2 receptor antagonists known in the state of the art, especially, improved selectivity, low toxicity, low drug drug interaction, improved bioavailability (especially with regard to oral administration), improved metabolic stability, improved stability in microsomal degradation assay, and improved solubility.

The present invention is now further illustrated by the following examples from which further features, embodiments and advantages of the present invention may be taken.

EXAMPLES

Preparation of Compounds

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

Abbreviations Used in the Following Examples are as Follows:

ACN is acetonitrile

BK is bradykinin

BSA is bovine serum albumin cpm is counts per minute

DCM is dichloromethane

DIBAL is diisobutylaluminum hydride

DIPEA is ethyl-diisopropyl-amine

DMF is dimethylformamide

DMSO is dimethylsulfoxide

EA is ethyl acetate

ELISA is enzyme-linked immunosorbentimmosorbent assay

HBTU is benzotriazol-1-yl-(bis-dimethylamino-methylene)-oxonium; hexafluorophosphate HBSS is Hanks' balanced salt solution HOAc is glacial acetic acid HPLC is high performance liquid chromatography LDA is lithium diisoprpylamide NMP is 1-methyl-pyrrolidin-2-one Pd(OAc)$_2$ is palladium (II) acetate PBS is phosphate-buffered saline PIPES is piperazine-N,N'-bis(2-ethanesulfonic acid)

p-TsOH is toluene-4-sulfonic acid

RT is room temperature

THF is tetrahydrofuran

THP is tetrahydropyranyl

TFA is trifluoroacetate or trifluoroacetic acid sat. is saturated

WSC is (3-dimethylamino-propyl)-ethyl-carbodiimide hydrochloride

Pd(dppf)Cl$_2$ is (1,1'-bis(diphenylphosphino)ferrocene)-dichloropalladium(II)•DCM The compounds shown in the following Table 1 are representative examples of compounds of formula (I) according to the present invention.

TABLE 1
| Example | Structure | M + H+ |
|---|---|---|
| 1. | 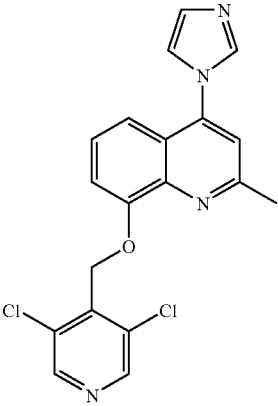 [SMILES: Cc1cc(-n2ccnc2)c2cccc(OCc3c(Cl)cncc3Cl)c2n1] | 385.5 |
| 2. | 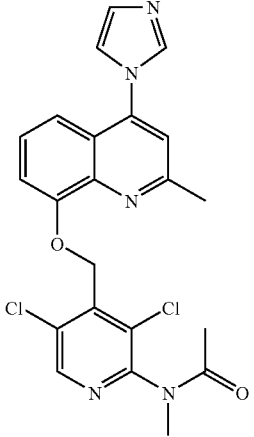 [SMILES: CC(=O)N(C)c1ncc(Cl)c(COc2cccc3c(-n4ccnc4)cc(C)nc23)c1Cl] | 456.6 |
| 3. | 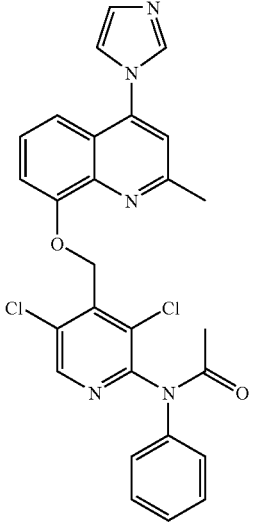 [SMILES: CC(=O)N(c1ccccc1)c1ncc(Cl)c(COc2cccc3c(-n4ccnc4)cc(C)nc23)c1Cl] | 518.9 |
TABLE 1-continued
| Example | Structure | M + H+ |
|---|---|---|
| 4. | 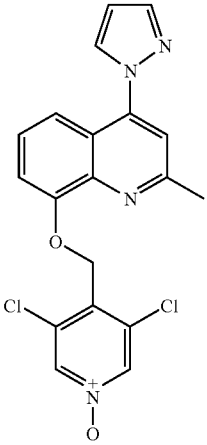 [SMILES: Cc1cc(-n2cccn2)c2cccc(OCc3c(Cl)c[n+](O)cc3Cl)c2n1] | 401.0 |
| 5 | 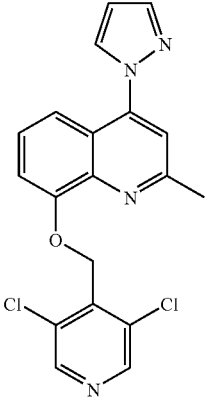 [SMILES: Cc1cc(-n2cccn2)c2cccc(OCc3c(Cl)cncc3Cl)c2n1] | 385.3 |
| 6. | 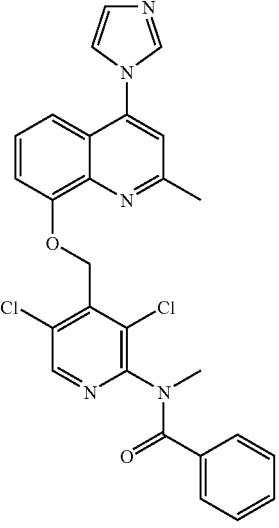 [SMILES: Cc1cc(-n2ccnc2)c2cccc(OCc3c(Cl)cnc(N(C)C(=O)c4ccccc4)c3Cl)c2n1] | 518.9 |

TABLE 1-continued
| Example | Structure | M + H+ |
|---|---|---|
| 7. | 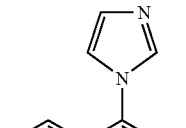 | 345.0 |
| 8. | 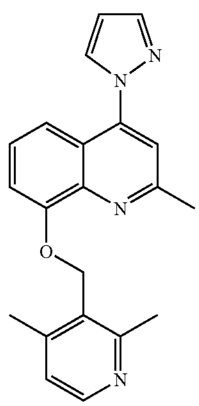 [SMILES: Cc1cc(-n2cccn2)c2cccc(OCc3c(C)ccnc3C)c2n1] | 345.0 |
| 9. | 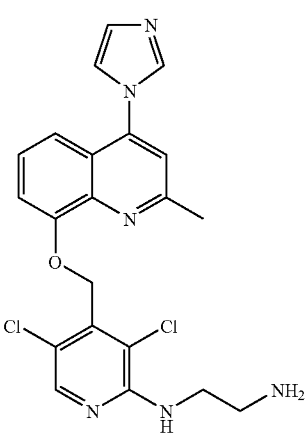 [SMILES: Cc1cc(-n2ccnc2)c2cccc(OCc3c(Cl)cnc(NCCN)c3Cl)c2n1] | 443.4 |
| 10. | | 414.3 |
| 11. | | 555.1 |
| 12. | | 485.3 |

TABLE 1-continued
| Example | Structure | M + H+ |
|---|---|---|
| 13. | 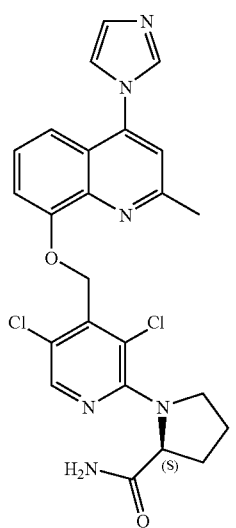 | 457.1 |
| 14. | 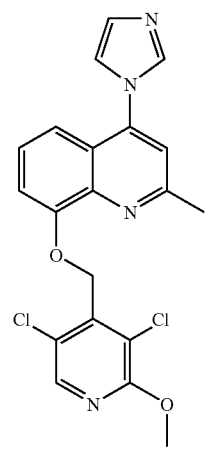 | 497.4 |
| 15. | 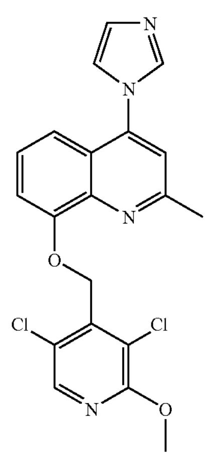 [SMILES: COc1ncc(Cl)c(COc2cccc3c(-n4ccnc4)cc(C)nc23)c1Cl] | 415.2 |
TABLE 1-continued
| Example | Structure | M + H+ |
|---|---|---|
| 16. | 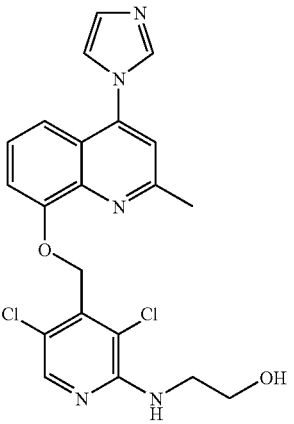 [SMILES: Cc1cc(-n2ccnc2)c2cccc(OCc3c(Cl)cnc(NCCO)c3Cl)c2n1] | 444.2 |
| 17. | 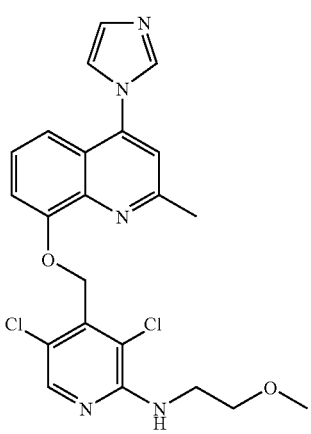 [SMILES: COCCNc1ncc(Cl)c(COc2cccc3c(-n4ccnc4)cc(C)nc23)c1Cl] | 458.5 |
| 18. | 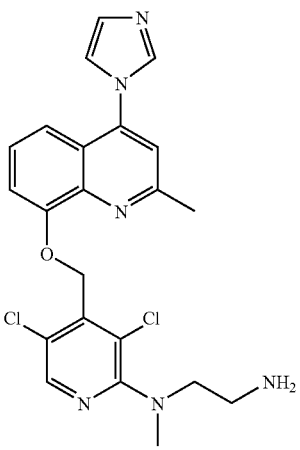 [SMILES: Cc1cc(-n2ccnc2)c2cccc(OCc3c(Cl)cnc(N(C)CCN)c3Cl)c2n1] | 457.3 |

TABLE 1-continued

| Example | Structure | M + H⁺ |
|---------|-----------|--------|
| 19. | 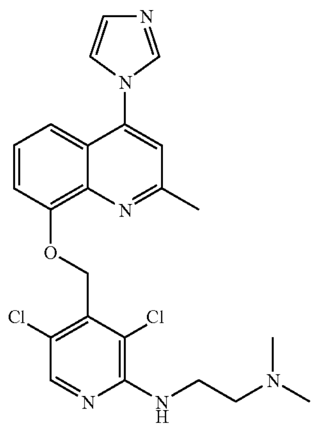 [SMILES: Cc1cc(-n2ccnc2)c2cccc(OCc3c(Cl)cnc(NCCN(C)C)c3Cl)c2n1] | 471.5 |
| 20. | 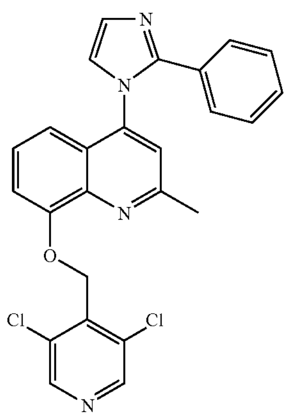 [SMILES: Cc1cc(-n2ccnc2-c2ccccc2)c2cccc(OCc3c(Cl)cncc3Cl)c2n1] | 461.9 |
| 21. | 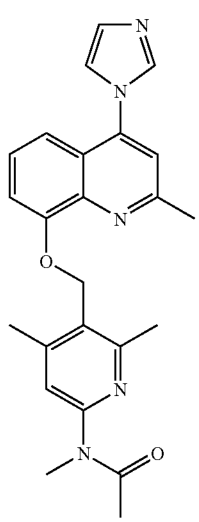 [SMILES: CC(=O)N(C)c1cc(C)c(COc2cccc3c(-n4ccnc4)cc(C)nc23)c(C)n1] | 417.0 |
| 22. | 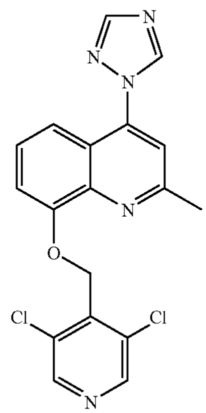 [SMILES: Cc1cc(-n2cncn2)c2cccc(OCc3c(Cl)cncc3Cl)c2n1] | 386.0 |
| 23. | 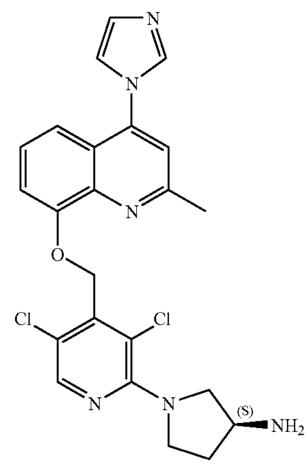 | 469.5 |
| 24. | 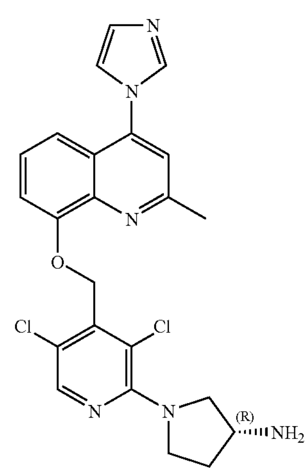 [SMILES: Cc1cc(-n2ccnc2)c2cccc(OCc3c(Cl)cnc(N4CC[C@@H](N)C4)c3Cl)c2n1] | 469.5 |

TABLE 1-continued

| Example | Structure | M + H⁺ |
|---|---|---|
| 25. | 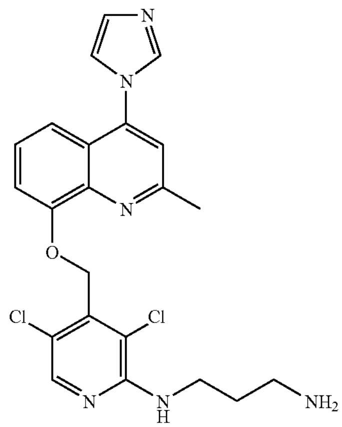 [SMILES: Cc1cc(-n2ccnc2)c2cccc(OCc3c(Cl)cnc(NCCCN)c3Cl)c2n1] | 457.3 |
| 26. | 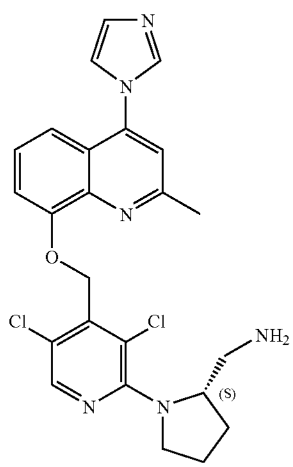 | 483.3 |
| 27. | 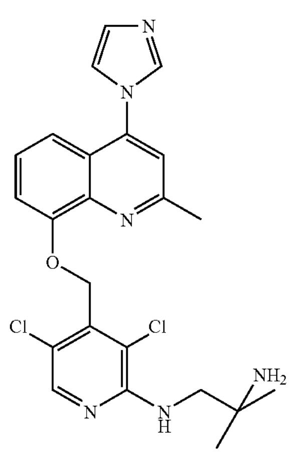 [SMILES: Cc1cc(-n2ccnc2)c2cccc(OCc3c(Cl)cnc(NCC(C)(C)N)c3Cl)c2n1] | 471.5 |
| 28. | 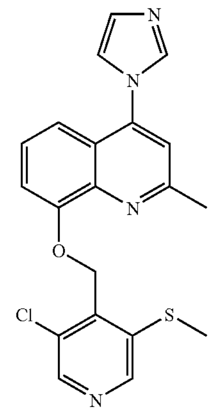 [SMILES: CSc1cncc(Cl)c1COc1cccc2c(-n3ccnc3)cc(C)nc12] | 397.3 |
| 29. | 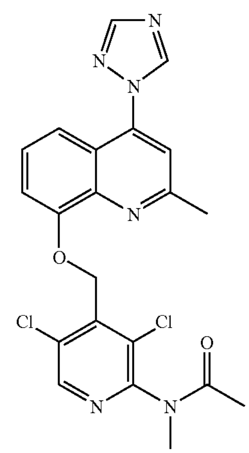 [SMILES: CC(=O)N(C)c1ncc(Cl)c(COc2cccc3c(-n4cncn4)cc(C)nc23)c1Cl] | 457.2 |
| 30. | 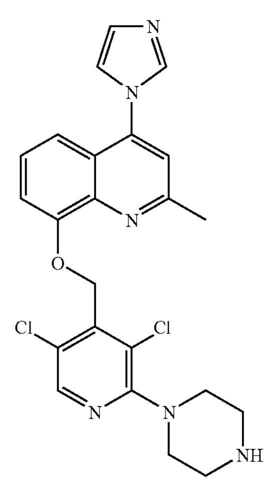 [SMILES: Cc1cc(-n2ccnc2)c2cccc(OCc3c(Cl)cnc(N4CCNCC4)c3Cl)c2n1] | 469.2 |

TABLE 1-continued

| Example | Structure | M + H+ |
|---------|-----------|--------|
| 31. | 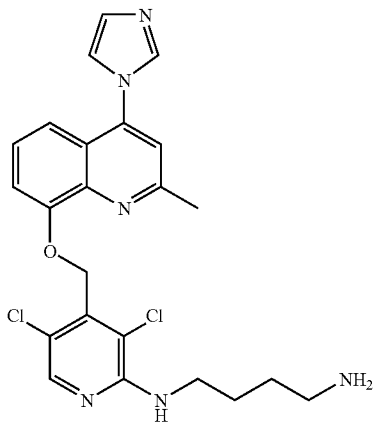 [SMILES: Cc1cc(-n2ccnc2)c2cccc(OCc3c(Cl)cnc(NCCCCN)c3Cl)c2n1] | 471.3 |
| 32. | 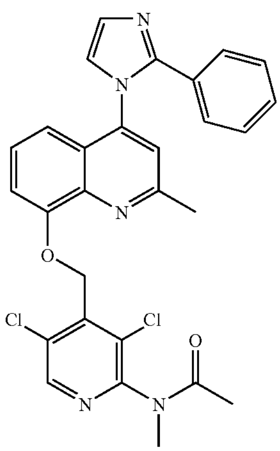 [SMILES: CC(=O)N(C)c1ncc(Cl)c(COc2cccc3c(-n4ccnc4-c4ccccc4)cc(C)nc23)c1Cl] | 532.2 |
| 33. | 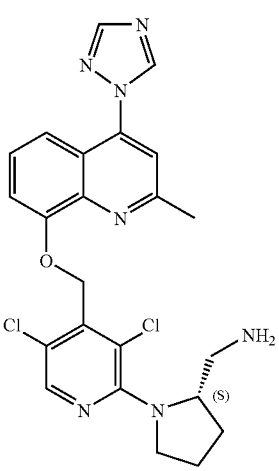 | 484.4 |
| 34. | | 559.5 |
| 35. | | 497.4 |
| 36. | | 471.4 |

TABLE 1-continued

| Example | Structure | M + H⁺ |
|---|---|---|
| 37. | 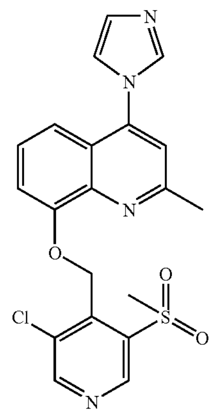 [SMILES: Cc1cc(-n2ccnc2)c2cccc(OCc3c(Cl)cncc3S(C)(=O)=O)c2n1] | 429.2 |
| 38. | 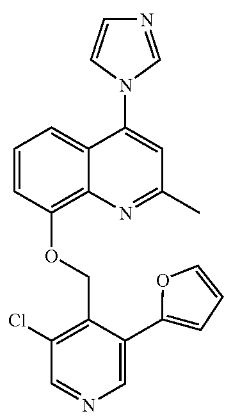 [SMILES: Cc1cc(-n2ccnc2)c2cccc(OCc3c(Cl)cncc3-c3ccco3)c2n1] | 417.2 |
| 39. | 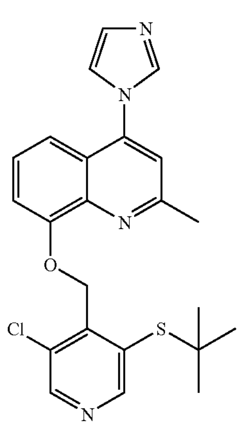 [SMILES: Cc1cc(-n2ccnc2)c2cccc(OCc3c(Cl)cncc3SC(C)(C)C)c2n1] | 439.8 |
| 40. | 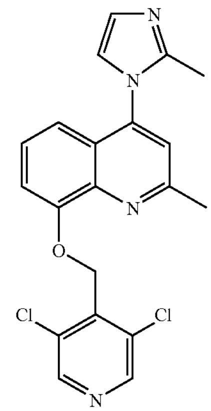 [SMILES: Cc1cc(-n2ccnc2C)c2cccc(OCc3c(Cl)cncc3Cl)c2n1] | 239.6 |
| 41. | 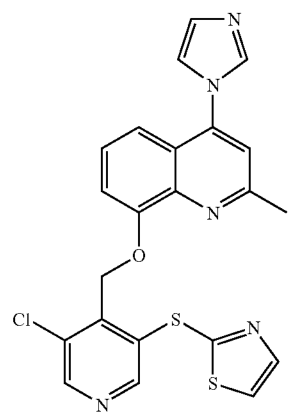 [SMILES: Cc1cc(-n2ccnc2)c2cccc(OCc3c(Cl)cncc3Sc3nccs3)c2n1] | 466.2 |
| 42. | 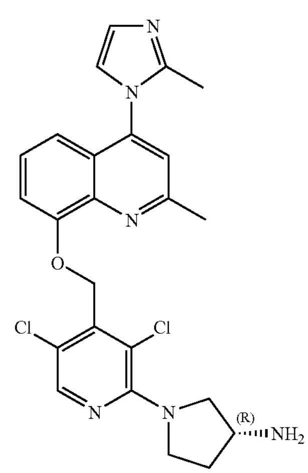 | 483.3 |

TABLE 1-continued

| Example | Structure | M + H+ |
|---------|-----------|--------|
| 43. | 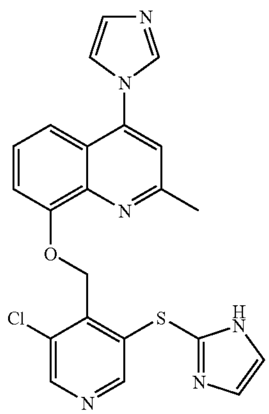 [SMILES: Cc1cc(-n2ccnc2)c2cccc(OCc3c(Cl)cncc3Sc3ncc[nH]3)c2n1] | 449.1 |
| 44. | 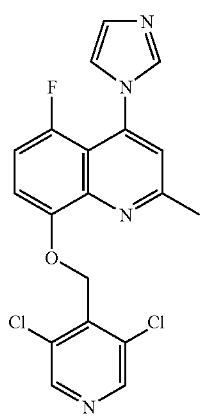 [SMILES: Cc1cc(-n2ccnc2)c2c(F)ccc(OCc3c(Cl)cncc3Cl)c2n1] | 403.6 |
| 45. | 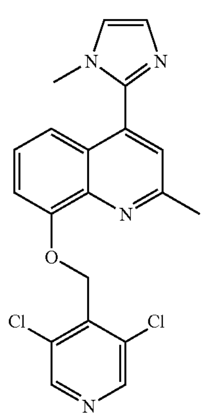 [SMILES: Cc1cc(-c2nccn2C)c2cccc(OCc3c(Cl)cncc3Cl)c2n1] | 399.8 |
| 46. | 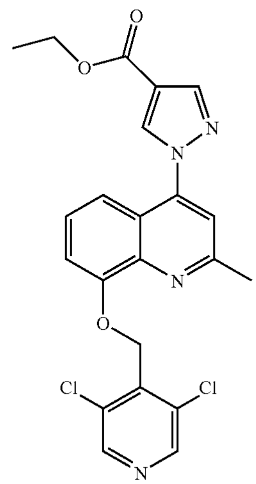 [SMILES: CCOC(=O)c1cnn(-c2cc(C)nc3c(OCc4c(Cl)cncc4Cl)cccc23)c1] | 457.3 |
| 47. | 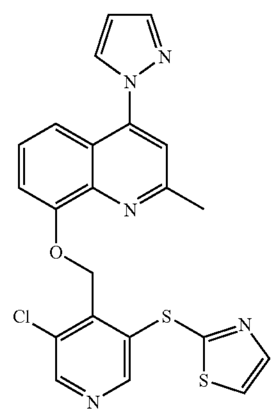 [SMILES: Cc1cc(-n2cccn2)c2cccc(OCc3c(Cl)cncc3Sc3nccs3)c2n1] | 466.1 |
| 48. | 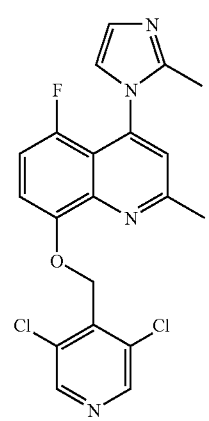 [SMILES: Cc1cc(-n2ccnc2C)c2c(F)ccc(OCc3c(Cl)cncc3Cl)c2n1] | 417.7 |

TABLE 1-continued

| Example | Structure | M + H⁺ |
|---------|-----------|--------|
| 49. | 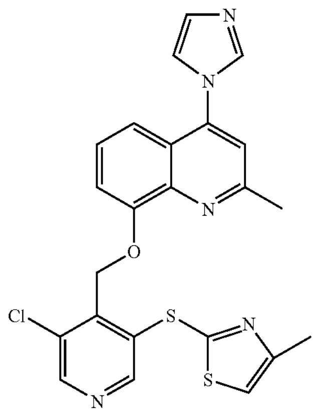 [SMILES: Cc1csc(Sc2cncc(Cl)c2COc2cccc3c(-n4ccnc4)cc(C)nc23)n1] | 480.0 |
| 50. | 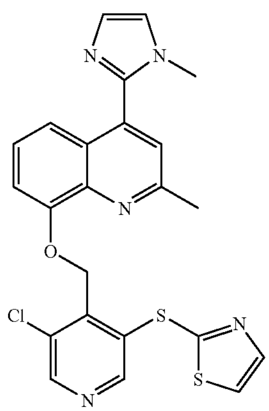 [SMILES: Cc1cc(-c2nccn2C)c2cccc(OCc3c(Cl)cncc3Sc3nccs3)c2n1] | 480.2 |
| 51. | 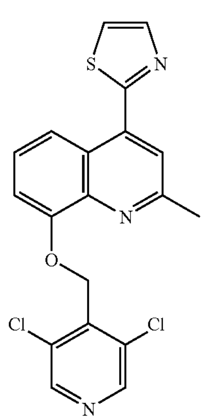 [SMILES: Cc1cc(-c2nccs2)c2cccc(OCc3c(Cl)cncc3Cl)c2n1] | 402.1 |
| 52. | | 483.4 |
| 53. | | 497.2 |
| 54. | | 457.2 |

TABLE 1-continued

| Example | Structure | M + H⁺ |
|---|---|---|
| 55. | 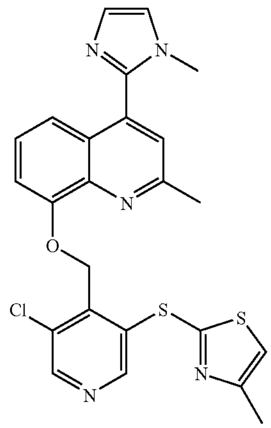 [SMILES: Cc1csc(Sc2cncc(Cl)c2COc2cccc3c(-c4nccn4C)cc(C)nc23)n1] | 494.2 |
| 56. | 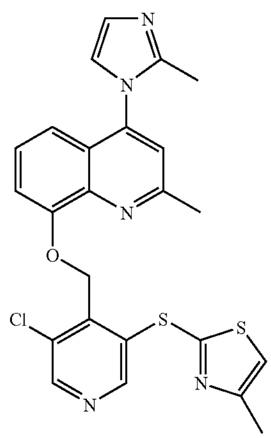 [SMILES: Cc1csc(Sc2cncc(Cl)c2COc2cccc3c(-n4ccnc4C)cc(C)nc23)n1] | 494.3 |
| 57. | 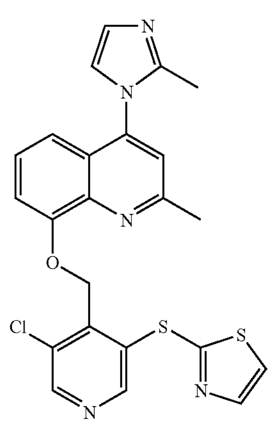 [SMILES: Cc1cc(-n2ccnc2C)c2cccc(OCc3c(Cl)cncc3Sc3nccs3)c2n1] | 480.3 |

TABLE 1-continued

| Example | Structure | M + H⁺ |
|---|---|---|
| 58. | 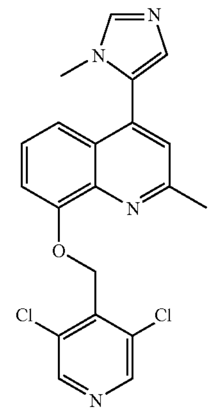 [SMILES: Cc1cc(-c2cncn2C)c2cccc(OCc3c(Cl)cncc3Cl)c2n1] | 399.3 |
| 59. | 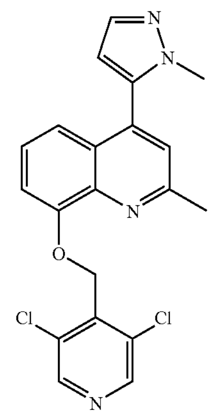 [SMILES: Cc1cc(-c2ccnn2C)c2cccc(OCc3c(Cl)cncc3Cl)c2n1] | 399.4 |
| 60. | 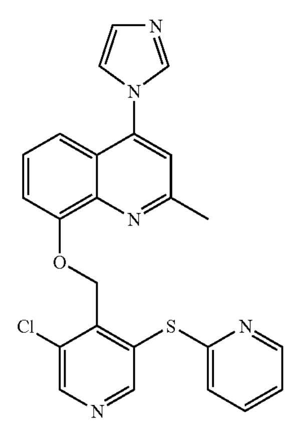 [SMILES: Cc1cc(-n2ccnc2)c2cccc(OCc3c(Cl)cncc3Sc3ccccn3)c2n1] | 460.0 |

TABLE 1-continued

| Example | Structure | M + H+ |
|---------|-----------|--------|
| 61. | 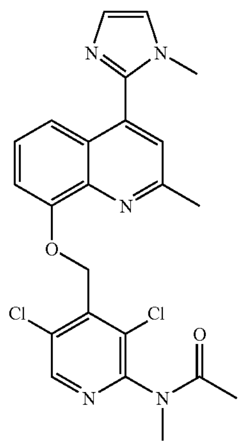 [SMILES: CC(=O)N(C)c1ncc(Cl)c(COc2cccc3c(-c4nccn4C)cc(C)nc23)c1Cl] | 470.2 |
| 62. | 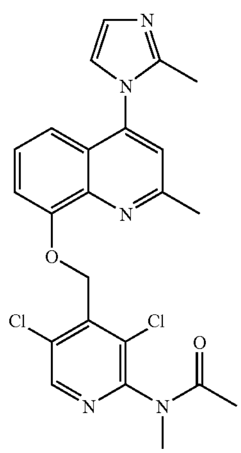 [SMILES: CC(=O)N(C)c1ncc(Cl)c(COc2cccc3c(-n4ccnc4C)cc(C)nc23)c1Cl] | 470.5 |
| 63. | 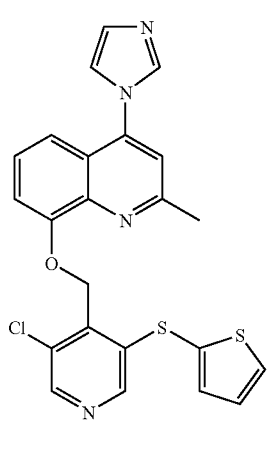 [SMILES: Cc1cc(-n2ccnc2)c2cccc(OCc3c(Cl)cncc3Sc3cccs3)c2n1] | 465.4 |
| 64. | | 479.6 |
| 65. | | 479.5 |
| 66. | | 482.1 |

TABLE 1-continued
| Example | Structure | M + H+ |
|---|---|---|
| 67. | 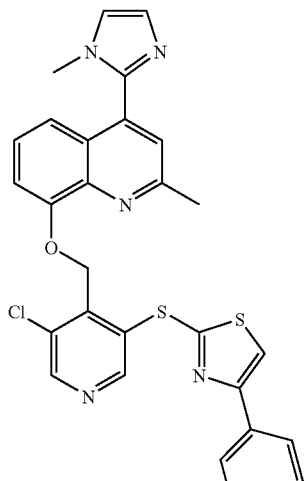 | 556.3 |
| 68. | 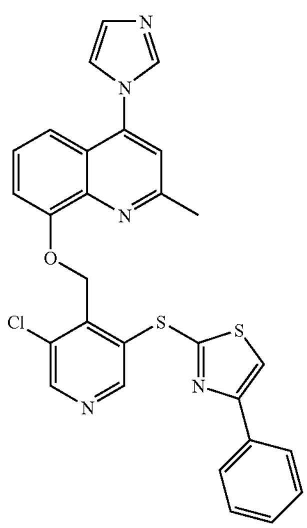 [SMILES: Cc1cc(-n2ccnc2)c2cccc(OCc3c(Cl)cncc3Sc3nc(-c4ccccc4)cs3)c2n1] | 542.2 |
| 69. | 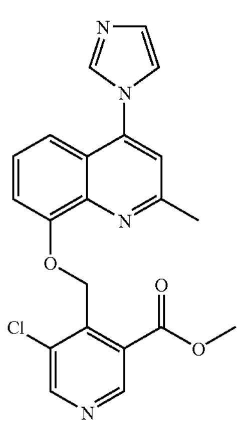 [SMILES: COC(=O)c1cncc(Cl)c1COc1cccc2c(-n3ccnc3)cc(C)nc12] | 409.1 |
TABLE 1-continued
| Example | Structure | M + H+ |
|---|---|---|
| 70. | 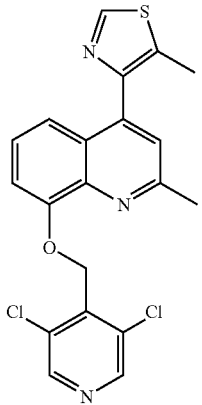 [SMILES: Cc1cc(-c2ncsc2C)c2cccc(OCc3c(Cl)cncc3Cl)c2n1] | 416.4 |
| 71. | 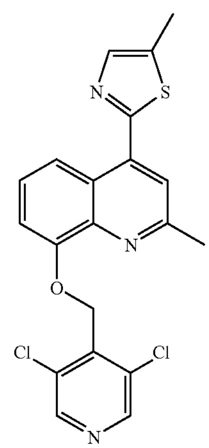 [SMILES: Cc1cc(-c2ncc(C)s2)c2cccc(OCc3c(Cl)cncc3Cl)c2n1] | 416.5 |
| 72. | 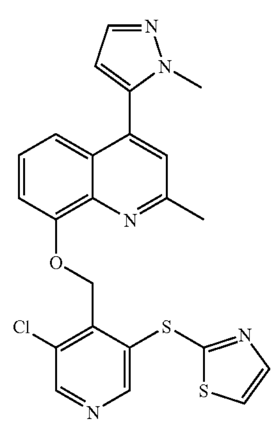 [SMILES: Cc1cc(-c2ccnn2C)c2cccc(OCc3c(Cl)cncc3Sc3nccs3)c2n1] | 480.2 |

TABLE 1-continued
| Example | Structure | M + H+ |
|---|---|---|
| 73. | 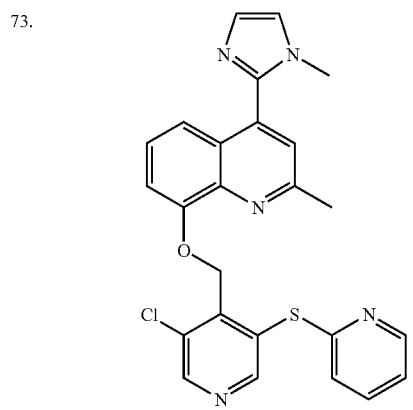 | 474.2 |
| 74. | 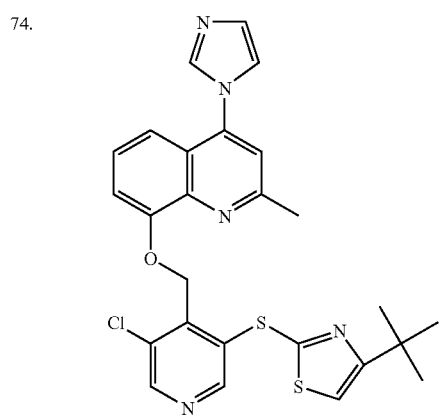 | 522.1 |
| 75. | 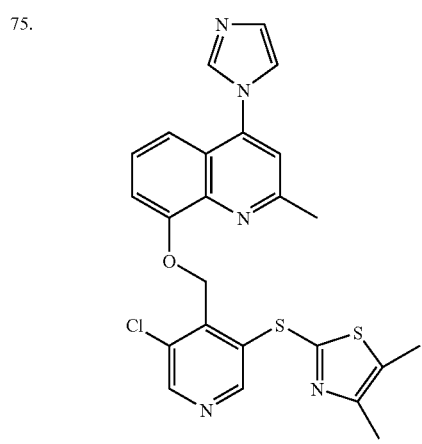 | 494.2 |
TABLE 1-continued
| Example | Structure | M + H+ |
|---|---|---|
| 76. | 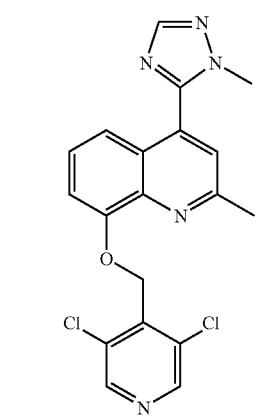 [SMILES: Cc1cc(-c2ncnn2C)c2cccc(OCc3c(Cl)cncc3Cl)c2n1] | 400.2 |
| 77. | 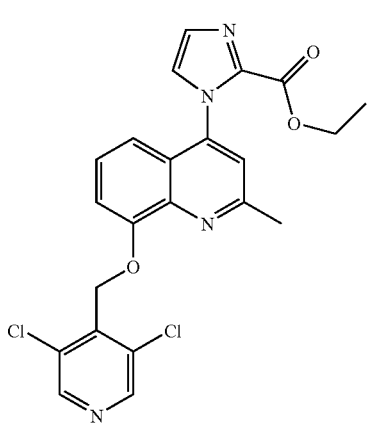 [SMILES: CCOC(=O)c1nccn1-c1cc(C)nc2c(OCc3c(Cl)cncc3Cl)cccc12] | 457.3 |
| 78. | 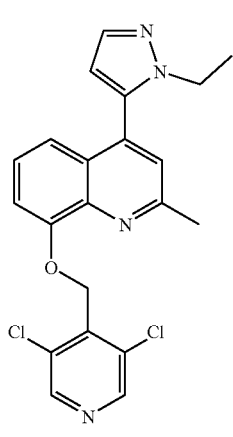 [SMILES: CCn1nccc1-c1cc(C)nc2c(OCc3c(Cl)cncc3Cl)cccc12] | 413.6 |

TABLE 1-continued
| Example | Structure | M + H⁺ |
|---|---|---|
| 79. | 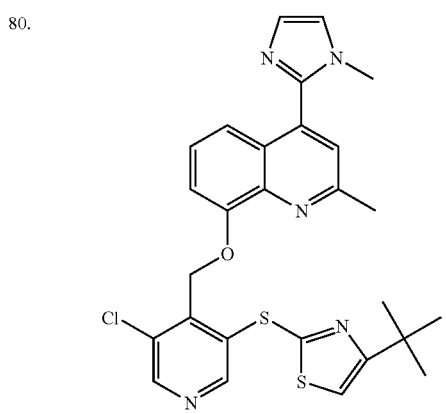 | 385.2 |
| 80. | 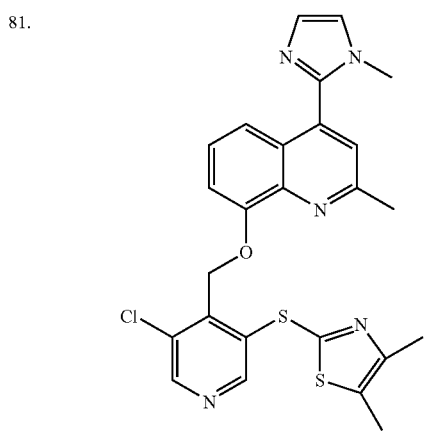 | 536.9 |
| 81. | 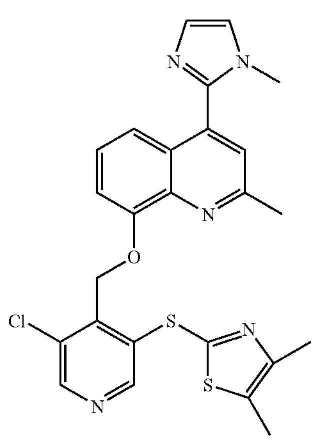 [SMILES: Cc1cc(-c2nccn2C)c2cccc(OCc3c(Cl)cncc3Sc3nc(C)c(C)s3)c2n1] | 508.4 |
TABLE 1-continued
| Example | Structure | M + H⁺ |
|---|---|---|
| 82. | 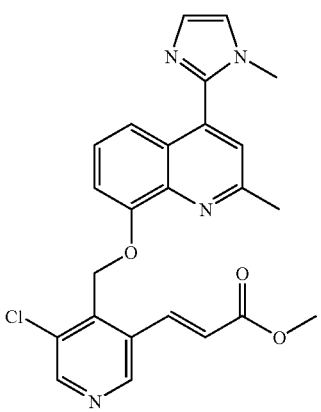 [SMILES: COC(=O)/C=C/c1cncc(Cl)c1COc1cccc2c(-c3nccn3C)cc(C)nc12] | 399.4 |
| 83. | 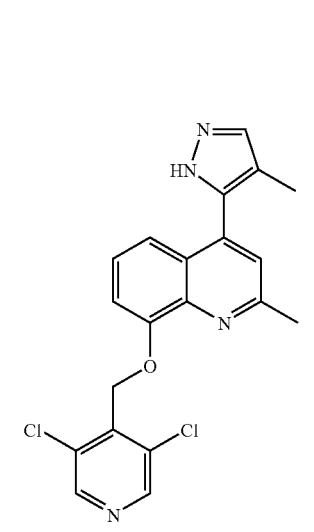 | 449.2 |
| 84. | 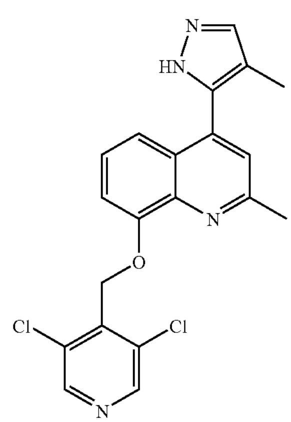 [SMILES: Cc1cc(-c2[nH]ncc2C)c2cccc(OCc3c(Cl)cncc3Cl)c2n1] | 399.1 |

TABLE 1-continued

| Example | Structure | M + H⁺ |
|---|---|---|
| 85. | 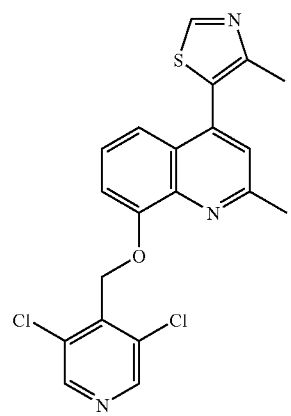 [SMILES: Cc1cc(-c2scnc2C)c2cccc(OCc3c(Cl)cncc3Cl)c2n1] | 416.6 |
| 86. | 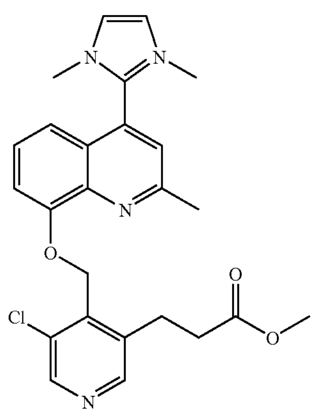 | 451.3 |
| 87. | 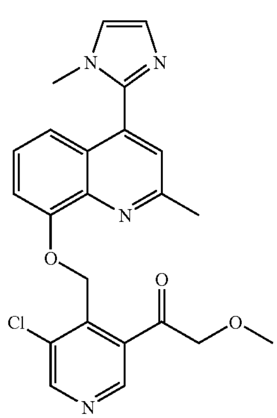 [SMILES: COCC(=O)c1cncc(Cl)c1COc1cccc2c(-c3nccn3C)cc(C)nc12] | 437.2 |

TABLE 1-continued

| Example | Structure | M + H⁺ |
|---|---|---|
| 88. | 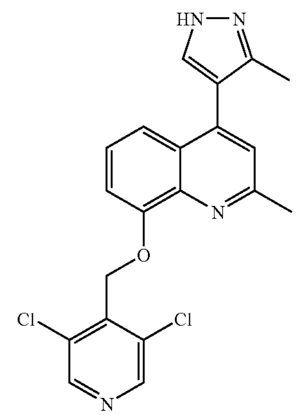 [SMILES: Cc1cc(-c2c[nH]nc2C)c2cccc(OCc3c(Cl)cncc3Cl)c2n1] | 399.1 |
| 89. | 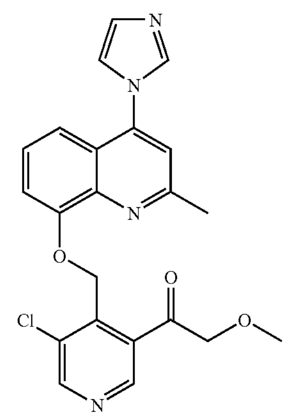 [SMILES: COCC(=O)c1cncc(Cl)c1COc1cccc2c(-n3ccnc3)cc(C)nc12] | 423.2 |
| 90. | 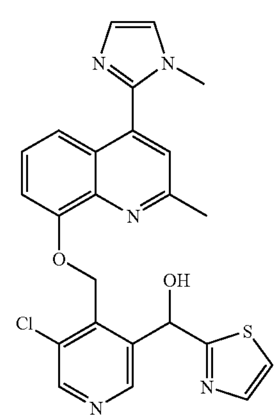 [SMILES: Cc1cc(-c2nccn2C)c2cccc(OCc3c(Cl)cncc3C(O)c3nccs3)c2n1] | 478.2 |

TABLE 1-continued
| Example | Structure | M + H⁺ |
|---|---|---|
| 91. | 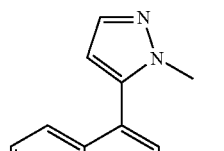 | 417.7 |
| 92. | 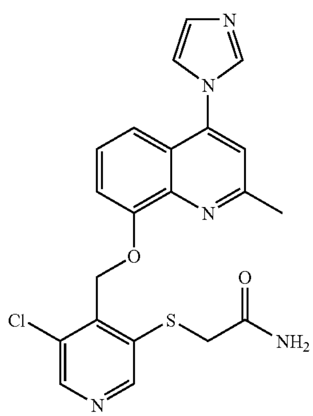 [SMILES: Cc1cc(-n2ccnc2)c2cccc(OCc3c(Cl)cncc3SCC(N)=O)c2n1] | 440.3 |
| 93. | 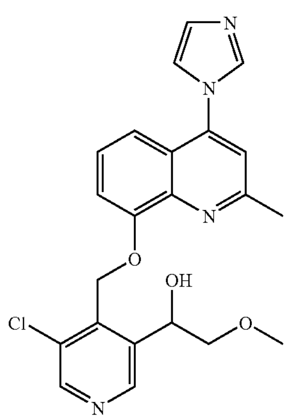 [SMILES: COCC(O)c1cncc(Cl)c1COc1cccc2c(-n3ccnc3)cc(C)nc12] | 425.2 |
| 94. | | 417.0 |
| 95. | | 455.1 |
| 96. | | 469.6 |

TABLE 1-continued

| Example | Structure | M + H+ |
|---|---|---|
| 97. | 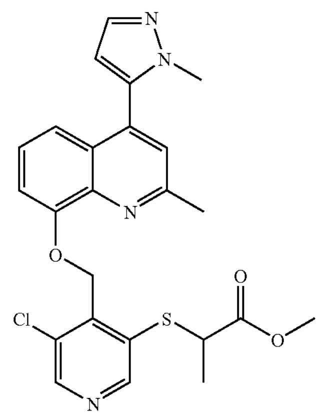 | 483.4 |
| 98. | 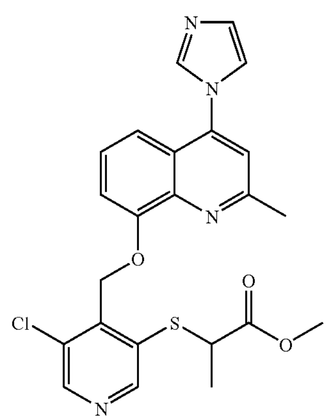 [SMILES: COC(=O)C(C)Sc1cncc(Cl)c1COc1cccc2c(-n3ccnc3)cc(C)nc12] | 469.6 |
| 99. | 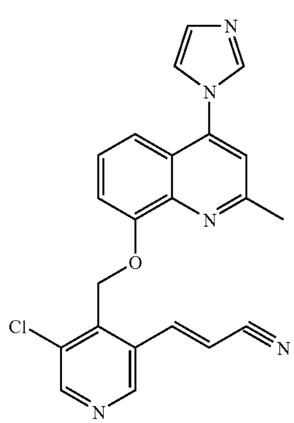 [SMILES: Cc1cc(-n2ccnc2)c2cccc(OCc3c(Cl)cncc3/C=C/C#N)c2n1] | 402.2 |

TABLE 1-continued

| Example | Structure | M + H+ |
|---|---|---|
| 100. | 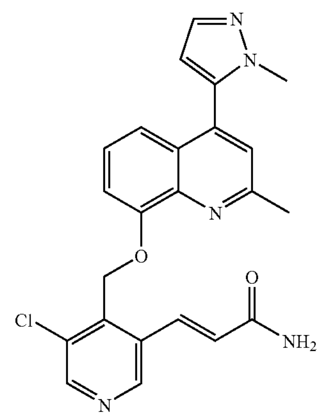 [SMILES: Cc1cc(-c2ccnn2C)c2cccc(OCc3c(Cl)cncc3/C=C/C(N)=O)c2n1] | 434.5 |
| 101. | 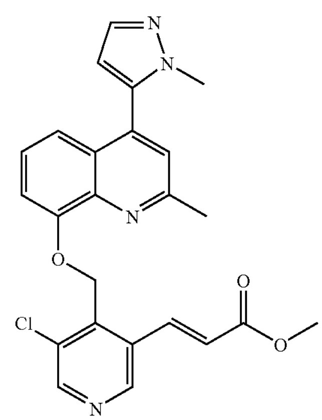 [SMILES: COC(=O)/C=C/c1cncc(Cl)c1COc1cccc2c(-c3ccnn3C)cc(C)nc12] | 449.3 |
| 102. | 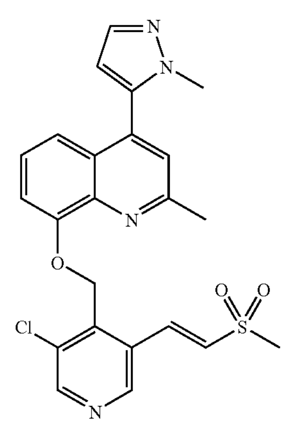 [SMILES: Cc1cc(-c2ccnn2C)c2cccc(OCc3c(Cl)cncc3/C=C/S(C)(=O)=O)c2n1] | 469.1 |

TABLE 1-continued

| Example | Structure | M + H+ |
|---------|-----------|--------|
| 103. | 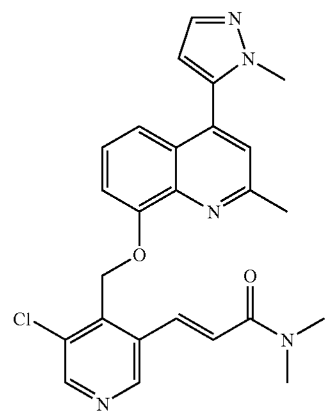 [SMILES: Cc1cc(-c2ccnn2C)c2cccc(OCc3c(Cl)cncc3/C=C/C(=O)N(C)C)c2n1] | 462.3 |
| 104. | 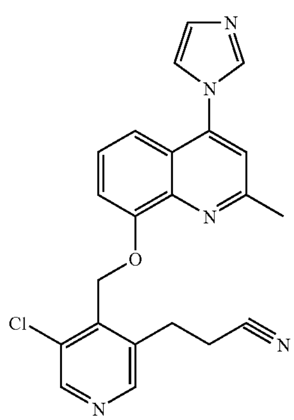 | 404.2 |
| 105. | 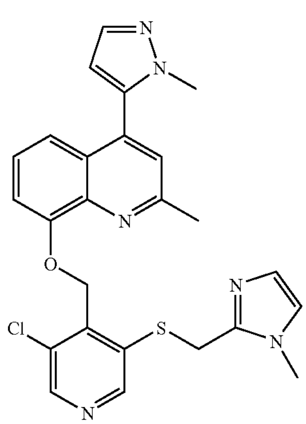 [SMILES: Cc1cc(-c2ccnn2C)c2cccc(OCc3c(Cl)cncc3SCc3nccn3C)c2n1] | 491.1 |
| 106. | | 477.0 |
| 107. | | 463.1 |
| 108. | | 436.1 |

TABLE 1-continued

| Example | Structure | M + H+ |
|---|---|---|
| 109. | 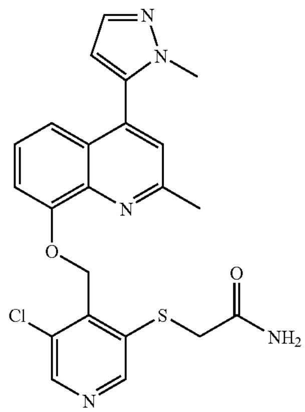 | 454.1 |
| 110. | 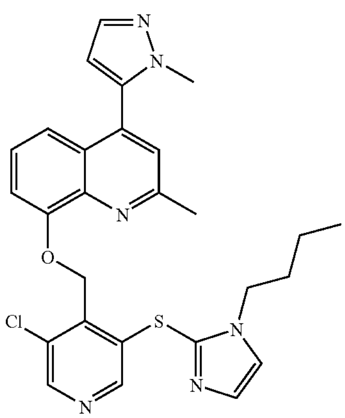 [SMILES: CCCCn1ccnc1Sc1cncc(Cl)c1COc1cccc2c(-c3ccnn3C)cc(C)nc12] | 519.1 |
| 111. | 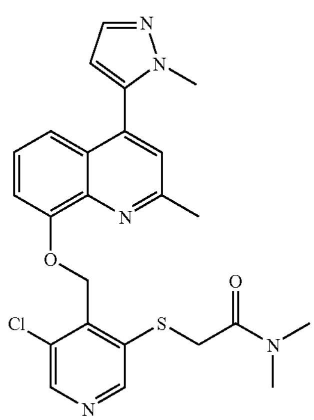 [SMILES: Cc1cc(-c2ccnn2C)c2cccc(OCc3c(Cl)cncc3SCC(=O)N(C)C)c2n1] | 482.2 |

TABLE 1-continued

| Example | Structure | M + H+ |
|---|---|---|
| 112. | 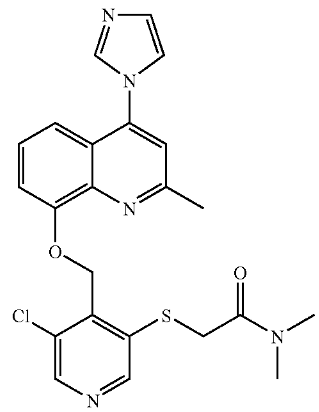 [SMILES: Cc1cc(-n2ccnc2)c2cccc(OCc3c(Cl)cncc3SCC(=O)N(C)C)c2n1] | 468.1 |
| 113. | 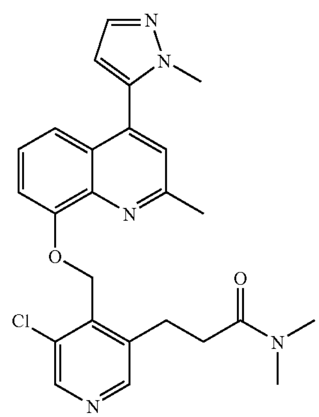 | 464.2 |
| 114. | 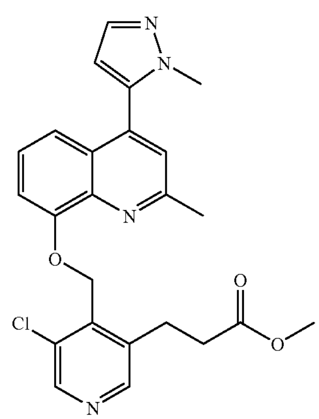 | 451.4 |

TABLE 1-continued

| Example | Structure | M + H+ |
|---------|-----------|--------|
| 115. | 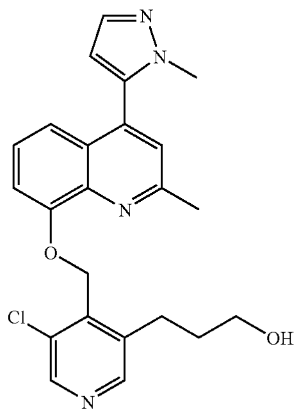 [SMILES: Cc1cc(-c2ccnn2C)c2cccc(OCc3c(Cl)cncc3CCCO)c2n1] | 423.2 |
| 116. | 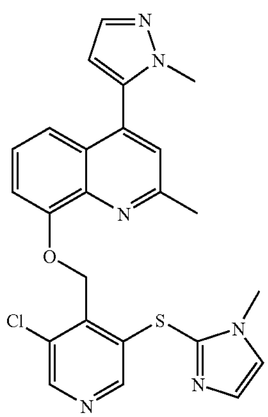 [SMILES: Cc1cc(-c2ccnn2C)c2cccc(OCc3c(Cl)cncc3Sc3nccn3C)c2n1] | 477.1 |
| 117. | 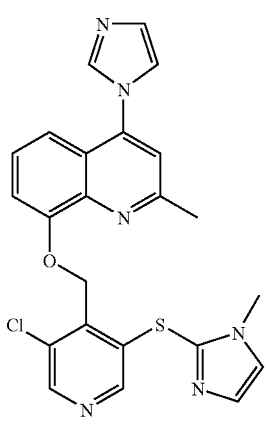 [SMILES: Cc1cc(-n2ccnc2)c2cccc(OCc3c(Cl)cncc3Sc3nccn3C)c2n1] | 463.0 |
| 118. | | 479.1 |
| 119. | | 465.0 |
| 120. | | 488.3 |

TABLE 1-continued
| Example | Structure | M + H⁺ |
|---------|-----------|--------|
| 121. | 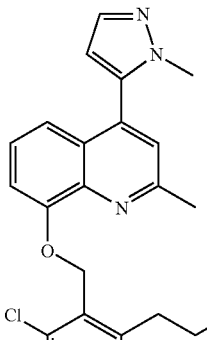 | 436.2 |
| 122. | 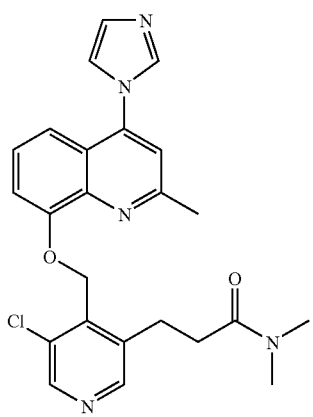 [SMILES: Cc1cc(-n2ccnc2)c2cccc(OCc3c(Cl)cncc3CCC(=O)N(C)C)c2n1] | 450.4 |
| 123. | 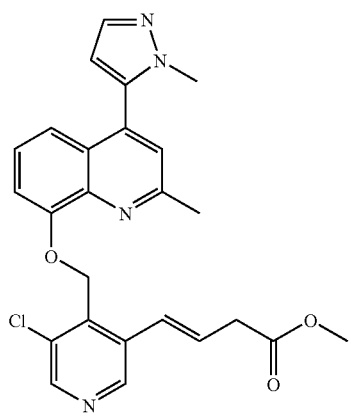 [SMILES: COC(=O)C/C=C/c1cncc(Cl)c1COc1cccc2c(-c3ccnn3C)cc(C)nc12] | 463.5 |
TABLE 1-continued
| Example | Structure | M + H⁺ |
|---------|-----------|--------|
| 124. | 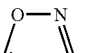 | 400.1 |
| 125. | 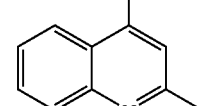 | 435.2 |
| 126. | 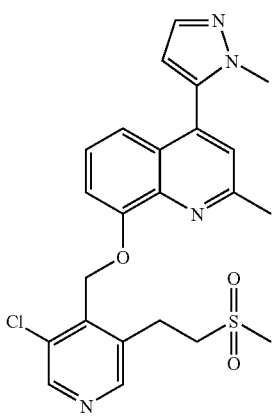 [SMILES: Cc1cc(-c2ccnn2C)c2cccc(OCc3c(Cl)cncc3CCS(C)(=O)=O)c2n1] | 471.3 |

TABLE 1-continued

| Example | Structure | M + H⁺ |
|---|---|---|
| 127. | 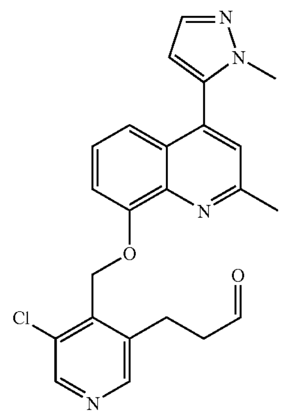 [SMILES: Cc1cc(-c2ccnn2C)c2cccc(OCc3c(Cl)cncc3CCC=O)c2n1] | 421.2 |
| 128. | 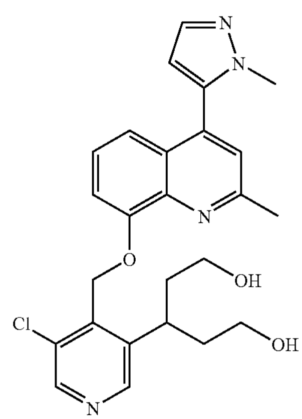 [SMILES: Cc1cc(-c2ccnn2C)c2cccc(OCc3c(Cl)cncc3C(CCO)CCO)c2n1] | 467.2 |
| 129. | 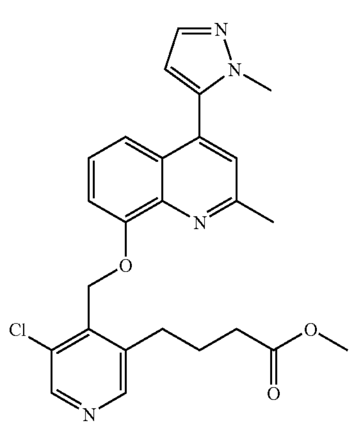 [SMILES: COC(=O)CCCc1cncc(Cl)c1COc1cccc2c(-c3ccnn3C)cc(C)nc12] | 465.2 |
| 130. | 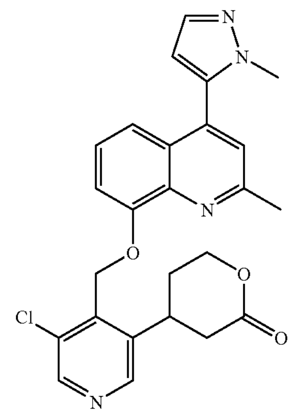 [SMILES: Cc1cc(-c2ccnn2C)c2cccc(OCc3c(Cl)cncc3C3CCOC(=O)C3)c2n1] | 463.1 |
| 131. | 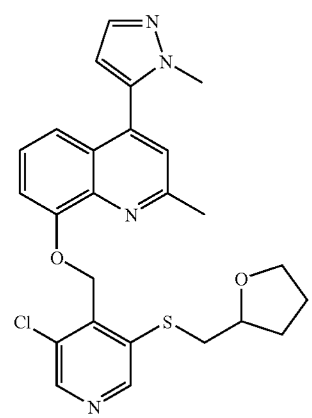 [SMILES: Cc1cc(-c2ccnn2C)c2cccc(OCc3c(Cl)cncc3SCC3CCCO3)c2n1] | 481.2 |
| 132. | 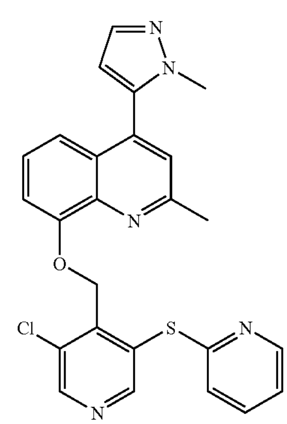 [SMILES: Cc1cc(-c2ccnn2C)c2cccc(OCc3c(Cl)cncc3Sc3ccccn3)c2n1] | 474.0 |

TABLE 1-continued

| Example | Structure | M + H+ |
|---|---|---|
| 133. | (structure) | 480.1 |
| 134. | (structure) | 494.1 |
| 135. | (structure) | 516.0 |
| 136. | (structure) | 530.1 |
| 137. | (structure) | 409.3 |
| 138. | (structure) | 395.2 |

TABLE 1-continued
| Example | Structure | M + H+ |
|---|---|---|
| 139. | 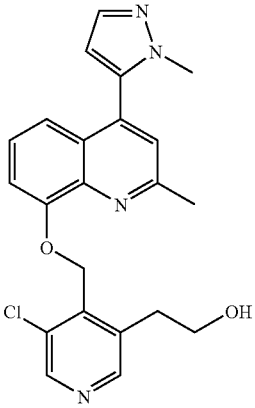 [SMILES: Cc1cc(-c2ccnn2C)c2cccc(OCc3c(Cl)cncc3CCO)c2n1] | 409.5 |
| 140. | 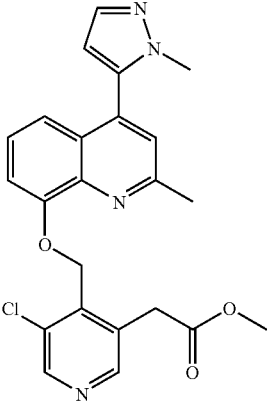 [SMILES: COC(=O)Cc1cncc(Cl)c1COc1cccc2c(-c3ccnn3C)cc(C)nc12] | 437.2 |
| 141. | 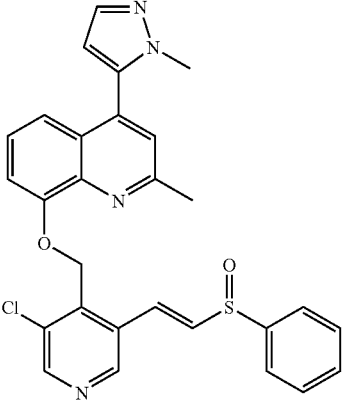 [SMILES: Cc1cc(-c2ccnn2C)c2cccc(OCc3c(Cl)cncc3/C=C/S(=O)c3ccccc3)c2n1] | 515.2 |
TABLE 1-continued
| Example | Structure | M + H+ |
|---|---|---|
| 142. | 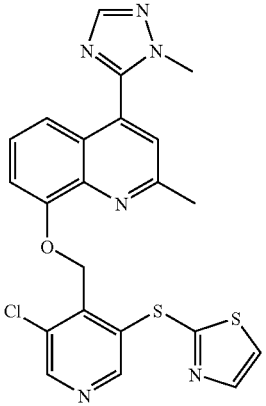 [SMILES: Cc1cc(-c2ncnn2C)c2cccc(OCc3c(Cl)cncc3Sc3nccs3)c2n1] | 481.4 |
| 143. | 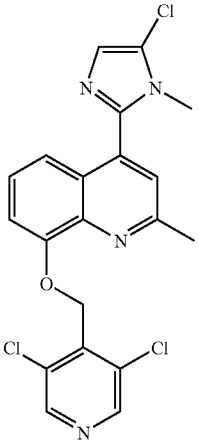 [SMILES: Cc1cc(-c2ncc(Cl)n2C)c2cccc(OCc3c(Cl)cncc3Cl)c2n1] | 433.6 |
| 144. | 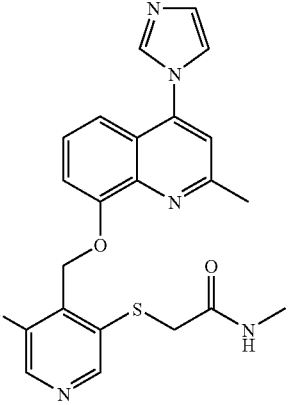 | 454.1 |

TABLE 1-continued
| Example | Structure | M + H⁺ |
|---|---|---|
| 145. | 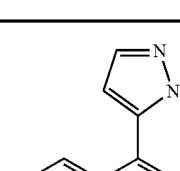 | 468.1 |
| 146. | 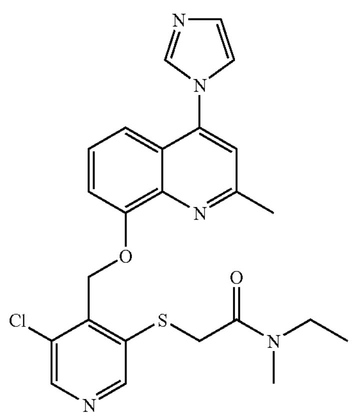 [SMILES: CCN(C)C(=O)CSc1cncc(Cl)c1COc1cccc2c(-n3ccnc3)cc(C)nc12] | 482.1 |
| 147. | 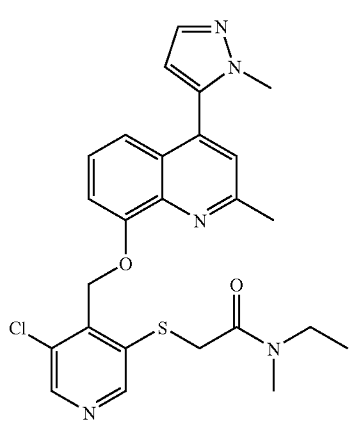 | 496.1 |
| 148. | | 399.1 |
| 149. | | 385.2 |
| 150. | | 508.1 |

TABLE 1-continued

| Example | Structure | M + H⁺ |
|---|---|---|
| 151. | 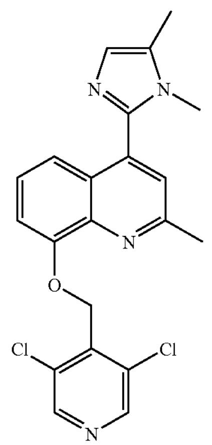 [SMILES: Cc1cc(-c2ncc(C)n2C)c2cccc(OCc3c(Cl)cncc3Cl)c2n1] | 413.5 |
| 152. | 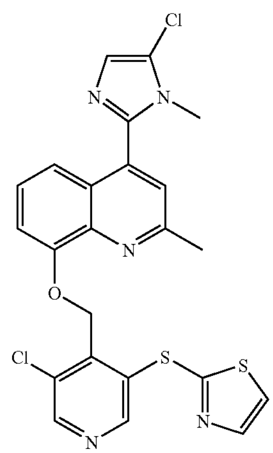 [SMILES: Cc1cc(-c2ncc(Cl)n2C)c2cccc(OCc3c(Cl)cncc3Sc3nccs3)c2n1] | 514.1 |
| 153. | 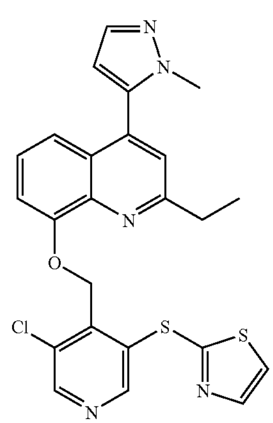 [SMILES: CCc1cc(-c2ccnn2C)c2cccc(OCc3c(Cl)cncc3Sc3nccs3)c2n1] | 494.3 |
| 154. | 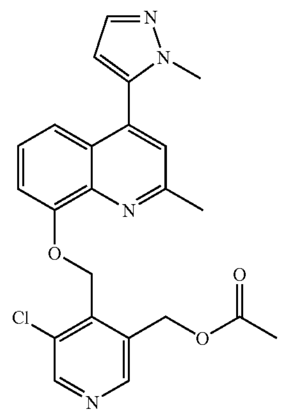 [SMILES: CC(=O)OCc1cncc(Cl)c1COc1cccc2c(-c3ccnn3C)cc(C)nc12] | 437.2 |
| 155. | 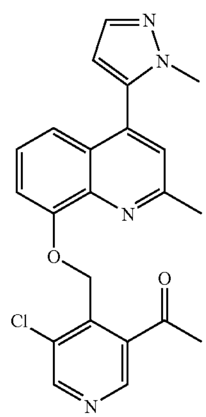 [SMILES: CC(=O)c1cncc(Cl)c1COc1cccc2c(-c3ccnn3C)cc(C)nc12] | 407.1 |
| 156. | 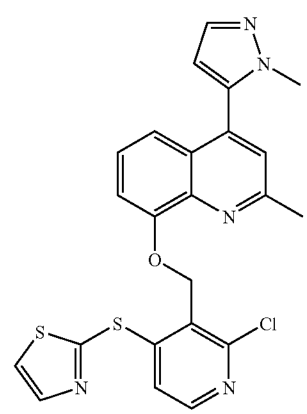 [SMILES: Cc1cc(-c2ccnn2C)c2cccc(OCc3c(Sc4nccs4)ccnc3Cl)c2n1] | 480.1 |

TABLE 1-continued

| Example | Structure | M + H⁺ |
|---------|-----------|--------|
| 157. | 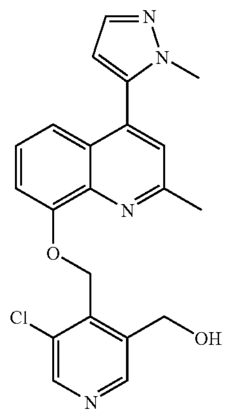 [SMILES: Cc1cc(-c2ccnn2C)c2cccc(OCc3c(Cl)cncc3CO)c2n1] | 395.1 |
| 158. | 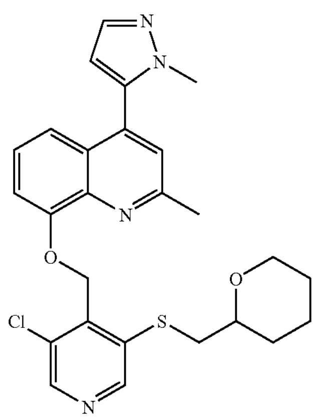 [SMILES: Cc1cc(-c2ccnn2C)c2cccc(OCc3c(Cl)cncc3SCC3CCCCO3)c2n1] | 495.2 |
| 159. | 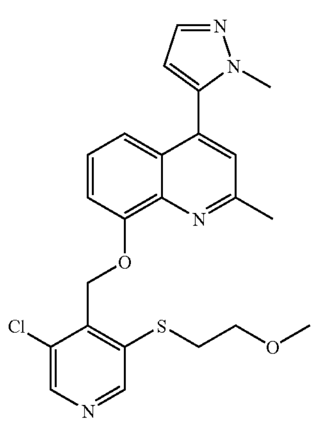 [SMILES: COCCSc1cncc(Cl)c1COc1cccc2c(-c3ccnn3C)cc(C)nc12] | 455.1 |

TABLE 1-continued

| Example | Structure | M + H⁺ |
|---------|-----------|--------|
| 160. | | 427.1 |
| 161. | | 441.1 |
| 162. | | 469.6 |

TABLE 1-continued

| Example | Structure | M + H⁺ |
|---------|-----------|--------|
| 163. | 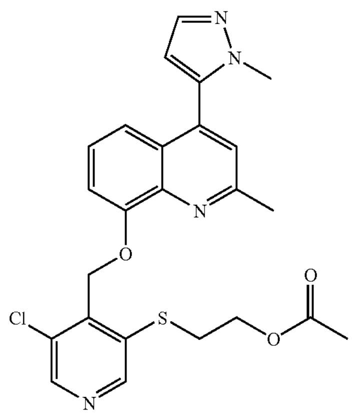 [SMILES: CC(=O)OCCSc1cncc(Cl)c1COc1cccc2c(-c3ccnn3C)cc(C)nc12] | 483.6 |
| 164. | 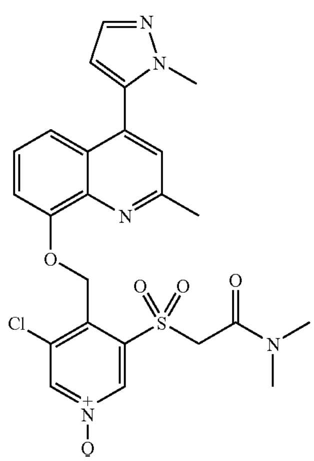 [SMILES: Cc1cc(-c2ccnn2C)c2cccc(OCc3c(Cl)c[n+]([O-])cc3S(=O)(=O)CC(=O)N(C)C)c2n1] | 530.0 |
| 165. | 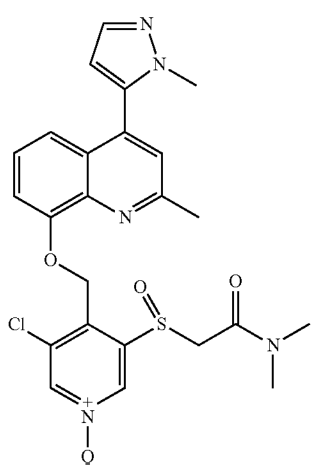 [SMILES: Cc1cc(-c2ccnn2C)c2cccc(OCc3c(Cl)c[n+]([O-])cc3S(=O)CC(=O)N(C)C)c2n1] | 514.0 |
| 166. | 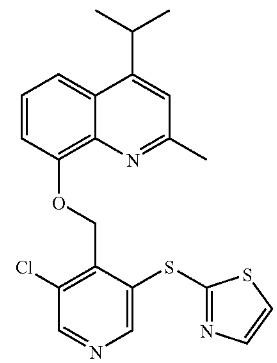 [SMILES: Cc1cc(C(C)C)c2cccc(OCc3c(Cl)cncc3Sc3nccs3)c2n1] | 442.1 |
| 167. | 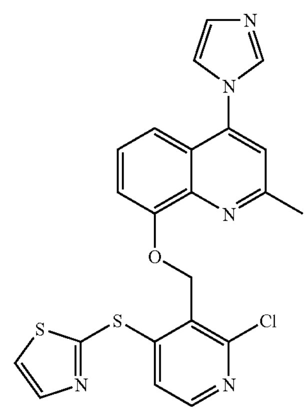 [SMILES: Cc1cc(-n2ccnc2)c2cccc(OCc3c(Sc4nccs4)ccnc3Cl)c2n1] | 466.0 |
| 168. | 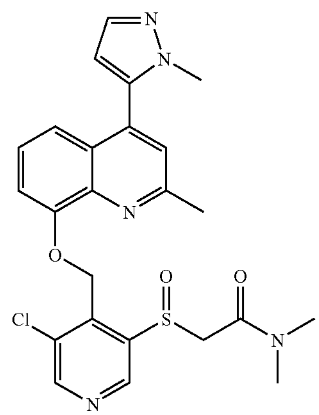 | 498.0 |
| 169. | 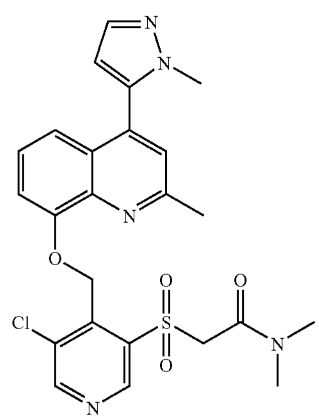 [SMILES: Cc1cc(-c2ccnn2C)c2cccc(OCc3c(Cl)cncc3S(=O)(=O)CC(=O)N(C)C)c2n1] | 514.1 |

TABLE 1-continued
| Example | Structure | M + H+ |
|---|---|---|
| 170. | 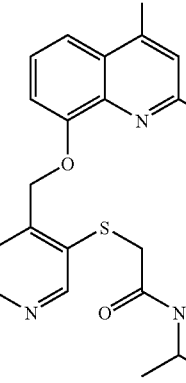 | 496.1 |
| 171. | 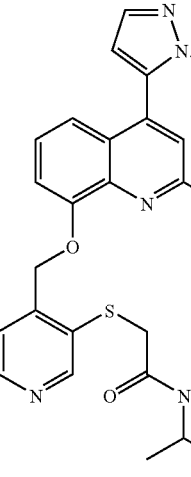 | 510.2 |
| 172. | 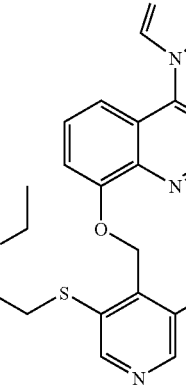 | 496.1 |
| 173. | 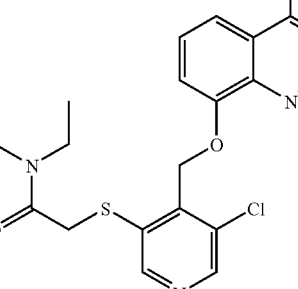 | 510.1 |
| 174. | 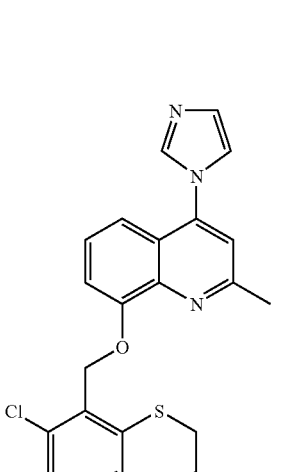 | 508.1 |
| 175. | 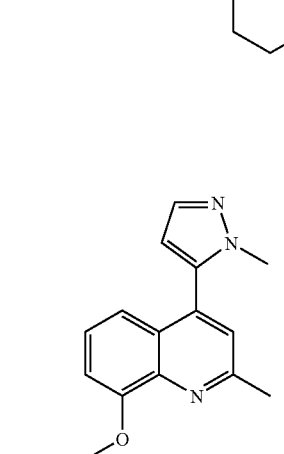 | 522.1 |

TABLE 1-continued

| Example | Structure | M + H+ |
|---|---|---|
| 176. | 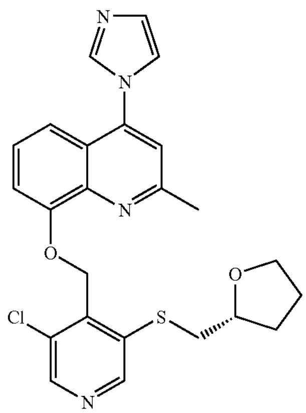 [SMILES: Cc1cc(-n2ccnc2)c2cccc(OCc3c(Cl)cncc3SC[C@H]3CCCO3)c2n1] | 467.1 |
| 177. | 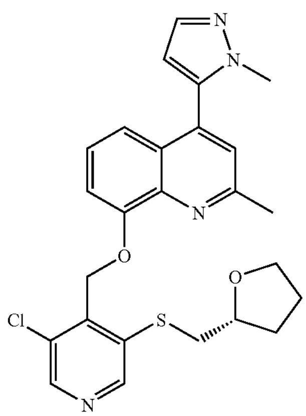 [SMILES: Cc1cc(-c2ccnn2C)c2cccc(OCc3c(Cl)cncc3SC[C@H]3CCCO3)c2n1] | 481.1 |
| 178. | 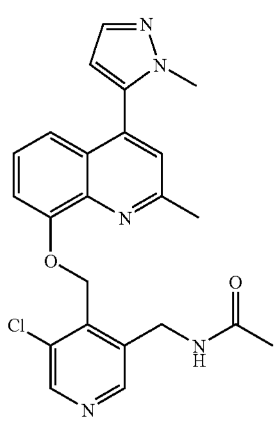 [SMILES: CC(=O)NCc1cncc(Cl)c1COc1cccc2c(-c3ccnn3C)cc(C)nc12] | 436.1 |
| 179. | 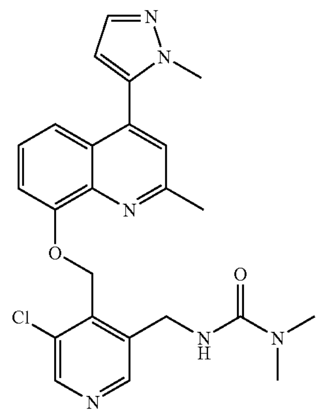 | 465.0 |
| 180. | 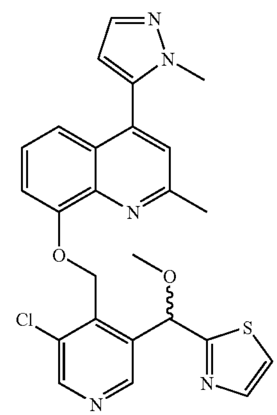 [SMILES: COC(c1nccs1)c1cncc(Cl)c1COc1cccc2c(-c3ccnn3C)cc(C)nc12] | 492.0 |
| 181. | 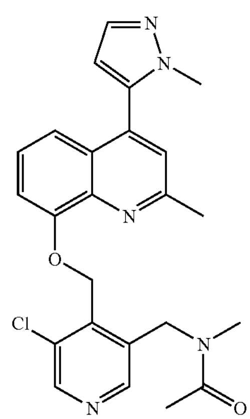 [SMILES: CC(=O)N(C)Cc1cncc(Cl)c1COc1cccc2c(-c3ccnn3C)cc(C)nc12] | 450.1 |

TABLE 1-continued
| Example | Structure | M + H+ |
|---|---|---|
| 182 | 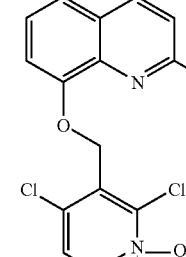 | 436.1 |
| 183. | | 466.0 |
| 184. | | 415.0 |
| 185. | 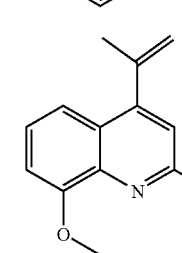 | 401.0 |
| 186. | 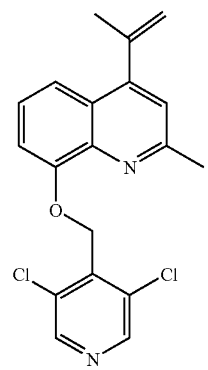 [SMILES: C=C(C)c1cc(C)nc2c(OCc3c(Cl)cncc3Cl)cccc12] | 359.0 |
| 187. | 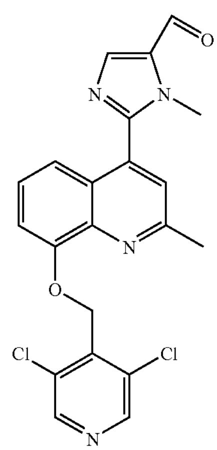 [SMILES: Cc1cc(-c2ncc(C=O)n2C)c2cccc(OCc3c(Cl)cncc3Cl)c2n1] | 427.0 |
| 188. | 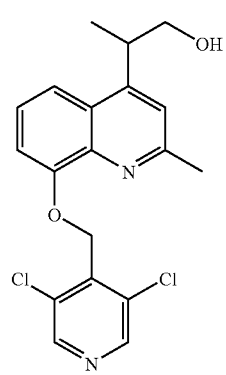 [SMILES: Cc1cc(C(C)CO)c2cccc(OCc3c(Cl)cncc3Cl)c2n1] | 377.0 |

TABLE 1-continued
| Example | Structure | M + H+ |
|---|---|---|
| 189. | 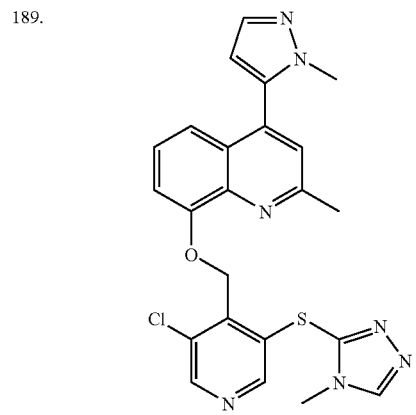 | 478.0 |
| 190. | 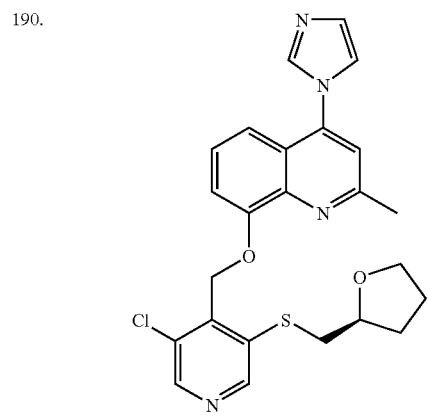 | 467.1 |
| 191. | 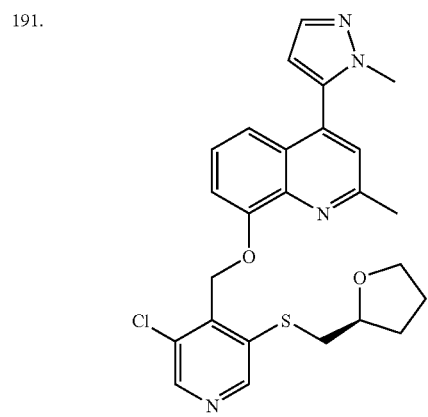 | 481.1 |
TABLE 1-continued
| Example | Structure | M + H+ |
|---|---|---|
| 192. | 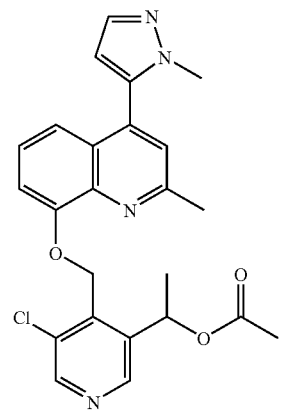 [SMILES: CC(=O)OC(C)c1cncc(Cl)c1COc1cccc2c(-c3ccnn3C)cc(C)nc12] | 451.0 |
| 193. | | 464.1 |
| 194. | 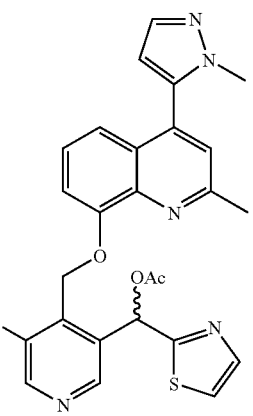 | 520.0 |

TABLE 1-continued
| Example | Structure | M + H+ |
|---|---|---|
| 195. | 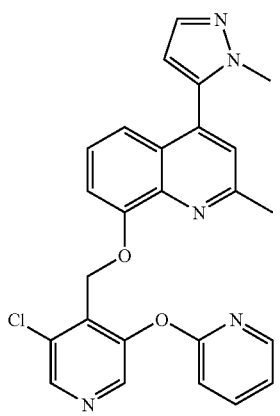 [SMILES: Cc1cc(-c2ccnn2C)c2cccc(OCc3c(Cl)cncc3Oc3ccccn3)c2n1] | 458.1 |
| 196. | 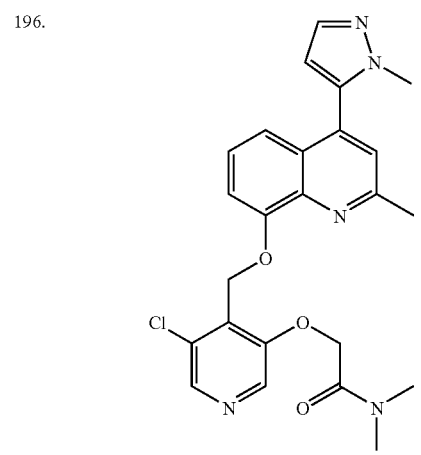 | 466.2 |
| 197. | 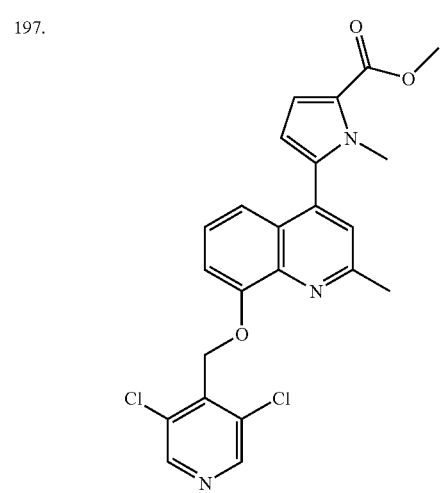 | 456 |
| 198. | 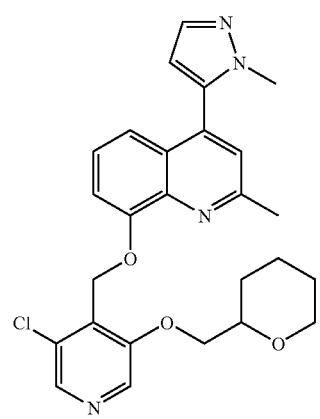 [SMILES: Cc1cc(-c2ccnn2C)c2cccc(OCc3c(Cl)cncc3OCC3CCCCO3)c2n1] | 479.2 |
| 199. | 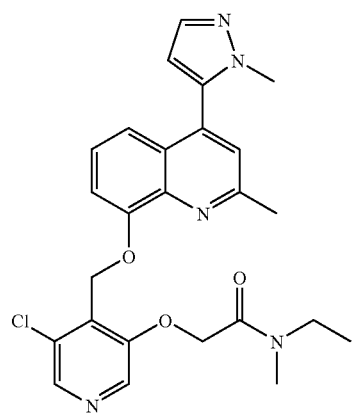 [SMILES: CCN(C)C(=O)COc1cncc(Cl)c1COc1cccc2c(-c3ccnn3C)cc(C)nc12] | 480.2 |
| 200. | 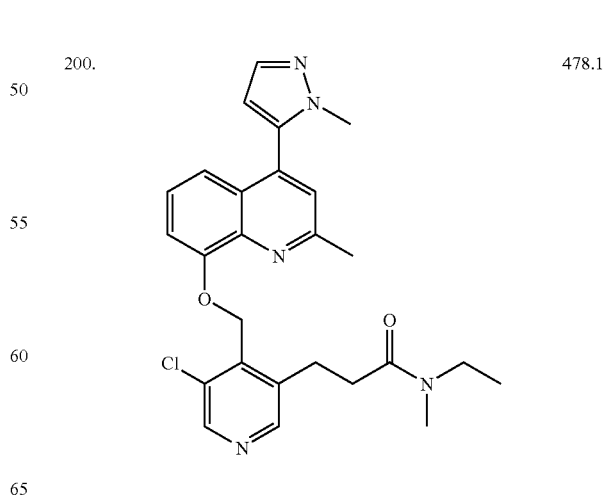 | 478.1 |

TABLE 1-continued

| Example | Structure | M + H⁺ |
|---------|-----------|--------|
| 201. | | 494.2 |
| 202. | | 457.0 |
| 203. | | 477.9 |
| 204. | 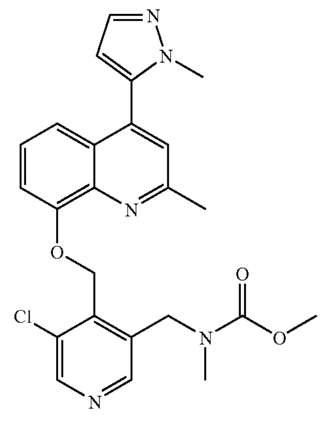 [SMILES: COC(=O)N(C)Cc1cncc(Cl)c1COc1cccc2c(-c3ccnn3C)cc(C)nc12] | 466.1 |
| 205. | 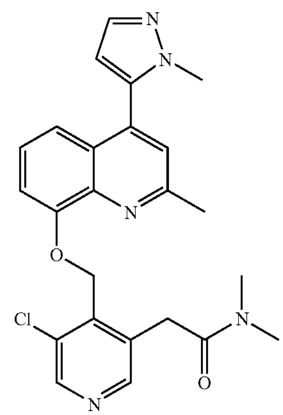 [SMILES: Cc1cc(-c2ccnn2C)c2cccc(OCc3c(Cl)cncc3CC(=O)N(C)C)c2n1] | 450.0 |
| 206. | 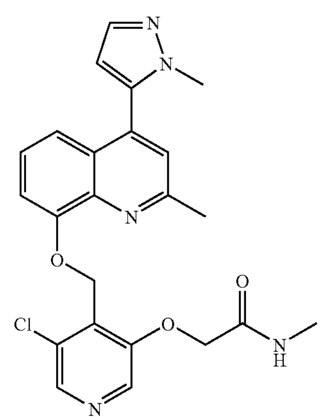 | 452.1 |
| 207. | 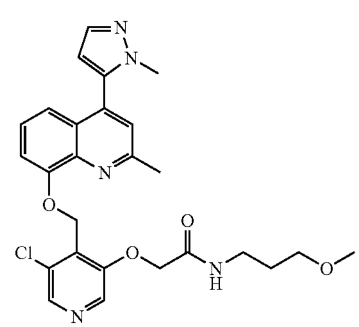 [SMILES: COCCCNC(=O)COc1cncc(Cl)c1COc1cccc2c(-c3ccnn3C)cc(C)nc12] | 510.2 |

TABLE 1-continued
| Example | Structure | M + H⁺ |
|---|---|---|
| 208. | 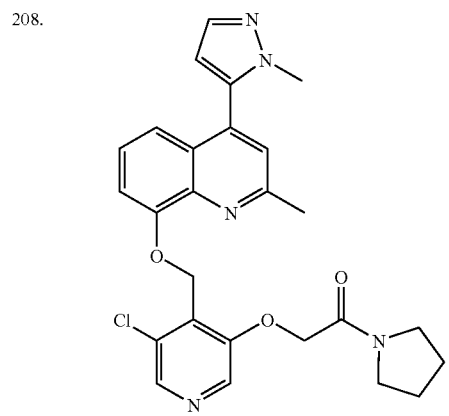 | 492.2 |
| 209. | 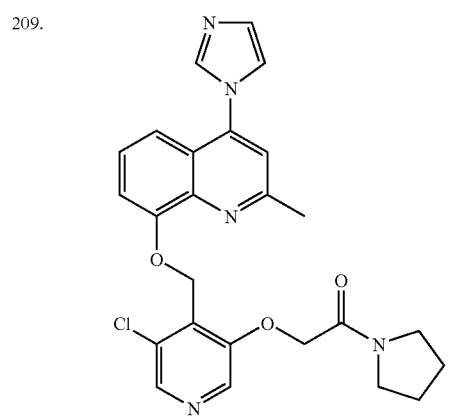 | 478.2 |
| 210. | 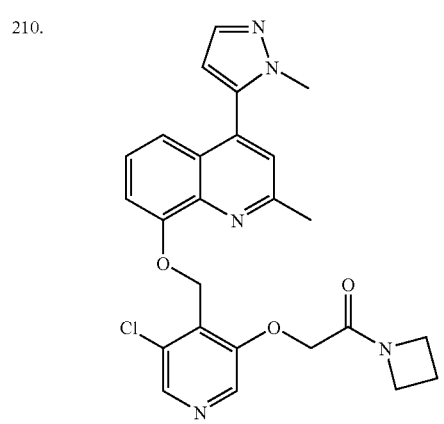 | 478.2 |
| 211. | 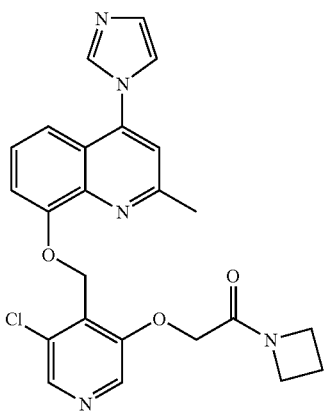 [SMILES: Cc1cc(-n2ccnc2)c2cccc(OCc3c(Cl)cncc3OCC(=O)N3CCC3)c2n1] | 464.1 |
| 212 | 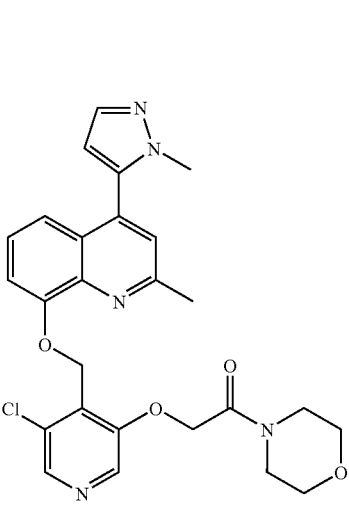 [SMILES: Cc1cc(-c2ccnn2C)c2cccc(OCc3c(Cl)cncc3OCC(=O)N3CCOCC3)c2n1] | 508.2 |
| 213. | 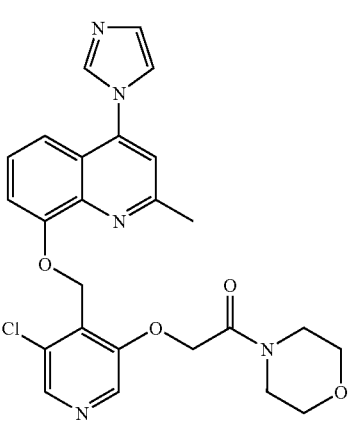 | 494.2 |

TABLE 1-continued
| Example | Structure | M + H+ |
|---|---|---|
| 214. | 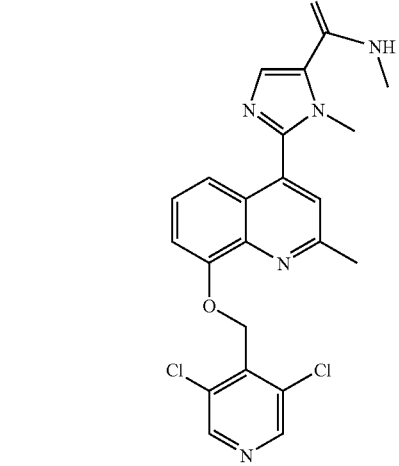 | 456.1 |
| 215. | 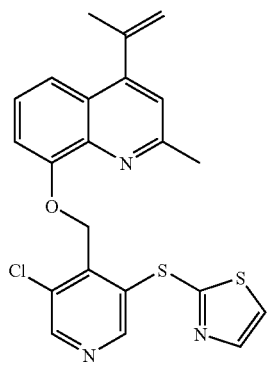 [SMILES: C=C(C)c1cc(C)nc2c(OCc3c(Cl)cncc3Sc3nccs3)cccc12] | 440 |
| 216. | 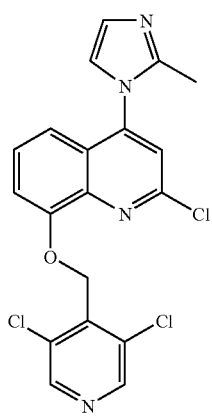 [SMILES: Cc1nccn1-c1cc(Cl)nc2c(OCc3c(Cl)cncc3Cl)cccc12] | 419.1 |
TABLE 1-continued
| Example | Structure | M + H+ |
|---|---|---|
| 217. | 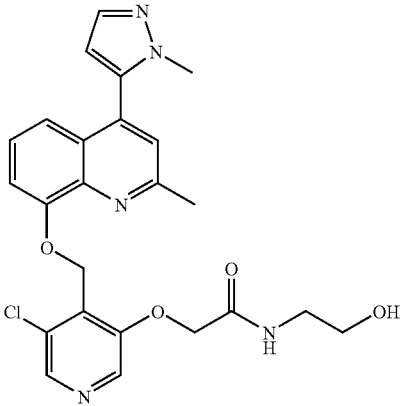 [SMILES: Cc1cc(-c2ccnn2C)c2cccc(OCc3c(Cl)cncc3OCC(=O)NCCO)c2n1] | 482.0 |
| 218. | 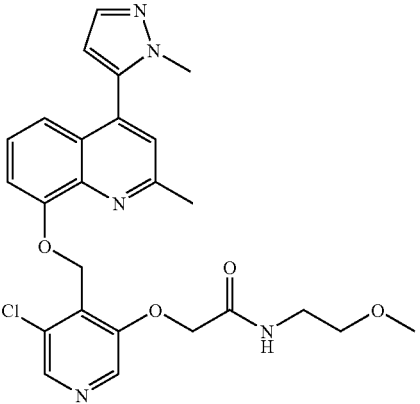 [SMILES: COCCNC(=O)COc1cncc(Cl)c1COc1cccc2c(-c3ccnn3C)cc(C)nc12] | 496.2 |
| 219. | 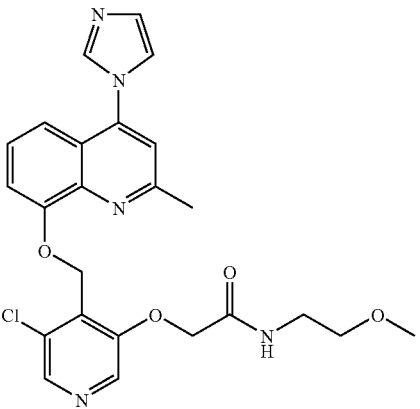 [SMILES: COCCNC(=O)COc1cncc(Cl)c1COc1cccc2c(-n3ccnc3)cc(C)nc12] | 482.2 |

TABLE 1-continued
| Example | Structure | M + H+ |
|---|---|---|
| 220. | 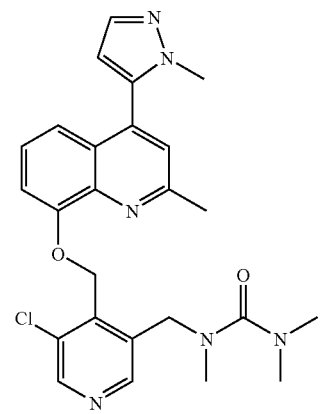 [SMILES: Cc1cc(-c2ccnn2C)c2cccc(OCc3c(Cl)cncc3CN(C)C(=O)C(C)C)c2n1] | 534.2 |
| 221. | 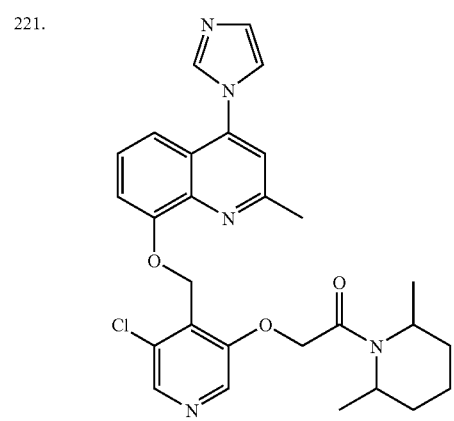 | 520.2 |
| 222. | 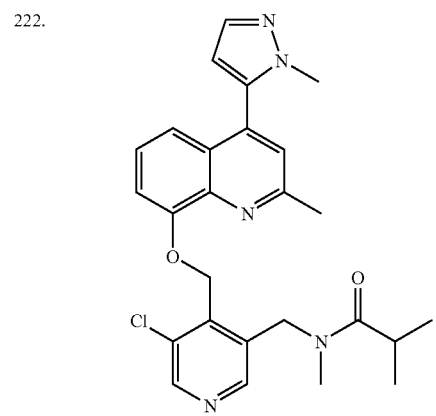 | 478.1 |
TABLE 1-continued
| Example | Structure | M + H+ |
|---|---|---|
| 223. | 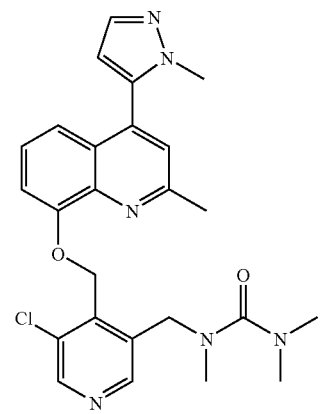 [SMILES: Cc1cc(-c2ccnn2C)c2cccc(OCc3c(Cl)cncc3CN(C)C(=O)C(C)C)c2n1] | 479.1 |
| 224. | 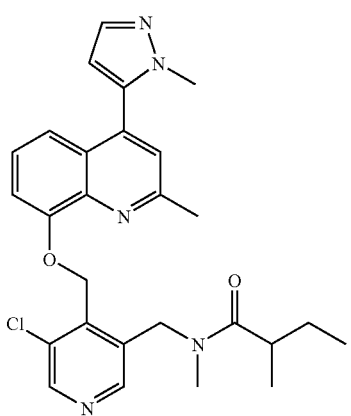 | 491.2 |
| 225. | 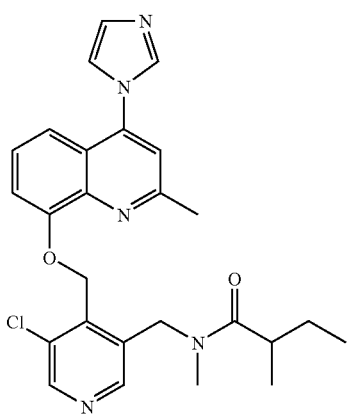 | 478.1 |

TABLE 1-continued

| Example | Structure | M + H+ |
|---|---|---|
| 226. | 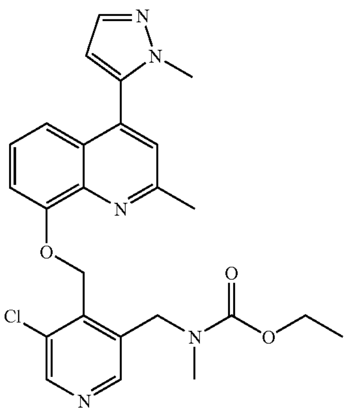 [SMILES: CCOC(=O)N(C)Cc1cncc(Cl)c1COc1cccc2c(-c3ccnn3C)cc(C)nc12] | 480.1 |
| 227. | 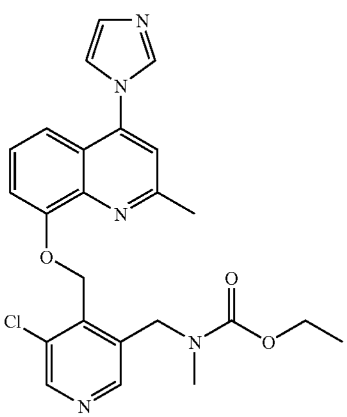 [SMILES: CCOC(=O)N(C)Cc1cncc(Cl)c1COc1cccc2c(-n3ccnc3)cc(C)nc12] | 466.1 |
| 228. | 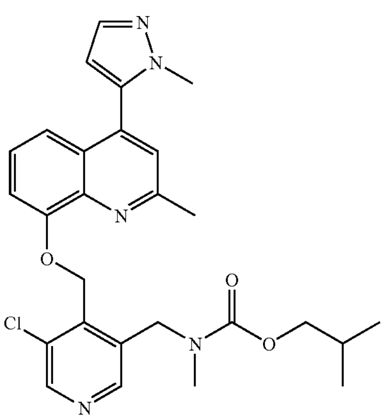 [SMILES: Cc1cc(-c2ccnn2C)c2cccc(OCc3c(Cl)cncc3CN(C)C(=O)OCC(C)C)c2n1] | 501. |

TABLE 1-continued

| Example | Structure | M + H+ |
|---|---|---|
| 229. | | 494.1 |
| 230. | | 514.1 |
| 231. | | 500.1 |

TABLE 1-continued
| Example | Structure | M + H⁺ |
|---|---|---|
| 232. | 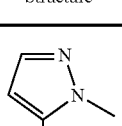 | 492.2 |
| 233. | 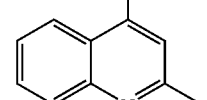 | 506.2 |
| 234. | 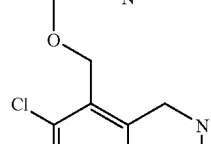 | 492.1 |
TABLE 1-continued
| Example | Structure | M + H⁺ |
|---|---|---|
| 235. | 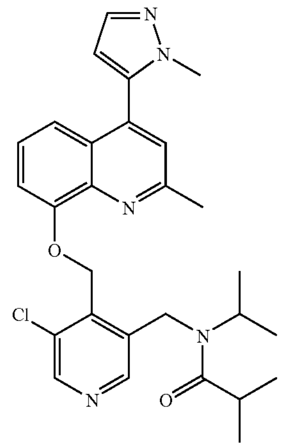 | 506.1 |
| 236. | 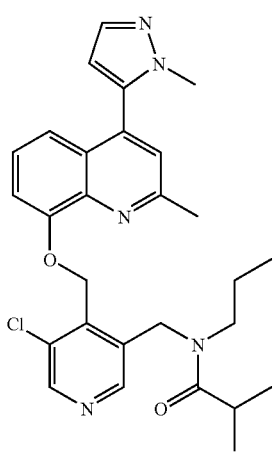 [SMILES: CCCN(Cc1cncc(Cl)c1COc1cccc2c(-c3ccnn3C)cc(C)nc12)C(=O)C(C)C] | 508.2 |
| 237 | 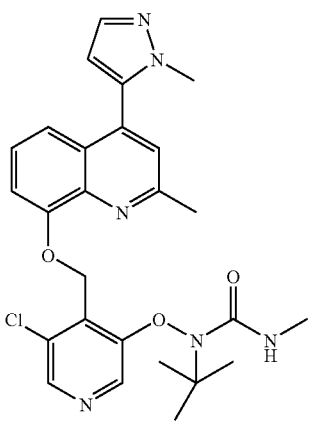 [SMILES: CNC(=O)N(Oc1cncc(Cl)c1COc1cccc2c(-c3ccnn3C)cc(C)nc12)C(C)(C)C] | 521.2 |

TABLE 1-continued

| Example | Structure | M + H⁺ |
|---|---|---|
| 238. | 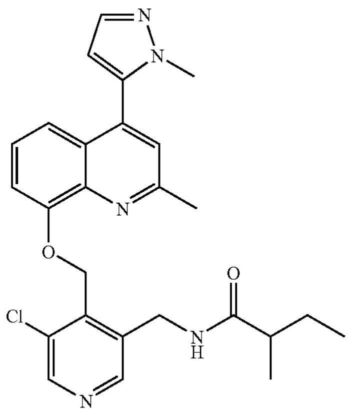 | 478.1 |
| 239. | 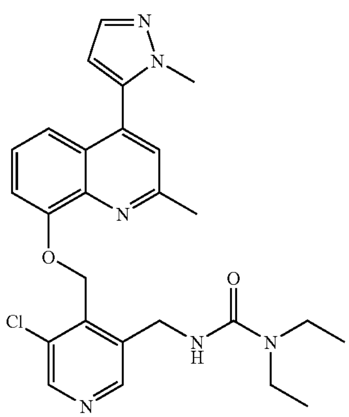 | 493.0 |
| 240. | 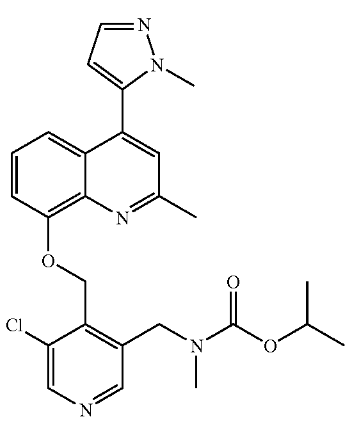 [SMILES: Cc1cc(-c2ccnn2C)c2cccc(OCc3c(Cl)cncc3CN(C)C(=O)OC(C)C)c2n1] | 494.1 |

TABLE 1-continued

| Example | Structure | M + H⁺ |
|---|---|---|
| 241. | | 480.1 |
| 242. | | 480.0 |
| 243. | | 493.0 |

TABLE 1-continued
| Example | Structure | M + H⁺ |
|---------|-----------|--------|
| 244. | 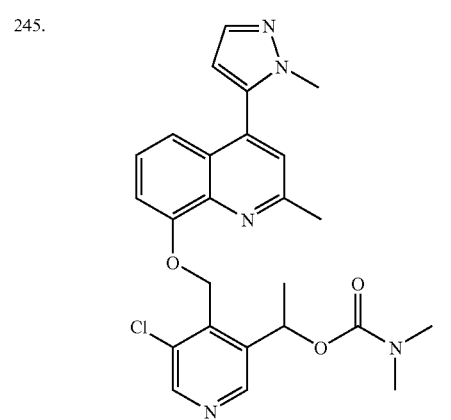 | 507.1 |
| 245. | 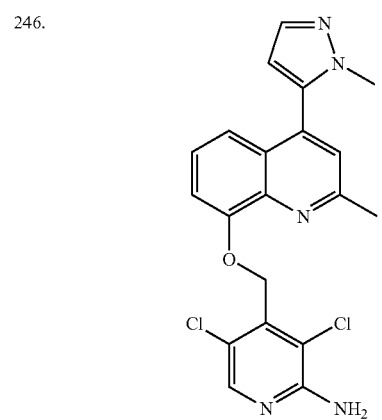 | 480.0 |
| 246. | 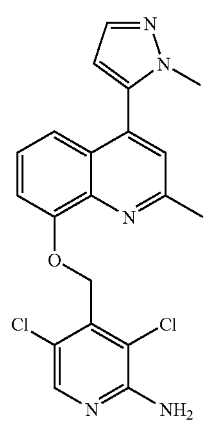 [SMILES: Cc1cc(-c2ccnn2C)c2cccc(OCc3c(Cl)cnc(N)c3Cl)c2n1] | 414.0 |
| 247. | 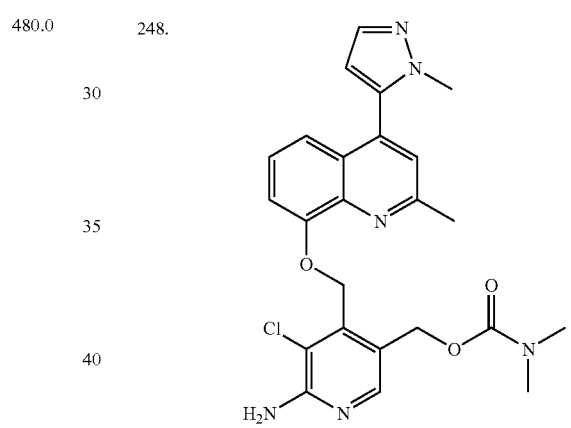 | 480.9 |
| 248. | 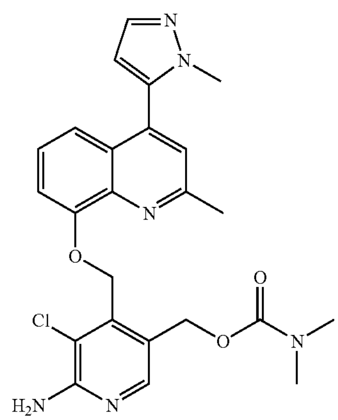 [SMILES: Cc1cc(-c2ccnn2C)c2cccc(OCc3c(COC(=O)N(C)C)cnc(N)c3Cl)c2n1] | 480.9 |
| 249. | 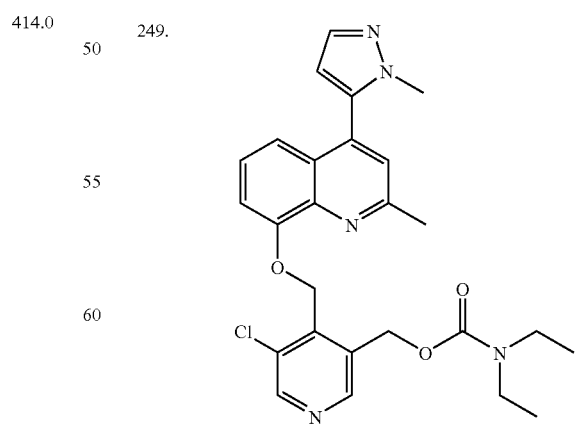 | 494.0 |

TABLE 1-continued
| Example | Structure | M + H+ |
|---------|-----------|--------|
| 250. | 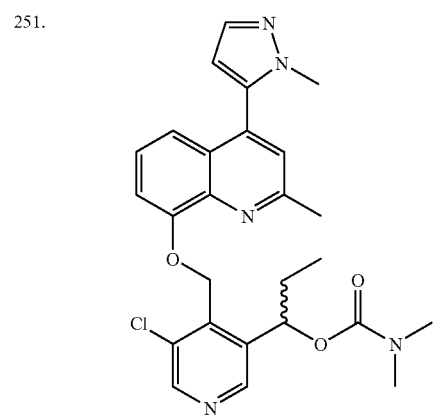 | 431.9 |
| 251. | 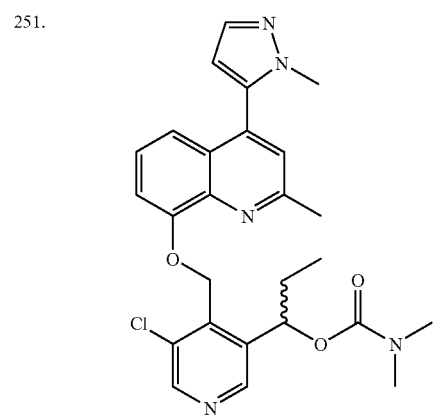 | 494.0 |
| 252. | 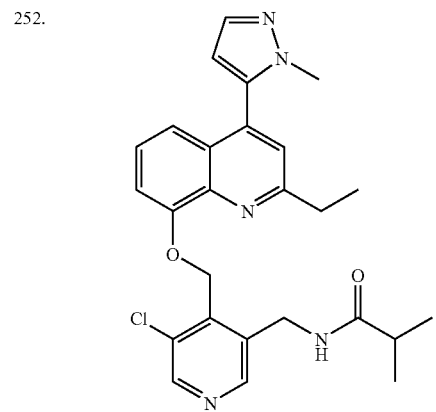 | 478.1 |
TABLE 1-continued
| Example | Structure | M + H+ |
|---------|-----------|--------|
| 253. | 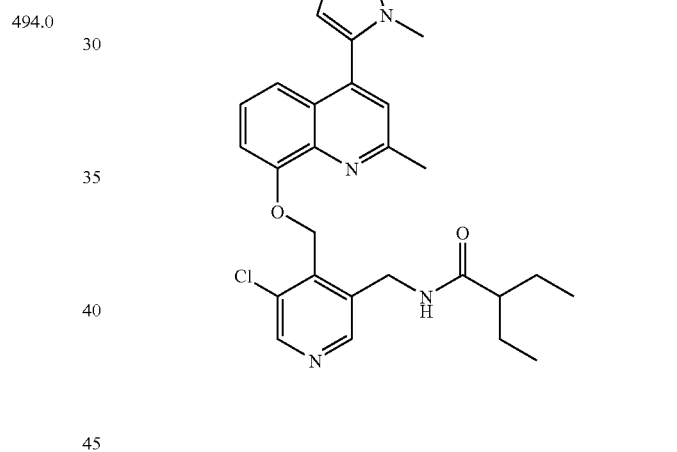 | 464.1 |
| 254. | 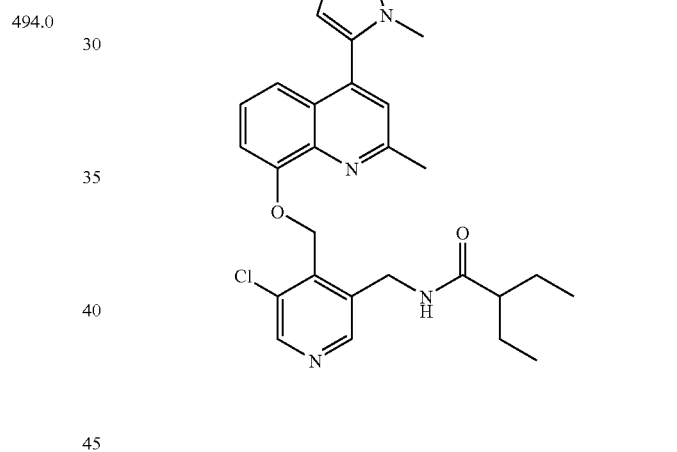 | 492.1 |
| 255. | 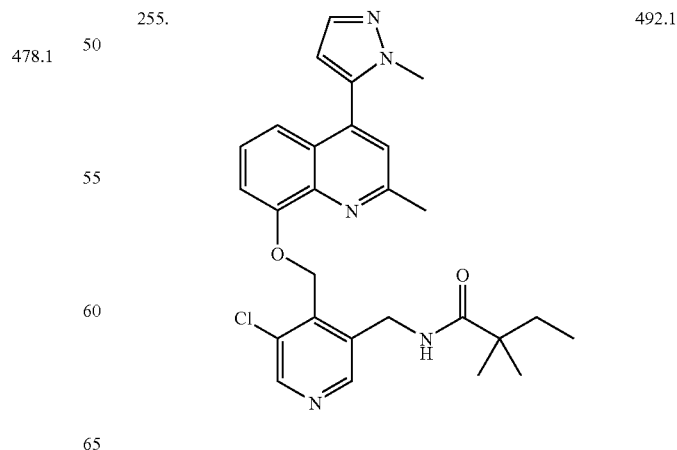 | 492.1 |

TABLE 1-continued
| Example | Structure | M + H⁺ |
|---|---|---|
| 256. | 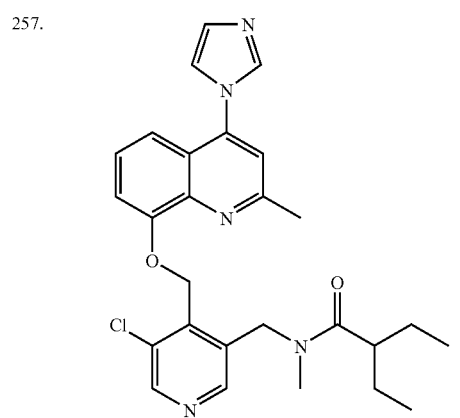 | 506.1 |
| 257. | | 492.1 |
| 258. | | 450.0 |
| Example | Structure | M + H⁺ |
|---|---|---|
| 259. | 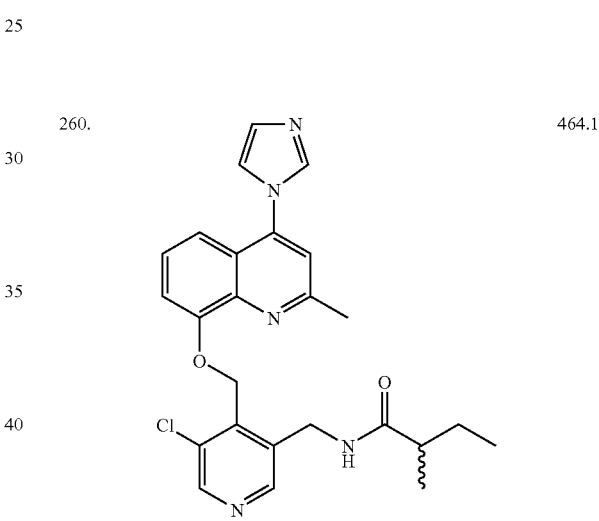 | 533.9 |
| 260. | | 464.1 |
| 261. | 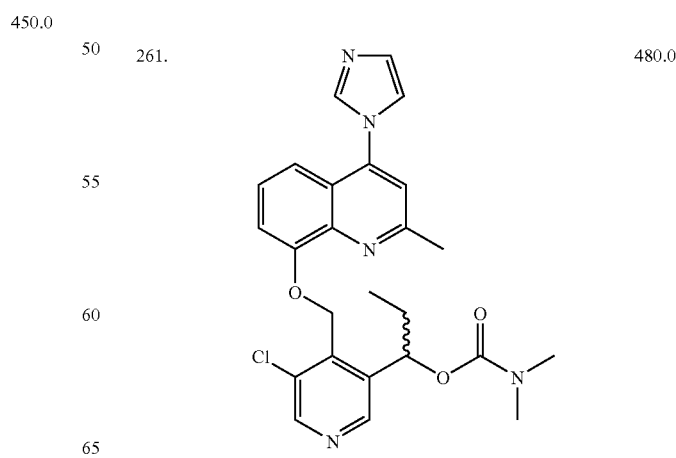 | 480.0 |

TABLE 1-continued

| Example | Structure | M + H+ |
|---|---|---|
| 262. | 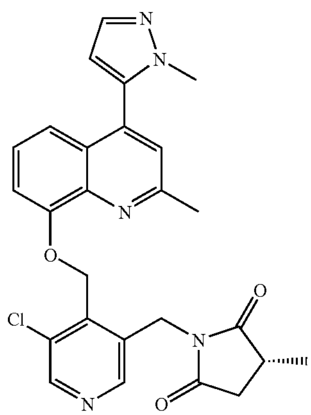 [SMILES: Cc1cc(-c2ccnn2C)c2cccc(OCc3c(Cl)cncc3CN3C(=O)C[C@@H](C)C3=O)c2n1] | 490.0 |
| 263. | 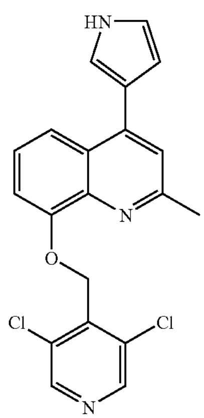 [SMILES: Cc1cc(-c2cc[nH]c2)c2cccc(OCc3c(Cl)cncc3Cl)c2n1] | 384.0 |
| 264. | 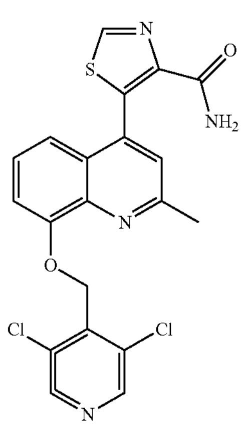 | 445.0 |

TABLE 1-continued

| Example | Structure | M + H+ |
|---|---|---|
| 265. | 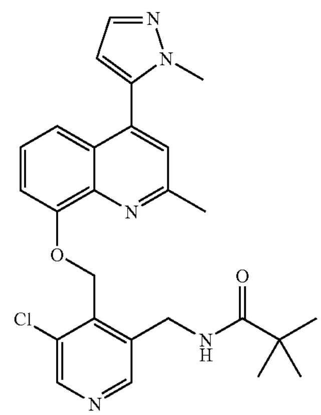 [SMILES: Cc1cc(-c2ccnn2C)c2cccc(OCc3c(Cl)cncc3CNC(=O)C(C)(C)C)c2n1] | 478.1 |
| 266. | 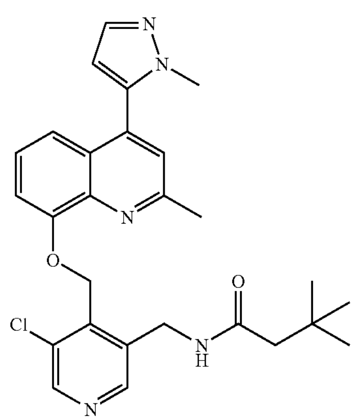 | 492.1 |
| 267. | 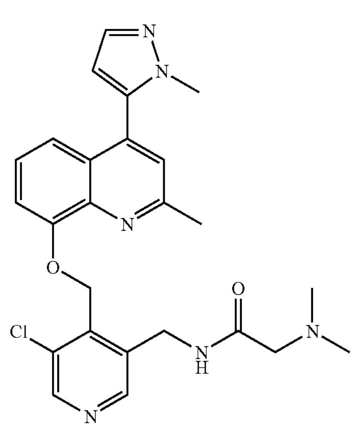 [SMILES: Cc1cc(-c2ccnn2C)c2cccc(OCc3c(Cl)cncc3CNC(=O)CN(C)C)c2n1] | 479.0 |

TABLE 1-continued

| Example | Structure | M + H⁺ |
|---------|-----------|--------|
| 268. | 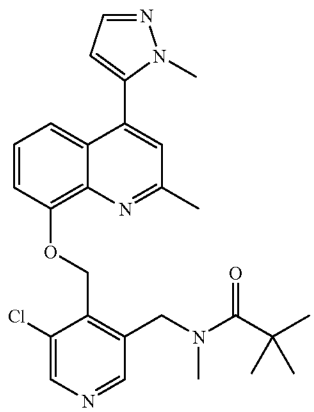 [SMILES: Cc1cc(-c2ccnn2C)c2cccc(OCc3c(Cl)cncc3CN(C)C(=O)C(C)(C)C)c2n1] | 492.1 |
| 269. | 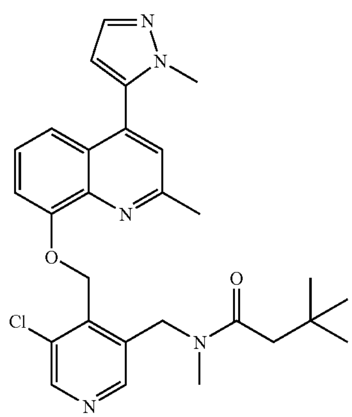 [SMILES: Cc1cc(-c2ccnn2C)c2cccc(OCc3c(Cl)cncc3CN(C)C(=O)CC(C)(C)C)c2n1] | 506.1 |
| 270. | 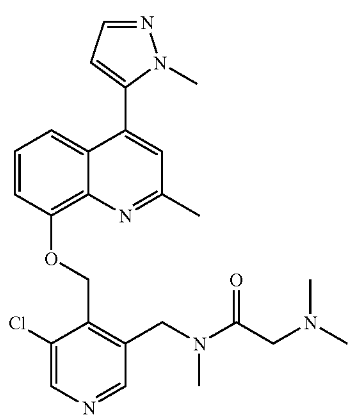 [SMILES: Cc1cc(-c2ccnn2C)c2cccc(OCc3c(Cl)cncc3CN(C)C(=O)CN(C)C)c2n1] | 493.1 |
| 271. | | 506.1 |
| 272. | | 504.3 |
| 273. | | 490.1 |

TABLE 1-continued

| Example | Structure | M + H+ |
|---|---|---|
| 274. | 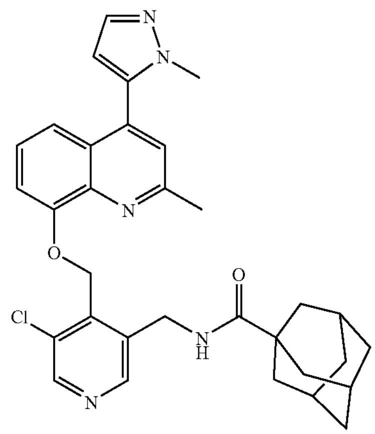 [SMILES: Cc1cc(-c2ccnn2C)c2cccc(OCc3c(Cl)cncc3CNC(=O)C34CC5CC(CC(C5)C3)C4)c2n1] | 556.2 |
| 275. | 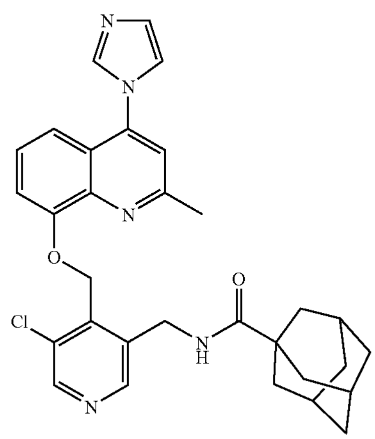 [SMILES: Cc1cc(-n2ccnc2)c2cccc(OCc3c(Cl)cncc3CNC(=O)C34CC5CC(CC(C5)C3)C4)c2n1] | 542.2 |
| 276. | 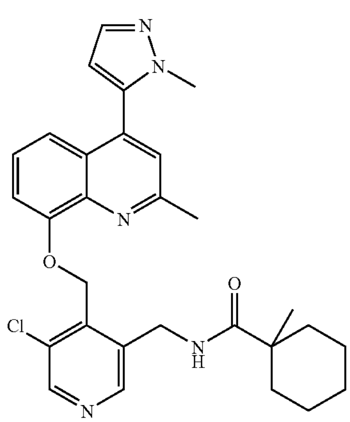 [SMILES: Cc1cc(-c2ccnn2C)c2cccc(OCc3c(Cl)cncc3CNC(=O)C3(C)CCCCC3)c2n1] | 518.2 |

TABLE 1-continued

| Example | Structure | M + H+ |
|---|---|---|
| 277. | 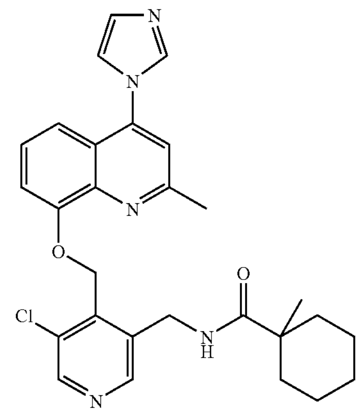 [SMILES: Cc1cc(-n2ccnc2)c2cccc(OCc3c(Cl)cncc3CNC(=O)C3(C)CCCCC3)c2n1] | 504.1 |
| 278. | 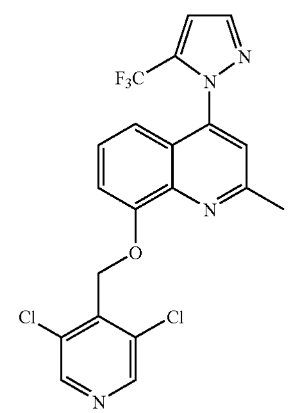 [SMILES: Cc1cc(-n2nccc2C(F)(F)F)c2cccc(OCc3c(Cl)cncc3Cl)c2n1] | 453.0 |
| 279. | 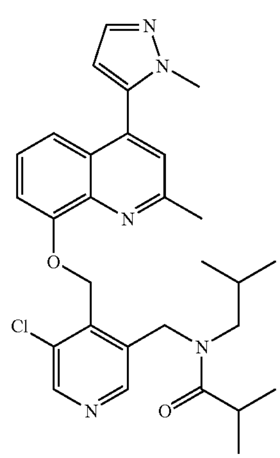 [SMILES: Cc1cc(-c2ccnn2C)c2cccc(OCc3c(Cl)cncc3CN(CC(C)C)C(=O)C(C)C)c2n1] | 520.2 |

TABLE 1-continued
| Example | Structure | M + H+ |
|---|---|---|
| 280. | 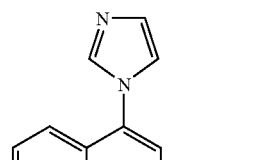 | 506.2 |
| 281. | 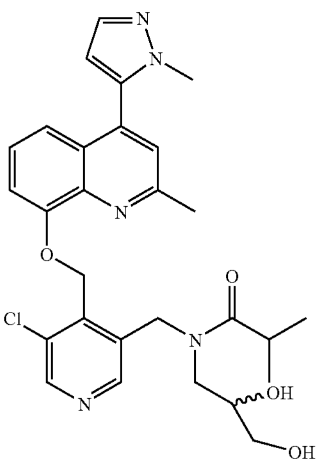 [SMILES: Cc1cc(-c2ccnn2C)c2cccc(OCc3c(Cl)cncc3CN(CC(O)CO)C(=O)C(C)C)c2n1] | 538.1 |
| 282. | 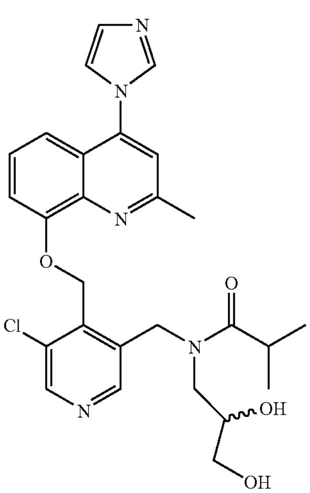 [SMILES: Cc1cc(-n2ccnc2)c2cccc(OCc3c(Cl)cncc3CN(CC(O)CO)C(=O)C(C)C)c2n1] | 524.1 |
| 283. | | 427.0 |
| 284. | | 481.1 |
| 285 | | 481.1 |

TABLE 1-continued
| Example | Structure | M + H⁺ |
|---------|-----------|--------|
| 286. | 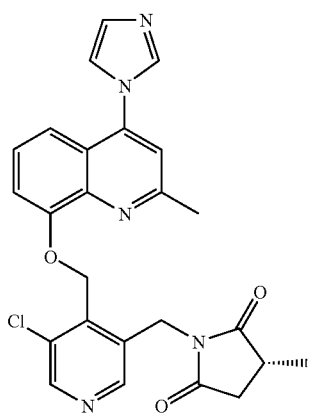 [SMILES: Cc1cc(-n2ccnc2)c2cccc(OCc3c(Cl)cncc3CN3C(=O)C[C@@H](C)C3=O)c2n1] | 478.1 |
| 287. | 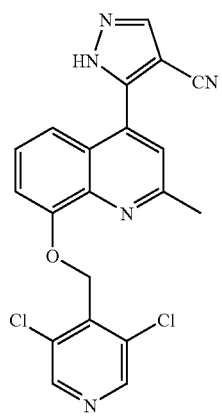 | 476.1 |
| 288. | 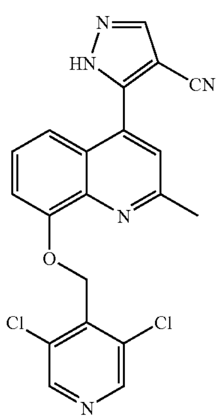 [SMILES: Cc1cc(-c2[nH]ncc2C#N)c2cccc(OCc3c(Cl)cncc3Cl)c2n1] | 410.0 |
TABLE 1-continued
| Example | Structure | M + H⁺ |
|---------|-----------|--------|
| 289. | 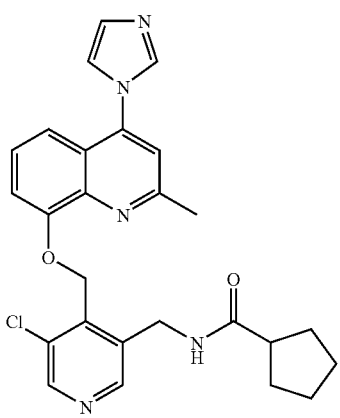 [SMILES: Cc1cc(-n2ccnc2)c2cccc(OCc3c(Cl)cncc3CNC(=O)C3CCCC3)c2n1] | 419.0 |
| 290. | 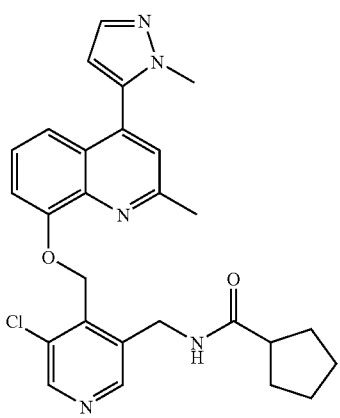 | 476.1 |
| 291. | 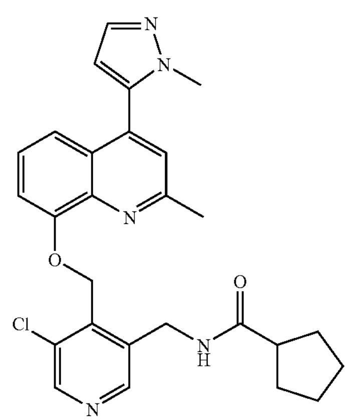 [SMILES: Cc1cc(-c2ccnn2C)c2cccc(OCc3c(Cl)cncc3CNC(=O)C3CCCC3)c2n1] | 490.1 |

TABLE 1-continued

| Example | Structure | M + H+ |
|---|---|---|
| 292. | 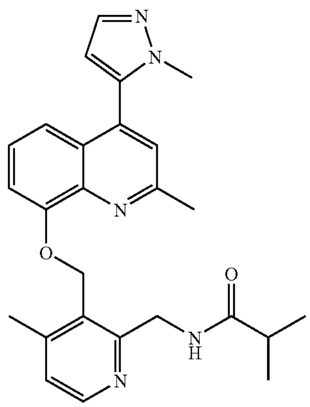 [SMILES: Cc1cc(-c2ccnn2C)c2cccc(OCc3c(C)ccnc3CNC(=O)C(C)C)c2n1] | 444.1 |
| 293. | 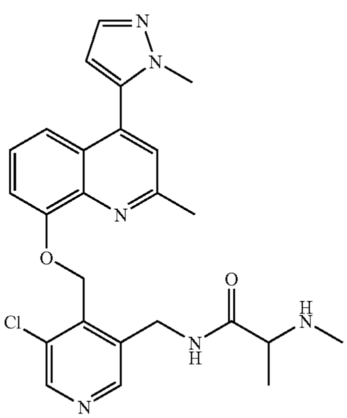 [SMILES: CNC(C)C(=O)NCc1cncc(Cl)c1COc1cccc2c(-c3ccnn3C)cc(C)nc12] | 479.1 |
| 294. | 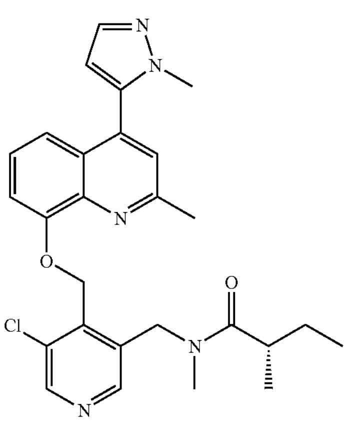 [SMILES: CC[C@H](C)C(=O)N(C)Cc1cncc(Cl)c1COc1cccc2c(-c3ccnn3C)cc(C)nc12] | 492.1 |
| 295. | 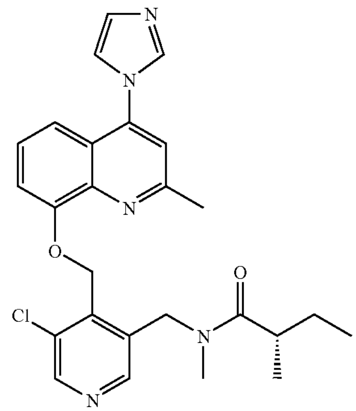 | 478.1 |
| 296. | 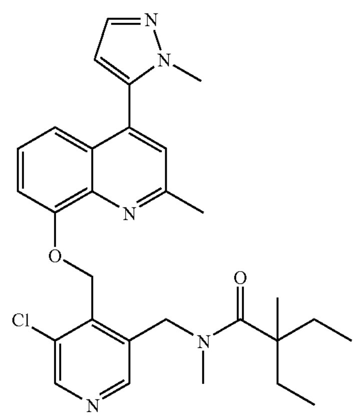 [SMILES: CCC(C)(CC)C(=O)N(C)Cc1cncc(Cl)c1COc1cccc2c(-c3ccnn3C)cc(C)nc12] | 520.2 |
| 297. | 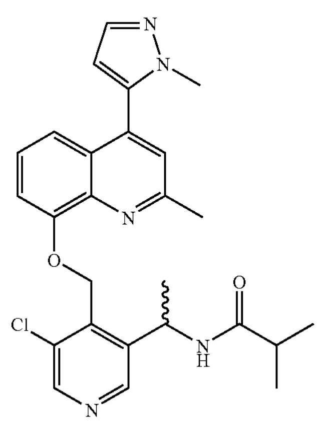 [SMILES: Cc1cc(-c2ccnn2C)c2cccc(OCc3c(Cl)cncc3C(C)NC(=O)C(C)C)c2n1] | 478.1 |

TABLE 1-continued

| Example | Structure | M + H⁺ |
|---------|-----------|--------|
| 298. | 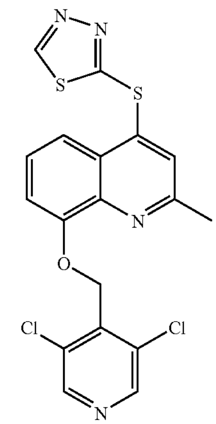 [SMILES: Cc1cc(Sc2nncs2)c2cccc(OCc3c(Cl)cncc3Cl)c2n1] | 435.0 |
| 299. | 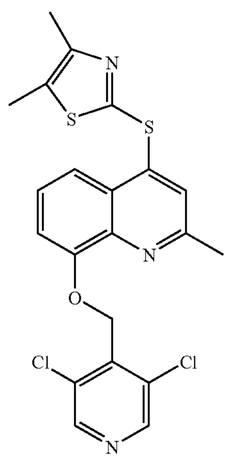 | 462 |
| 300. | 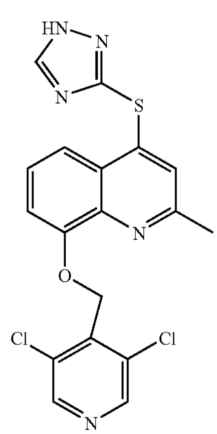 [SMILES: Cc1cc(Sc2nc[nH]n2)c2cccc(OCc3c(Cl)cncc3Cl)c2n1] | 418.0 |
| 301. | 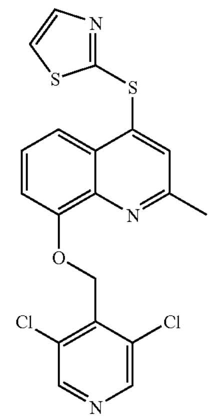 [SMILES: Cc1cc(Sc2nccs2)c2cccc(OCc3c(Cl)cncc3Cl)c2n1] | 433.9 |
| 302. | 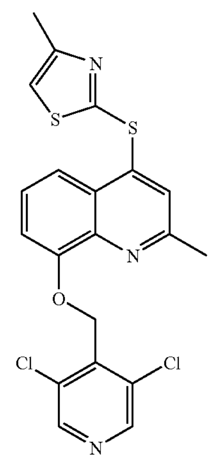 [SMILES: Cc1csc(Sc2cc(C)nc3c(OCc4c(Cl)cncc4Cl)cccc23)n1] | 447.9 |
| 303. | 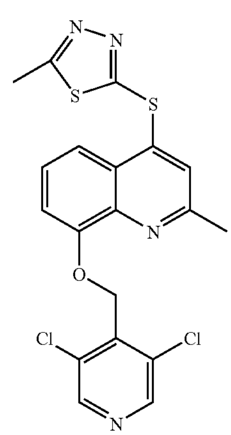 | 448.9 |

TABLE 1-continued

| Example | Structure | M + H+ |
|---|---|---|
| 304. | 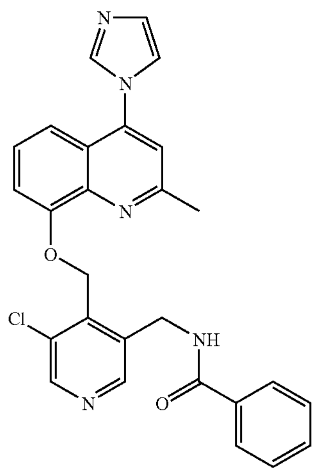 [SMILES: Cc1cc(-n2ccnc2)c2cccc(OCc3c(Cl)cncc3CNC(=O)c3ccccc3)c2n1] | 484.0 |
| 305. | 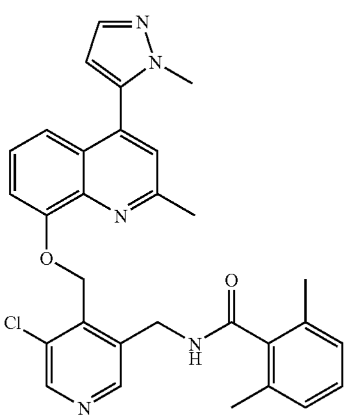 [SMILES: Cc1cc(-c2ccnn2C)c2cccc(OCc3c(Cl)cncc3CNC(=O)c3c(C)cccc3C)c2n1] | 526.1 |
| 306. | 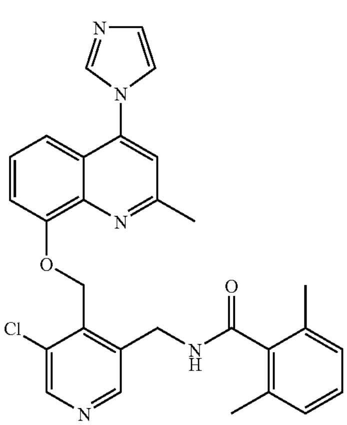 [SMILES: Cc1cc(-n2ccnc2)c2cccc(OCc3c(Cl)cncc3CNC(=O)c3c(C)cccc3C)c2n1] | 512.1 |
| 307. | | 518.2 |
| 308. | | 504.2 |
| 309. | | 500.1 |

TABLE 1-continued

| Example | Structure | M + H+ |
|---------|-----------|--------|
| 310. | 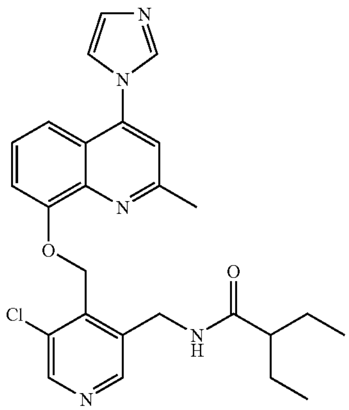 | 478.1 |
| 311. | 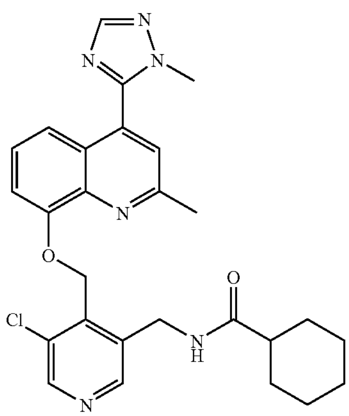 [SMILES: Cc1cc(-c2ncnn2C)c2cccc(OCc3c(Cl)cncc3CNC(=O)C3CCCCC3)c2n1] | 505.1 |
| 312. | 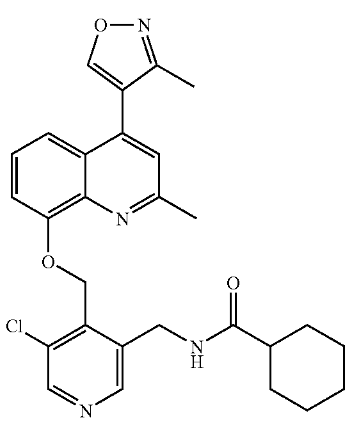 [SMILES: Cc1cc(-c2conc2C)c2cccc(OCc3c(Cl)cncc3CNC(=O)C3CCCCC3)c2n1] | 505.1 |

TABLE 1-continued

| Example | Structure | M + H+ |
|---------|-----------|--------|
| 313. | | 518.1 |
| 314. | | 191.1 |
| 315. | | 524.1 |

TABLE 1-continued

| Example | Structure | M + H⁺ |
|---------|-----------|--------|
| 316. | 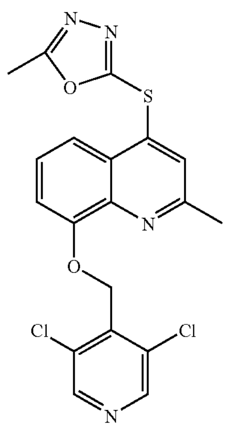 | 432.9 |
| 317. | 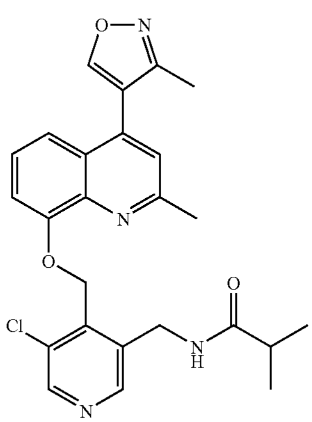 [SMILES: Cc1cc(-c2conc2C)c2cccc(OCc3c(Cl)cncc3CNC(=O)C(C)C)c2n1] | 465.1 |
| 318. | 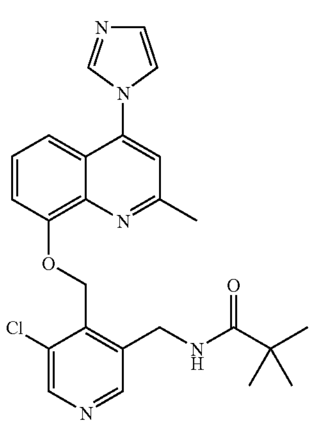 [SMILES: Cc1cc(-n2ccnc2)c2cccc(OCc3c(Cl)cncc3CNC(=O)C(C)(C)C)c2n1] | 464.1 |
| 319. | | 437.9 |
| 320. | | 504.2 |
| 321. | | 518.2 |

TABLE 1-continued
| Example | Structure | M + H+ |
|---|---|---|
| 322. | 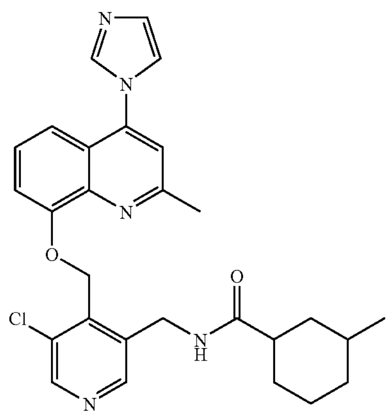 [SMILES: Cc1cc(-n2ccnc2)c2cccc(OCc3c(Cl)cncc3CNC(=O)C3CCCC(C)C3)c2n1] | 504.2 |
| 323. | 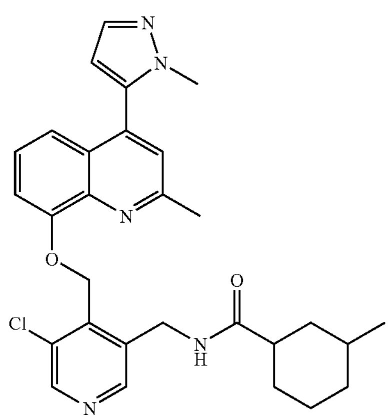 [SMILES: Cc1cc(-c2ccnn2C)c2cccc(OCc3c(Cl)cncc3CNC(=O)C3CCCC(C)C3)c2n1] | 518.3 |
| 324. | 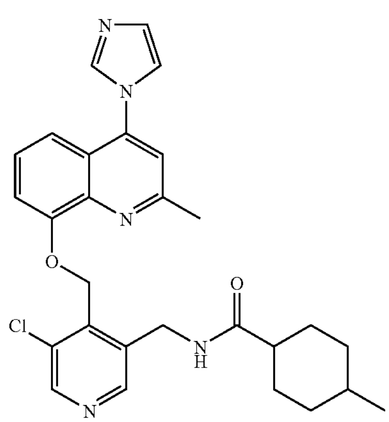 [SMILES: Cc1cc(-n2ccnc2)c2cccc(OCc3c(Cl)cncc3CNC(=O)C3CCC(C)CC3)c2n1] | 504.2 |
| 325. | 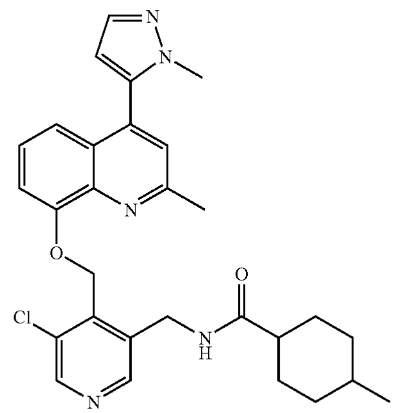 | 518.3 |
| 326. | 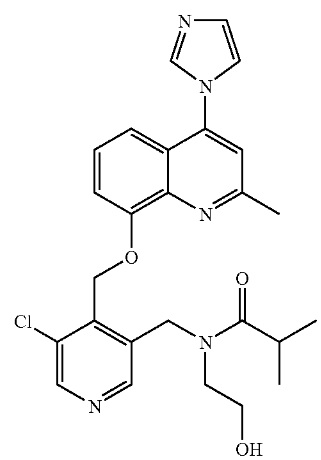 [SMILES: Cc1cc(-n2ccnc2)c2cccc(OCc3c(Cl)cncc3CN(CCO)C(=O)C(C)C)c2n1] | 494.1 |
| 327. | 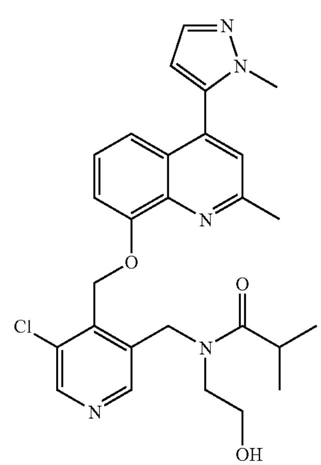 [SMILES: Cc1cc(-c2ccnn2C)c2cccc(OCc3c(Cl)cncc3CN(CCO)C(=O)C(C)C)c2n1] | 508.1 |

TABLE 1-continued
| Example | Structure | M + H+ |
|---|---|---|
| 328. | 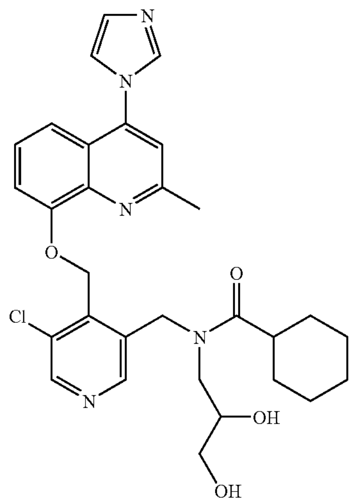 [SMILES: Cc1cc(-n2ccnc2)c2cccc(OCc3c(Cl)cncc3CN(CC(O)CO)C(=O)C3CCCCC3)c2n1] | 564.2 |
| 329. | 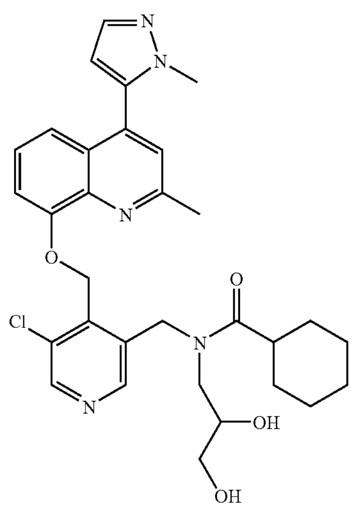 [SMILES: Cc1cc(-c2ccnn2C)c2cccc(OCc3c(Cl)cncc3CN(CC(O)CO)C(=O)C3CCCCC3)c2n1] | 578.2 |
| 330. | 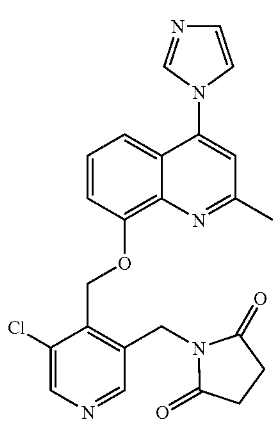 [SMILES: Cc1cc(-n2ccnc2)c2cccc(OCc3c(Cl)cncc3CN3C(=O)CCC3=O)c2n1] | 462.1 |
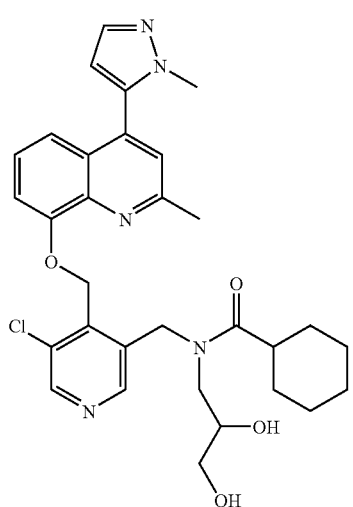
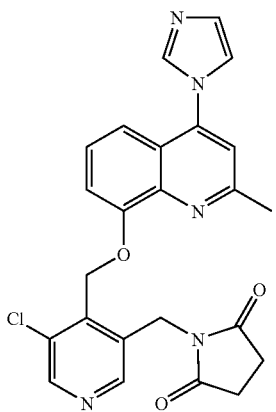
TABLE 1-continued
| Example | Structure | M + H+ |
|---|---|---|
| 331. | 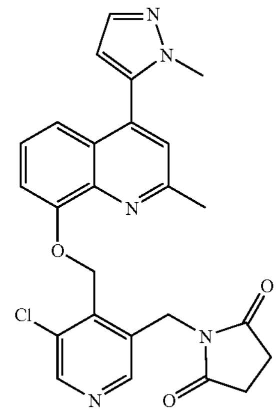 | 476.1 |
| 332. | 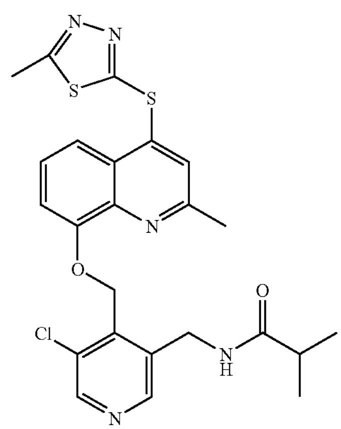 [SMILES: Cc1cc(Sc2nnc(C)s2)c2cccc(OCc3c(Cl)cncc3CNC(=O)C(C)C)c2n1] | 514.0 |
| 333. | 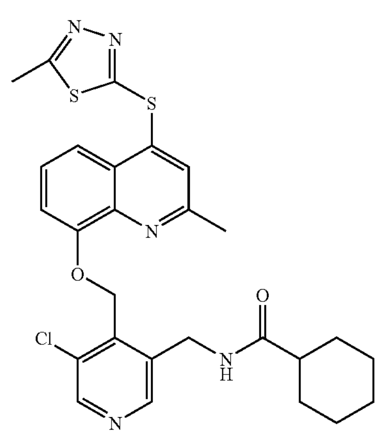 [SMILES: Cc1cc(Sc2nnc(C)s2)c2cccc(OCc3c(Cl)cncc3CNC(=O)C3CCCCC3)c2n1] | 554.0 |
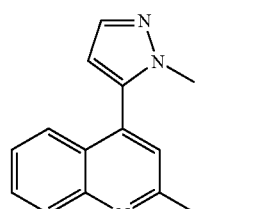
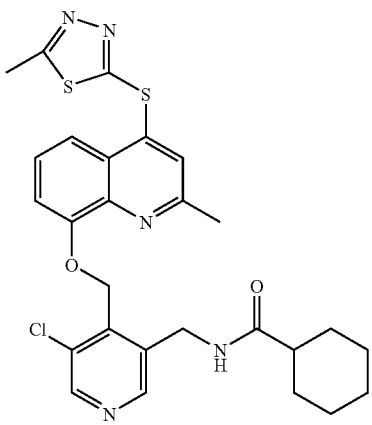

TABLE 1-continued
| Example | Structure | M + H+ |
|---|---|---|
| 334. | 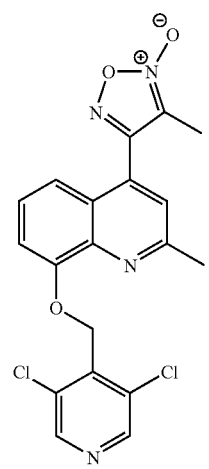 | 401.0 |
| 335. | 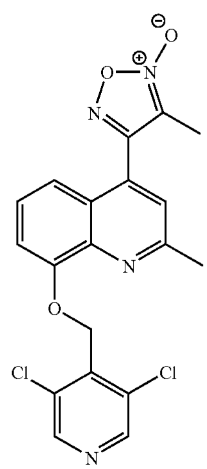 [SMILES: Cc1cc(-c2no[n+]([O-])c2C)c2cccc(OCc3c(Cl)cncc3Cl)c2n1] | 416.9 |
| 336. | 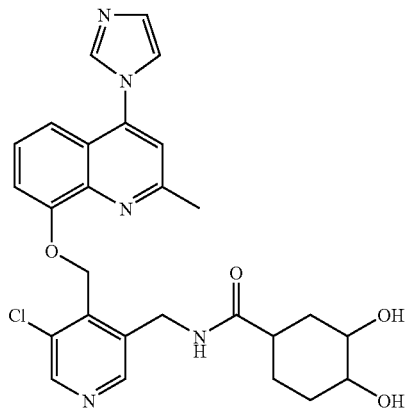 [SMILES: Cc1cc(-n2ccnc2)c2cccc(OCc3c(Cl)cncc3CNC(=O)C3CCC(O)C(O)C3)c2n1] | 522.0 |
TABLE 1-continued
| Example | Structure | M + H+ |
|---|---|---|
| 337. | 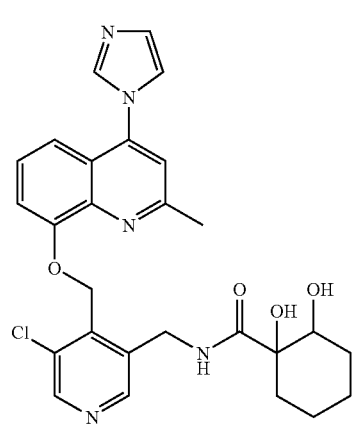 | 536.1 |
| 338. | 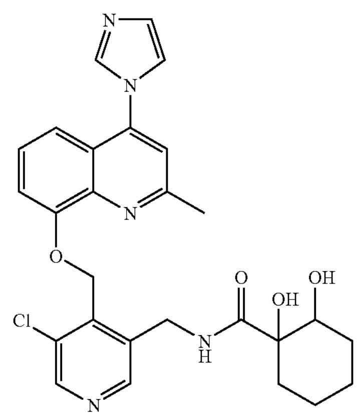 [SMILES: Cc1cc(-n2ccnc2)c2cccc(OCc3c(Cl)cncc3CNC(=O)C3(O)CCCCC3O)c2n1] | 522.0 |
| 339. | 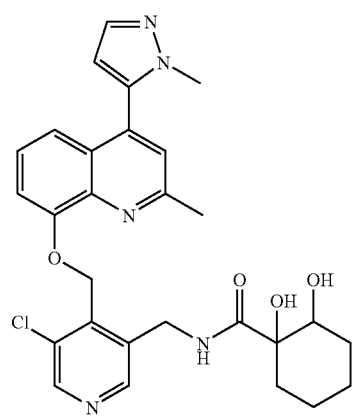 [SMILES: Cc1cc(-c2ccnn2C)c2cccc(OCc3c(Cl)cncc3CNC(=O)C3(O)CCCCC3O)c2n1] | 536.1 |

141
TABLE 1-continued
| Example | Structure | M + H⁺ |
|---|---|---|
| 340. | 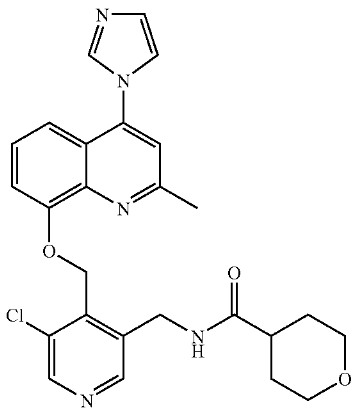 [SMILES: Cc1cc(-n2ccnc2)c2cccc(OCc3c(Cl)cncc3CNC(=O)C3CCOCC3)c2n1] | 492.1 |
| 341. | 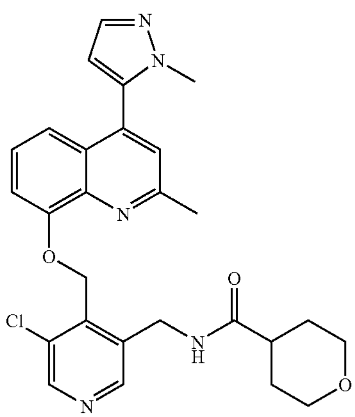 [SMILES: Cc1cc(-c2ccnn2C)c2cccc(OCc3c(Cl)cncc3CNC(=O)C3CCOCC3)c2n1] | 506.2 |
| 342. | 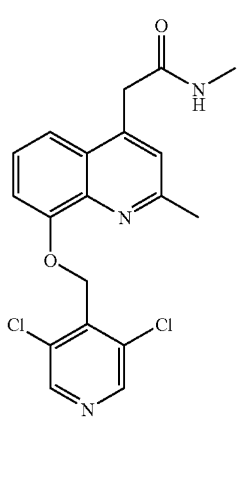 [SMILES: CNC(=O)Cc1cc(C)nc2c(OCc3c(Cl)cncc3Cl)cccc12] | 390.0 |
142
TABLE 1-continued
| Example | Structure | M + H⁺ |
|---|---|---|
| 343. | 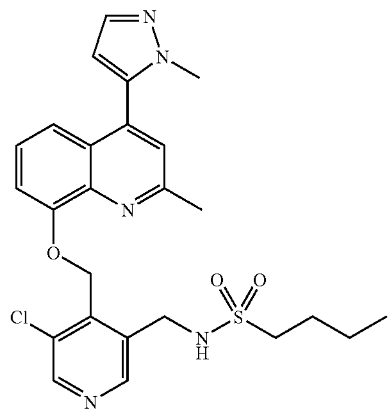 [SMILES: CCCCS(=O)(=O)NCc1cncc(Cl)c1COc1cccc2c(-c3ccnn3C)cc(C)nc12] | 514.1 |
| 344. | 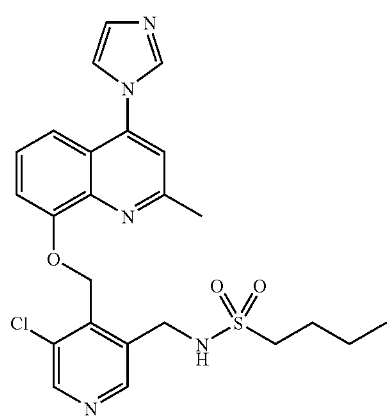 [SMILES: CCCCS(=O)(=O)NCc1cncc(Cl)c1COc1cccc2c(-n3ccnc3)cc(C)nc12] | 500.1 |
| 345. | 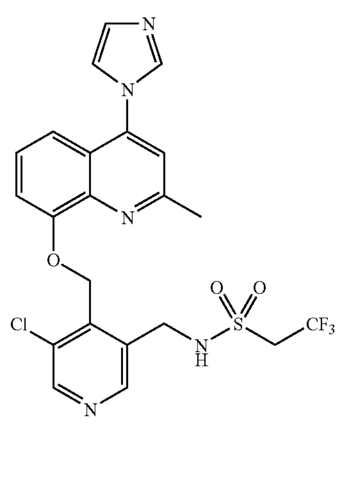 [SMILES: Cc1cc(-n2ccnc2)c2cccc(OCc3c(Cl)cncc3CNS(=O)(=O)CC(F)(F)F)c2n1] | 526.1 |
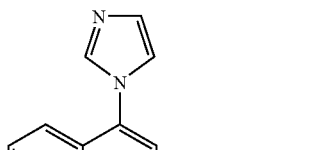
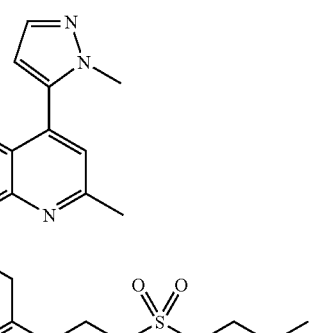

TABLE 1-continued

| Example | Structure | M + H⁺ |
|---|---|---|
| 346. | 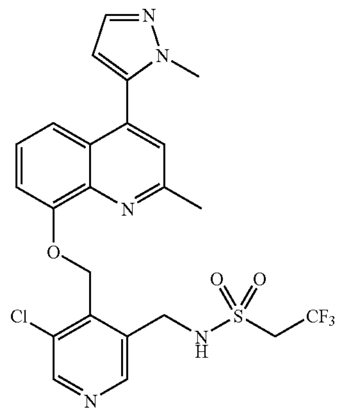 [SMILES: Cc1cc(-c2ccnn2C)c2cccc(OCc3c(Cl)cncc3CNS(=O)(=O)CC(F)(F)F)c2n1] | 540.0 |
| 347. | 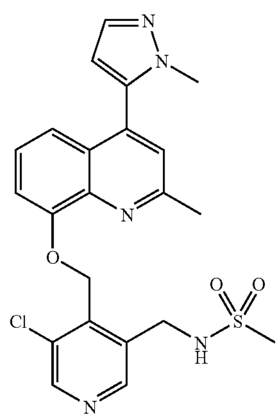 [SMILES: Cc1cc(-c2ccnn2C)c2cccc(OCc3c(Cl)cncc3CNS(C)(=O)=O)c2n1] | 472.1 |
| 348. | 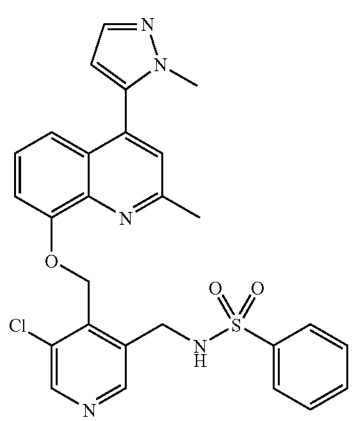 [SMILES: Cc1cc(-c2ccnn2C)c2cccc(OCc3c(Cl)cncc3CNS(=O)(=O)c3ccccc3)c2n1] | 534.0 |
| 349. | 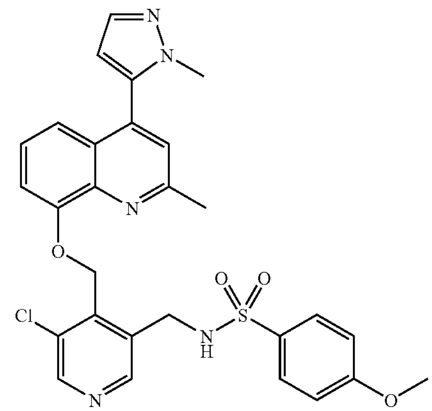 [SMILES: COc1ccc(S(=O)(=O)NCc2cncc(Cl)c2COc2cccc3c(-c4ccnn4C)cc(C)nc23)cc1] | 564.1 |
| 350. | 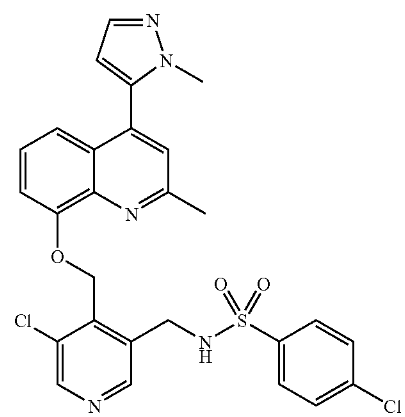 [SMILES: Cc1cc(-c2ccnn2C)c2cccc(OCc3c(Cl)cncc3CNS(=O)(=O)c3ccc(Cl)cc3)c2n1] | 568.0 |
| 351. | 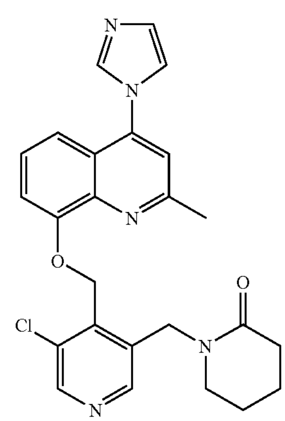 [SMILES: Cc1cc(-n2ccnc2)c2cccc(OCc3c(Cl)cncc3CN3CCCCC3=O)c2n1] | 462.1 |

TABLE 1-continued

| Example | Structure | M + H+ |
|---|---|---|
| 352. | 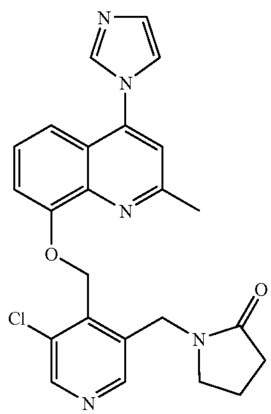 [SMILES: Cc1cc(-n2ccnc2)c2cccc(OCc3c(Cl)cncc3CN3CCCC3=O)c2n1] | 448.1 |
| 353. | 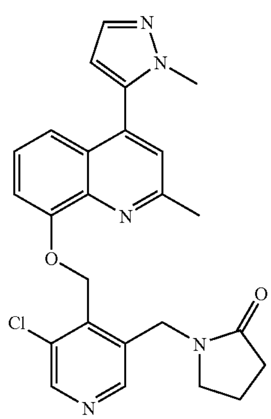 [SMILES: Cc1cc(-c2ccnn2C)c2cccc(OCc3c(Cl)cncc3CN3CCCC3=O)c2n1] | 462.1 |
| 354. | 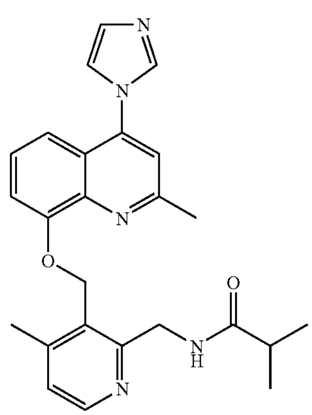 [SMILES: Cc1cc(-n2ccnc2)c2cccc(OCc3c(C)ccnc3CNC(=O)C(C)C)c2n1] | 430.0 |
| 355. | | 540.0 |
| 356. | | 476.2 |
| 357. | | 490.2 |

TABLE 1-continued

| Example | Structure | M + H⁺ |
|---|---|---|
| 358. | 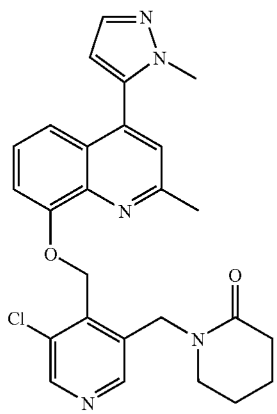 [SMILES: Cc1cc(-c2ccnn2C)c2cccc(OCc3c(Cl)cncc3CN3CCCCC3=O)c2n1] | 476.1 |
| 359. | 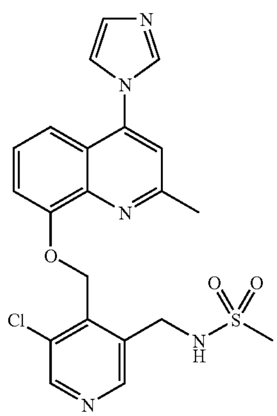 [SMILES: Cc1cc(-n2ccnc2)c2cccc(OCc3c(Cl)cncc3CNS(C)(=O)=O)c2n1] | 458.1 |
| 360. | 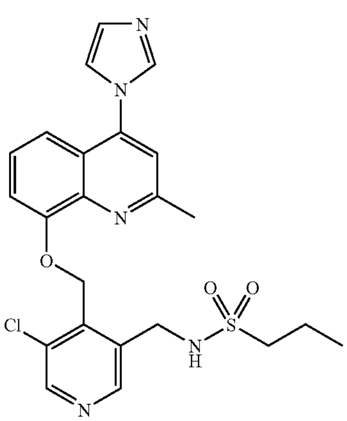 [SMILES: CCCS(=O)(=O)NCc1cncc(Cl)c1COc1cccc2c(-n3ccnc3)cc(C)nc12] | 486.1 |

TABLE 1-continued

| Example | Structure | M + H⁺ |
|---|---|---|
| 361. | 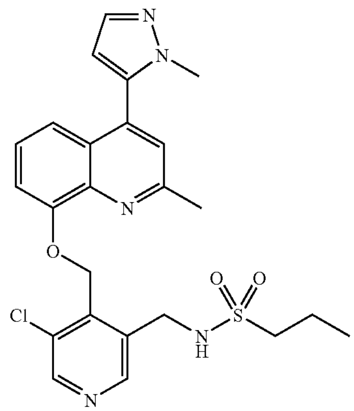 [SMILES: CCCS(=O)(=O)NCc1cncc(Cl)c1COc1cccc2c(-c3ccnn3C)cc(C)nc12] | 500.1 |
| 362. | 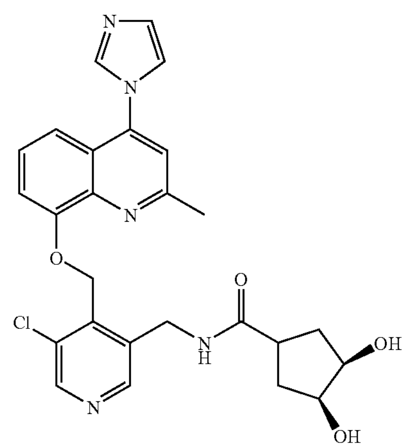 [SMILES: Cc1cc(-n2ccnc2)c2cccc(OCc3c(Cl)cncc3CNC(=O)C3C[C@@H](O)[C@@H](O)C3)c2n1] | 508.0 |
| 363. | 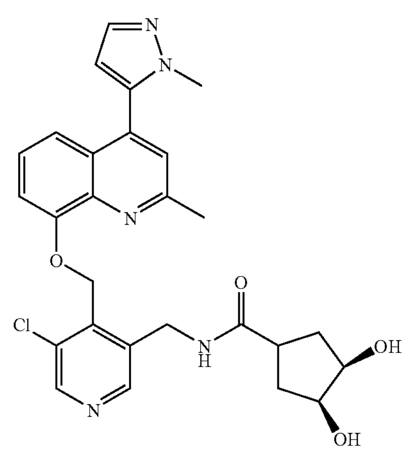 [SMILES: Cc1cc(-c2ccnn2C)c2cccc(OCc3c(Cl)cncc3CNC(=O)C3C[C@@H](O)[C@@H](O)C3)c2n1] | 522.1 |

TABLE 1-continued

| Example | Structure | M + H+ |
|---------|-----------|--------|
| 364. | 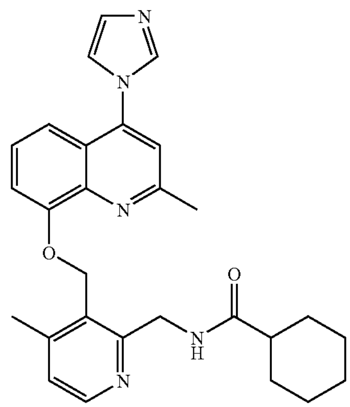 [SMILES: Cc1cc(-n2ccnc2)c2cccc(OCc3c(C)ccnc3CNC(=O)C3CCCCC3)c2n1] | 470.1 |
| 365. | 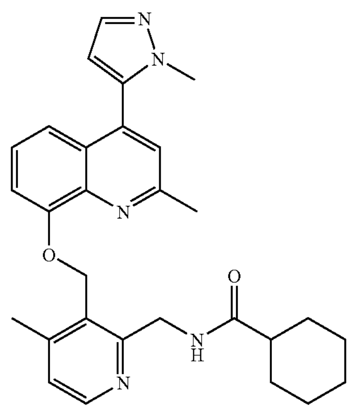 [SMILES: Cc1cc(-c2ccnn2C)c2cccc(OCc3c(C)ccnc3CNC(=O)C3CCCCC3)c2n1] | 484.1 |
| 366. | 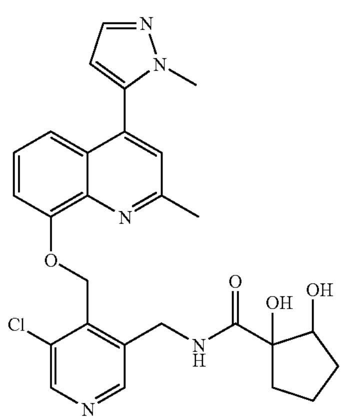 [SMILES: Cc1cc(-c2ccnn2C)c2cccc(OCc3c(Cl)cncc3CNC(=O)C3(O)CCCC3O)c2n1] | 522.2 |
| 367. | | 458.1 |
| 368. | | 489.4 |
| 369. | | 475.3 |

TABLE 1-continued
| Example | Structure | M + H+ |
|---|---|---|
| 370. | 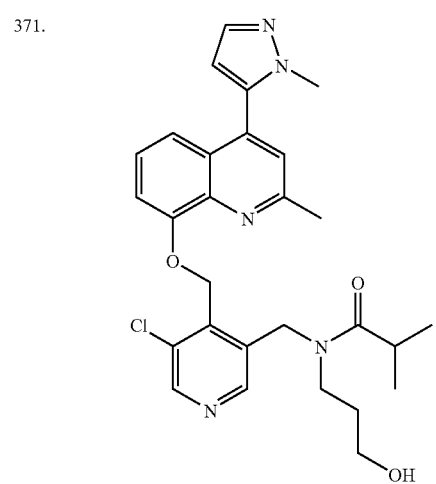 | 501.0 |
| 371. | 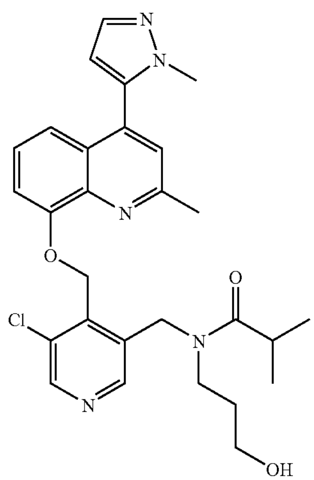 [SMILES: Cc1cc(-c2ccnn2C)c2cccc(OCc3c(Cl)cncc3CN(CCCO)C(=O)C(C)C)c2n1] | 522.2 |
| 372. | 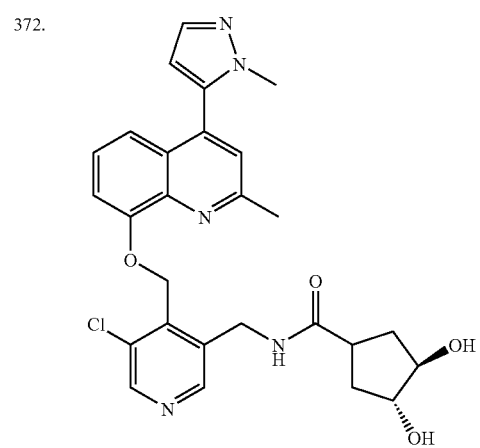 | 522.1 |
TABLE 1-continued
| Example | Structure | M + H+ |
|---|---|---|
| 373. | 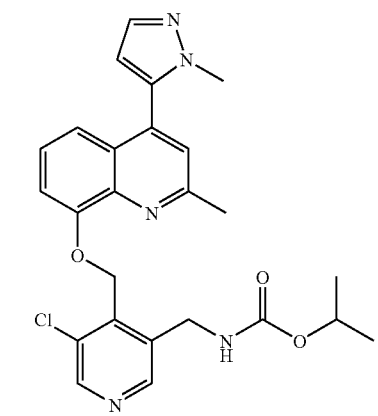 [SMILES: Cc1cc(-c2ccnn2C)c2cccc(OCc3c(Cl)cncc3CNC(=O)OC(C)C)c2n1] | 508.1 |
| 374. | 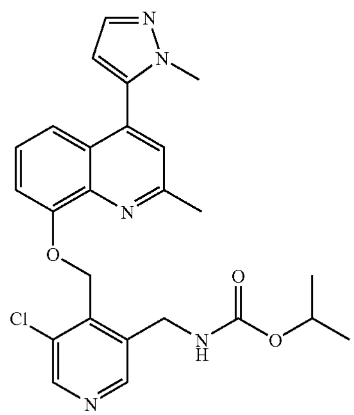 | 480.1 |
| 375. | 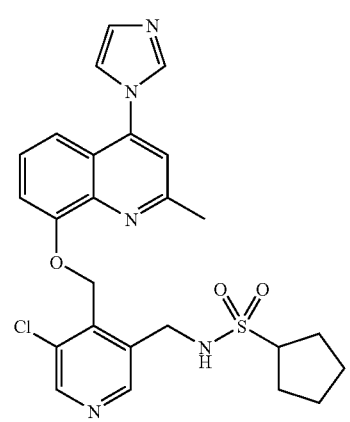 [SMILES: Cc1cc(-n2ccnc2)c2cccc(OCc3c(Cl)cncc3CNS(=O)(=O)C3CCCC3)c2n1] | 512.2 |

TABLE 1-continued
| Example | Structure | M + H+ |
|---|---|---|
| 376. | 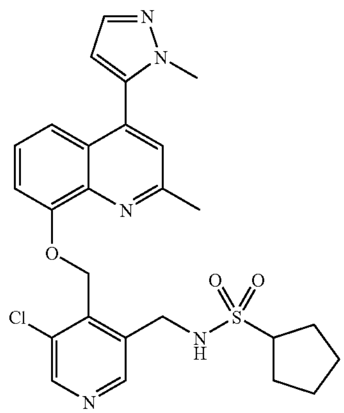 [SMILES: Cc1cc(-c2ccnn2C)c2cccc(OCc3c(Cl)cncc3CNS(=O)(=O)C3CCCC3)c2n1] | 526.2 |
| 377. | 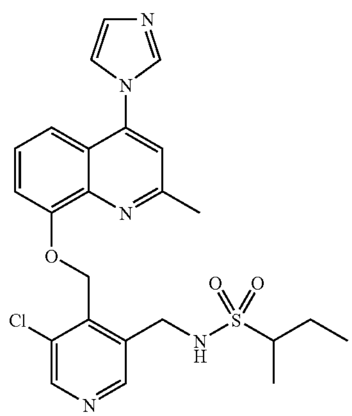 [SMILES: CCC(C)S(=O)(=O)NCc1cncc(Cl)c1COc1cccc2c(-n3ccnc3)cc(C)nc12] | 500.1 |
| 378. | 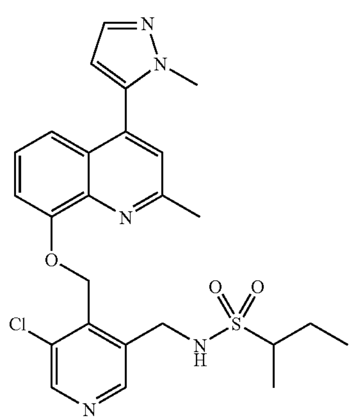 [SMILES: CCC(C)S(=O)(=O)NCc1cncc(Cl)c1COc1cccc2c(-c3ccnn3C)cc(C)nc12] | 514.2 |
| 379. | | 540.2 |
| 380. | | 526.2 |
| 381. | | 451.9 |
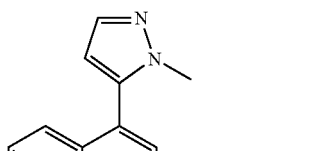

TABLE 1-continued

| Example | Structure | M + H⁺ |
|---------|-----------|--------|
| 382. | 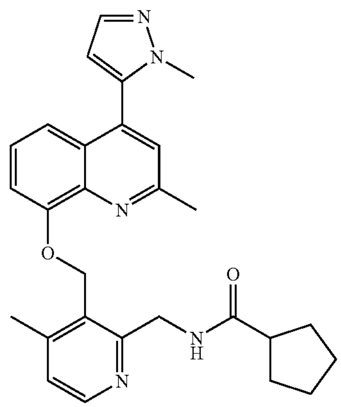 [SMILES: Cc1cc(-c2ccnn2C)c2cccc(OCc3c(C)ccnc3CNC(=O)C3CCCC3)c2n1] | 470.1 |
| 383. | 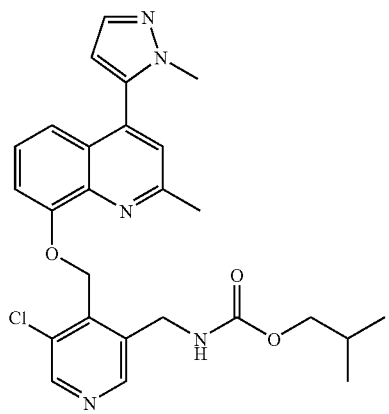 [SMILES: Cc1cc(-c2ccnn2C)c2cccc(OCc3c(Cl)cncc3CNC(=O)OCC(C)C)c2n1] | 494.1 |
| 384. | 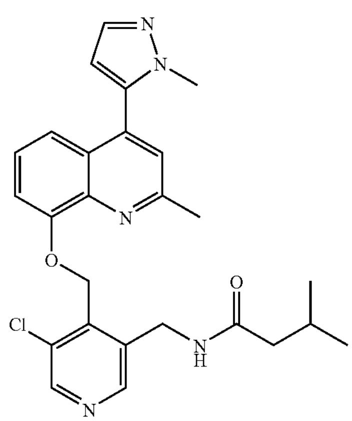 [SMILES: Cc1cc(-c2ccnn2C)c2cccc(OCc3c(Cl)cncc3CNC(=O)CC(C)C)c2n1] | 478.2 |
| 385. | 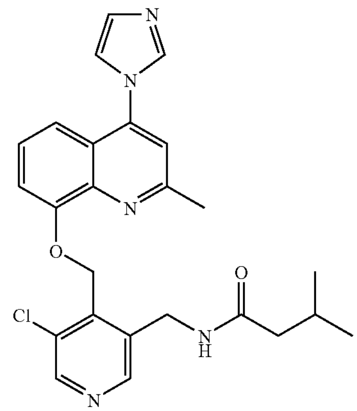 [SMILES: Cc1cc(-n2ccnc2)c2cccc(OCc3c(Cl)cncc3CNC(=O)CC(C)C)c2n1] | 464.1 |
| 386. | 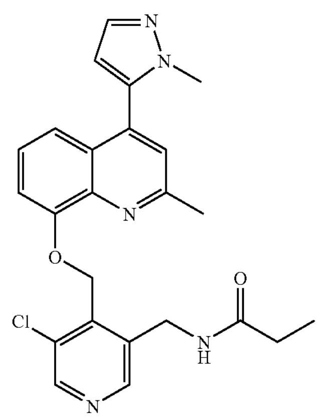 [SMILES: CCC(=O)NCc1cncc(Cl)c1COc1cccc2c(-c3ccnn3C)cc(C)nc12] | 450.1 |
| 387. | 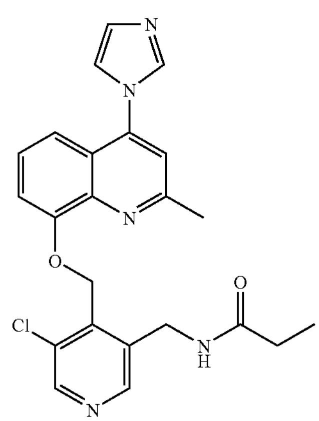 [SMILES: CCC(=O)NCc1cncc(Cl)c1COc1cccc2c(-n3ccnc3)cc(C)nc12] | 436.1 |

TABLE 1-continued

| Example | Structure | M + H+ |
|---|---|---|
| 388. | 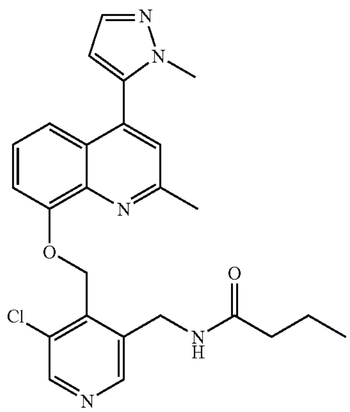 [SMILES: CCCC(=O)NCc1cncc(Cl)c1COc1cccc2c(-c3ccnn3C)cc(C)nc12] | 464.2 |
| 389. | 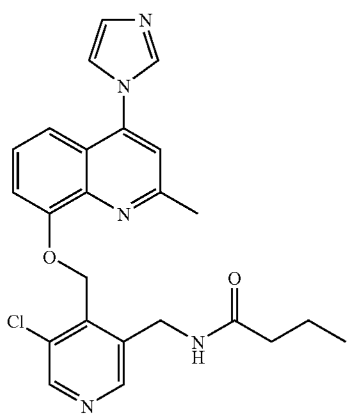 [SMILES: CCCC(=O)NCc1cncc(Cl)c1COc1cccc2c(-n3ccnc3)cc(C)nc12] | 450.1 |
| 390. | 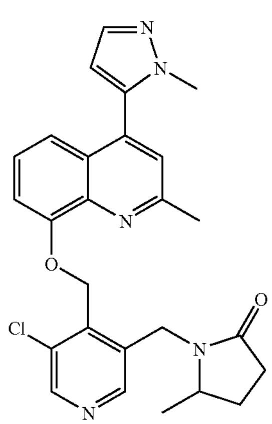 [SMILES: Cc1cc(-c2ccnn2C)c2cccc(OCc3c(Cl)cncc3CN3C(=O)CCC3C)c2n1] | 476.1 |

TABLE 1-continued

| Example | Structure | M + H+ |
|---|---|---|
| 391. | 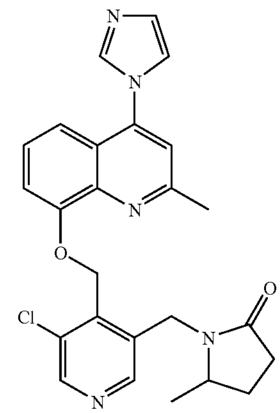 [SMILES: Cc1cc(-n2ccnc2)c2cccc(OCc3c(Cl)cncc3CN3C(=O)CCC3C)c2n1] | 462.1 |
| 392. | 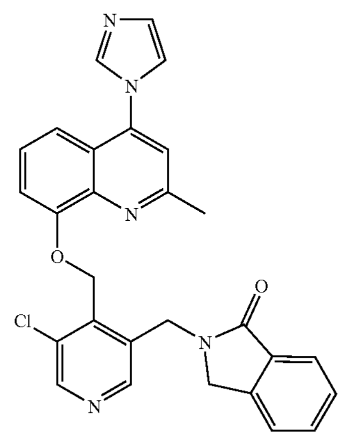 [SMILES: Cc1cc(-n2ccnc2)c2cccc(OCc3c(Cl)cncc3CN3Cc4ccccc4C3=O)c2n1] | 496.1 |
| 393. | 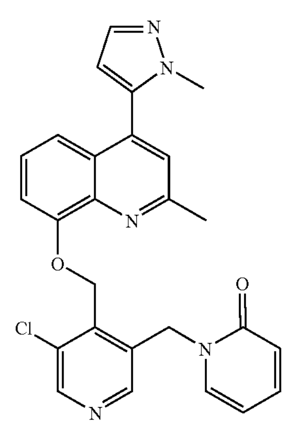 [SMILES: Cc1cc(-c2ccnn2C)c2cccc(OCc3c(Cl)cncc3Cn3ccccc3=O)c2n1] | 472.1 |

TABLE 1-continued

| Example | Structure | M + H⁺ |
|---------|-----------|--------|
| 394. | 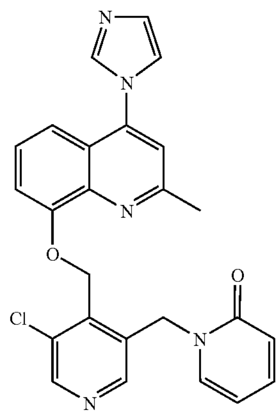 [SMILES: Cc1cc(-n2ccnc2)c2cccc(OCc3c(Cl)cncc3Cn3ccccc3=O)c2n1] | 458.1 |
| 395. | 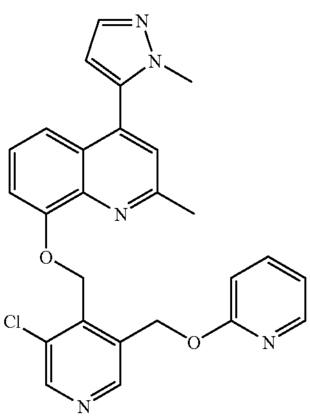 [SMILES: Cc1cc(-c2ccnn2C)c2cccc(OCc3c(Cl)cncc3COc3ccccn3)c2n1] | 472.0 |
| 396. | 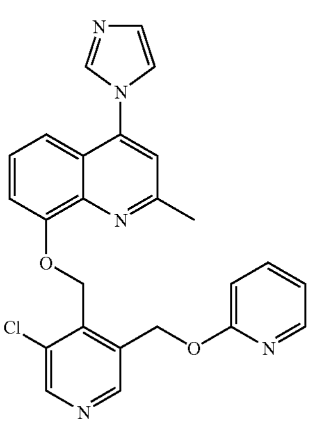 [SMILES: Cc1cc(-n2ccnc2)c2cccc(OCc3c(Cl)cncc3COc3ccccn3)c2n1] | 458.0 |
| 397. | | 456.1 |
| 398. | | 481.1 |
| 399. | | 510.1 |

TABLE 1-continued

| Example | Structure | M + H+ |
|---------|-----------|--------|
| 400. | 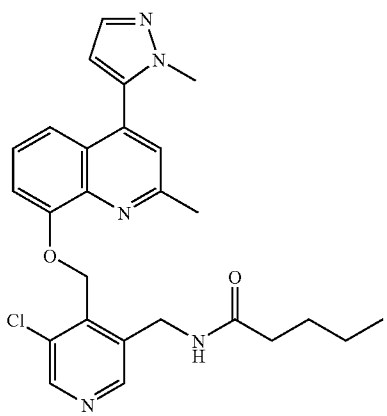 [SMILES: CCCCC(=O)NCc1cncc(Cl)c1COc1cccc2c(-c3ccnn3C)cc(C)nc12] | 478.2 |
| 401. | 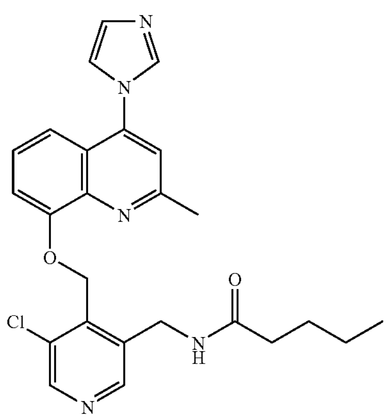 [SMILES: CCCCC(=O)NCc1cncc(Cl)c1COc1cccc2c(-n3ccnc3)cc(C)nc12] | 464.1 |
| 402. | 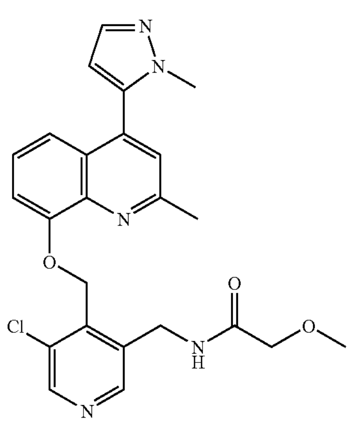 [SMILES: COCC(=O)NCc1cncc(Cl)c1COc1cccc2c(-c3ccnn3C)cc(C)nc12] | 466.1 |
| 403. | 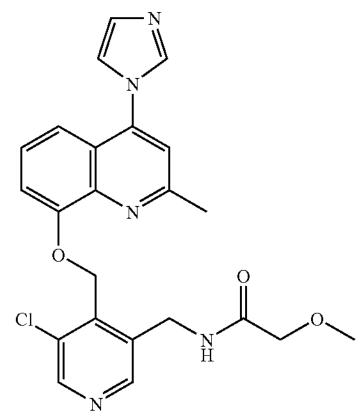 [SMILES: COCC(=O)NCc1cncc(Cl)c1COc1cccc2c(-n3ccnc3)cc(C)nc12] | 452.1 |
| 404. | 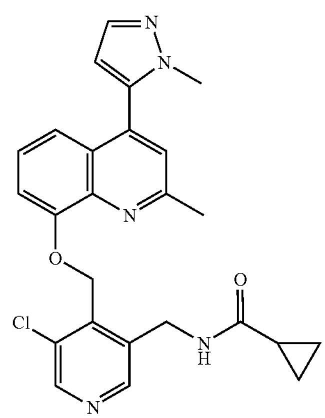 [SMILES: Cc1cc(-c2ccnn2C)c2cccc(OCc3c(Cl)cncc3CNC(=O)C3CC3)c2n1] | 462.1 |
| 405. | 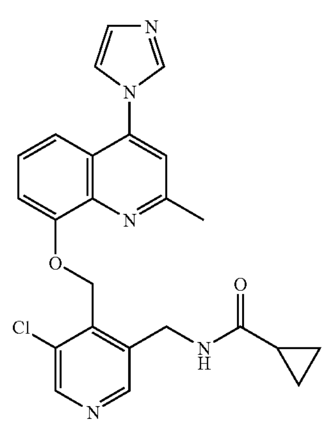 [SMILES: Cc1cc(-n2ccnc2)c2cccc(OCc3c(Cl)cncc3CNC(=O)C3CC3)c2n1] | 448.1 |

TABLE 1-continued
| Example | Structure | M + H⁺ |
|---|---|---|
| 406. | 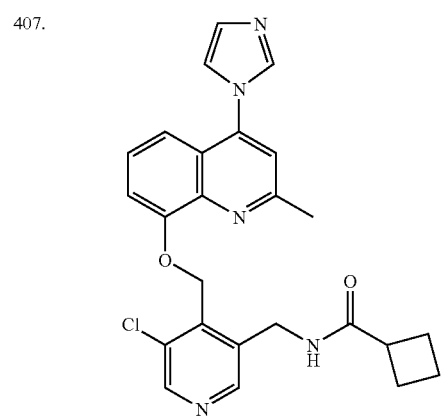 | 476.1 |
| 407. | 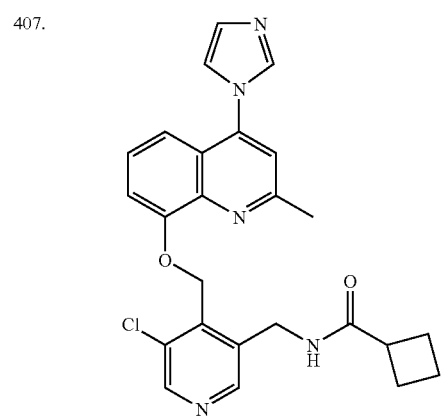 | 462.1 |
| 408. | 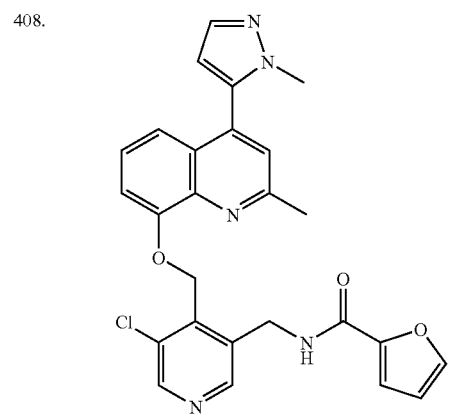 | 488.1 |
TABLE 1-continued
| Example | Structure | M + H⁺ |
|---|---|---|
| 409. | 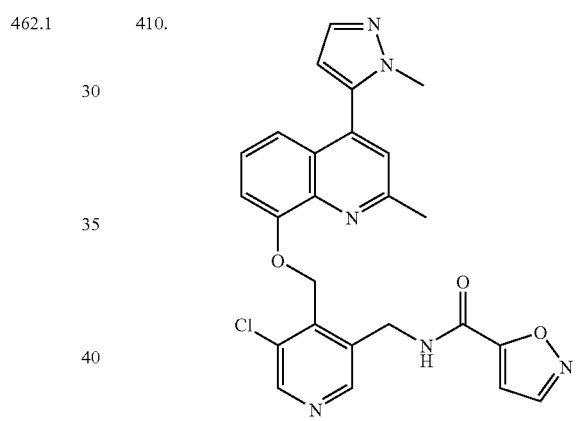 | 474.1 |
| 410. | 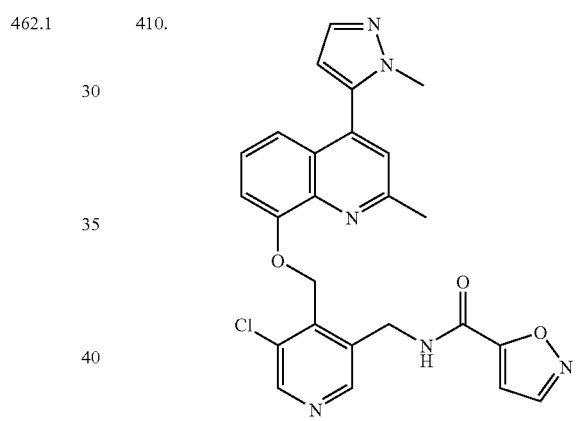 | 489.1 |
| 411. | 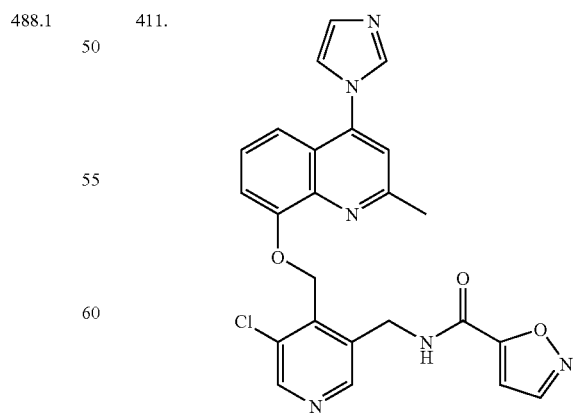 | 475.1 |

TABLE 1-continued
| Example | Structure | M + H⁺ |
|---|---|---|
| 412. | 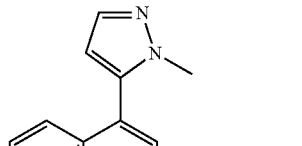 | 472.1 |
| 413. | 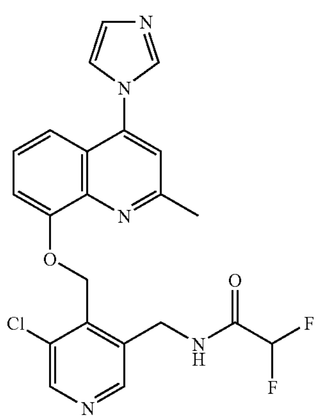 [SMILES: Cc1cc(-n2ccnc2)c2cccc(OCc3c(Cl)cncc3CNC(=O)C(F)F)c2n1] | 458.0 |
| 414. | 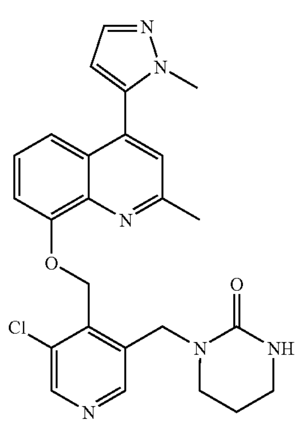 [SMILES: Cc1cc(-c2ccnn2C)c2cccc(OCc3c(Cl)cncc3CN3CCCNC3=O)c2n1] | 477.2 |
TABLE 1-continued
| Example | Structure | M + H⁺ |
|---|---|---|
| 415. | 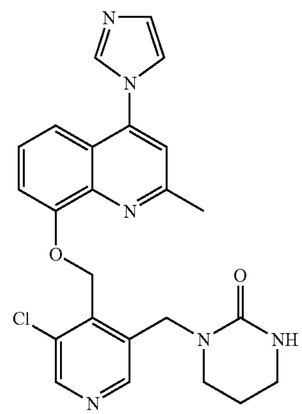 [SMILES: Cc1cc(-n2ccnc2)c2cccc(OCc3c(Cl)cncc3CN3CCCNC3=O)c2n1] | 463.2 |
| 416. | 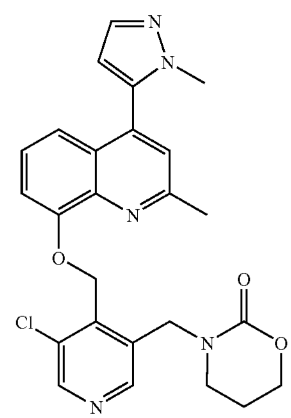 [SMILES: Cc1cc(-c2ccnn2C)c2cccc(OCc3c(Cl)cncc3CN3CCCOC3=O)c2n1] | 478.2 |
| 417. | 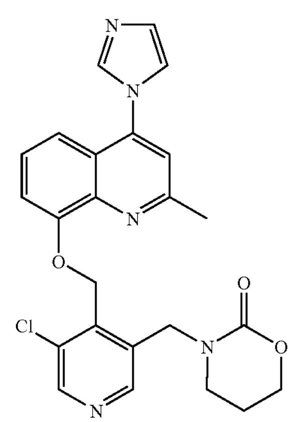 [SMILES: Cc1cc(-n2ccnc2)c2cccc(OCc3c(Cl)cncc3CN3CCCOC3=O)c2n1] | 464.1 |
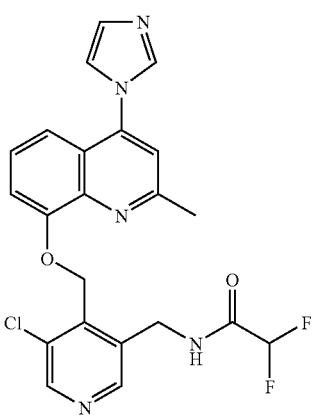
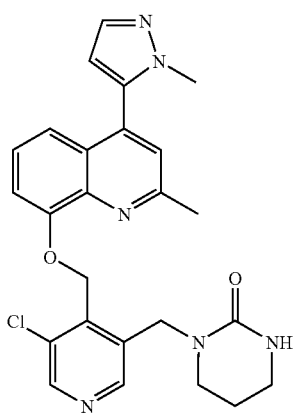

TABLE 1-continued
| Example | Structure | M + H⁺ |
|---------|-----------|--------|
| 418. | 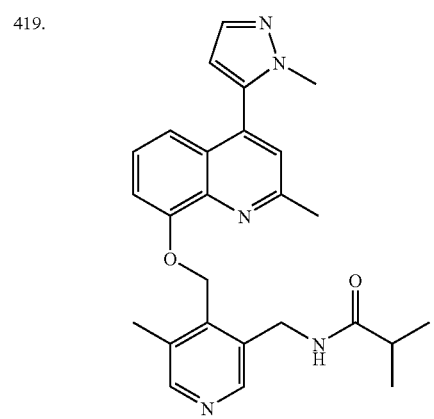 | 415.9 |
| 419. | 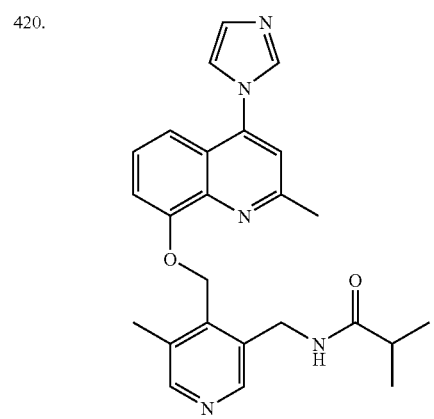 | 444.1 |
| 420. | 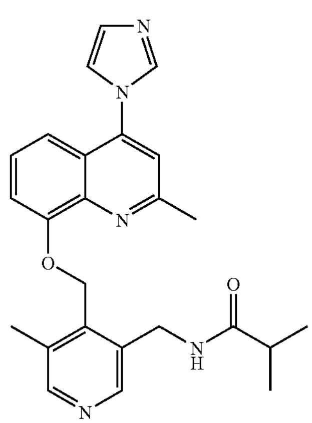 [SMILES: Cc1cc(-n2ccnc2)c2cccc(OCc3c(C)cncc3CNC(=O)C(C)C)c2n1] | 430.1 |
TABLE 1-continued
| Example | Structure | M + H⁺ |
|---------|-----------|--------|
| 421. | 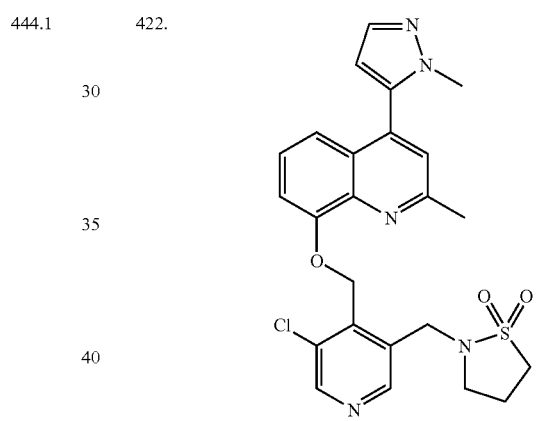 | 484.1 |
| 422. | 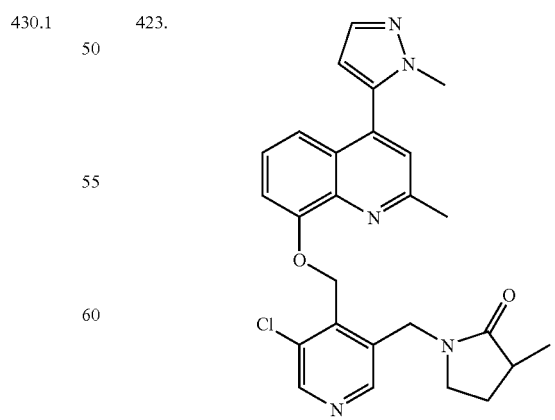 | 498.1 |
| 423. | | 476.2 |

TABLE 1-continued

| Example | Structure | M + H+ |
|---|---|---|
| 424. | 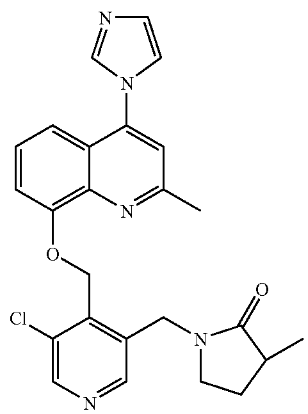 [SMILES: Cc1cc(-n2ccnc2)c2cccc(OCc3c(Cl)cncc3CN3CCC(C)C3=O)c2n1] | 462.2 |
| 425. | 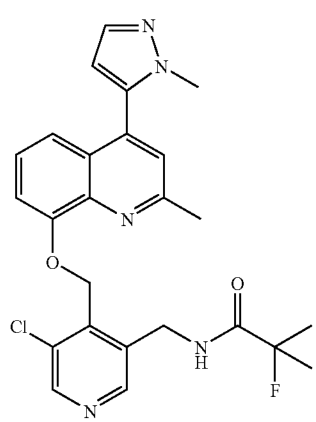 [SMILES: Cc1cc(-c2ccnn2C)c2cccc(OCc3c(Cl)cncc3CNC(=O)C(C)(C)F)c2n1] | 482.1 |
| 426. | 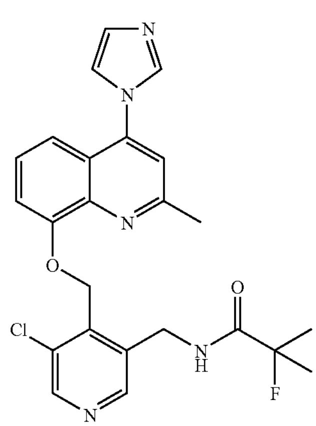 [SMILES: Cc1cc(-n2ccnc2)c2cccc(OCc3c(Cl)cncc3CNC(=O)C(C)(C)F)c2n1] | 468.2 |

TABLE 1-continued

| Example | Structure | M + H+ |
|---|---|---|
| 427. | 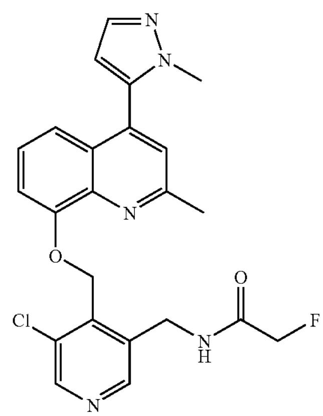 [SMILES: Cc1cc(-c2ccnn2C)c2cccc(OCc3c(Cl)cncc3CNC(=O)CF)c2n1] | 454.1 |
| 428. | 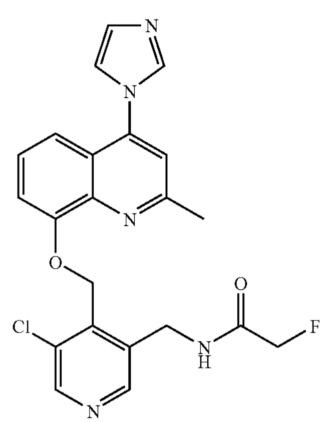 [SMILES: Cc1cc(-n2ccnc2)c2cccc(OCc3c(Cl)cncc3CNC(=O)CF)c2n1] | 440.1 |
| 429. | 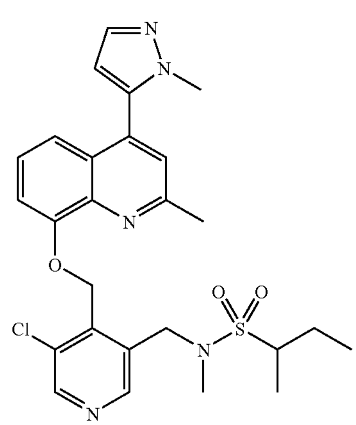 [SMILES: CCC(C)S(=O)(=O)N(C)Cc1cncc(Cl)c1COc1cccc2c(-c3ccnn3C)cc(C)nc12] | 528.2 |

TABLE 1-continued

| Example | Structure | M + H+ |
|---------|-----------|--------|
| 430. | 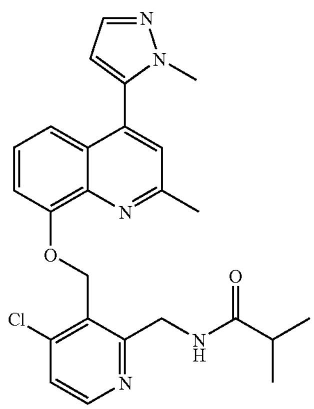 [SMILES: Cc1cc(-c2ccnn2C)c2cccc(OCc3c(Cl)ccnc3CNC(=O)C(C)C)c2n1] | 464.1 |
| 431. | 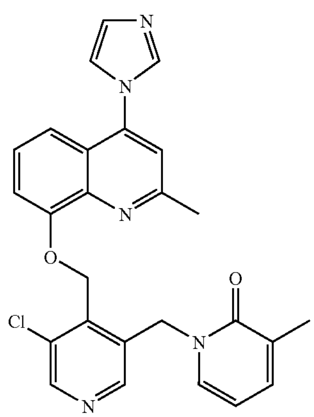 [SMILES: Cc1cc(-n2ccnc2)c2cccc(OCc3c(Cl)cncc3Cn3cccc(C)c3=O)c2n1] | 472.1 |
| 432. | 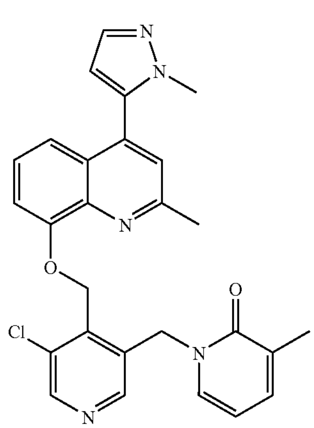 [SMILES: Cc1cc(-c2ccnn2C)c2cccc(OCc3c(Cl)cncc3Cn3cccc(C)c3=O)c2n1] | 486.1 |
| 433. | | 526.1 |
| 434. | | 540.1 |
| 435. | | 507.1 |

TABLE 1-continued

| Example | Structure | M + H⁺ |
|---|---|---|
| 436. | 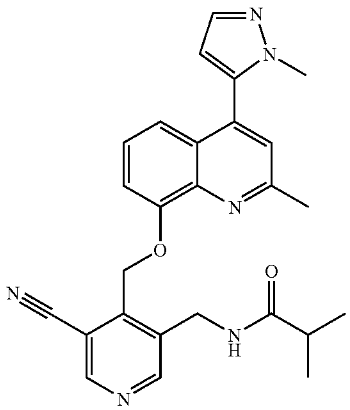 [SMILES: Cc1cc(-c2ccnn2C)c2cccc(OCc3c(C#N)cncc3CNC(=O)C(C)C)c2n1] | 455.1 |
| 437. | 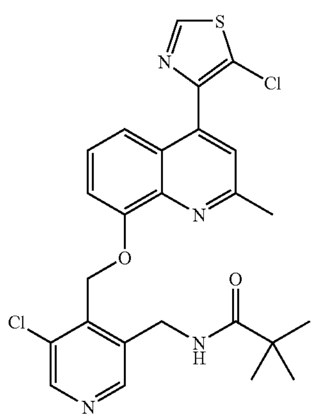 [SMILES: Cc1cc(-c2ncsc2Cl)c2cccc(OCc3c(Cl)cncc3CNC(=O)C(C)(C)C)c2n1] | 515.1 |
| 438. | 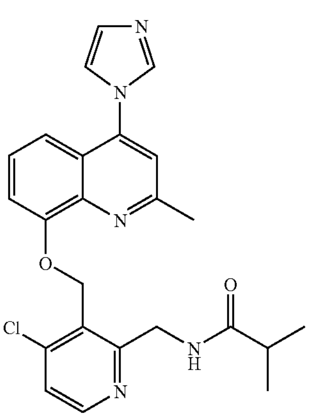 [SMILES: Cc1cc(-n2ccnc2)c2cccc(OCc3c(Cl)ccnc3CNC(=O)C(C)C)c2n1] | 450.2 |

TABLE 1-continued

| Example | Structure | M + H⁺ |
|---|---|---|
| 439. | 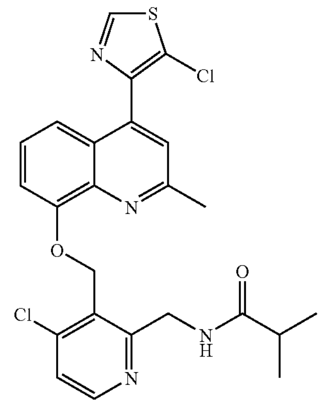 [SMILES: Cc1cc(-c2ncsc2Cl)c2cccc(OCc3c(Cl)ccnc3CNC(=O)C(C)C)c2n1] | 501.1 |
| 440. | 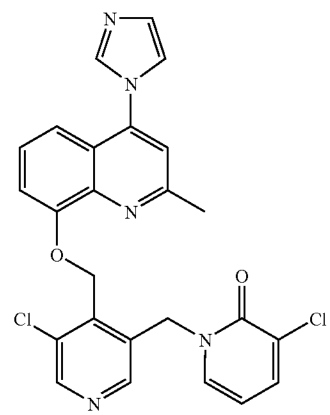 [SMILES: Cc1cc(-n2ccnc2)c2cccc(OCc3c(Cl)cncc3Cn3cccc(Cl)c3=O)c2n1] | 492.1 |
| 441. | 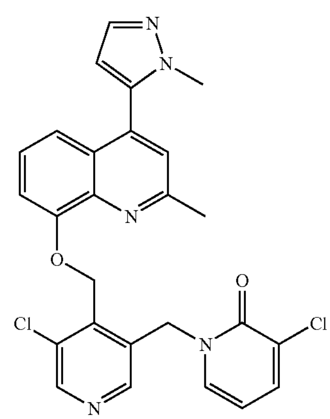 [SMILES: Cc1cc(-c2ccnn2C)c2cccc(OCc3c(Cl)cncc3Cn3cccc(Cl)c3=O)c2n1] | 506.1 |

TABLE 1-continued
| Example | Structure | M + H⁺ |
|---|---|---|
| 442. | 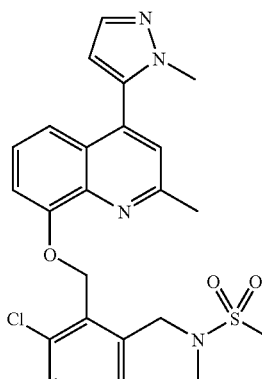 | 512.2 |
| 443. | 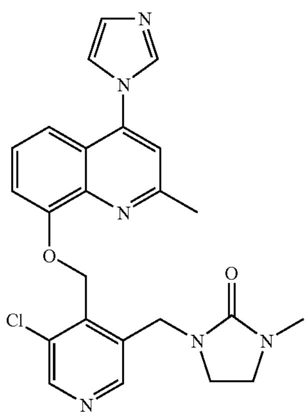 [SMILES: Cc1cc(-n2ccnc2)c2cccc(OCc3c(Cl)cncc3CN3CCN(C)C3=O)c2n1] | 463.1 |
| 444. | 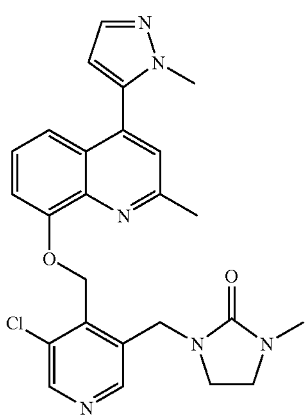 [SMILES: Cc1cc(-c2ccnn2C)c2cccc(OCc3c(Cl)cncc3CN3CCN(C)C3=O)c2n1] | 477.1 |
| 445. | 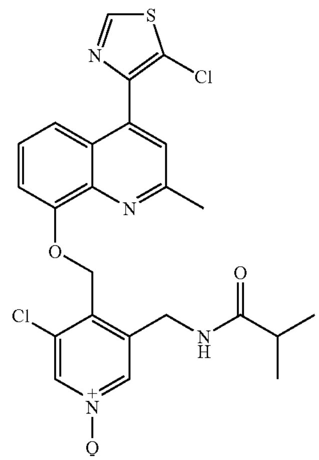 [SMILES: Cc1cc(-c2ncsc2Cl)c2cccc(OCc3c(Cl)c[n+]([O-])cc3CNC(=O)C(C)C)c2n1] | 517.0 |
| 446. | 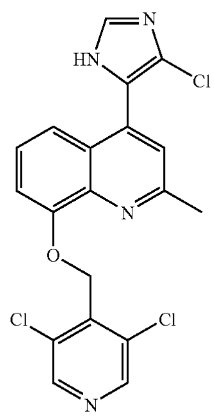 [SMILES: Cc1cc(-c2[nH]cnc2Cl)c2cccc(OCc3c(Cl)cncc3Cl)c2n1] | 418.9 |
| 447. | 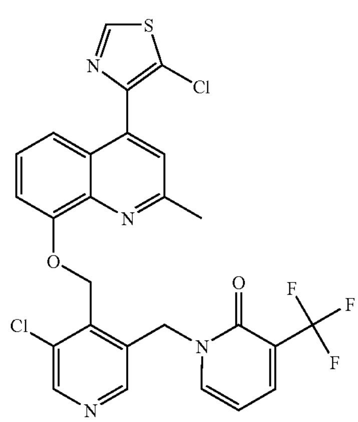 [SMILES: Cc1cc(-c2ncsc2Cl)c2cccc(OCc3c(Cl)cncc3Cn3cccc(C(F)(F)F)c3=O)c2n1] | 577.1 |

TABLE 1-continued

| Example | Structure | M + H⁺ |
|---|---|---|
| 448. | 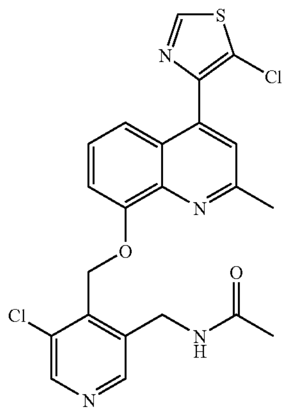 [SMILES: CC(=O)NCc1cncc(Cl)c1COc1cccc2c(-c3ncsc3Cl)cc(C)nc12] | 473.1 |
| 449. | 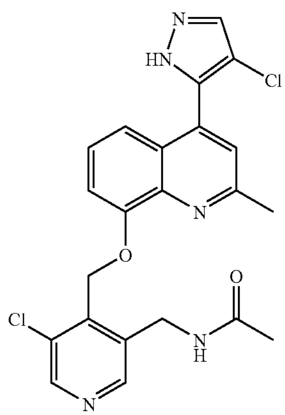 [SMILES: CC(=O)NCc1cncc(Cl)c1COc1cccc2c(-c3[nH]ncc3Cl)cc(C)nc12] | 456.0 |
| 450. | 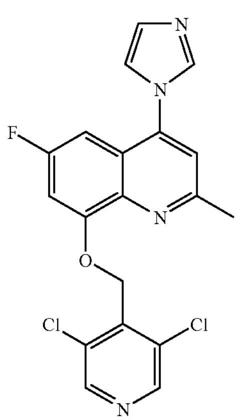 [SMILES: Cc1cc(-n2ccnc2)c2cc(F)cc(OCc3c(Cl)cncc3Cl)c2n1] | 403.0 |

TABLE 1-continued

| Example | Structure | M + H⁺ |
|---|---|---|
| 451. | 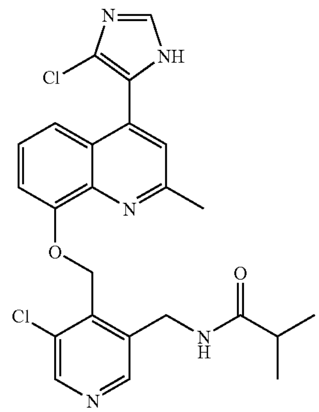 [SMILES: Cc1cc(-c2[nH]cnc2Cl)c2cccc(OCc3c(Cl)cncc3CNC(=O)C(C)C)c2n1] | 484.1 |
| 452. | 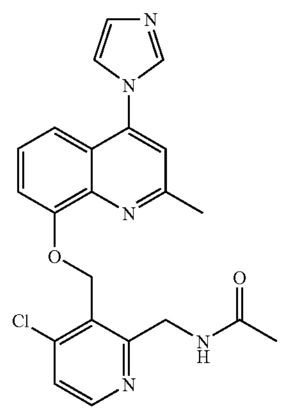 [SMILES: CC(=O)NCc1nccc(Cl)c1COc1cccc2c(-n3ccnc3)cc(C)nc12] | 422.0 |
| 453. | 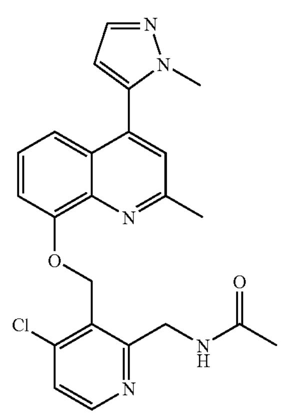 [SMILES: CC(=O)NCc1nccc(Cl)c1COc1cccc2c(-c3ccnn3C)cc(C)nc12] | 436.0 |

TABLE 1-continued
| Example | Structure | M + H⁺ |
|---|---|---|
| 454. | 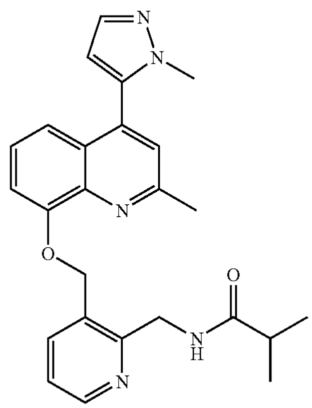 [SMILES: Cc1cc(-c2ccnn2C)c2cccc(OCc3cccnc3CNC(=O)C(C)C)c2n1] | 430.2 |
| 455. | 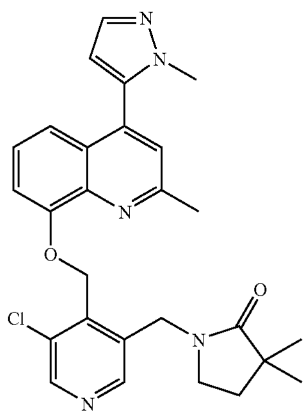 [SMILES: Cc1cc(-c2ccnn2C)c2cccc(OCc3c(Cl)cncc3CN3CCC(C)(C)C3=O)c2n1] | 490.1 |
| 456. | 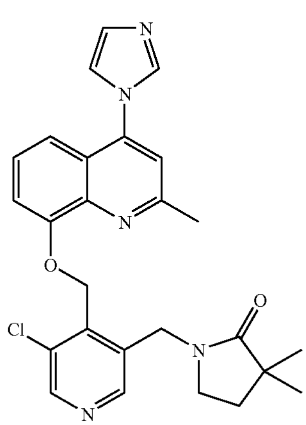 [SMILES: Cc1cc(-n2ccnc2)c2cccc(OCc3c(Cl)cncc3CN3CCC(C)(C)C3=O)c2n1] | 476.1 |
| 457. | 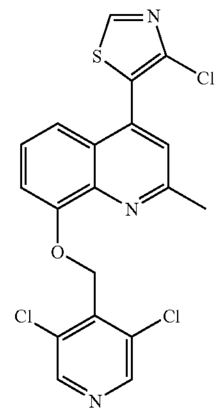 [SMILES: Cc1cc(-c2scnc2Cl)c2cccc(OCc3c(Cl)cncc3Cl)c2n1] | 435.9 |
| 458. | 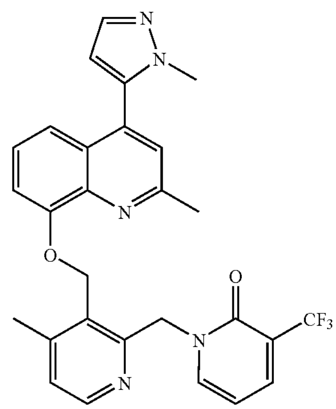 [SMILES: Cc1cc(-c2ccnn2C)c2cccc(OCc3c(C)ccnc3Cn3cccc(C(F)(F)F)c3=O)c2n1] | 520.1 |
| 459. | 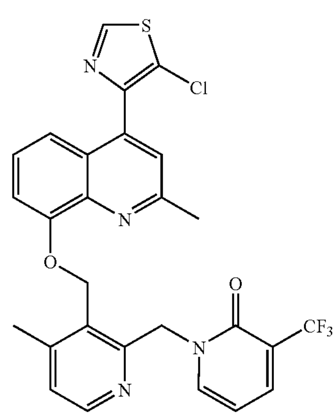 [SMILES: Cc1cc(-c2ncsc2Cl)c2cccc(OCc3c(C)ccnc3Cn3cccc(C(F)(F)F)c3=O)c2n1] | 557.0 |
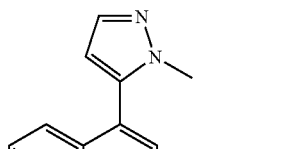

TABLE 1-continued

| Example | Structure | M + H+ |
|---|---|---|
| 460. | 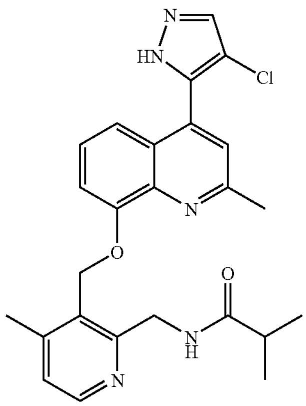 [SMILES: Cc1cc(-c2[nH]ncc2Cl)c2cccc(OCc3c(C)ccnc3CNC(=O)C(C)C)c2n1] | 464.1 |
| 461. | 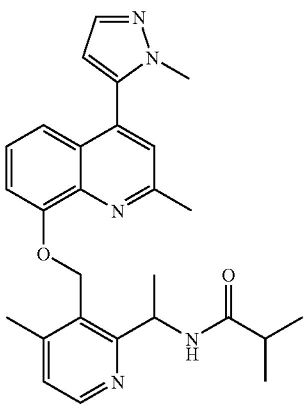 [SMILES: Cc1cc(-c2ccnn2C)c2cccc(OCc3c(C)ccnc3C(C)NC(=O)C(C)C)c2n1] | 458.2 |
| 462. | 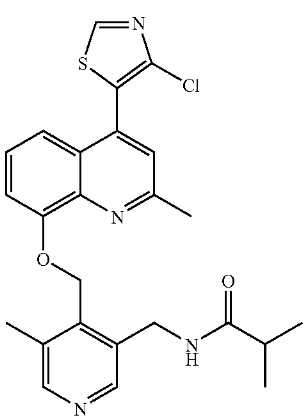 [SMILES: Cc1cc(-c2scnc2Cl)c2cccc(OCc3c(C)cncc3CNC(=O)C(C)C)c2n1] | 481.0 |

TABLE 1-continued

| Example | Structure | M + H+ |
|---|---|---|
| 463. | | 416.1 |
| 464. | | 430.1 |
| 465. | | 450.1 |

TABLE 1-continued

| Example | Structure | M + H⁺ |
|---|---|---|
| 466. | 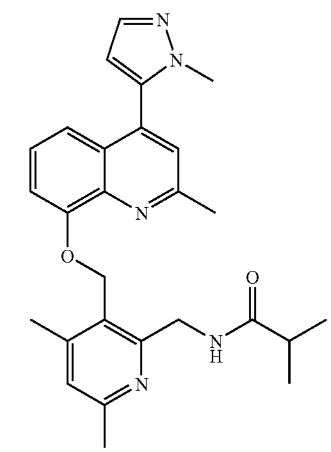 [SMILES: Cc1cc(C)c(COc2cccc3c(-c4ccnn4C)cc(C)nc23)c(CNC(=O)C(C)C)n1] | 458.1 |
| 467. | 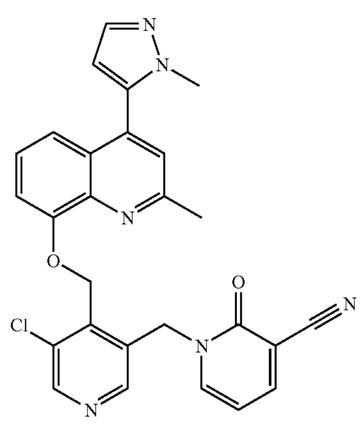 [SMILES: Cc1cc(-c2ccnn2C)c2cccc(OCc3c(Cl)cncc3Cn3cccc(C#N)c3=O)c2n1] | 497.1 |
| 468. | 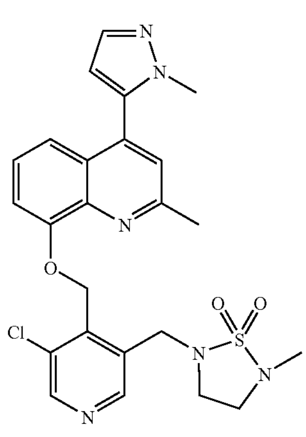 [SMILES: Cc1cc(-c2ccnn2C)c2cccc(OCc3c(Cl)cncc3CN3CCN(C)S3(=O)=O)c2n1] | 513.1 |

TABLE 1-continued

| Example | Structure | M + H⁺ |
|---|---|---|
| 469. | | 498.2 |
| 470. | | 470.1 |
| 471. | | 419.9 |

TABLE 1-continued

| Example | Structure | M + H⁺ |
|---|---|---|
| 472. | 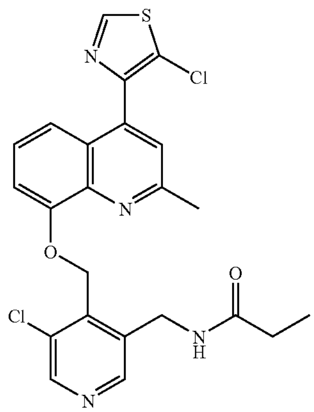 [SMILES: CCC(=O)NCc1cncc(Cl)c1COc1cccc2c(-c3ncsc3Cl)cc(C)nc12] | 487.0 |
| 473. | 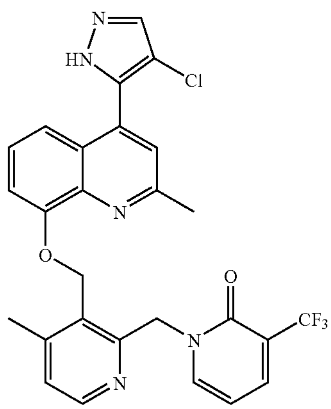 [SMILES: Cc1cc(-c2[nH]ncc2Cl)c2cccc(OCc3c(C)ccnc3Cn3cccc(C(F)(F)F)c3=O)c2n1] | 540.0 |
| 474. | 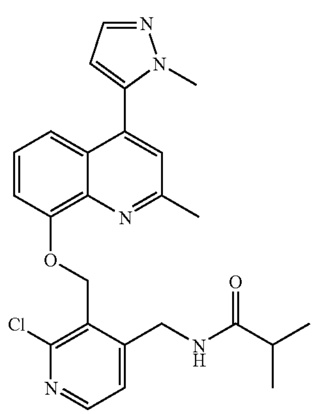 | 464.1 |

TABLE 1-continued

| Example | Structure | M + H⁺ |
|---|---|---|
| 475. | | 437.9 |
| 476. | | 495.1 |
| 477. | | 515.0 |

TABLE 1-continued

| Example | Structure | M + H⁺ |
|---|---|---|
| 478. | 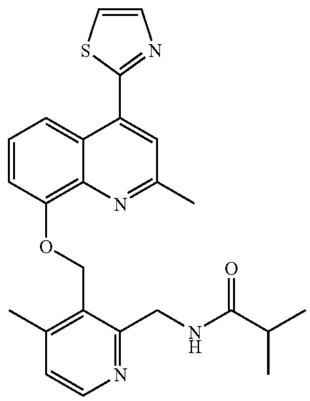 [SMILES: Cc1cc(-c2nccs2)c2cccc(OCc3c(C)ccnc3CNC(=O)C(C)C)c2n1] | 447.1 |
| 479. | 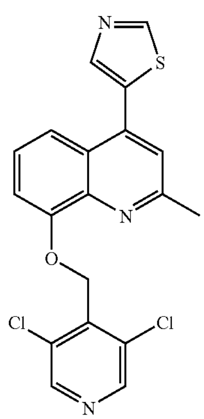 [SMILES: Cc1cc(-c2cncs2)c2cccc(OCc3c(Cl)cncc3Cl)c2n1] | 402.0 |
| 480. | 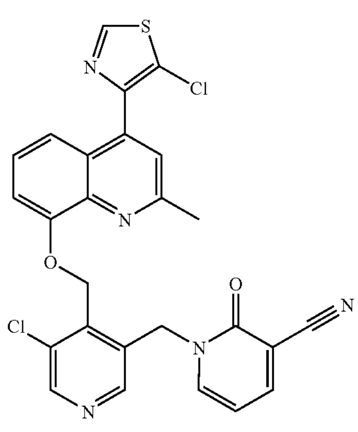 [SMILES: Cc1cc(-c2ncsc2Cl)c2cccc(OCc3c(Cl)cncc3Cn3cccc(C#N)c3=O)c2n1] | 534.1 |

TABLE 1-continued

| Example | Structure | M + H⁺ |
|---|---|---|
| 481. | | 494.1 |
| 482. | | 591.0 |
| 483. | | 554.1 |

TABLE 1-continued

| Example | Structure | M + H+ |
|---------|-----------|--------|
| 484. | 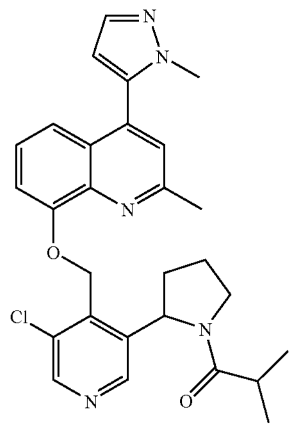 [SMILES: Cc1cc(-c2ccnn2C)c2cccc(OCc3c(Cl)cncc3C3CCCN3C(=O)C(C)C)c2n1] | 504.2 |
| 485. | 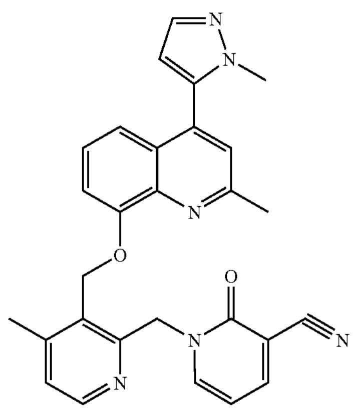 [SMILES: Cc1cc(-c2ccnn2C)c2cccc(OCc3c(C)ccnc3Cn3cccc(C#N)c3=O)c2n1] | 477.1 |
| 486. | 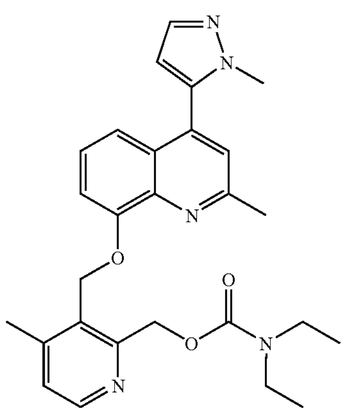 [SMILES: CCN(CC)C(=O)OCc1nccc(C)c1COc1cccc2c(-c3ccnn3C)cc(C)nc12] | 474.1 |
| 487. | | 548.1 |
| 488. | | 511.1 |
| 489. | | 490.1 |

TABLE 1-continued
| Example | Structure | M + H+ |
|---|---|---|
| 490. | 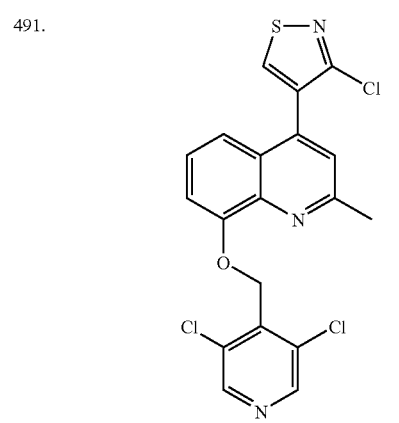 | 490.1 |
| 491. | 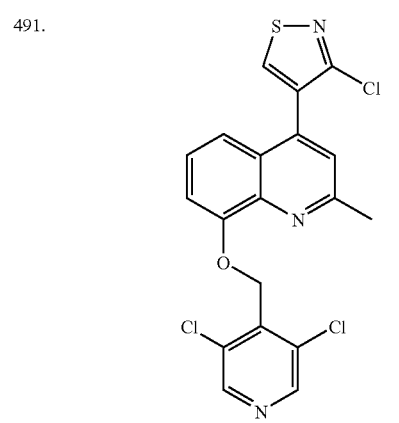 | 437.9 |
| 492. | 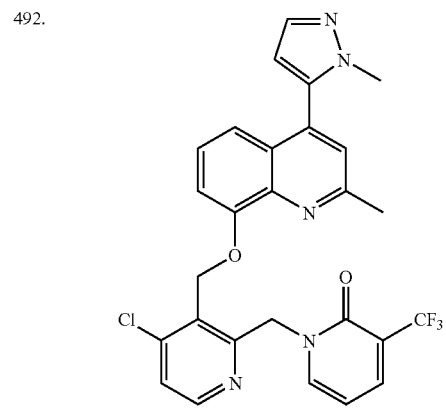 | 540.1 |
TABLE 1-continued
| Example | Structure | M + H+ |
|---|---|---|
| 493. | 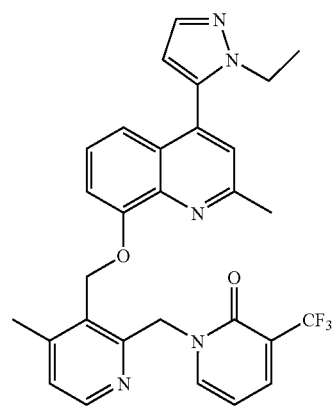 [SMILES: CCn1nccc1-c1cc(C)nc2c(OCc3c(C)ccnc3Cn3cccc(C(F)(F)F)c3=O)cccc12] | 577.0 |
| 494. | 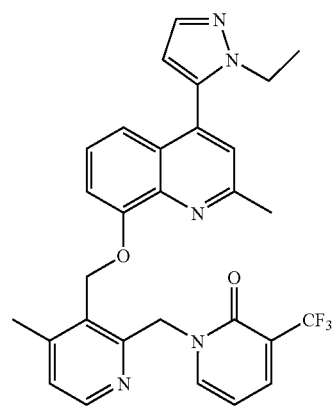 [SMILES: CCn1nccc1-c1cc(C)nc2c(OCc3c(C)ccnc3Cn3cccc(C(F)(F)F)c3=O)cccc12] | 534.1 |
| 495. | 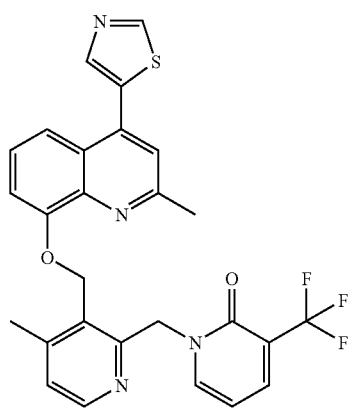 [SMILES: Cc1cc(-c2cncs2)c2cccc(OCc3c(C)ccnc3Cn3cccc(C(F)(F)F)c3=O)c2n1] | 523.0 |

TABLE 1-continued
| Example | Structure | M + H+ |
|---|---|---|
| 496. | 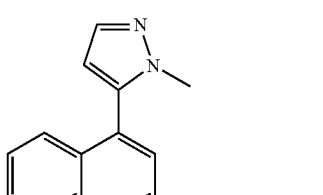 | 502.1 |
| 497. | 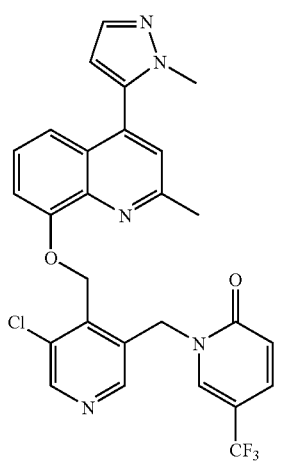 [SMILES: Cc1cc(-c2ccnn2C)c2cccc(OCc3c(Cl)cncc3Cn3cc(C(F)(F)F)ccc3=O)c2n1] | 540.1 |
| 498. | 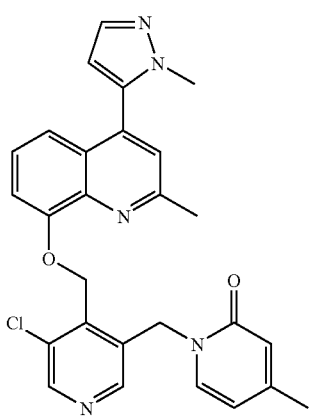 [SMILES: Cc1ccn(Cc2cncc(Cl)c2COc2cccc3c(-c4ccnn4C)cc(C)nc23)c(=O)c1] | 486.1 |
| 499. | 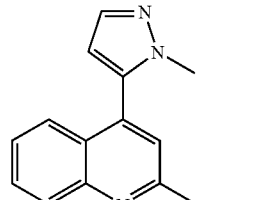 | 486.1 |
| 500. | | 486.1 |
| 501. | 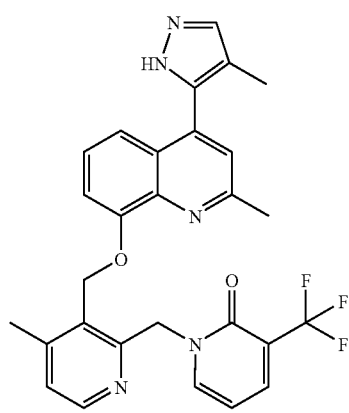 [SMILES: Cc1cc(-c2[nH]ncc2C)c2cccc(OCc3c(C)ccnc3Cn3cccc(C(F)(F)F)c3=O)c2n1] | 520.1 |

TABLE 1-continued
| Example | Structure | M + H+ |
|---|---|---|
| 502. | 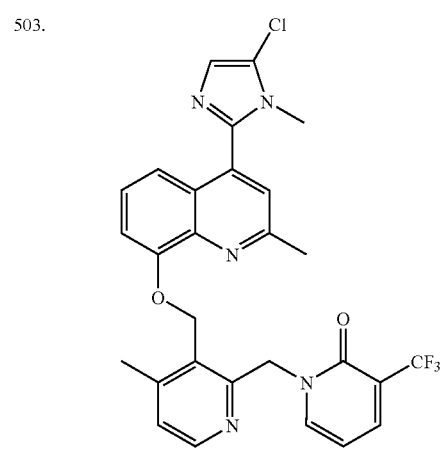 | 401.9 |
| 503. | 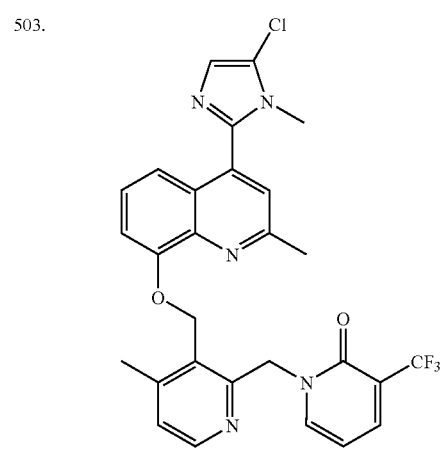 | 554.1 |
| 504. | 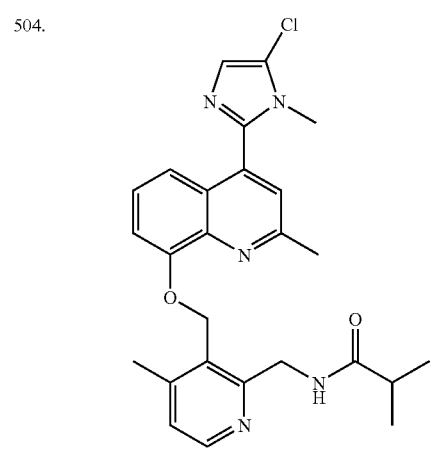 | 478.1 |
TABLE 1-continued
| Example | Structure | M + H+ |
|---|---|---|
| 505. | 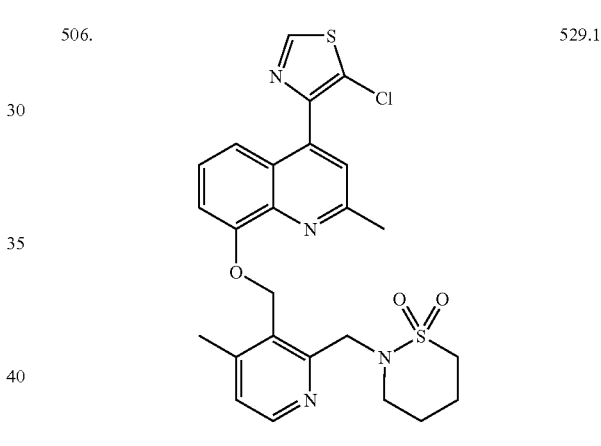 | 492.2 |
| 506. | 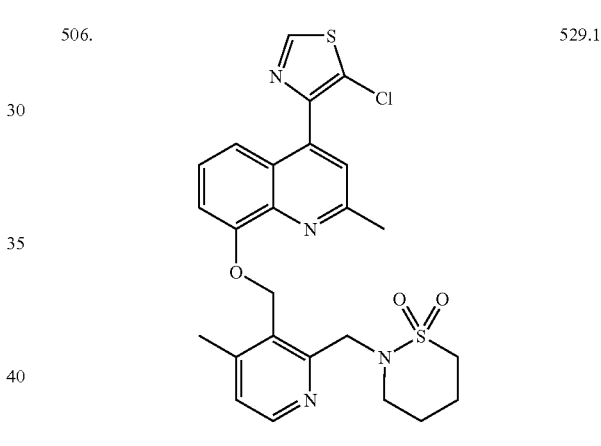 | 529.1 |
| 507. | 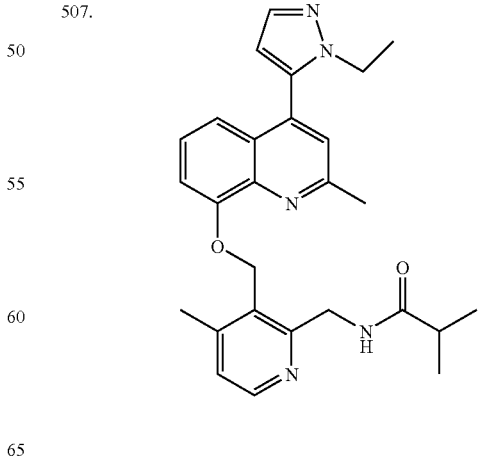 | 457.1 |

TABLE 1-continued
| Example | Structure | M + H+ |
|---|---|---|
| 508. | 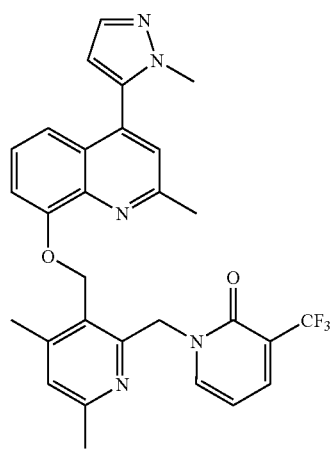 [SMILES: Cc1cc(C)c(COc2cccc3c(-c4ccnn4C)cc(C)nc23)c(Cn2cccc(C(F)(F)F)c2=O)n1] | 447.1 |
| 509. | 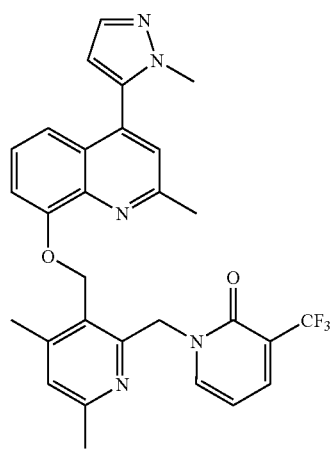 [SMILES: Cc1cc(C)c(COc2cccc3c(-c4ccnn4C)cc(C)nc23)c(Cn2cccc(C(F)(F)F)c2=O)n1] | 534.0 |
| 510. | 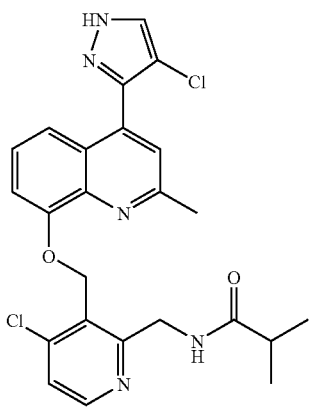 | 484.1 |
| 511. | | 571.0 |
| 512. | | 523.1 |
| 513. | 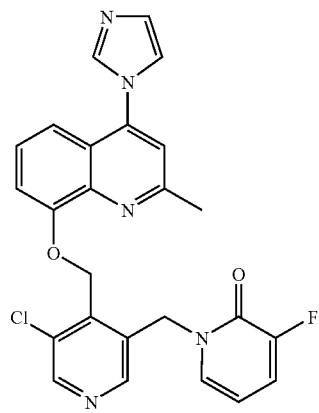 [SMILES: Cc1cc(-n2ccnc2)c2cccc(OCc3c(Cl)cncc3Cn3cccc(F)c3=O)c2n1] | 476.1 |

TABLE 1-continued
| Example | Structure | M + H+ |
|---|---|---|
| 514. | 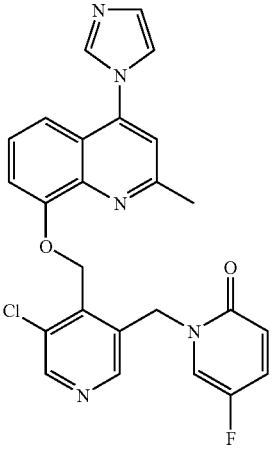 [SMILES: Cc1cc(-n2ccnc2)c2cccc(OCc3c(Cl)cncc3Cn3cc(F)ccc3=O)c2n1] | 476.0 |
| 515. | 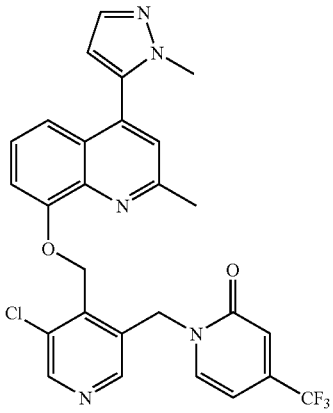 [SMILES: Cc1cc(-c2ccnn2C)c2cccc(OCc3c(Cl)cncc3Cn3ccc(C(F)(F)F)cc3=O)c2n1] | 540.1 |
| 516. | 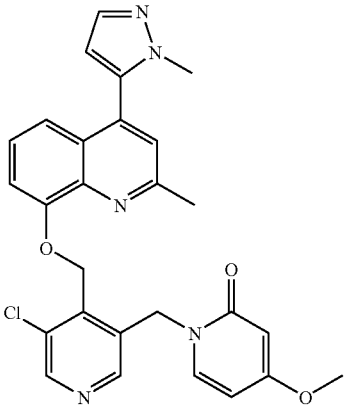 [SMILES: COc1ccn(Cc2cncc(Cl)c2COc2cccc3c(-c4ccnn4C)cc(C)nc23)c(=O)c1] | 502.1 |
| 517. | 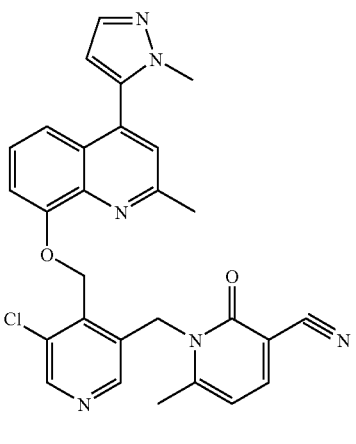 [SMILES: Cc1cc(-c2ccnn2C)c2cccc(OCc3c(Cl)cncc3Cn3c(C)ccc(C#N)c3=O)c2n1] | 511.1 |
| 518. | 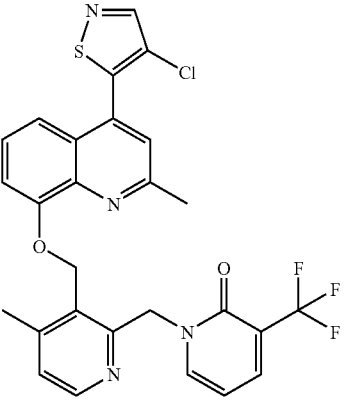 [SMILES: Cc1cc(-c2sncc2Cl)c2cccc(OCc3c(C)ccnc3Cn3cccc(C(F)(F)F)c3=O)c2n1] | 557.0 |
| 519. | 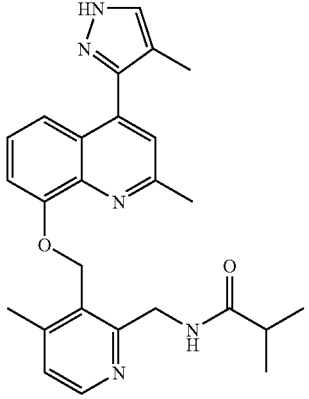 [SMILES: Cc1cc(-c2n[nH]cc2C)c2cccc(OCc3c(C)ccnc3CNC(=O)C(C)C)c2n1] | 444.1 |

TABLE 1-continued
| Example | Structure | M + H+ |
|---|---|---|
| 520. | 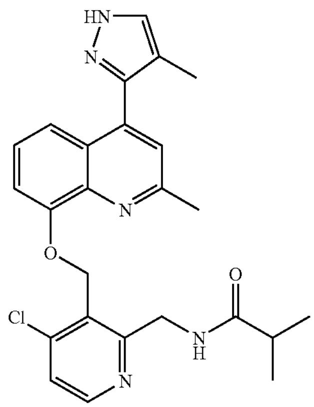 [SMILES: Cc1cc(-c2n[nH]cc2C)c2cccc(OCc3c(Cl)ccnc3CNC(=O)C(C)C)c2n1] | 464.1 |
| 521. | 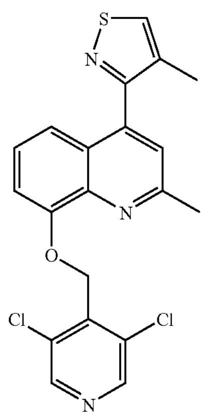 [SMILES: Cc1cc(-c2nscc2C)c2cccc(OCc3c(Cl)cncc3Cl)c2n1] | 415.9 |
| 522. | 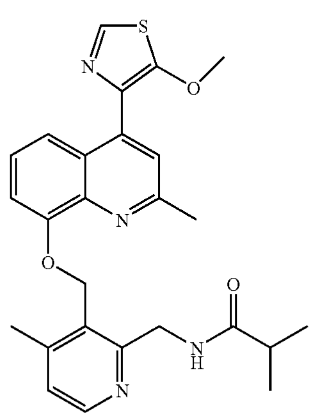 [SMILES: COc1scnc1-c1cc(C)nc2c(OCc3c(C)ccnc3CNC(=O)C(C)C)cccc12] | 477.1 |
| 523. | | 541.0 |
| 524. | | 490.0 |
| 525. | | 506.0 |
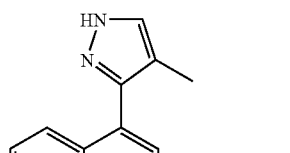

TABLE 1-continued
| Example | Structure | M + H+ |
|---|---|---|
| 526. | 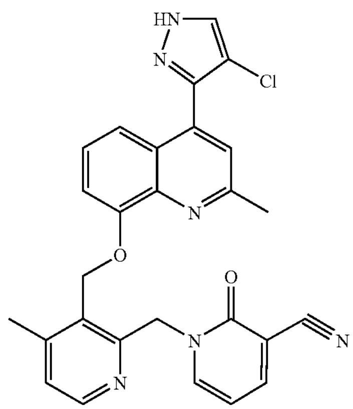 [SMILES: Cc1cc(-c2n[nH]cc2Cl)c2cccc(OCc3c(C)ccnc3Cn3cccc(C#N)c3=O)c2n1] | 497.1 |
| 527. | 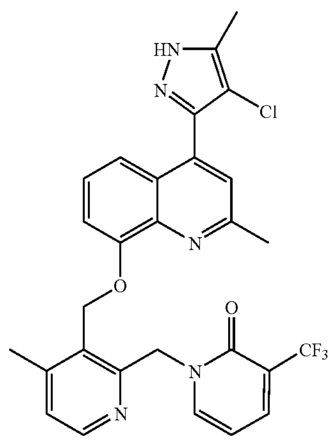 [SMILES: Cc1cc(-c2n[nH]c(C)c2Cl)c2cccc(OCc3c(C)ccnc3Cn3cccc(C(F)(F)F)c3=O)c2n1] | 554.1 |
| 528. | 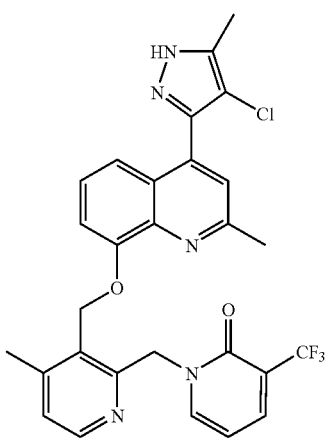 | 478.1 |
| 529. | | 520.1 |
| 530. | | 540.1 |
| 531. | | 520.1 |
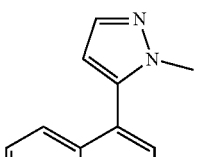
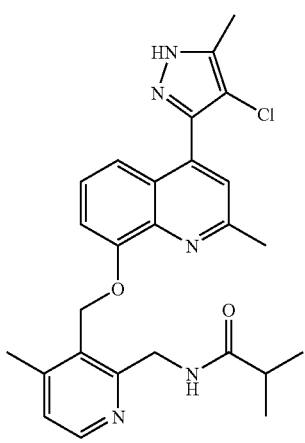 [SMILES: Cc1cc(-c2n[nH]c(C)c2Cl)c2cccc(OCc3c(C)ccnc3CNC(=O)C(C)C)c2n1]

TABLE 1-continued
| Example | Structure | M + H+ |
|---|---|---|
| 532. | 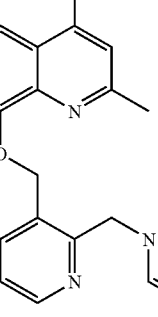 | 540.1 |
| 533. | 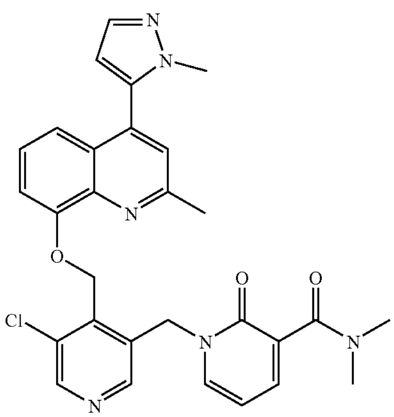 [SMILES: Cc1cc(-c2ccnn2C)c2cccc(OCc3c(Cl)cncc3Cn3cccc(C(=O)N(C)C)c3=O)c2n1] | 543.1 |
| 534. | 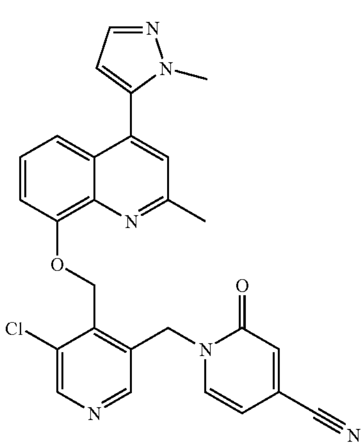 [SMILES: Cc1cc(-c2ccnn2C)c2cccc(OCc3c(Cl)cncc3Cn3ccc(C#N)cc3=O)c2n1] | 497.1 |
| 535. | 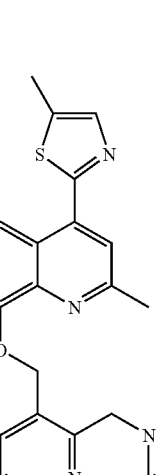 | 537.1 |
| 536. | 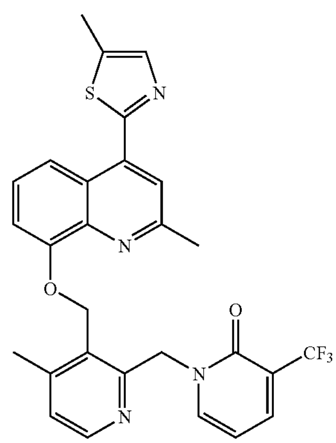 [SMILES: Cc1cc(-c2ncc(C)s2)c2cccc(OCc3c(C)ccnc3Cn3cccc(C(F)(F)F)c3=O)c2n1] | 537.1 |
| 537. | 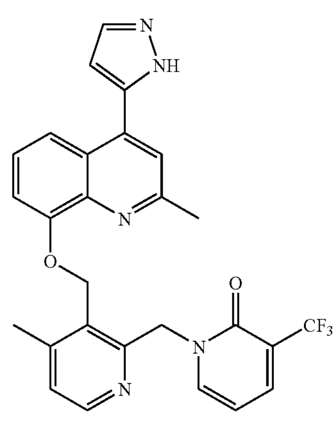 [SMILES: Cc1cc(-c2ccn[nH]2)c2cccc(OCc3c(C)ccnc3Cn3cccc(C(F)(F)F)c3=O)c2n1] | 506.0 |

TABLE 1-continued
| Example | Structure | M + H+ |
|---|---|---|
| 538. | 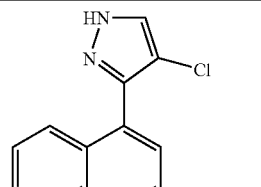 | 490.0 |
| 539. | 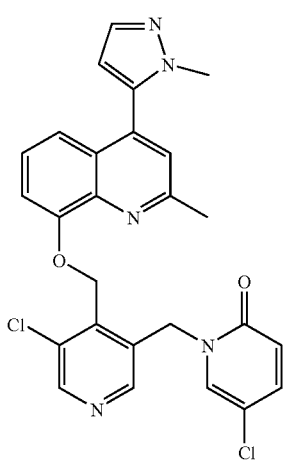 [SMILES: Cc1cc(-c2ccnn2C)c2cccc(OCc3c(Cl)cncc3Cn3cc(Cl)ccc3=O)c2n1] | 506.0 |
| 540. | 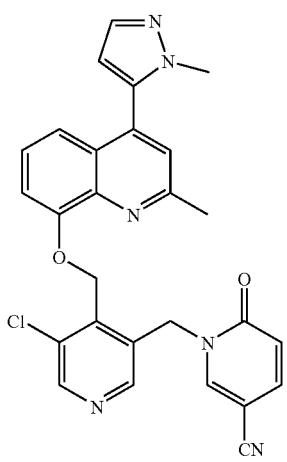 [SMILES: Cc1cc(-c2ccnn2C)c2cccc(OCc3c(Cl)cncc3Cn3cc(C#N)ccc3=O)c2n1] | 497.0 |
TABLE 1-continued
| Example | Structure | M + H+ |
|---|---|---|
| 541. | 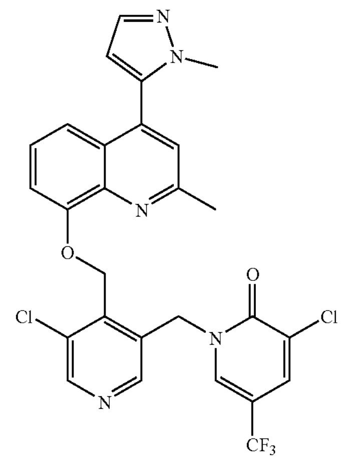 [SMILES: Cc1cc(-c2ccnn2C)c2cccc(OCc3c(Cl)cncc3Cn3cc(C(F)(F)F)cc(Cl)c3=O)c2n1] | 474.1 |
| 542. | 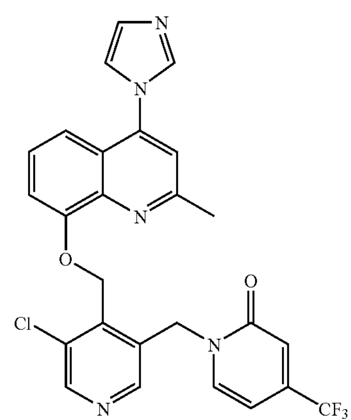 [SMILES: Cc1cc(-n2ccnc2)c2cccc(OCc3c(Cl)cncc3Cn3ccc(C(F)(F)F)cc3=O)c2n1] | 526.1 |
| 543. | 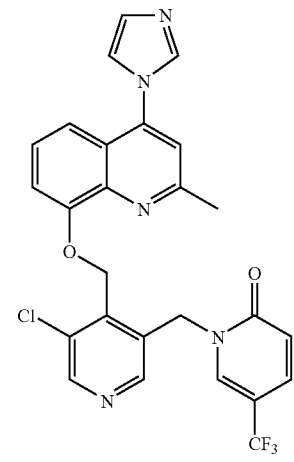 [SMILES: Cc1cc(-n2ccnc2)c2cccc(OCc3c(Cl)cncc3Cn3cc(C(F)(F)F)ccc3=O)c2n1] | 526.1 |

TABLE 1-continued
| Example | Structure | M + H+ |
|---|---|---|
| 544. | 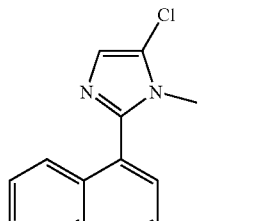 | 554.1 |
| 545. | 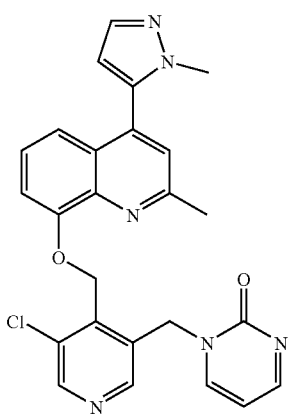 [SMILES: Cc1cc(-c2ccnn2C)c2cccc(OCc3c(Cl)cncc3Cn3cccnc3=O)c2n1] | 473.0 |
| 546. | 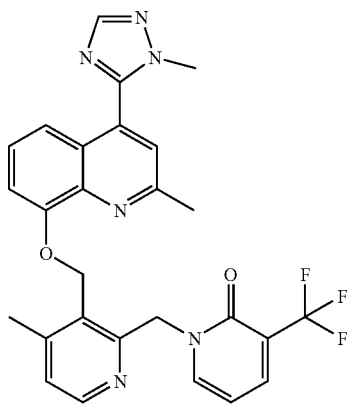 [SMILES: Cc1cc(-c2ncnn2C)c2cccc(OCc3c(C)ccnc3Cn3cccc(C(F)(F)F)c3=O)c2n1] | 521.1 |
| 547. | 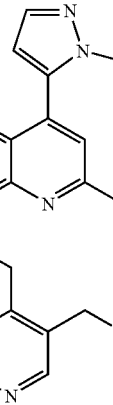 | 473.1 |
| 548. | | 473.0 |
| 549. | 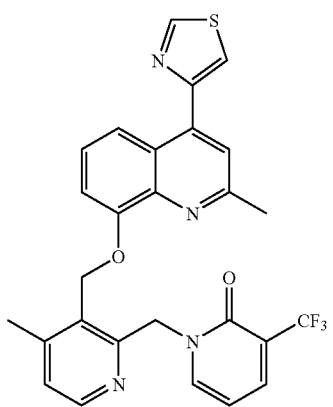 [SMILES: Cc1cc(-c2cscn2)c2cccc(OCc3c(C)ccnc3Cn3cccc(C(F)(F)F)c3=O)c2n1] | 523.1 |

TABLE 1-continued

| Example | Structure | M + H⁺ |
|---|---|---|
| 550. | 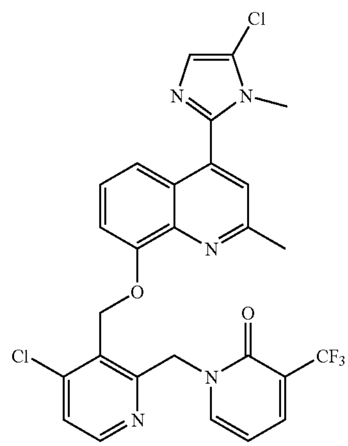 [SMILES: Cc1cc(-c2ncc(Cl)n2C)c2cccc(OCc3c(Cl)ccnc3Cn3cccc(C(F)(F)F)c3=O)c2n1] | 574.0 |
| 551. | 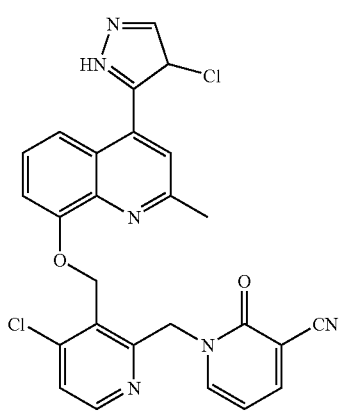 [SMILES: Cc1cc(C2=NN=CC2Cl)c2cccc(OCc3c(Cl)ccnc3Cn3cccc(C#N)c3=O)c2n1] | 517.1 |
| 552. | 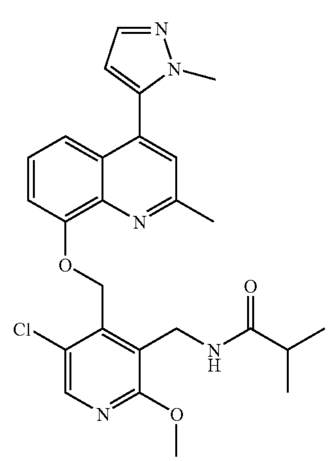 [SMILES: COc1ncc(Cl)c(COc2cccc3c(-c4ccnn4C)cc(C)nc23)c1CNC(=O)C(C)C] | 494.2 |
| 553. | 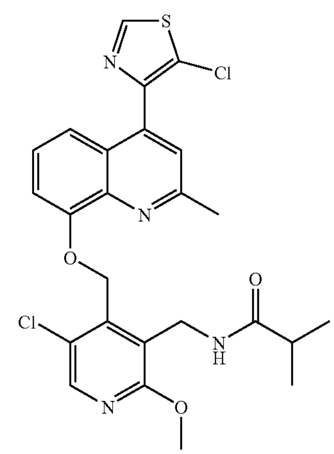 [SMILES: COc1ncc(Cl)c(COc2cccc3c(-c4ncsc4Cl)cc(C)nc23)c1CNC(=O)C(C)C] | 531.1 |
| 554. | 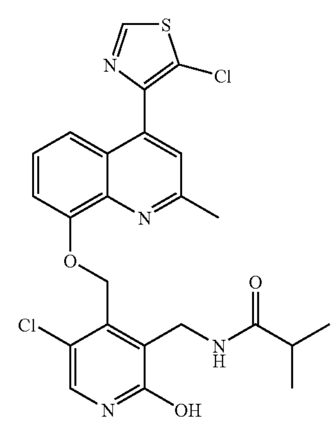 [SMILES: Cc1cc(-c2ncsc2Cl)c2cccc(OCc3c(Cl)cnc(O)c3CNC(=O)C(C)C)c2n1] | 517.0 |
| 555. | 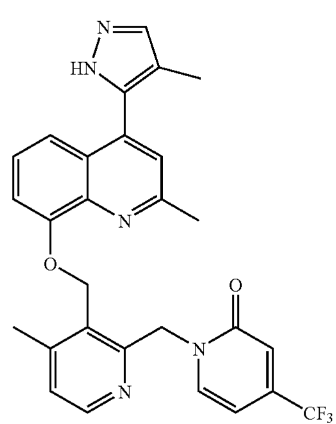 [SMILES: Cc1cc(-c2[nH]ncc2C)c2cccc(OCc3c(C)ccnc3Cn3ccc(C(F)(F)F)cc3=O)c2n1] | 520.1 |

TABLE 1-continued

| Example | Structure | M + H⁺ |
|---|---|---|
| 556. | 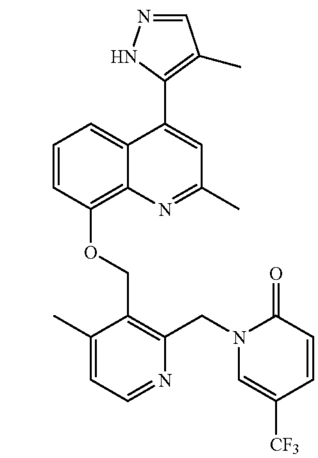 [SMILES: Cc1cc(-c2[nH]ncc2C)c2cccc(OCc3c(C)ccnc3Cn3cc(C(F)(F)F)ccc3=O)c2n1] | 520.1 |
| 557. | 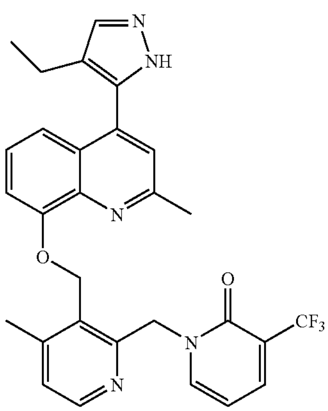 [SMILES: CCc1cn[nH]c1-c1cc(C)nc2c(OCc3c(C)ccnc3Cn3cccc(C(F)(F)F)c3=O)cccc12] | 534.1 |
| 558. | 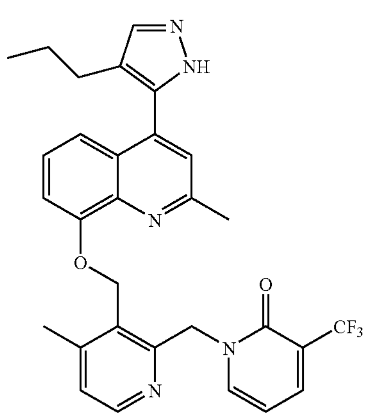 [SMILES: CCCc1cn[nH]c1-c1cc(C)nc2c(OCc3c(C)ccnc3Cn3cccc(C(F)(F)F)c3=O)cccc12] | 548.1 |

TABLE 1-continued

| Example | Structure | M + H⁺ |
|---|---|---|
| 559. | | 487.2 |
| 560. | | 522.1 |
| 561. | | 526.1 |

TABLE 1-continued
| Example | Structure | M + H+ |
|---------|-----------|--------|
| 562. | 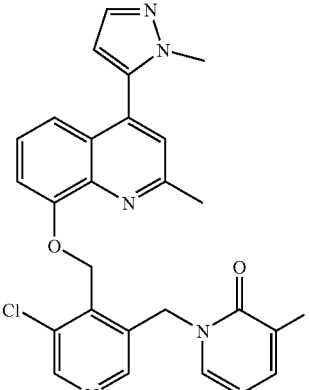 | 558.1 |
| 563. | 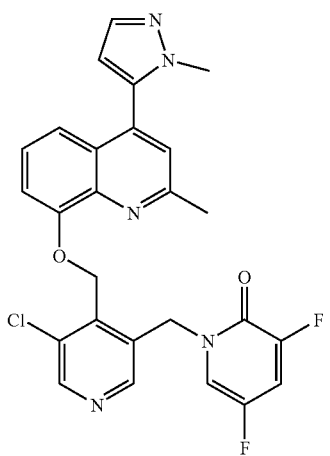 [SMILES: Cc1cc(-c2ccnn2C)c2cccc(OCc3c(Cl)cncc3Cn3cc(F)cc(F)c3=O)c2n1] | 508.1 |
| 564. | 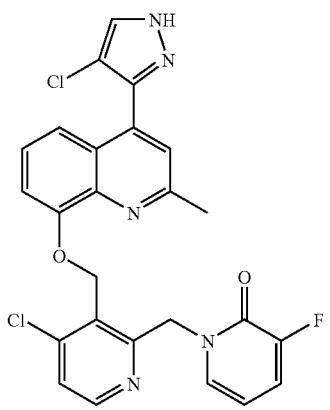 [SMILES: Cc1cc(-c2n[nH]cc2Cl)c2cccc(OCc3c(Cl)ccnc3Cn3cccc(F)c3=O)c2n1] | 510.1 |
TABLE 1-continued
| Example | Structure | M + H+ |
|---------|-----------|--------|
| 565. | 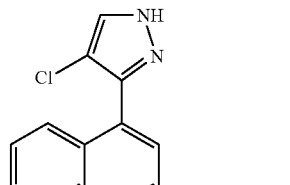 | 508.1 |
| 566. | 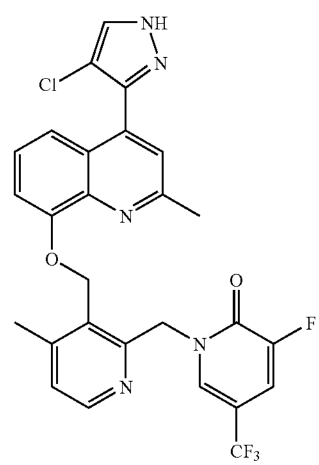 [SMILES: Cc1cc(-c2n[nH]cc2Cl)c2cccc(OCc3c(C)ccnc3Cn3cc(C(F)(F)F)cc(F)c3=O)c2n1] | 558.2 |
| 567. | 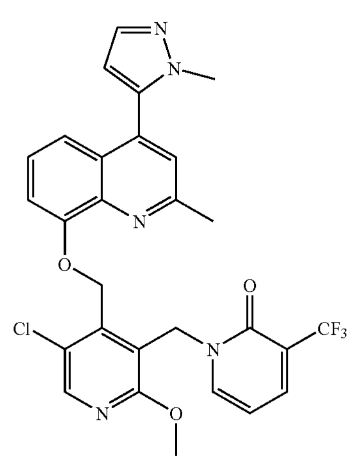 [SMILES: COc1ncc(Cl)c(COc2cccc3c(-c4ccnn4C)cc(C)nc23)c1Cn1cccc(C(F)(F)F)c1=O] | 570.1 |

TABLE 1-continued
| Example | Structure | M + H+ |
|---|---|---|
| 568. | 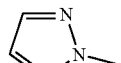 | 521.1 |
| 569. | 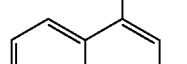 | 541.2 |
| 570. | 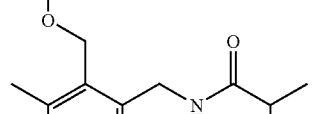 | 497.1 |
| 571. | 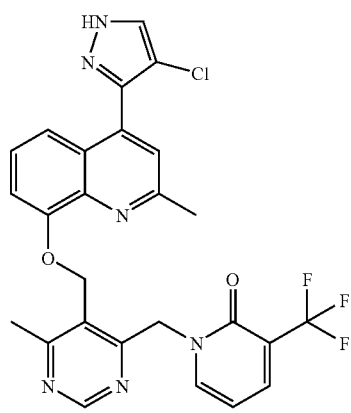 [SMILES: Cc1cc(-c2n[nH]cc2Cl)c2cccc(OCc3c(C)ncnc3Cn3cccc(C(F)(F)F)c3=O)c2n1] | 462.2 |
| 572. | 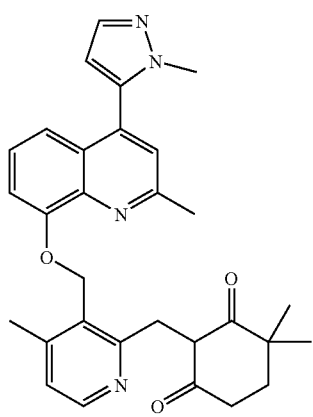 [SMILES: Cc1cc(-c2ccnn2C)c2cccc(OCc3c(C)ccnc3CC3C(=O)CCC(C)(C)C3=O)c2n1] | 571.2 |
| 573. | 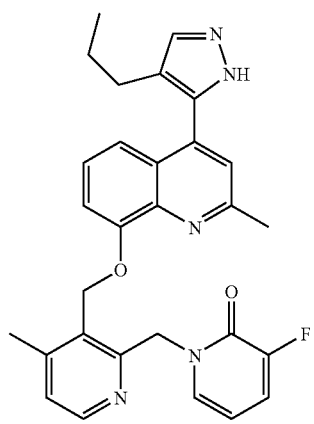 [SMILES: CCCc1cn[nH]c1-c1cc(C)nc2c(OCc3c(C)ccnc3Cn3cccc(F)c3=O)cccc12] | 498.1 |

TABLE 1-continued

| Example | Structure | M + H+ |
|---|---|---|
| 574. | 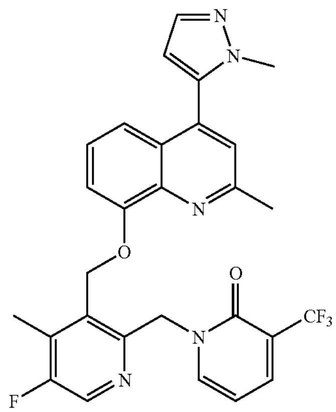 [SMILES: Cc1cc(-c2ccnn2C)c2cccc(OCc3c(Cn4cccc(C(F)(F)F)c4=O)ncc(F)c3C)c2n1] | 538.2 |
| 575. | 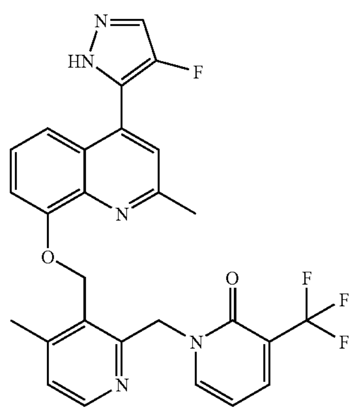 [SMILES: Cc1cc(-c2[nH]ncc2F)c2cccc(OCc3c(C)ccnc3Cn3cccc(C(F)(F)F)c3=O)c2n1] | 524.1 |
| 576. | 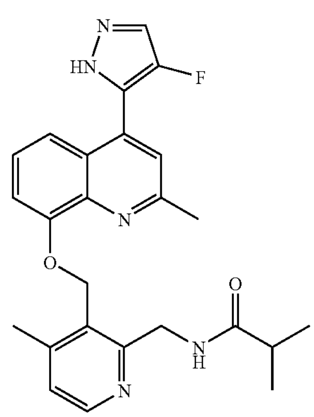 [SMILES: Cc1cc(-c2[nH]ncc2F)c2cccc(OCc3c(C)ccnc3CNC(=O)C(C)C)c2n1] | 448.1 |

TABLE 1-continued

| Example | Structure | M + H+ |
|---|---|---|
| 577. | 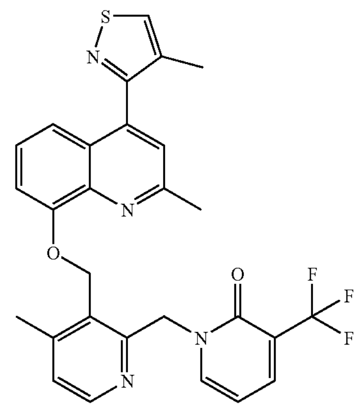 [SMILES: Cc1cc(-c2nscc2C)c2cccc(OCc3c(C)ccnc3Cn3cccc(C(F)(F)F)c3=O)c2n1] | 537.1 |
| 578. | 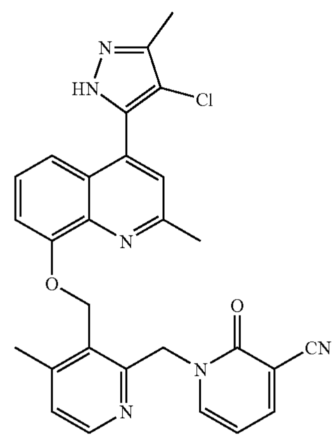 [SMILES: Cc1cc(-c2[nH]nc(C)c2Cl)c2cccc(OCc3c(C)ccnc3Cn3cccc(C#N)c3=O)c2n1] | 511.1 |
| 579. | 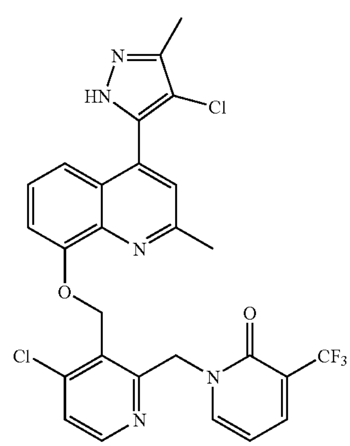 [SMILES: Cc1cc(-c2[nH]nc(C)c2Cl)c2cccc(OCc3c(Cl)ccnc3Cn3cccc(C(F)(F)F)c3=O)c2n1] | 574.0 |

TABLE 1-continued
| Example | Structure | M + H+ |
|---|---|---|
| 580. | 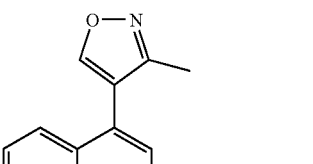 | 521.2 |
| 581. | 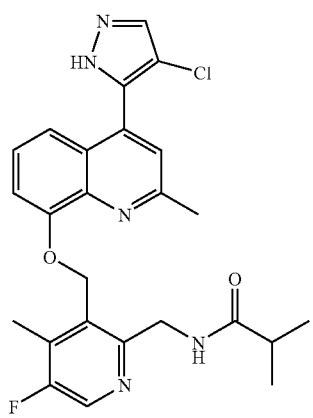 [SMILES: Cc1cc(-c2[nH]ncc2Cl)c2cccc(OCc3c(CNC(=O)C(C)C)ncc(F)c3C)c2n1] | 482.2 |
| 582. | 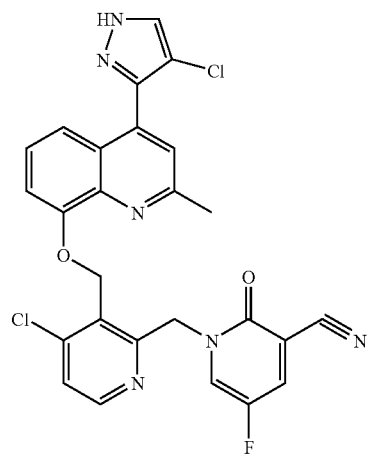 [SMILES: Cc1cc(-c2n[nH]cc2Cl)c2cccc(OCc3c(Cl)ccnc3Cn3cc(F)cc(C#N)c3=O)c2n1] | 535.1 |
| 583. | | 574.0 |
| 584 | | 557.0 |
| 585. | 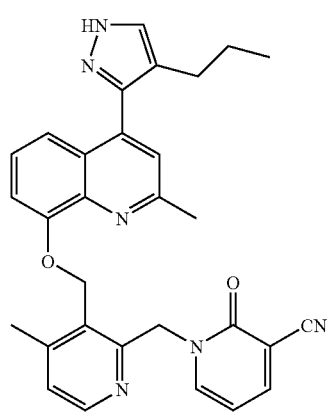 [SMILES: CCCc1c[nH]nc1-c1cc(C)nc2c(OCc3c(C)ccnc3Cn3cccc(C#N)c3=O)cccc12] | 505.2 |

TABLE 1-continued
| Example | Structure | M + H⁺ |
|---|---|---|
| 586. | 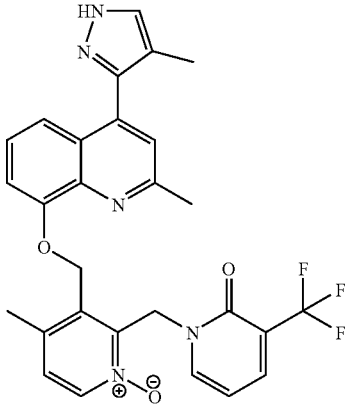 [SMILES: Cc1cc(-c2n[nH]cc2C)c2cccc(OCc3c(C)cc[n+]([O-])c3Cn3cccc(C(F)(F)F)c3=O)c2n1] | 536.0 |
| 587. | 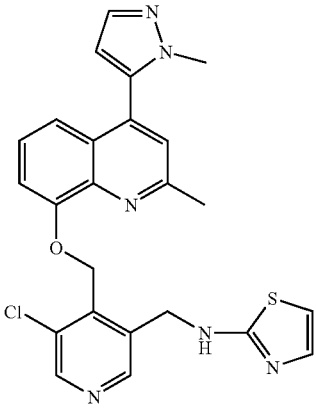 [SMILES: Cc1cc(-c2ccnn2C)c2cccc(OCc3c(Cl)cncc3CNc3nccs3)c2n1] | 477.0 |
| 588. | 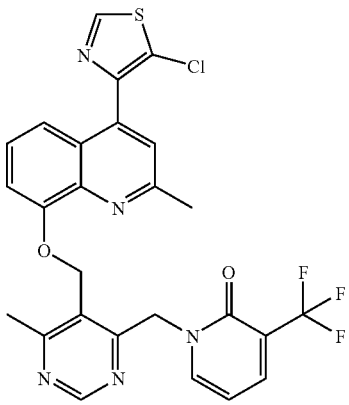 [SMILES: Cc1cc(-c2ncsc2Cl)c2cccc(OCc3c(C)ncnc3Cn3cccc(C(F)(F)F)c3=O)c2n1] | 558.0 |
TABLE 1-continued
| Example | Structure | M + H⁺ |
|---|---|---|
| 589. | 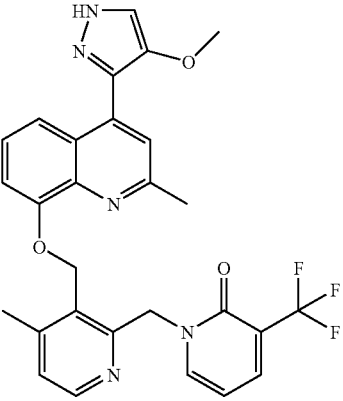 | 536.2 |
| 590. | 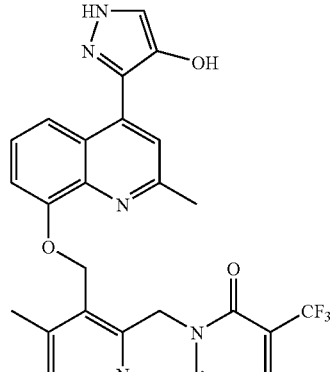 | 522.1 |
| 591. | 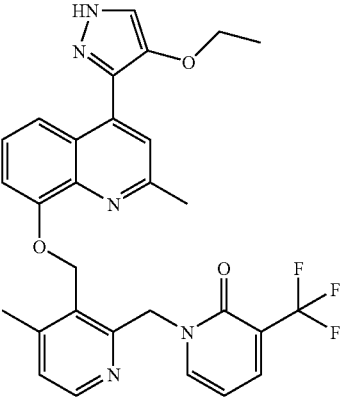 [SMILES: CCOc1c[nH]nc1-c1cc(C)nc2c(OCc3c(C)ccnc3Cn3cccc(C(F)(F)F)c3=O)cccc12] | 550.1 |

TABLE 1-continued
| Example | Structure | M + H+ |
|---|---|---|
| 592. | 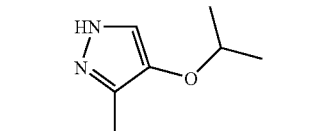 | 564.1 |
| 593. | 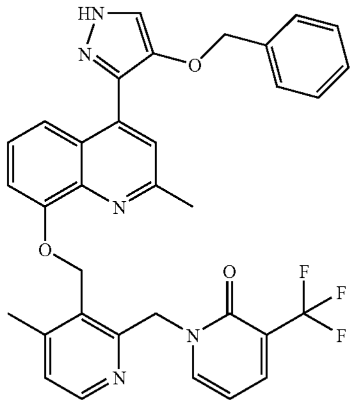 [SMILES: Cc1cc(-c2n[nH]cc2OCc2ccccc2)c2cccc(OCc3c(C)ccnc3Cn3cccc(C(F)(F)F)c3=O)c2n1] | 612.1 |
| 594. | 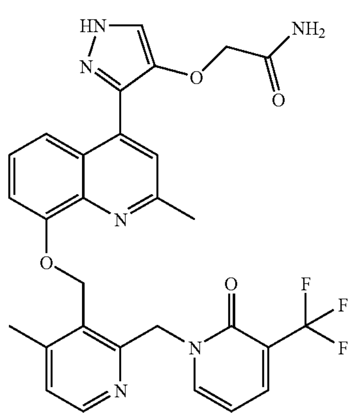 [SMILES: Cc1cc(-c2n[nH]cc2OCC(N)=O)c2cccc(OCc3c(C)ccnc3Cn3cccc(C(F)(F)F)c3=O)c2n1] | 579.1 |
| 595. | | 530.1 |
| 596. | | 516.1 |
| 597. | | 536.1 |

TABLE 1-continued
| Example | Structure | M + H+ |
|---------|-----------|--------|
| 598. | 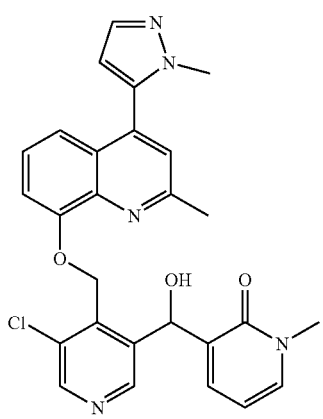 | 521.1 |
| 599. | 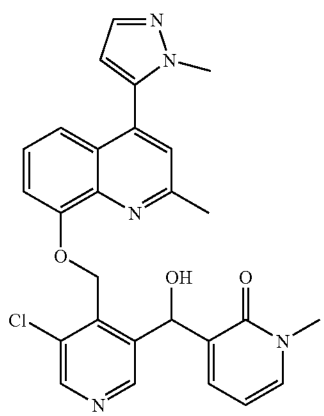 [SMILES: Cc1cc(-c2ccnn2C)c2cccc(OCc3c(Cl)cncc3C(O)c3cccn(C)c3=O)c2n1] | 502.1 |
| 600. | 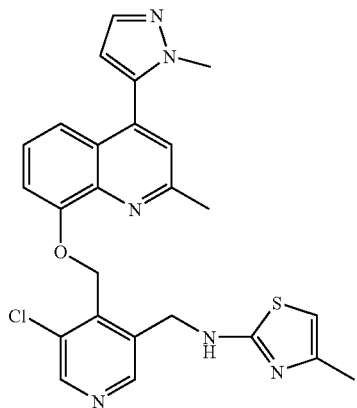 [SMILES: Cc1csc(NCc2cncc(Cl)c2COc2cccc3c(-c4ccnn4C)cc(C)nc23)n1] | 491.0 |
| 601. | 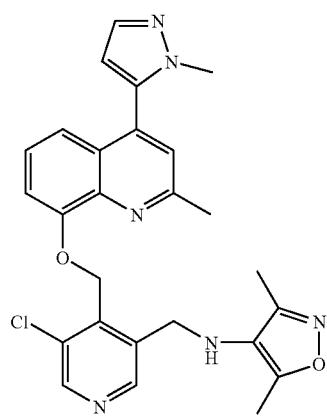 [SMILES: Cc1cc(-c2ccnn2C)c2cccc(OCc3c(Cl)cncc3CNc3c(C)noc3C)c2n1] | 461.1 |
| 602. | | 489.1 |
| 603. | 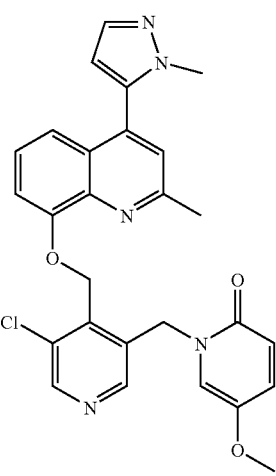 [SMILES: COc1ccc(=O)n(Cc2cncc(Cl)c2COc2cccc3c(-c4ccnn4C)cc(C)nc23)c1] | 502.1 |

TABLE 1-continued
| Example | Structure | M + H+ |
|---------|-----------|--------|
| 604. | 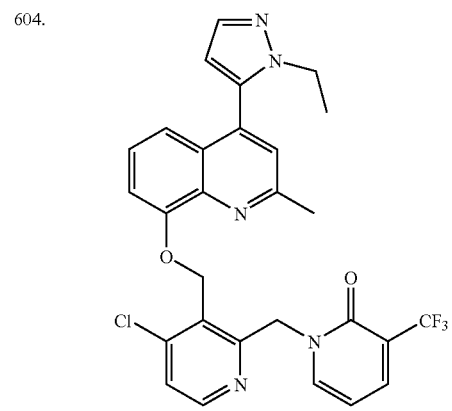 | 554.2 |
| 605. | 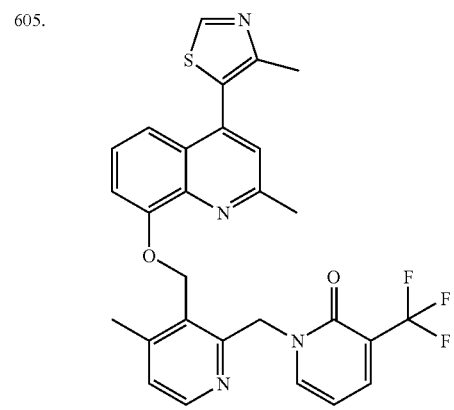 | 537.1 |
| 606. | 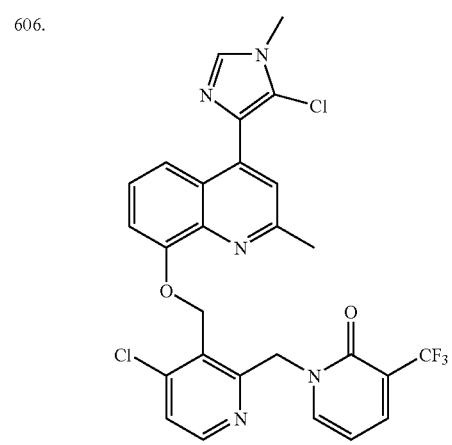 | 574.1 |
TABLE 1-continued
| Example | Structure | M + H+ |
|---------|-----------|--------|
| 607. | 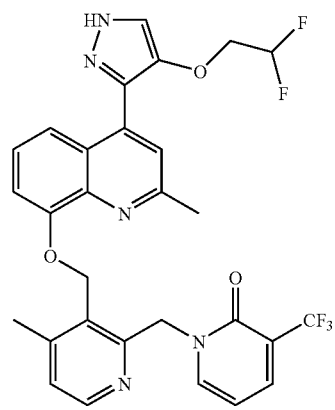 [SMILES: Cc1cc(-c2n[nH]cc2OCC(F)F)c2cccc(OCc3c(C)ccnc3Cn3cccc(C(F)(F)F)c3=O)c2n1] | 586.1 |
| 608. | 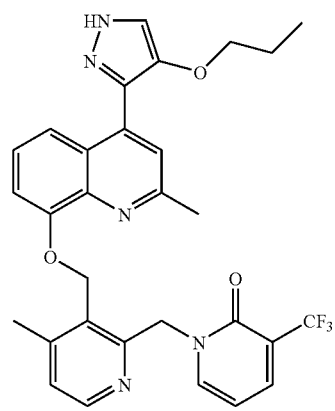 [SMILES: CCCOc1c[nH]nc1-c1cc(C)nc2c(OCc3c(C)ccnc3Cn3cccc(C(F)(F)F)c3=O)cccc12] | 564.1 |
| 609. | 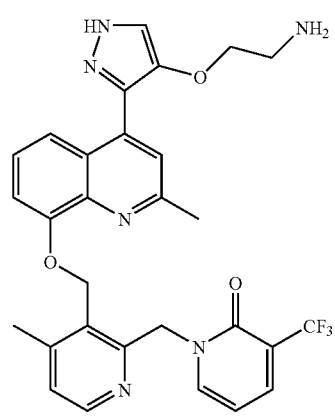 [SMILES: Cc1cc(-c2n[nH]cc2OCCN)c2cccc(OCc3c(C)ccnc3Cn3cccc(C(F)(F)F)c3=O)c2n1] | 565.1 |

TABLE 1-continued

| Example | Structure | M + H+ |
|---|---|---|
| 610. | 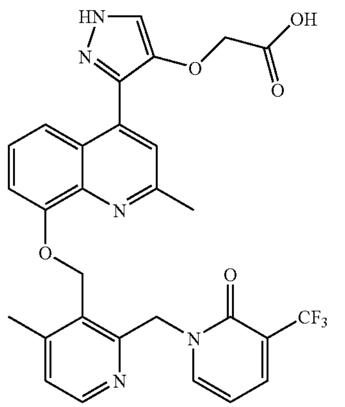 [SMILES: Cc1cc(-c2n[nH]cc2OCC(=O)O)c2cccc(OCc3c(C)ccnc3Cn3cccc(C(F)(F)F)c3=O)c2n1] | 580.1 |
| 611. | 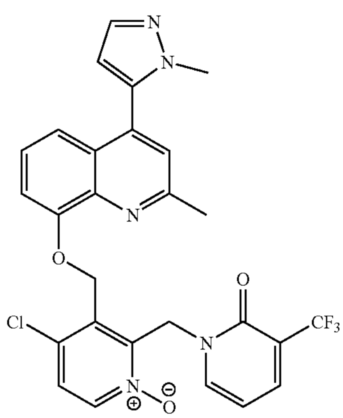 [SMILES: Cc1cc(-c2ccnn2C)c2cccc(OCc3c(Cl)cc[n+]([O-])c3Cn3cccc(C(F)(F)F)c3=O)c2n1] | 556.0 |
| 612. | 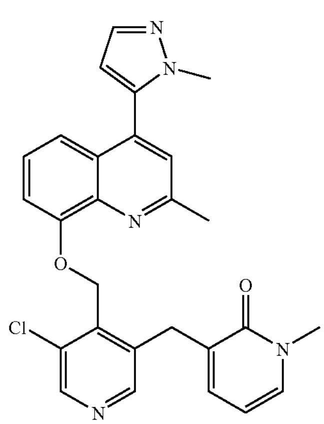 [SMILES: Cc1cc(-c2ccnn2C)c2cccc(OCc3c(Cl)cncc3Cc3cccn(C)c3=O)c2n1] | 486.1 |

TABLE 1-continued

| Example | Structure | M + H+ |
|---|---|---|
| 613. | | 557.1 |
| 614. | | 557.1 |
| 615. | | 554.1 |

TABLE 1-continued
| Example | Structure | M + H+ |
|---------|-----------|--------|
| 616. | 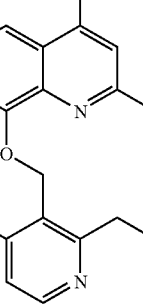 | 534.1 |
| 617. | 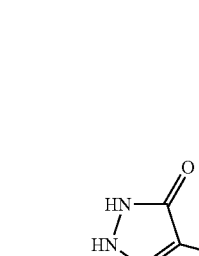 | 538.0 |
| 618. | 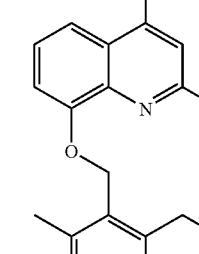 | 558.0 |
| 619. | 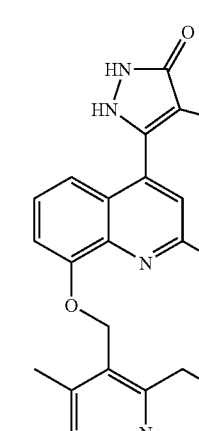 | 584.0 |
| 620. | 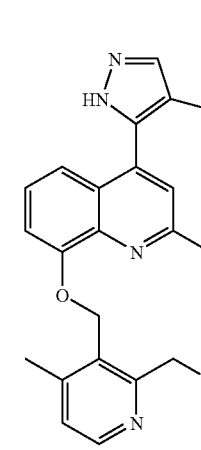 | 536.0 |
| 621. | 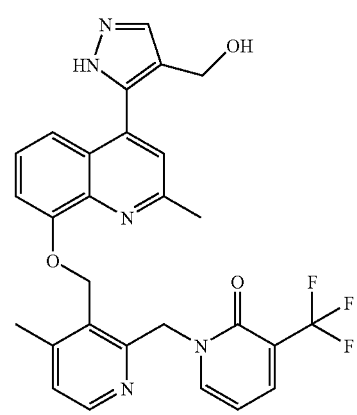 [SMILES: Cc1cc(-c2[nH]ncc2CO)c2cccc(OCc3c(C)ccnc3Cn3cccc(C(F)(F)F)c3=O)c2n1] | 536.1 |

TABLE 1-continued

| Example | Structure | M + H+ |
|---|---|---|
| 622. | 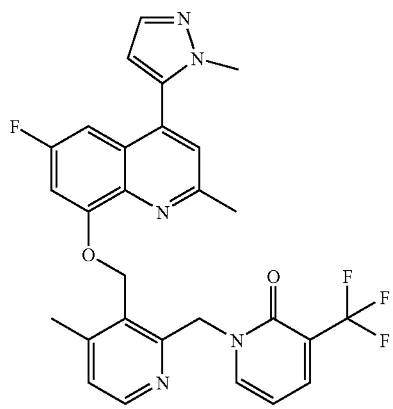 [SMILES: Cc1cc(-c2ccnn2C)c2cc(F)cc(OCc3c(C)ccnc3Cn3cccc(C(F)(F)F)c3=O)c2n1] | 538.1 |
| 623. | 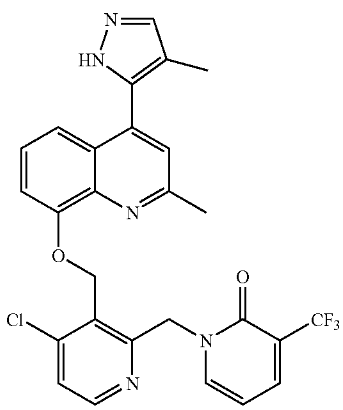 [SMILES: Cc1cc(-c2[nH]ncc2C)c2cccc(OCc3c(Cl)ccnc3Cn3cccc(C(F)(F)F)c3=O)c2n1] | 540.1 |
| 624. | 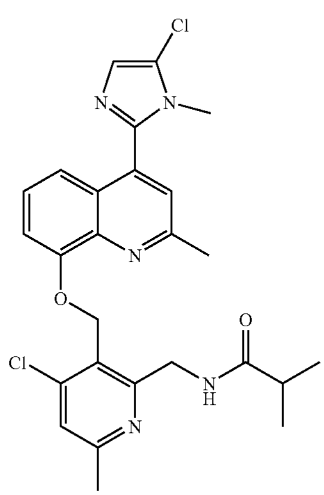 [SMILES: Cc1cc(Cl)c(COc2cccc3c(-c4ncc(Cl)n4C)cc(C)nc23)c(CNC(=O)C(C)C)n1] | 512.1 |
| 625. | 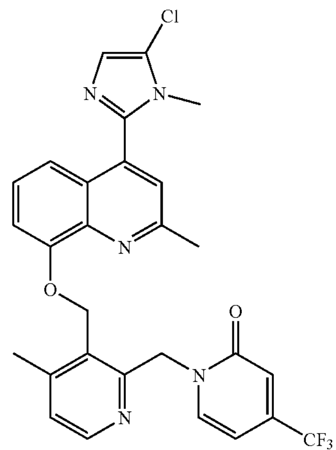 [SMILES: Cc1cc(-c2ncc(Cl)n2C)c2cccc(OCc3c(C)ccnc3Cn3ccc(C(F)(F)F)cc3=O)c2n1] | 554.1 |
| 626. | 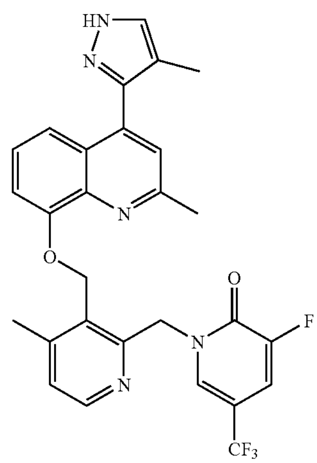 [SMILES: Cc1cc(-c2n[nH]cc2C)c2cccc(OCc3c(C)ccnc3Cn3cc(C(F)(F)F)cc(F)c3=O)c2n1] | 538.1 |
| 627. | 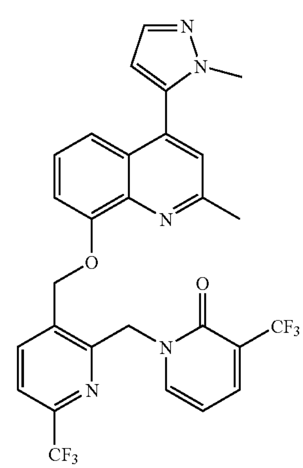 [SMILES: Cc1cc(-c2ccnn2C)c2cccc(OCc3ccc(C(F)(F)F)nc3Cn3cccc(C(F)(F)F)c3=O)c2n1] | 574.1 |

TABLE 1-continued
| Example | Structure | M + H+ |
|---|---|---|
| 628. | 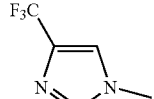 | 608.0 |
| 629. | 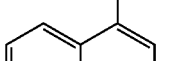 | 545.1 |
| 630. | 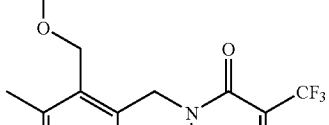 | 588.1 |
TABLE 1-continued
| Example | Structure | M + H+ |
|---|---|---|
| 631. | 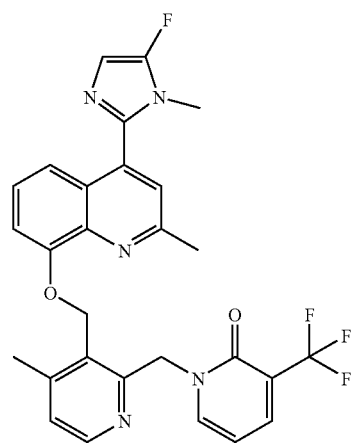 [SMILES: Cc1cc(-c2ncc(F)n2C)c2cccc(OCc3c(C)ccnc3Cn3cccc(C(F)(F)F)c3=O)c2n1] | 588.0 |
| 632. | 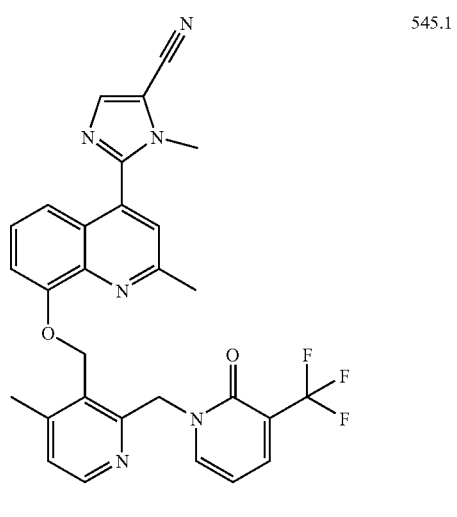 | 538.1 |
| 633. | 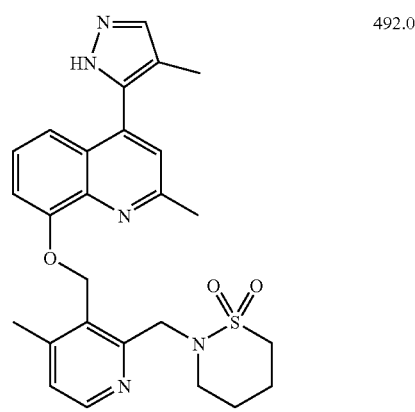 | 492.0 |

TABLE 1-continued
| Example | Structure | M + H+ |
|---|---|---|
| 634. | 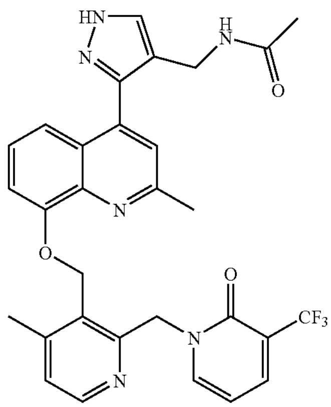 [SMILES: CC(=O)NCc1c[nH]nc1-c1cc(C)nc2c(OCc3c(C)ccnc3Cn3cccc(C(F)(F)F)c3=O)cccc12] | 577.1 |
| 635. | 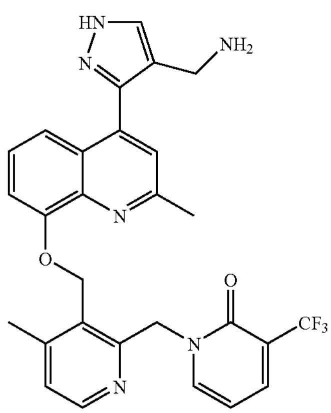 [SMILES: Cc1cc(-c2n[nH]cc2CN)c2cccc(OCc3c(C)ccnc3Cn3cccc(C(F)(F)F)c3=O)c2n1] | 535.1 |
| 636. | 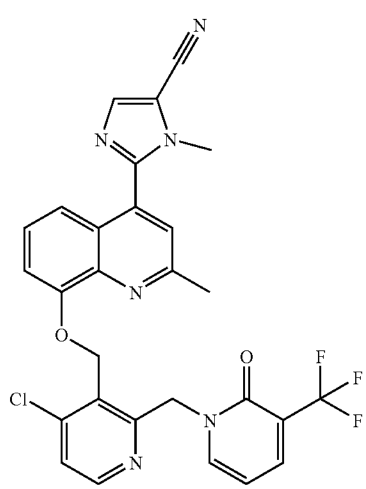 [SMILES: Cc1cc(-c2ncc(C#N)n2C)c2cccc(OCc3c(Cl)ccnc3Cn3cccc(C(F)(F)F)c3=O)c2n1] | 565.0 |
TABLE 1-continued
| Example | Structure | M + H+ |
|---|---|---|
| 637. | 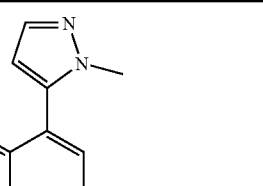 | 450.0 |
| 638. | 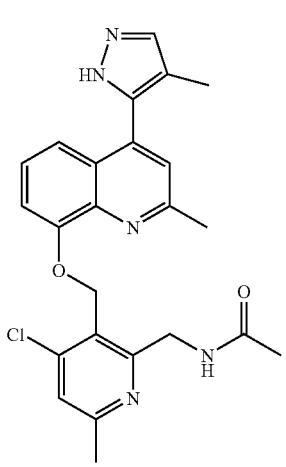 [SMILES: CC(=O)NCc1nc(C)cc(Cl)c1COc1cccc2c(-c3[nH]ncc3C)cc(C)nc12] | 450.0 |
| 639. | 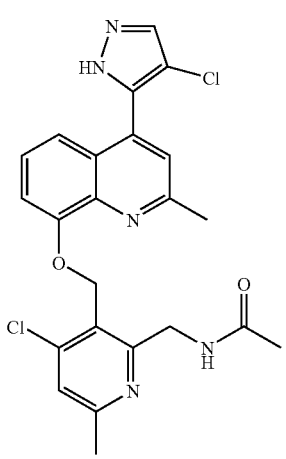 [SMILES: CC(=O)NCc1nc(C)cc(Cl)c1COc1cccc2c(-c3[nH]ncc3Cl)cc(C)nc12] | 470.0 |
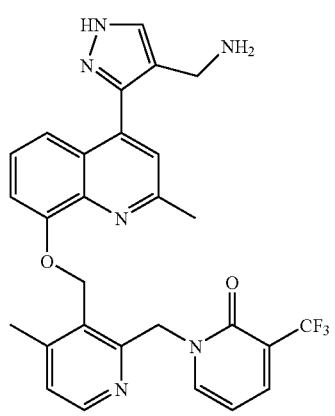
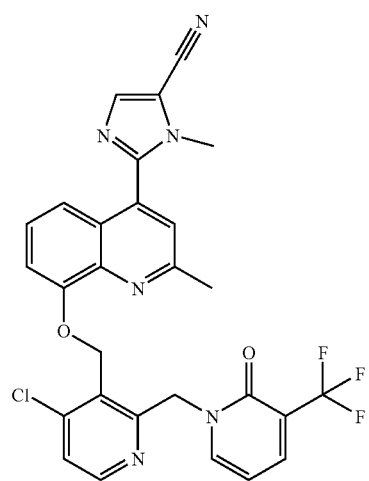

TABLE 1-continued
| Example | Structure | M + H+ |
|---|---|---|
| 640. | 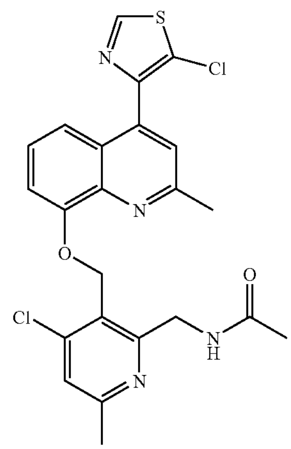 [SMILES: CC(=O)NCc1nc(C)cc(Cl)c1COc1cccc2c(-c3ncsc3Cl)cc(C)nc12] | 486.9 |
| 641. | 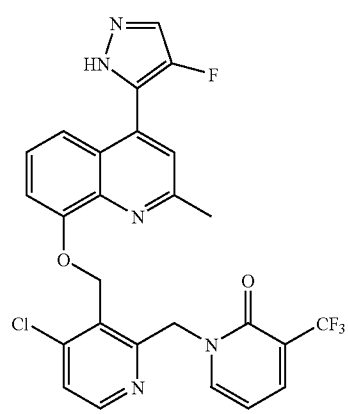 | 544.0 |
| 642. | 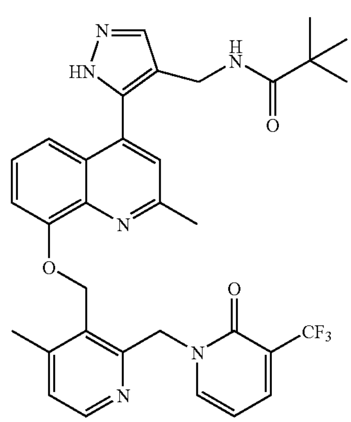 [SMILES: Cc1cc(-c2[nH]ncc2CNC(=O)C(C)(C)C)c2cccc(OCc3c(C)ccnc3Cn3cccc(C(F)(F)F)c3=O)c2n1] | 619.1 |
| 643. | | 639.1 |
| 644. | | 613.0 |
| 645. | | 591.1 |
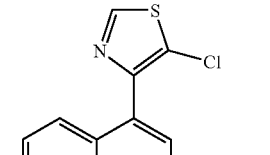

TABLE 1-continued
| Example | Structure | M + H⁺ |
|---|---|---|
| 646. | 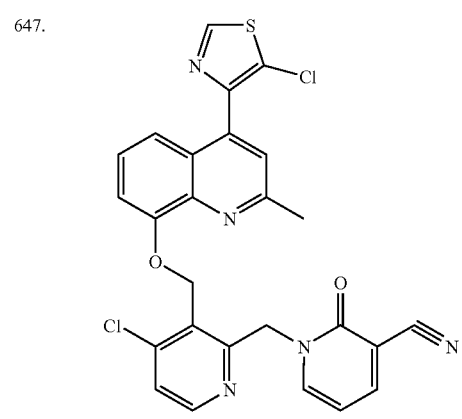 | 542.9 |
| 647. | 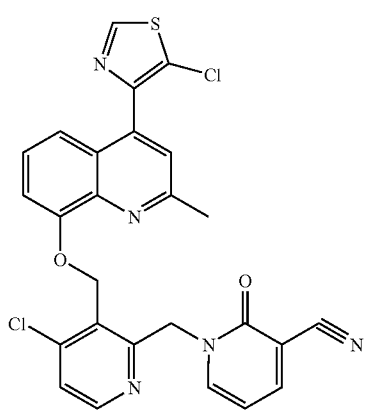 [SMILES: Cc1cc(-c2ncsc2Cl)c2cccc(OCc3c(Cl)ccnc3Cn3cccc(C#N)c3=O)c2n1] | 534.0 |
| 648. | 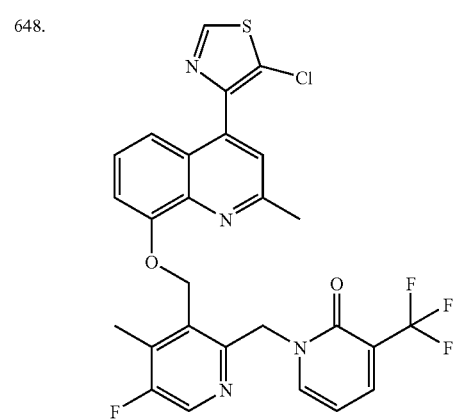 | 575.0 |
TABLE 1-continued
| Example | Structure | M + H⁺ |
|---|---|---|
| 649. | 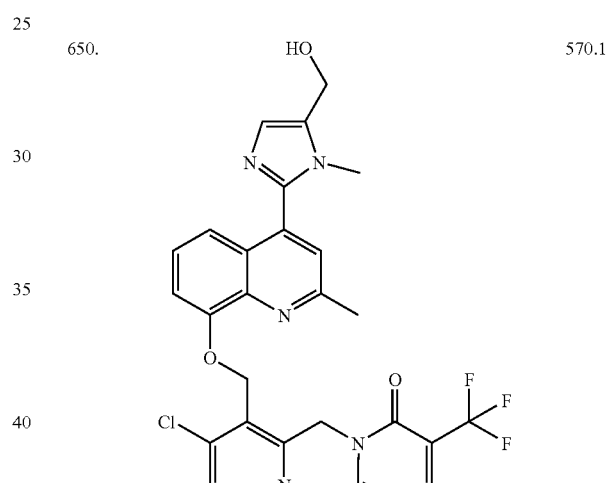 | 597.0 |
| 650. | 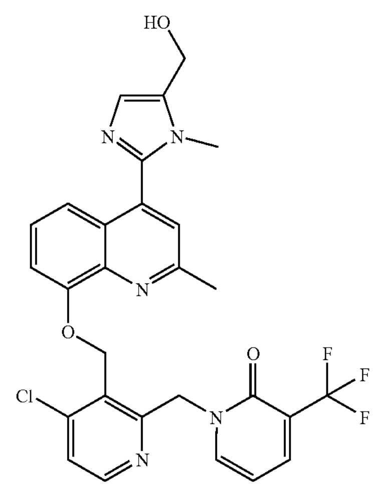 [SMILES: Cc1cc(-c2ncc(CO)n2C)c2cccc(OCc3c(Cl)ccnc3Cn3cccc(C(F)(F)F)c3=O)c2n1] | 570.1 |
| 651 | 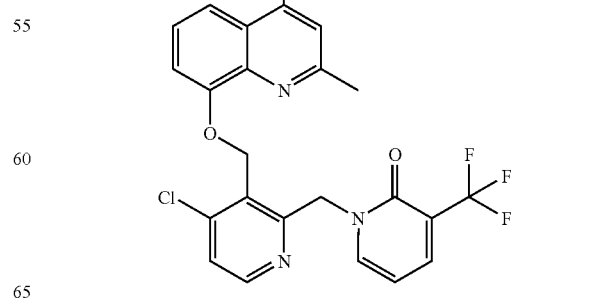 | 558.1 |

TABLE 1-continued
| Example | Structure | M + H⁺ |
|---|---|---|
| 652. | 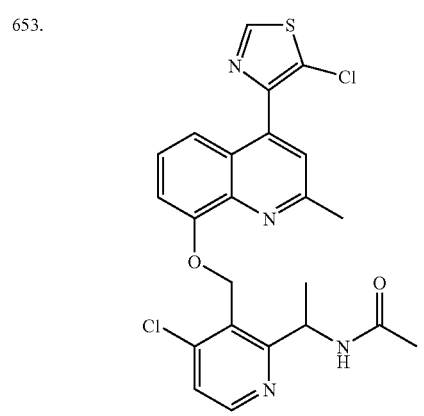 | 538.1 |
| 653. | 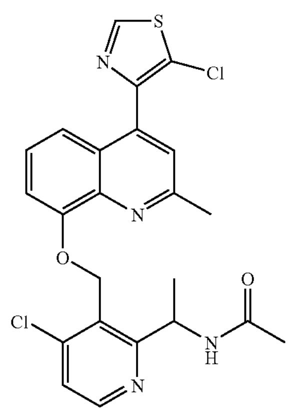 [SMILES: CC(=O)NC(C)c1nccc(Cl)c1COc1cccc2c(-c3ncsc3Cl)cc(C)nc12] | 487.1 |
| 654. | 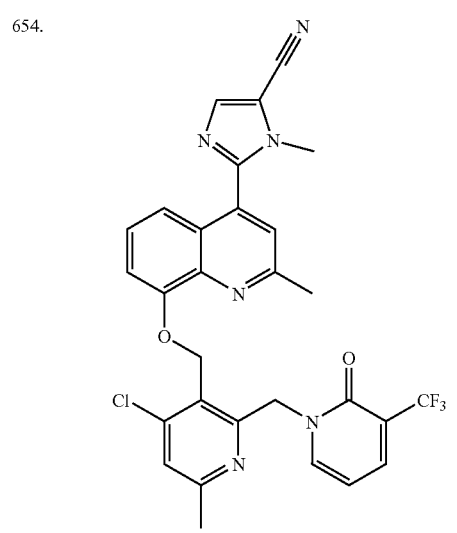 | 579.0 |
| 655. | 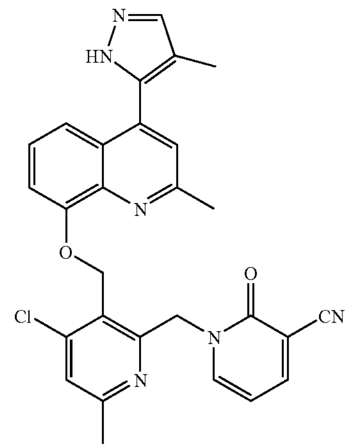 [SMILES: Cc1cc(Cl)c(COc2cccc3c(-c4[nH]ncc4C)cc(C)nc23)c(Cn2cccc(C#N)c2=O)n1] | 511.0 |
| 656. | 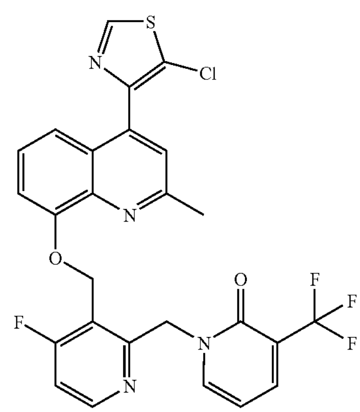 [SMILES: Cc1cc(-c2ncsc2Cl)c2cccc(OCc3c(F)ccnc3Cn3cccc(C(F)(F)F)c3=O)c2n1] | 561.0 |
| 657. | 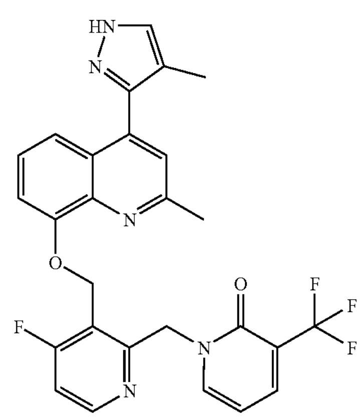 [SMILES: Cc1cc(-c2n[nH]cc2C)c2cccc(OCc3c(F)ccnc3Cn3cccc(C(F)(F)F)c3=O)c2n1] | 524.1 |

TABLE 1-continued
| Example | Structure | M + H+ |
|---|---|---|
| 658. | 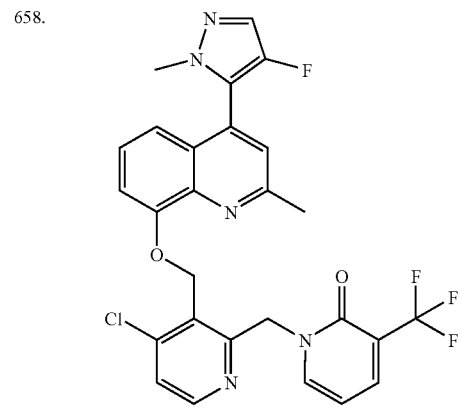 | 558.0 |
| 659. | 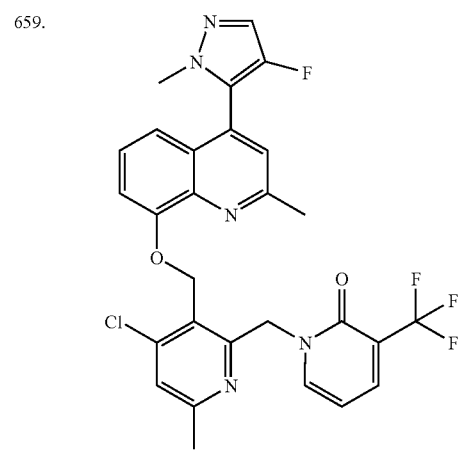 | 572.1 |
| 660. | 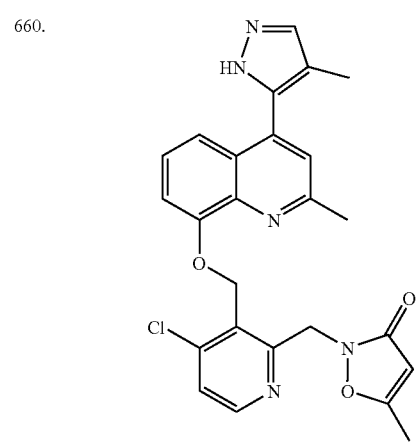 | 476.0 |
TABLE 1-continued
| Example | Structure | M + H+ |
|---|---|---|
| 661. | 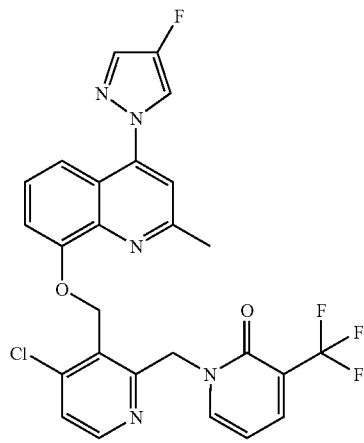 [SMILES: Cc1cc(-n2cc(F)cn2)c2cccc(OCc3c(Cl)ccnc3Cn3cccc(C(F)(F)F)c3=O)c2n1] | 544.0 |
| 662. | 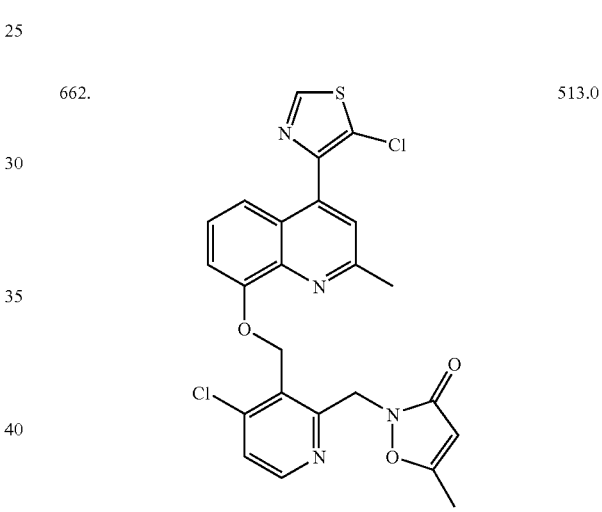 | 513.0 |
| 663. | 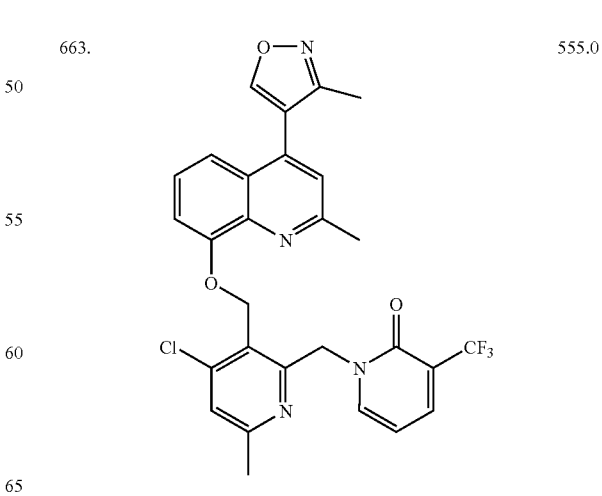 | 555.0 |

TABLE 1-continued
| Example | Structure | M + H⁺ |
|---|---|---|
| 664. | 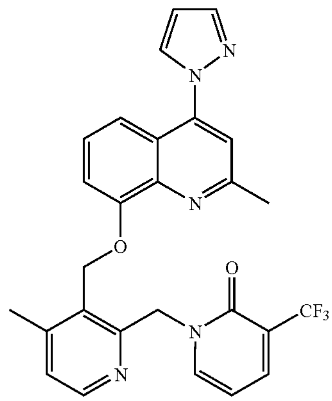 [SMILES: Cc1cc(-n2cccn2)c2cccc(OCc3c(C)ccnc3Cn3cccc(C(F)(F)F)c3=O)c2n1] | 506.0 |
| 665. | 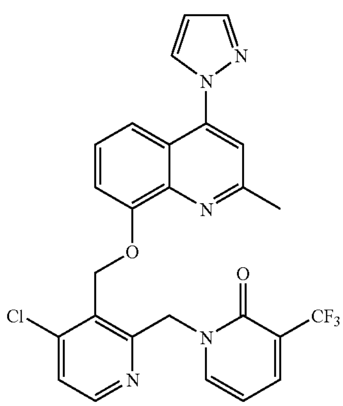 [SMILES: Cc1cc(-n2cccn2)c2cccc(OCc3c(Cl)ccnc3Cn3cccc(C(F)(F)F)c3=O)c2n1] | 526.0 |
| 666. | 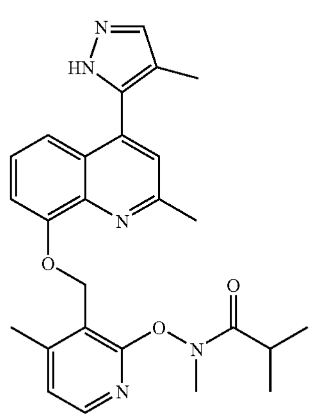 [SMILES: Cc1cc(-c2[nH]ncc2C)c2cccc(OCc3c(C)ccnc3ON(C)C(=O)C(C)C)c2n1] | 460.0 |
| 667. | | 554.0 |
| 668. | | 578.2 |
| 669. | | 536.0 |
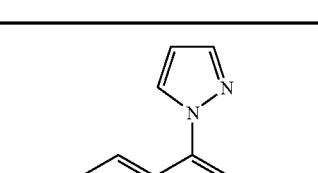

TABLE 1-continued

| Example | Structure | M + H+ |
|---|---|---|
| 670. | 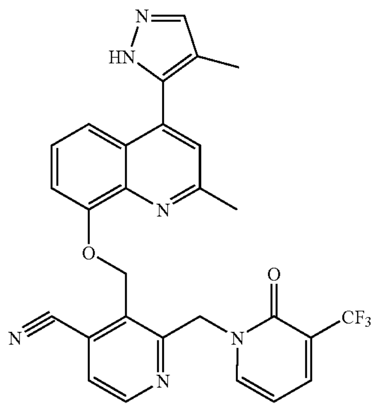 [SMILES: Cc1cc(-c2[nH]ncc2C)c2cccc(OCc3c(C#N)ccnc3Cn3cccc(C(F)(F)F)c3=O)c2n1] | 531.1 |
| 671. | 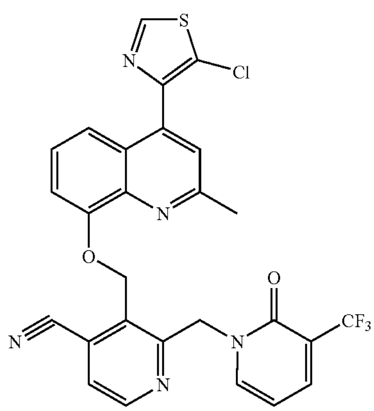 [SMILES: Cc1cc(-c2ncsc2Cl)c2cccc(OCc3c(C#N)ccnc3Cn3cccc(C(F)(F)F)c3=O)c2n1] | 568.0 |
| 672. | 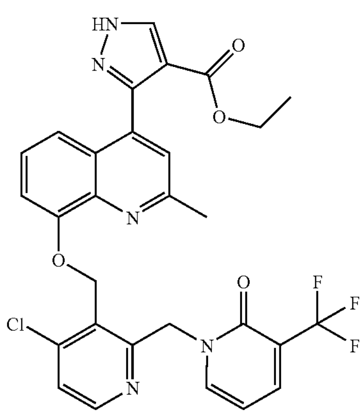 [SMILES: CCOC(=O)c1c[nH]nc1-c1cc(C)nc2c(OCc3c(Cl)ccnc3Cn3cccc(C(F)(F)F)c3=O)cccc12] | 598.0 |

TABLE 1-continued

| Example | Structure | M + H+ |
|---|---|---|
| 673. | | 565.0 |
| 674. | | 591.0 |
| 675. | | 548.0 |

TABLE 1-continued

| Example | Structure | M + H+ |
|---------|-----------|--------|
| 676. | 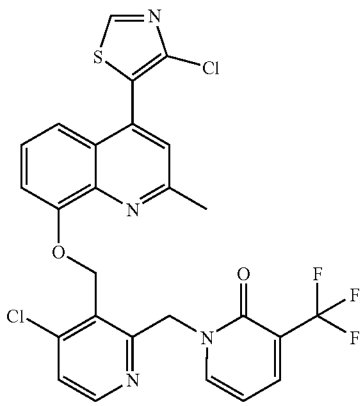 [SMILES: Cc1cc(-c2scnc2Cl)c2cccc(OCc3c(Cl)ccnc3Cn3cccc(C(F)(F)F)c3=O)c2n1] | 577.0 |
| 677. | 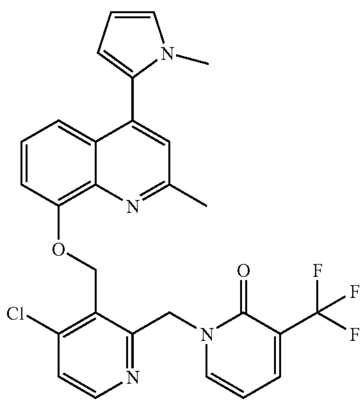 [SMILES: Cc1cc(-c2cccn2C)c2cccc(OCc3c(Cl)ccnc3Cn3cccc(C(F)(F)F)c3=O)c2n1] | 539.1 |
| 678. | 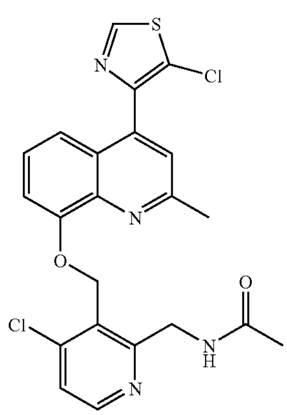 [SMILES: CC(=O)NCc1nccc(Cl)c1COc1cccc2c(-c3ncsc3Cl)cc(C)nc12] | 473.0 |
| 679. | | 500.9 |
| 680. | | 464.0 |
| 681. | | 598.0 |

TABLE 1-continued

| Example | Structure | M + H+ |
|---------|-----------|--------|
| 682. | 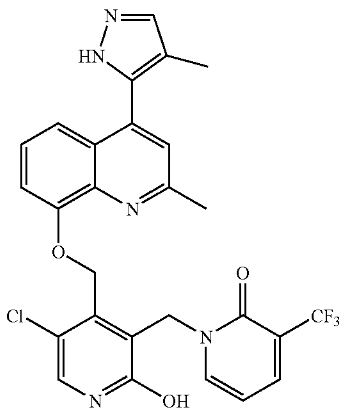 [SMILES: Cc1cc(-c2[nH]ncc2C)c2cccc(OCc3c(Cl)cnc(O)c3Cn3cccc(C(F)(F)F)c3=O)c2n1] | 556.0 |
| 683. | 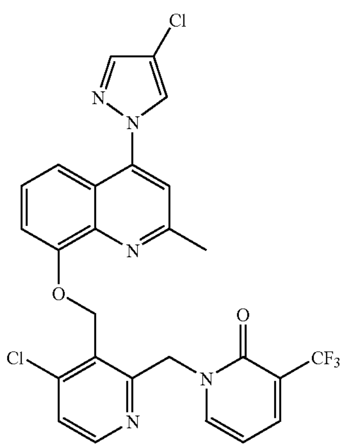 [SMILES: Cc1cc(-n2cc(Cl)cn2)c2cccc(OCc3c(Cl)ccnc3Cn3cccc(C(F)(F)F)c3=O)c2n1] | 560.0 |
| 684. | 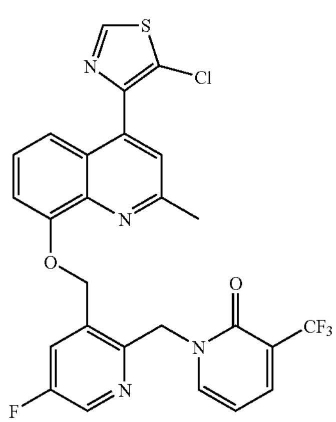 [SMILES: Cc1cc(-c2ncsc2Cl)c2cccc(OCc3cc(F)cnc3Cn3cccc(C(F)(F)F)c3=O)c2n1] | 561.0 |
| 685. | 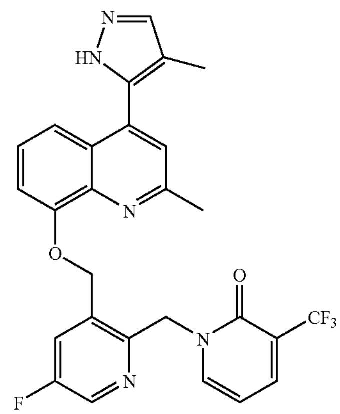 [SMILES: Cc1cc(-c2[nH]ncc2C)c2cccc(OCc3cc(F)cnc3Cn3cccc(C(F)(F)F)c3=O)c2n1] | 524.1 |
| 686. | 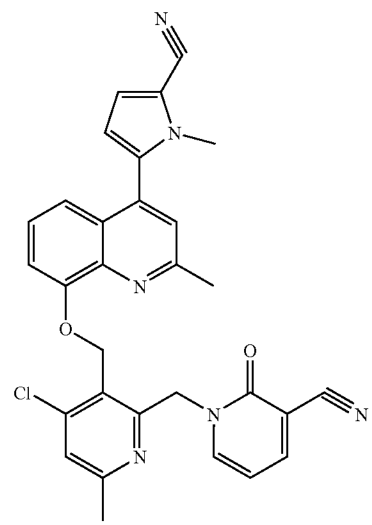 [SMILES: Cc1cc(Cl)c(COc2cccc3c(-c4ccc(C#N)n4C)cc(C)nc23)c(Cn2cccc(C#N)c2=O)n1] | 535.1 |
| 687. | 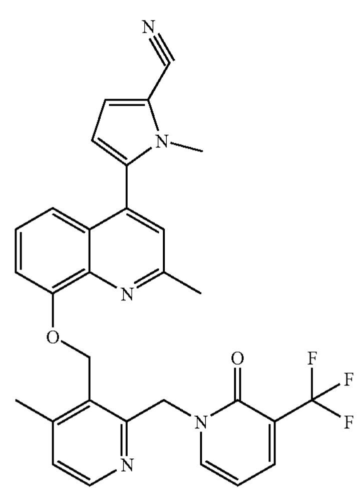 [SMILES: Cc1cc(-c2ccc(C#N)n2C)c2cccc(OCc3c(C)ccnc3Cn3cccc(C(F)(F)F)c3=O)c2n1] | 544.1 |

TABLE 1-continued
| Example | Structure | M + H⁺ |
|---|---|---|
| 688. | 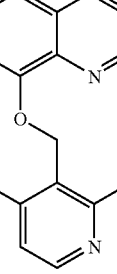 | 540.1 |
| 689. | 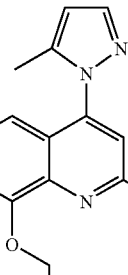 | 520.1 |
| 690. | 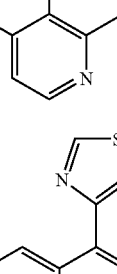 | 573.0 |
| 691. | 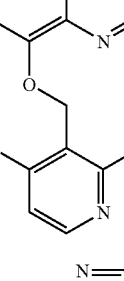 | 536.0 |
TABLE 1-continued
| Example | Structure | M + H⁺ |
|---|---|---|
| 692 | 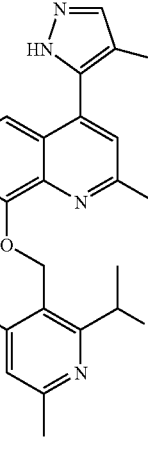 | 518.0 |
| 693. | 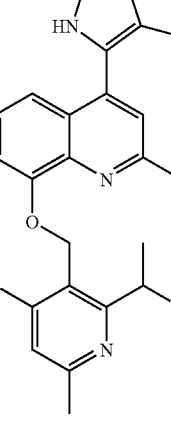 | 492.0 |
| 694. | 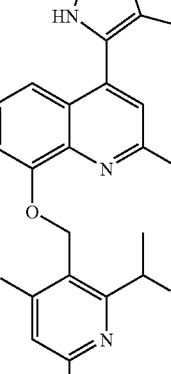 | 478.0 |

TABLE 1-continued
| Example | Structure | M + H⁺ |
|---------|-----------|--------|
| 695. | 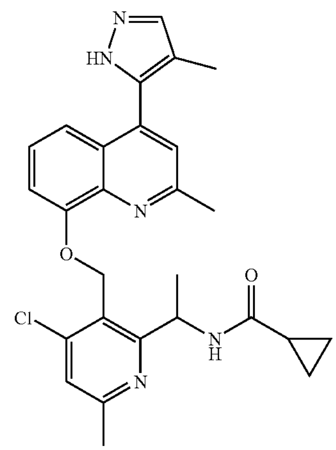 [SMILES: Cc1cc(Cl)c(COc2cccc3c(-c4[nH]ncc4C)cc(C)nc23)c(C(C)NC(=O)C2CC2)n1] | 490.0 |
| 696. | 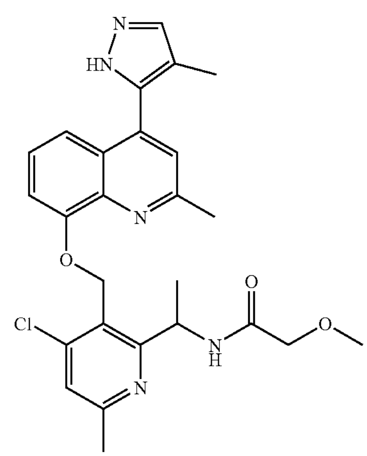 [SMILES: COCC(=O)NC(C)c1nc(C)cc(Cl)c1COc1cccc2c(-c3[nH]ncc3C)cc(C)nc12] | 494.0 |
| 697. | 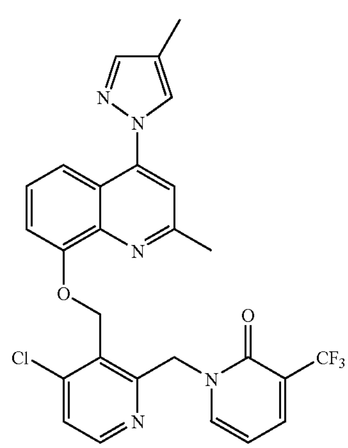 [SMILES: Cc1cnn(-c2cc(C)nc3c(OCc4c(Cl)ccnc4Cn4cccc(C(F)(F)F)c4=O)cccc23)c1] | 540.0 |
| 698. | 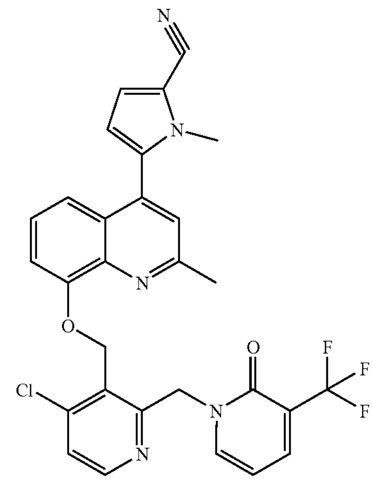 [SMILES: Cc1cc(-c2ccc(C#N)n2C)c2cccc(OCc3c(Cl)ccnc3Cn3cccc(C(F)(F)F)c3=O)c2n1] | 564.0 |
| 699. | 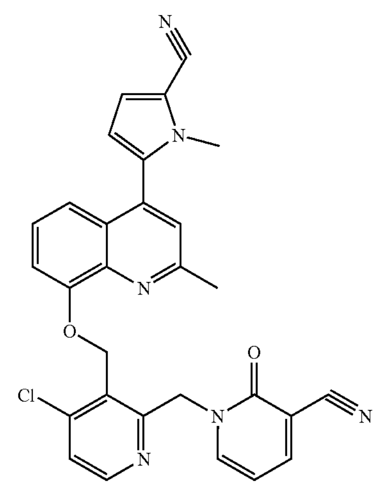 [SMILES: Cc1cc(-c2ccc(C#N)n2C)c2cccc(OCc3c(Cl)ccnc3Cn3cccc(C#N)c3=O)c2n1] | 521.0 |
| 700. | 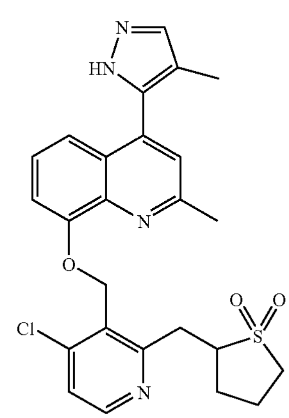 [SMILES: Cc1cc(-c2[nH]ncc2C)c2cccc(OCc3c(Cl)ccnc3CC3CCCS3(=O)=O)c2n1] | 497.0 |
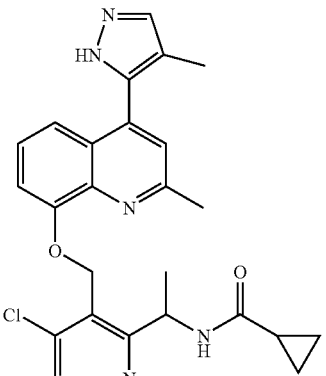

TABLE 1-continued

| Example | Structure | M + H+ |
|---------|-----------|--------|
| 701. | 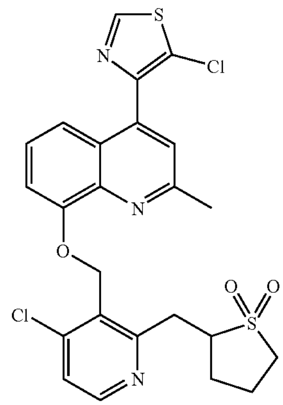 [SMILES: Cc1cc(-c2ncsc2Cl)c2cccc(OCc3c(Cl)ccnc3CC3CCCS3(=O)=O)c2n1] | 533.9 |
| 702. | 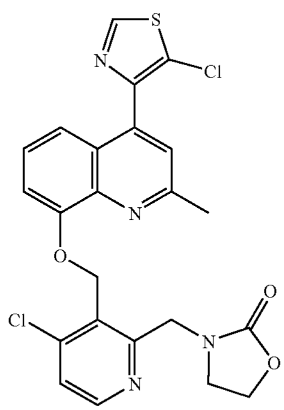 [SMILES: Cc1cc(-c2ncsc2Cl)c2cccc(OCc3c(Cl)ccnc3CN3CCOC3=O)c2n1] | 501.0 |
| 703. | 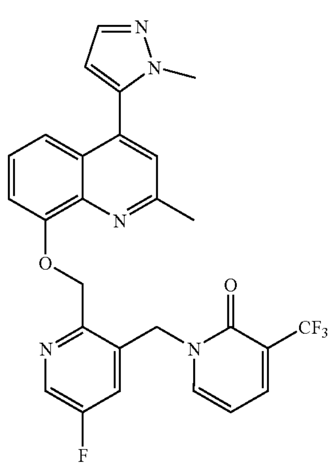 [SMILES: Cc1cc(-c2ccnn2C)c2cccc(OCc3ncc(F)cc3Cn3cccc(C(F)(F)F)c3=O)c2n1] | 524.1 |
| 704. | | 517.0 |
| 705. | | 553.9 |
| 706. | | 584.0 |

TABLE 1-continued

| Example | Structure | M + H+ |
|---|---|---|
| 707. | 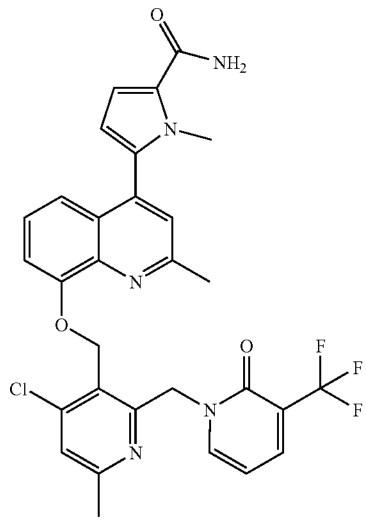 [SMILES: Cc1cc(Cl)c(COc2cccc3c(-c4ccc(C(N)=O)n4C)cc(C)nc23)c(Cn2cccc(C(F)(F)F)c2=O)n1] | 596.0 |
| 708. | 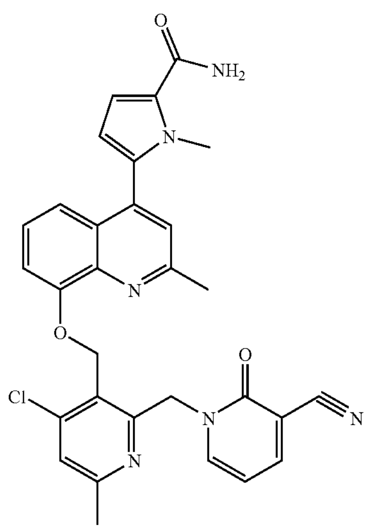 [SMILES: Cc1cc(Cl)c(COc2cccc3c(-c4ccc(C(N)=O)n4C)cc(C)nc23)c(Cn2cccc(C#N)c2=O)n1] | 553.0 |
| 709. | 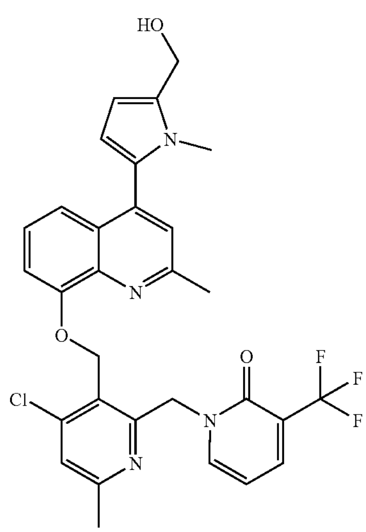 [SMILES: Cc1cc(Cl)c(COc2cccc3c(-c4ccc(CO)n4C)cc(C)nc23)c(Cn2cccc(C(F)(F)F)c2=O)n1] | 583.0 |
| 710. | | 544.1 |
| 711. | | 517.0 |
| 712. | | 556.0 |

TABLE 1-continued

| Example | Structure | M + H+ |
|---------|-----------|--------|
| 713. | 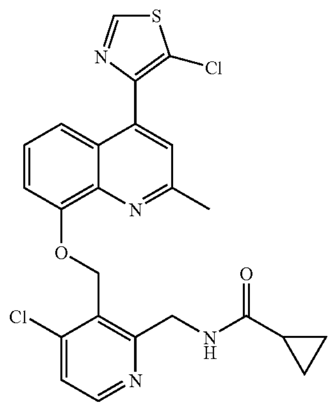 [SMILES: Cc1cc(-c2ncsc2Cl)c2cccc(OCc3c(Cl)ccnc3CNC(=O)C3CC3)c2n1] | 498.6 |
| 714. | 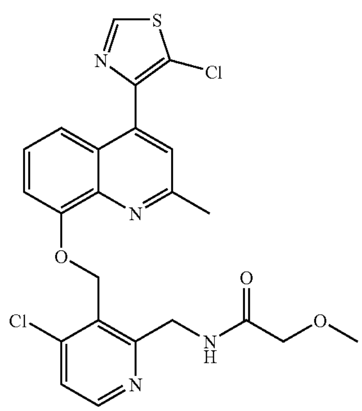 [SMILES: COCC(=O)NCc1nccc(Cl)c1COc1cccc2c(-c3ncsc3Cl)cc(C)nc12] | 502.6 |
| 715. | 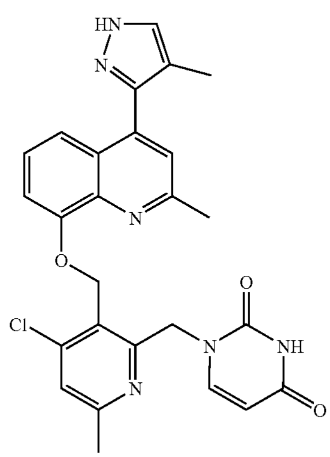 [SMILES: Cc1cc(Cl)c(COc2cccc3c(-c4n[nH]cc4C)cc(C)nc23)c(Cn2ccc(=O)[nH]c2=O)n1] | 503.0 |
| 716. | 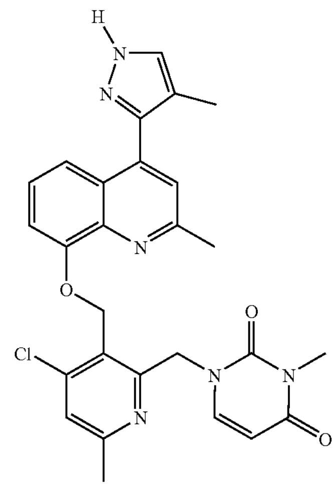 [SMILES: Cc1cc(Cl)c(COc2cccc3c(-c4n[nH]cc4C)cc(C)nc23)c(Cn2ccc(=O)n(C)c2=O)n1] | 517.0 |
| 717. | 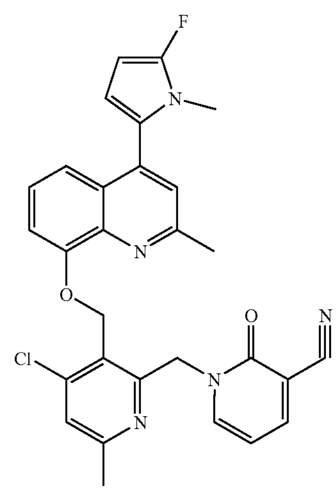 [SMILES: Cc1cc(Cl)c(COc2cccc3c(-c4ccc(F)n4C)cc(C)nc23)c(Cn2cccc(C#N)c2=O)n1] | 528.0 |
| 718. | 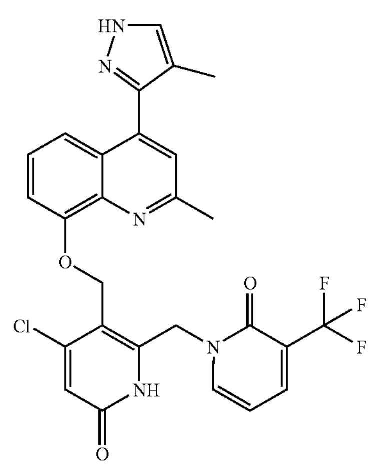 [SMILES: Cc1cc(-c2n[nH]cc2C)c2cccc(OCc3c(Cl)cc(=O)[nH]c3Cn3cccc(C(F)(F)F)c3=O)c2n1] | 556.0 |

TABLE 1-continued

| Example | Structure | M + H⁺ |
|---------|-----------|--------|
| 719. | 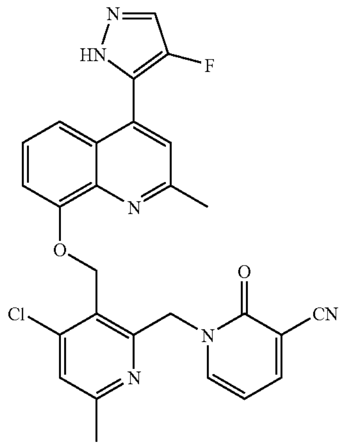 [SMILES: Cc1cc(Cl)c(COc2cccc3c(-c4[nH]ncc4F)cc(C)nc23)c(Cn2cccc(C#N)c2=O)n1] | 515.0 |
| 720. | 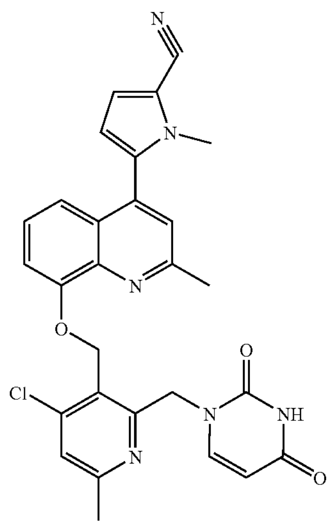 [SMILES: Cc1cc(Cl)c(COc2cccc3c(-c4ccc(C#N)n4C)cc(C)nc23)c(Cn2ccc(=O)[nH]c2=O)n1] | 527.0 |
| 721. | 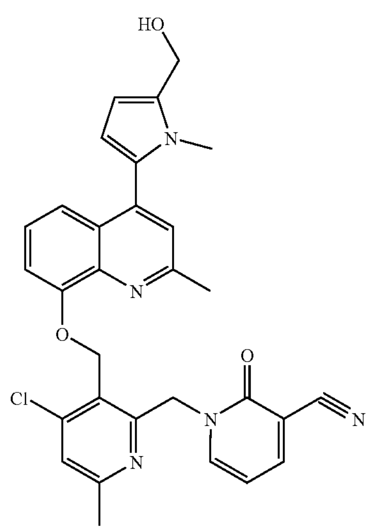 [SMILES: Cc1cc(Cl)c(COc2cccc3c(-c4ccc(CO)n4C)cc(C)nc23)c(Cn2cccc(C#N)c2=O)n1] | 540.1 |
| 722. | 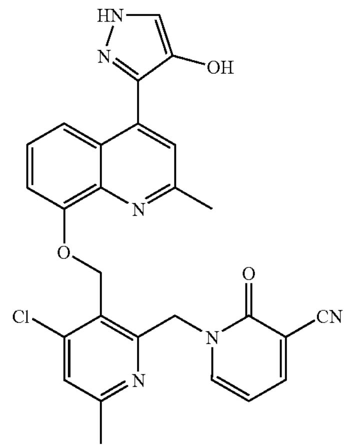 [SMILES: Cc1cc(Cl)c(COc2cccc3c(-c4n[nH]cc4O)cc(C)nc23)c(Cn2cccc(C#N)c2=O)n1] | 513.0 |
| 723. | 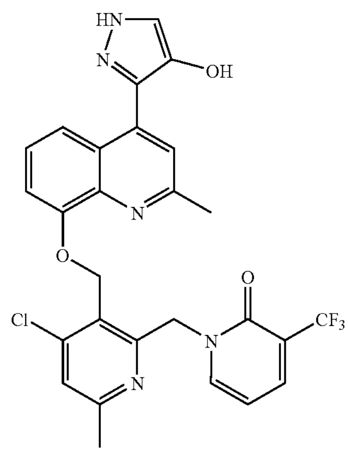 | 556.0 |
| 724. | 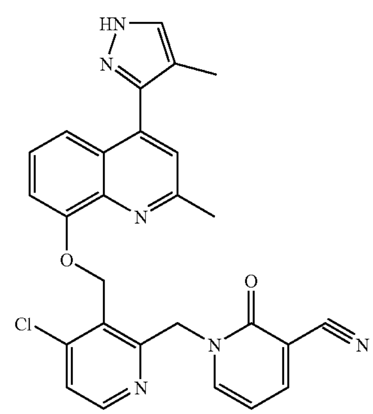 [SMILES: Cc1cc(-c2n[nH]cc2C)c2cccc(OCc3c(Cl)ccnc3Cn3cccc(C#N)c3=O)c2n1] | 497.0 |

TABLE 1-continued
| Example | Structure | M + H+ |
|---|---|---|
| 725. | 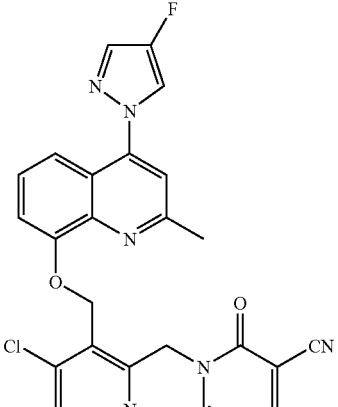 | 515.0 |
| 726. | 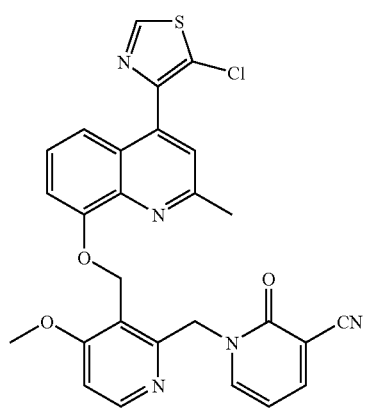 [SMILES: COc1ccnc(Cn2cccc(C#N)c2=O)c1COc1cccc2c(-c3ncsc3Cl)cc(C)nc12] | 530.0 |
| 727. | 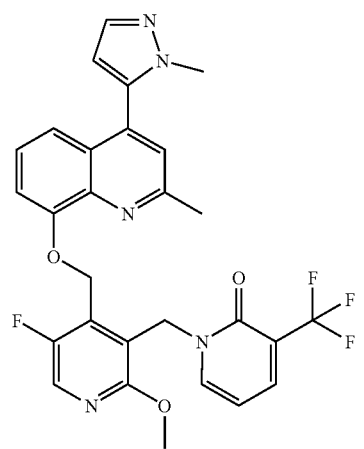 [SMILES: COc1ncc(F)c(COc2cccc3c(-c4ccnn4C)cc(C)nc23)c1Cn1cccc(C(F)(F)F)c1=O] | 553.7 |
| 728. | 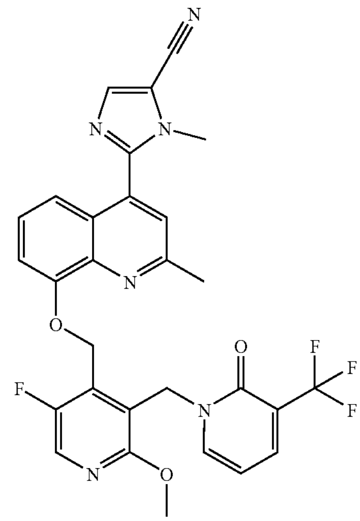 [SMILES: COc1ncc(F)c(COc2cccc3c(-c4ncc(C#N)n4C)cc(C)nc23)c1Cn1cccc(C(F)(F)F)c1=O] | 578.7 |
| 729. | 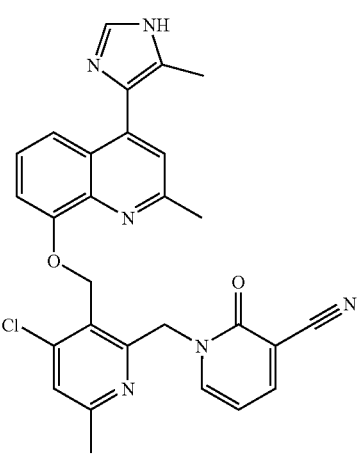 [SMILES: Cc1cc(Cl)c(COc2cccc3c(-c4nc[nH]c4C)cc(C)nc23)c(Cn2cccc(C#N)c2=O)n1] | 511.0 |
| 730. | 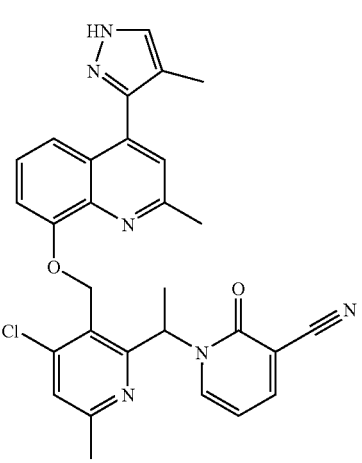 [SMILES: Cc1cc(Cl)c(COc2cccc3c(-c4n[nH]cc4C)cc(C)nc23)c(C(C)n2cccc(C#N)c2=O)n1] | 525.1 |

TABLE 1-continued
| Example | Structure | M + H⁺ |
|---|---|---|
| 731. | 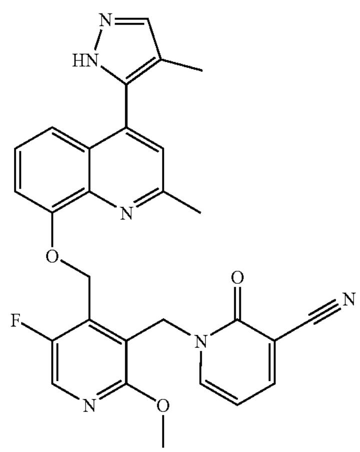 [SMILES: COc1ncc(F)c(COc2cccc3c(-c4[nH]ncc4C)cc(C)nc23)c1Cn1cccc(C#N)c1=O] | 511.0 |
| 732. | 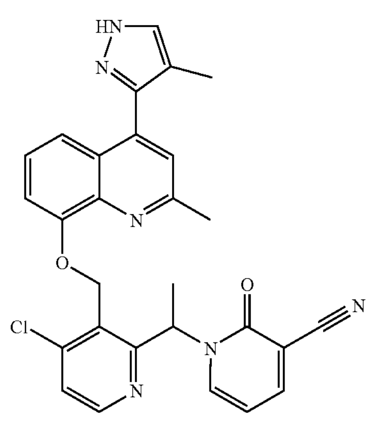 [SMILES: Cc1cc(-c2n[nH]cc2C)c2cccc(OCc3c(Cl)ccnc3C(C)n3cccc(C#N)c3=O)c2n1] | 511.1 |
| 733. | 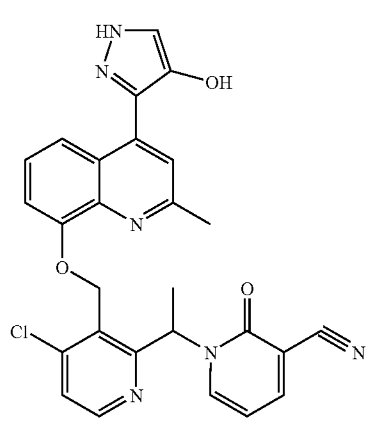 [SMILES: Cc1cc(-c2n[nH]cc2O)c2cccc(OCc3c(Cl)ccnc3C(C)n3cccc(C#N)c3=O)c2n1] | 513.0 |
| 734. | 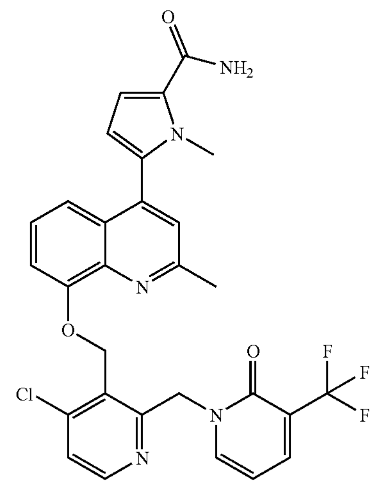 [SMILES: Cc1cc(-c2ccc(C(N)=O)n2C)c2cccc(OCc3c(Cl)ccnc3Cn3cccc(C(F)(F)F)c3=O)c2n1] | 581.6 |
| 735. | 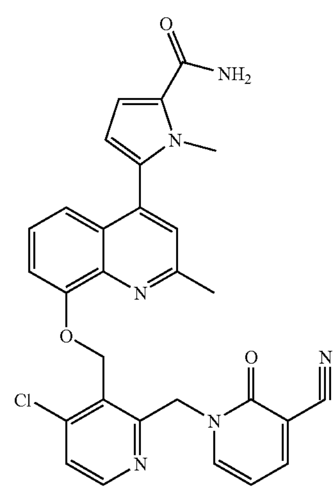 [SMILES: Cc1cc(-c2ccc(C(N)=O)n2C)c2cccc(OCc3c(Cl)ccnc3Cn3cccc(C#N)c3=O)c2n1] | 538.6 |
| 736. | 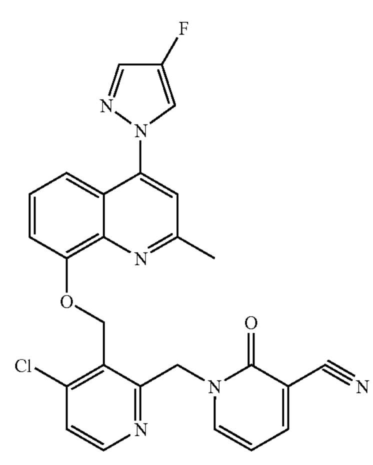 [SMILES: Cc1cc(-n2cc(F)cn2)c2cccc(OCc3c(Cl)ccnc3Cn3cccc(C#N)c3=O)c2n1] | 500.6 |
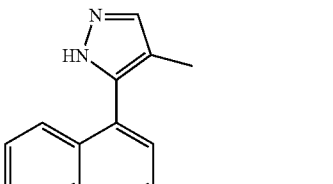

TABLE 1-continued

| Example | Structure | M + H⁺ |
|---------|-----------|--------|
| 737. | 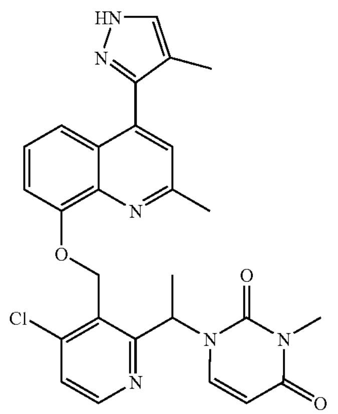 [SMILES: Cc1cc(-c2n[nH]cc2C)c2cccc(OCc3c(Cl)ccnc3C(C)n3ccc(=O)n(C)c3=O)c2n1] | 517.1 |
| 738. | 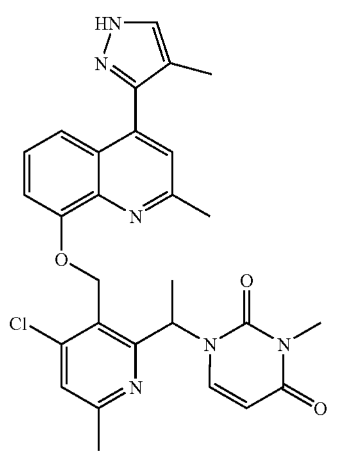 [SMILES: Cc1cc(Cl)c(COc2cccc3c(-c4n[nH]cc4C)cc(C)nc23)c(C(C)n2ccc(=O)n(C)c2=O)n1] | 531.0 |
| 739. | 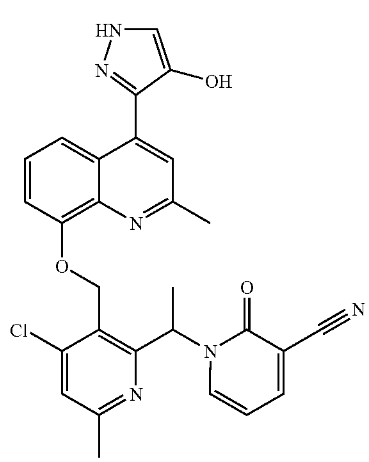 [SMILES: Cc1cc(Cl)c(COc2cccc3c(-c4n[nH]cc4O)cc(C)nc23)c(C(C)n2cccc(C#N)c2=O)n1] | 527.0 |
| 740. | | 538.9 |
| 741. | | 511.7 |
| 742. | | 537.0 |

TABLE 1-continued
| Example | Structure | M + H+ |
|---|---|---|
| 743. | 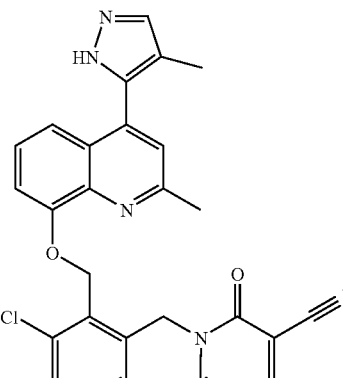 | 513.0 |
| 744. | 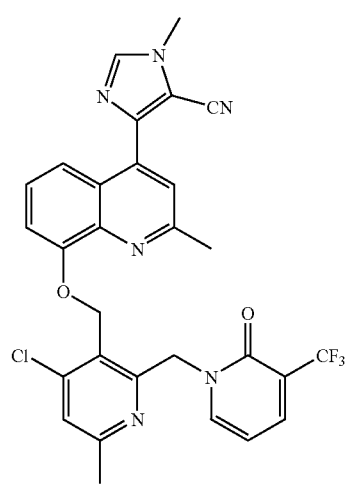 [SMILES: Cc1cc(Cl)c(COc2cccc3c(-c4ncn(C)c4C#N)cc(C)nc23)c(Cn2cccc(C(F)(F)F)c2=O)n1] | 579.0 |
| 745. | 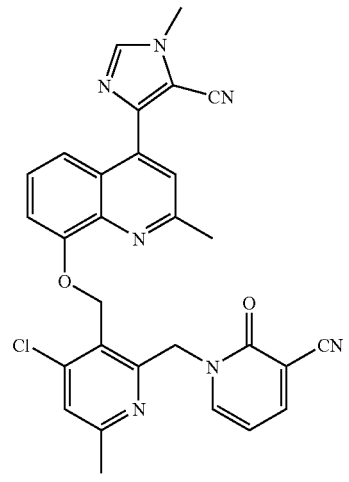 [SMILES: Cc1cc(Cl)c(COc2cccc3c(-c4ncn(C)c4C#N)cc(C)nc23)c(Cn2cccc(C#N)c2=O)n1] | 536.0 |
TABLE 1-continued
| Example | Structure | M + H+ |
|---|---|---|
| 746. | 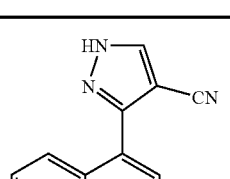 | 565.0 |
| 747. | 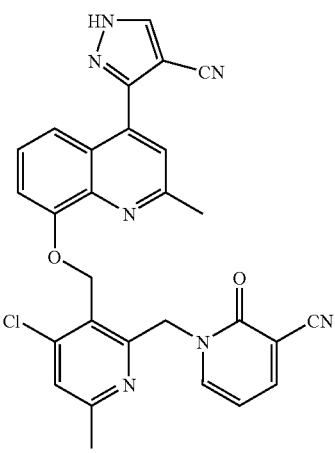 | 522.0 |
| 748. | 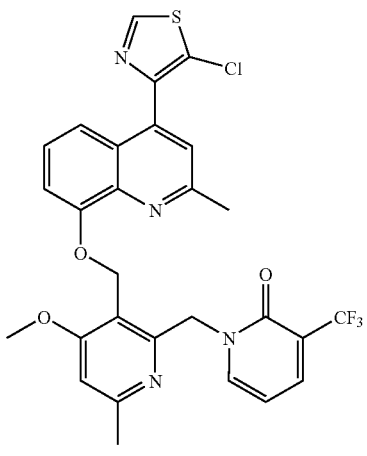 [SMILES: COc1cc(C)nc(Cn2cccc(C(F)(F)F)c2=O)c1COc1cccc2c(-c3ncsc3Cl)cc(C)nc12] | 586.9 |

TABLE 1-continued

| Example | Structure | M + H⁺ |
|---|---|---|
| 749. | 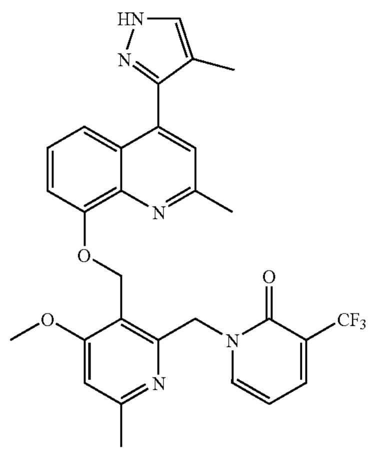 [SMILES: COc1cc(C)nc(Cn2cccc(C(F)(F)F)c2=O)c1COc1cccc2c(-c3n[nH]cc3C)cc(C)nc12] | 550.0 |
| 750. | 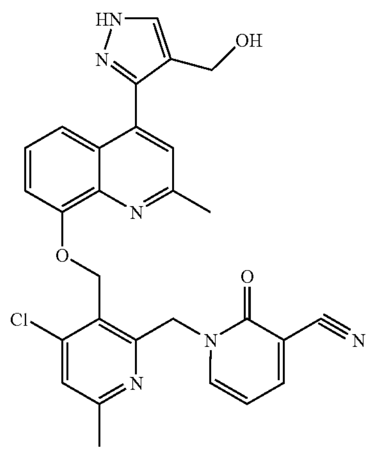 [SMILES: Cc1cc(Cl)c(COc2cccc3c(-c4n[nH]cc4CO)cc(C)nc23)c(Cn2cccc(C#N)c2=O)n1] | 527.04 |
| 751. | 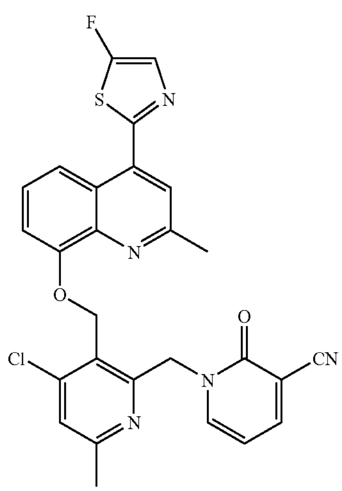 [SMILES: Cc1cc(Cl)c(COc2cccc3c(-c4ncc(F)s4)cc(C)nc23)c(Cn2cccc(C#N)c2=O)n1] | 532.0 |
| 752. | | 543.97 |
| 753. | | 507.1 |

Specific examples for the preparation of compounds of formula (I) are provided in the following examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied including additional steps employed to produce compounds encompassed by the present invention.

Example 1

Synthesis of 8-(3,5-dichloro-pyridin-4-ylmethoxy)-4-imidazol-1-yl-2-methylquinoline A. 4-Imidazol-1-yl-2-methyl-quinolin-8-ol A mixture of 4-chloro-2-methyl-quinolin-8-ol (2.0 g, 10 mmol) and imidazole (3.53 g, 51.8 mmol) in dioxane (20 mL) was heated to reflux for 28 h. The solvent was removed in vacuo and the residue was purified by flash chromatography on silica gel (elution with DCM/methanol 10:1) to give the title compound. MS (m/z): 226.3 [M+H⁺].

B. (3,5-Dichloro-pyridin-4-yl)-methanol

NaBH₄ (0.838 g, 22.2 mmol) was added to a stirred solution of 3,5-dichloro-pyridine-4-carbaldehyde (3.0 g, 17 mmol) in ethanol (40 mL). After stirring for 35 min at room temperature, the reaction mixture was concentrated in vacuo, the residue was redissolved in ethyl acetate (200 mL) and washed with water (50 mL). The organic layer was dried over $Na_2SO_4$, filtered, and concentrated in vacuo to give the title compound. MS (m/z): 178.1 [M+H$^+$].

C. 3,5-Dichloro-4-chloromethyl-pyridine $SOCl_2$ (2.3 mL, 32 mmol) was added dropwise to a stirred solution of (3,5-dichloropyridin-4-yl)-methanol (2.83 g, 15.9 mmol) in DCM (20 mL) over 10 min. After stirring for 35 min at room temperature, saturated aqueous $Na_2CO_3$ solution (40 mL) and DCM (60 mL) was added to the reaction mixture. The organic layer was dried over $Na_2SO_4$, filtered, and concentrated in vacuo. The residue was purified by flash chromatography on silica gel (elution with EA/hexane 1:4) to give the title compound. MS (m/z): 196.0 [M+H$^+$].

D. 8-(3,5-Dichloro-pyridin-4-ylmethoxy)-4-imidazol-1-yl-2-methyl-quinoline $Cs_2CO_3$ (59 mg, 0.18 mmol) was added to a vigorously stirred solution of 3,5-dichloro-4-chloromethyl-pyridine (48 mg, 0.25 mmol) and 4-imidazol-1-yl-2-methyl-quinolin-8-ol (20 mg, 89 µmol) in DMF (1 mL). After stirring for 18 h at room temperature, the solvent was removed in vacuo. The residue was purified by reversed phase HPLC using a gradient of acetonitrile in water with 0.1% TFA to give the title compound as the TFA salt. MS (m/z): 385.5 [M+H$^+$].

Example 2

Synthesis of N-[3,5-dichloro-4-(4-imidazol-1-yl-2-methyl-quinolin-8-yloxymethyl)-pyridin-2-yl]-N-methyl-acetamide A. 3,5-Dichloro-4-chloromethyl-pyridine 1-oxide To a solution of 3,5-dichloro-4-chloromethyl-pyridine (0.55 g, 2.8 mmol) in DCM (10 mL) 3-methyl-benzenecarboperoxoic acid (2.9 g, 16.8 mmol) was added. After stirring for 50 h at room temperature, saturated aqueous $Na_2CO_3$ solution (20 mL) and DCM (40 mL) were added to the reaction mixture. The organic layer was dried over $Na_2SO_4$, filtered, and concentrated in vacuo. The residue was purified by flash chromatography over silica gel (elution with EA/hexane 1:2) to give the title compound. MS (m/z): 214.2 [M+H$^+$].

B. N-(3,5-dichloro-4-chloromethyl-pyridin-2-yl)-N-methyl-acetamide

Oxalyl dichloride (45 µL, 0.47 mmol) was added dropwise to a solution of N-methylacetamide (36 µL, 0.47 mmol) and 2,6-dimethyl-pyridine (55 µL, 0.47 mmol) in anhydrous DCM (10 mL) at 0° C. After stirring for 20 min, 3,5-dichloro-4-chloromethyl-pyridine 1-oxide (10 mg, 0.047 mmol) was added to it and stirring was continued overnight at 45° C. Saturated aqueous $Na_2CO_3$ solution (20 mL) and DCM (40 mL) were added to the reaction mixture. The organic layer was dried over $Na_2SO_4$, filtered, and concentrated in vacuo. The residue was purified by flash chromatography over silica gel (elution with EA/hexane 1:3) to give the title compound. MS (m/z): 267.4 [M+H$^+$].

C. N-[3,5-dichloro-4-(4-imidazol-1-yl-2-methyl-quinolin-8-yloxymethyl)-pyridin-2-yl]-N-methyl-acetamide N-(3,5-dichloro-4-chloromethyl-pyridin-2-yl)-N-methyl-acetamide (48 mg, 0.18 mmol) was reacted with 4-imidazol-1-yl-2-methyl-quinolin-8-ol (20 mg, 89 µmol) according to the synthesis of 8-(3,5-dichloro-pyridin-4-ylmethoxy)-4-imidazol-1-yl-2-methyl-quinoline to give the title compound as the TFA salt. MS (m/z): 456.6 [M+H$^+$].

Example 9

Synthesis of N1-[3,5-dichloro-4-(4-imidazol-1-yl-2-methyl-quinolin-8-yloxymethyl)-pyridin-2-yl]-ethane-1,2-diamine A. 4-Imidazol-1-yl-2-methyl-8-(2,3,5-trichloro-pyridin-4-ylmethoxy)-quinoline A solution of 3,5-dichloro-4-chloromethyl-pyridine 1-oxide (0.93 g, 4.4 mmol) in $POCl_3$ (15 mL) was stirred at 100° C. overnight. After removal of the solvent in vacuo, saturated aqueous $Na_2CO_3$ solution (20 mL) and DCM (40 mL) was added to the reaction mixture. The organic layer was dried over $Na_2SO_4$, filtered, and concentrated in vacuo and the residue was used in the following step without further purification. 2,3,5-Trichloro-4-chloromethyl-pyridine (0.15 g, 0.67 mmol) was reacted with 4-imidazol-1-yl-2-methyl-quinolin-8-ol (0.10 g, 0.45 mmol) according to the synthesis of 8-(3,5-dichloro-pyridin-4-ylmethoxy)-4-imidazol-1-yl-2-methyl-quinoline to give the title compound as the TFA salt. MS (m/z): 421.4 [M+H$^+$].

B. N1-[3,5-dichloro-4-(4-imidazol-1-yl-2-methyl-quinolin-8-yloxymethyl)-pyridin-2-yl]-ethane-1,2-diamine 4-Imidazol-1-yl-2-methyl-8-(2,3,5-trichloro-pyridin-4-ylmethoxy)-quinoline (20 mg, 48 µM) was stirred in ethane-1,2-diamine (1 mL) at 100° C. for 1 h. At completion of the reaction, the solvent was removed in vacuo and the residue was purified by reversed phase HPLC to give the title compound as the TFA salt. MS (m/z): 443.4 [M+H$^+$].

Example 15

Synthesis of 8-(3,5-dichloro-2-methoxy-pyridin-4-ylmethoxy)-4-imidazol-1-yl-2-methyl-quinoline To a solution of 4-imidazol-1-yl-2-methyl-8-(2,3,5-trichloro-pyridin-4-ylmethoxy)-quinoline (10 mg, 24 µM) in anhydrous methanol (2 mL) sodium methanolate (13 mg, 0.24 mmol) was added. After stirring at 60° C. for 2 h, the solvent was removed in vacuo and the residue was purified by reversed phase HPLC to give the title compound as the TFA salt. MS (m/z): 415.2 [M+H$^+$].

Example 44

Synthesis of 8-(3,5-dichloro-pyridin-4-ylmethoxy)-5-fluoro-4-imidazol-1-yl-2-methyl-quinoline A. 5-Fluoro-8-methoxy-2-methyl-quinolin-4-ol A suspension of 5-fluoro-2-methoxy-phenylamine (3.3 g, 23 mmol), 3-oxo-butyric acid ethyl ester (3.0 g, 23 mmol), acetic acid (120 µL), and Drierite® (12.0 g) in ethanol (20 mL) was heated to reflux for 5 d. The reaction mixture was cooled to room temperature and filtered. The filtrate was concentrated in vacuo and purified by flash chromatography on silica gel (elution with EA/hexane 1:3) to give crude 3-(5-fluoro-2-methoxy-phenylamino)-but-2-enoic acid ethyl ester.

A solution of 3-(5-fluoro-2-methoxy-phenylamino)-but-2-enoic acid ethyl ester (1.8 g, 6.7 mmol) in diphenyl ether (10.7 mL) was heated to 250° C. for 25 min. The reaction mixture was cooled to room temperature, diluted with hexane, and filtered to give the title compound. MS (m/z): 208.1 [M+H$^+$].

B. 4-Chloro-5-fluoro-8-methoxy-2-methyl-quinoline

POCl$_3$ (3.4 mL, 36 mmol) was added dropwise to 5-fluoro-8-methoxy-2-methyl-quinolin-4-ol (0.56 g, 2.7 mmol) at 0° C. The reaction vessel was equipped with a drying tube containing P$_4$O$_{10}$ and heated to 118° C. for 2 h. The reaction mixture was concentrated in vacuo and partitioned between DCM (30 mL), water (2 mL), and concentrated aqueous NH$_3$ (2 mL). The organic layer was dried over Na$_2$SO$_4$, filtered, and concentrated in vacuo. The residue was purified by flash chromatography on silica gel (elution with EA/DCM 1:15) to give the title compound. MS (m/z): 226.5 [M+H$^+$]

C. 4-Chloro-5-fluoro-2-methyl-quinolin-8-ol

4-Chloro-5-fluoro-8-methoxy-2-methyl-quinoline (0.440 g, 1.95 mmol) was coevaporated in anhydrous toluene (2×15 mL). The residue was dissolved in anhydrous DCM (25 mL) and BBr$_3$ (1 M in DCM, 9.8 mL, 9.8 mmol) was added dropwise at –75° C. The reaction mixture was allowed to warm to room temperature over 3.5 h. The reaction mixture was then concentrated in vacuo and the residue was partitioned between DCM (10 mL) and water (7 mL). The pH of the aqueous layer was adjusted to 8 by the addition of saturated aqueous NaHCO$_3$ solution and the aqueous layer was extracted with DCM (2×30 mL). The combined organic layers were dried over Na$_2$SO$_4$, filtered, and concentrated in vacuo to give the title compound. MS (m/z): 212.3 [M+H$^+$].

D. 8-(3,5-dichloro-pyridin-4-ylmethoxy)-5-fluoro-4-imidazol-1-yl-2-methyl-quinoline 4-Chloro-5-fluoro-2-methyl-quinolin-8-ol (100 mg, 0.47 mmol) was reacted with imidazole according to the synthesis of 4-imidazol-1-yl-2-methyl-quinolin-8-ol. The resulting phenol was alkylated according to the synthesis of 8-(3,5-dichloro-pyridin-4-ylmethoxy)-4-imidazol-1-yl-2-methyl-quinoline to give the title compound as the TFA salt. MS (m/z): 403.6 [M+H$^+$].

Example 45

Synthesis of 8-(3,5-dichloro-pyridin-4-ylmethoxy)-2-methyl-4-(1-methyl-1H-imidazol-2-yl)-quinoline A. 4-Bromo-8-methoxy-2-methyl-quinoline 8-Methoxy-2-methyl-quinolin-4-ol (9.0 g, 48 mmol) and POBr$_3$ (53 g, 185 mmol) was placed in a round-bottomed flask, equipped with a drying tube containing P$_4$O$_{10}$. After stirring for 40 min at 120° C., the reaction mixture was cooled to room temperature and poured on ice. The mixture was then extracted with DCM (2×200 mL). The combined organic layers were dried over Na$_2$SO$_4$, filtered, and concentrated in vacuo. The residue was purified by flash chromatography on silica gel (elution with DCM/EA 10:1) to give the title compound. MS (m/z): 252.4 [M+H$^+$].

B. 4-Bromo-2-methyl-quinolin-8-ol

BBr$_3$ (1 M in DCM, 108 mL, 108 mmol) was added dropwise to a stirred solution of 4-bromo-8-methoxy-2-methyl-quinoline (7.8 g, 31 mmol) and triisopropyl-silane (6.2 mL, 31 mmol) in anhydrous DCM (300 mL) at –80° C. The reaction mixture was allowed to warm to room temperature over 4 h. The reaction mixture was then concentrated in vacuo and the residue was partitioned between DCM (300 mL), water (50 mL), and concentrated aqueous NH$_3$ (20 mL). The aqueous layer was extracted with DCM (2×300 mL). The combined organic layers were dried over Na$_2$SO$_4$, filtered, and concentrated in vacuo. The residue was purified by flash chromatography on silica gel (elution with DCM/EA 10:1) to give the title compound. MS (m/z): 238.3 [M+H$^+$].

C. 2-Methyl-4-(1-methyl-1H-imidazol-2-yl)-quinolin-8-ol n-Butyllithium (1.6 M in hexane, 6.0 mL, 9.7 mmol) was added dropwise to a stirred solution of 1-methyl-1H-imidazole (0.83 mL, 11 mmol) in anhydrous THF (60 mL) at –78° C. The reaction mixture was allowed to warm to –40° C. A solution of ZnCl$_2$ (3.9 g, 28 mmol) in anhydrous THF (28 mL) was than added dropwise at –40° C. The reaction mixture was allowed to reach room temperature and was then transferred to a suspension of Pd(PPh$_4$)$_4$ (340 mg, 0.29 mmol) and 4-bromo-2-methyl-quinolin-8-ol (1.0 g, 4.2 mmol) in anhydrous dioxane (20 mL). After stirring for 90 min at 80° C., the reaction mixture was cooled to room temperature, MeOH (5 mL) was added and the solvent was removed in vacuo. The residue was partitioned between DCM (150 mL) and water (50 mL). The pH of the aqueous layer was adjusted to 11 by addition of concentrated aqueous NH$_3$ solution and the aqueous layer was extracted with DCM (2×100 mL). The combined organic layers were dried over Na$_2$SO$_4$, filtered, and concentrated in vacuo. The residue was purified by flash chromatography on silica gel (elution with DCM/MeOH 20:1) to give the title compound. MS (m/z): 240.2 [M+H$^+$].

D. 8-(3,5-Dichloro-pyridin-4-ylmethoxy)-2-methyl-4-(1-methyl-1H-imidazol-2-yl)-quinoline 2-Methyl-4-(1-methyl-1H-imidazol-2-yl)-quinolin-8-ol (16 mg, 67 µmol) was alkylated according to the synthesis of 8-(3,5-dichloro-pyridin-4-ylmethoxy)-4-imidazol-1-yl-2-methylquinoline to give the title compound as the TFA salt. MS (m/z): 399.8 [M+H$^+$].

Example 50

Synthesis of 8-[3-chloro-5-(thiazol-2-ylsulfanyl)-pyridin-4-ylmethoxy]-2-methyl-4-(1-methyl-1H-imidazol-2-yl)-quinoline Cs$_2$CO$_3$ (0.22 g, 0.68 mmol) was added to a solution of 3,5-dichloro-pyridine-4-carbaldehyde (0.10 g, 0.57 mmol) and thiazole-2-thiol (0.10 g, 0.85 mmol) in THF (10 mL). After stirring at room temperature overnight, the solvent was removed in vacuo and saturated aqueous NaCl solution (20 mL) and EA (40 mL) were added to the reaction mixture. The organic layer was dried over Na$_2$SO$_4$, filtered, and concentrated in vacuo and the residue was used in the following step without further purification. The aldehyde group in 3-chloro-5-(thiazol-2-ylsulfanyl)-pyridine-4-carbaldehyde was reduced as described for the synthesis of (3,5-dichloro-pyridin-4-yl)-methanol to give [3-chloro-5-(thiazol-2-ylsulfanyl)-pyridin-4-yl]-methanol which was used in the following step without further purification. Conversion of [3-chloro-5-(thiazol-2-ylsulfanyl)-pyridin-4-yl]-methanol into 3-chloro-4-chloromethyl-5-(thiazol-2-ylsulfanyl)-pyridine according to the synthesis of 3,5-dichloro-4-chloromethyl-pyridine and subsequent reaction with 2-methyl-4-(1-methyl-1H-imidazol-2-yl)-quinolin-8-ol according to the synthesis of 8-(3,5-dichloro-pyridin-4-ylmethoxy)-4-imidazol-1-yl-2-methylquinoline yielded the title compound as the TFA salt. MS (m/z): 480.2 [M+H$^+$].

Example 69

Synthesis of 5-chloro-4-(4-imidazol-1-yl-2-methyl-quinolin-8-yloxymethyl)-nicotinic acid methyl ester A. 5-Chloro-4-(tetrahydro-pyran-2-yloxymethyl)-nicotinic acid methyl ester A mixture of 3,5-dichloro-4-(tetrahydro-pyran-2-yloxymethyl)-pyridine (400 mg, 1.533 mmol), triethylamine (278 µL, 1.993 mmol), (1,1'-bis(diphenylphosphino)ferrocene)-dichloropalladium(II)•DCM (PdCl$_2$(dppf)$_2$•DCM, 63 mg, 0.077 mmol) and 4 Å molecular sieves (600 mg) in MeOH (10 mL) was stirred at 120° C. for 5 h under an atmosphere of carbon monoxide (15 bar). The reaction was filtered and the solvent was removed in vacuo. The residue was purified by flash chromatography on silica gel (elution with mixtures of hexane/EA) to give the title compound. MS (m/z): 286.0 [M+H$^+$].

B. 5-Chloro-4-hydroxymethyl-nicotinic acid methyl ester p-Toluenesulfonic acid monohydrate (26.7 mg, 0.140 mmol) was added to a stirred solution of 5-chloro-4-(tetrahydro-pyran-2-yloxymethyl)-nicotinic acid methyl ester (20 mg, 0.070 mmol) in MeOH (4 mL). After stirring for 60 min at room temperature, the reaction mixture was concentrated in vacuo and the residue was partitioned between EA (10 mL) and saturated NaHCO$_3$ solution (10 mL). After extraction of the aqueous layer with DCM (2×10 mL) the combined organic layers were dried over Na$_2$SO$_4$, filtered, and concentrated in vacuo. The resulting title compound was used for the next reaction without purification. MS (m/z): 202.0 [M+H$^+$].

C. 5-Chloro-4-chloromethyl-nicotinic acid methyl ester

Polymer bound triphenylphosphine (3 mmol/g, 234 mg, 0.702 mmol) and CCl$_4$ (400 µL) were added to a stirred solution of 5-chloro-4-hydroxymethyl-nicotinic acid methyl ester (14.2 mg, 0.070 mmol) in DCM (4 mL). After stirring for 2 h at room temperature, the reaction mixture was filtered and concentrated in vacuo. The resulting title compound was used for the next reaction without purification. MS (m/z): 220.1 [M+H$^+$].

D. 5-Chloro-4-(4-imidazol-1-yl-2-methyl-quinolin-8-yloxymethyl)-nicotinic acid methyl ester 4-Imidazol-1-yl-2-methyl-quinolin-8-ol (19 mg, 0.084 mmol) was alkylated with 5-chloro-4-chloromethyl-nicotinic acid methyl ester (25 mg, 0.077 mmol) according to the synthesis of 8-(3,5-dichloro-pyridin-4-ylmethoxy)-4-imidazol-1-yl-2-methyl-quinoline for 3 d at RT. Purification by reversed phase HPLC using a gradient of acetonitrile in water with 0.1% TFA to give the title compound as the TFA salt. MS (m/z): 409.1 [M+H$^+$].

Example 70

Synthesis of 8-(3,5-dichloro-pyridin-4-ylmethoxy)-2-methyl-4-(5-methyl-thiazol-4-yl)-quinoline and 8-(3,5-dichloro-pyridin-4-ylmethoxy)-2-methyl-4-(5-methyl-thiazol-2-yl)-quinoline A. 4-Bromo-5-methyl-thiazole Br$_2$ (3.4 mL, 66 mmol) was added dropwise to a stirred solution of 5-methyl-thiazole (3.0 g, 30 mmol) in acetic acid at room temperature. After stirring for 3.5 h at room temperature, the reaction mixture was warmed to 50° C. After stirring for 2 d at 50° C., Br$_2$ (3.4 mL, 66 mmol) was added. After stirring for 4 d at 35° C., the reaction mixture was partitioned between DCM (150 mL) and concentrated aqueous NaCl (50 mL). The aqueous layer was extracted with DCM (150 mL). The combined organic layers were washed with aqueous Na$_2$CO$_3$ (1 M, 150 mL), aqueous sodium thiosulfate pentahydrate (1.2 M, 2×50 mL), dried over Na$_2$SO$_4$, filtered, and concentrated in vacuo. The residue was purified by flash chromatography on silica gel (elution with EA/hexane 1:10) to give the title compound. MS (m/z): 180.1 [M+H$^+$].

B. 2-Methyl-4-(5-methyl-thiazol-4-yl)-quinolin-8-ol and 2-methyl-4-(5-methyl-thiazol-2-yl)-quinolin-8-ol A solution of 4-bromo-5-methyl-thiazole (129 mg, 0.725 mmol) in anhydrous THF (2.0 mL) was added dropwise to a stirred solution of tert.-butyllithium (1.7 M in pentane, 1.28 mL, 2.17 mmol) in anhydrous THF (2.0 mL) at −95° C. The reaction mixture was allowed to warm to −40° C. A solution of ZnCl$_2$ (0.302 g, 2.21 mmol) in anhydrous THF (28 mL) was then added dropwise at −40° C. The reaction mixture was allowed to reach room temperature and was then transferred to a suspension of Pd(PPh$_4$)$_4$ (75 mg, 0.32 mmol) and 4-bromo-2-methyl-quinolin-8-ol (73 mg, 0.063 mmol) in anhydrous dioxane (1.5 mL). After stirring for 90 min at 80° C., the reaction mixture was cooled to room temperature, MeOH (1 mL) was added and the solvent was removed in vacuo. The residue was partitioned between DCM (30 mL) and water (5 mL). The pH of the aqueous layer was adjusted to 11 by the addition of concentrated aqueous NH$_3$ solution and the aqueous layer was extracted with DCM (2×20 mL) The combined organic layers were dried over Na$_2$SO$_4$, filtered, and concentrated in vacuo. The residue was purified by flash chromatography on silica gel (elution with DCM/MeOH 20:1) to give a mixture of the title compounds. MS (m/z): 257.2 [M+H$^+$].

C. 8-(3,5-Dichloro-pyridin-4-ylmethoxy)-2-methyl-4-(5-methyl-thiazol-4-yl)-quinoline and 8-(3,5-dichloro-pyridin-4-ylmethoxy)-2-methyl-4-(5-methyl-thiazol-2-yl)-quinoline A mixture of 2-methyl-4-(5-methyl-thiazol-4-yl)-quinolin-8-ol and 2-methyl-4-(5-methyl-thiazol-2-yl)-quinolin-8-ol (38 mg, 0.15 mmol) was alkyalted according to the synthesis of 8-(3,5-dichloro-pyridin-4-ylmethoxy)-4-imidazol- 1-yl-2-methyl-quinoline to give the pure title compounds as the TFA salt. MS (m/z): 416.1 [M+H$^+$].

Example 79

Synthesis of 8-(3,5-dichloro-pyridin-4-ylmethoxy)-2-methyl-4-(2H-pyrazol-3-yl)-quinoline A. 1-Benzyloxymethyl-1H-pyrazole Chloromethoxymethyl-benzene (purity ~60%, 2.0 mL, 14 mmol) was added dropwise to a stirred solution of 1H-pyrazole (1.93 g, 28.4 mmol) in DMF (10 mL) at 0° C. The reaction mixture was allowed to warm to room temperature and stirred for an additional 1.5 h. The reaction was then quenched by the addition of concentrated aqueous NH$_3$ (1 mL). The reaction mixture was concentrated in vacuo and the residue was purified by flash chromatography on silica gel (elution with DCM/MeOH 1:20) to give the title compound. MS (m/z): 189.0 [M+H$^+$].

B. 4-(2-Benzyloxymethyl-2H-pyrazol-3-yl)-8-(3,5-dichloro-pyridin-4-ylmethoxy)-2-methyl-quinoline 1-Benzyloxymethyl-1H-pyrazole (158 mg, 0.84 mmol) was reacted with 4-bromo-2-methyl-quinolin-8-ol (80 mg, 0.340 mmol) according to the synthesis of 2-methyl-4-(1-methyl-1H-imidazol-2-yl)-quinolin-8-ol. The resulting product was alkylated according to the synthesis of 8-(3,5-dichloro-pyridin-4-ylmethoxy)-4-imidazol-1-yl-2-methyl-quinoline to give the title compound as the TFA salt. MS (m/z): 505.84 [M+H$^+$].

C. 8-(3,5-Dichloro-pyridin-4-ylmethoxy)-2-methyl-4-(2H-pyrazol-3-yl)-quinoline

A solution of 4-(2-benzyloxymethyl-2H-pyrazol-3-yl)-8-(3,5-dichloro-pyridin-4-ylmethoxy)-2-methyl-quinoline TFA salt (10 mg) in TFA (1.35 mL) and DCM (0.15 mL) was stirred in a sealed reaction vessel at 80° C. for 2.5 h. The solvent was removed in vacuo and the residue was purified by reversed phase HPLC using a gradient of acetonitrile in water with 0.1% TFA to give the title compound as the TFA salt. MS (m/z): 385.0 [M+H$^+$].

Example 85

Synthesis of 8-(3,5-dichloro-pyridin-4-ylmethoxy)-2-methyl-4-(4-methyl-thiazol-5-yl)-quinoline A. 8-((3,5-Dichloropyridin-4-yl)methoxy)-2-methylquinolin-4-ylboronic acid A suspension of bis(pinacolato)diborane (0.77 g, 3.0 mmol), 4-bromo-8-(3,5-dichloropyridin-4-ylmethoxy)-2-methyl-quinoline (0.40 g, 1.0 mmol), potassium acetate (0.30 g, 3.0 mmol), and Pd(dppf)Cl$_2$ (82 mg, 0.10 mmol) in deoxygenated anhydrous DMSO (7 mL) was heated to 85° C. for 2 h. The solvent was then removed in vacuo and the residue was purified by reversed phase HPLC using a gradient of acetonitrile in water with 0.1% TFA to give the title compound as the TFA salt. MS (m/z): 362.9 [M+H$^+$].

B. 8-(3,5-Dichloro-pyridin-4-ylmethoxy)-2-methyl-4-(4-methyl-thiazol-5-yl)-quinoline A suspension of 8-(3,5-dichloropyridin-4-yl)methoxy)-2-methylquinolin-4-ylboronic acid TFA salt (14.6 mg), 5-bromo-4-methyl-thiazole (Takeda; Minato; Yakugaku Zasshi; 71; 1951; 1242; Chem. Abstr.; 1952; 5583) (6.0 mg, 24 µmol), Pd(PPh$_3$)$_4$ (2 mg, 2 µmol), and Na$_2$CO$_3$ (12 mg, 0.11 mmol) in deoxygenated dioxane (0.7 mL) and deoxygenated H$_2$O (70 µL) was stirred in a sealed reaction vessel at 100° C. for 22 h. The solvent was removed in vacuo and the residue was purified by reversed phase HPLC using a gradient of acetonitrile in water with 0.1% TFA to give the title compound as the TFA salt. MS (m/z): 416.4 [M+H$^+$].

Example 86

Synthesis of 3-{5-chloro-4-[2-methyl-4-(1-methyl-1H-imidazol-2-yl)-quinolin-8-yloxymethyl]-pyridin-3-yl}-propionic acid methyl ester A. (3-Bromo-5-chloro-pyridin-4-yl)-methanol A solution of LDA (7.94 mL, 1.8 M in THF/heptane/ethylbenzene, 14.3 mmol) in anhydrous THF (30 mL) at −78° C. under Ar was treated dropwise with a solution of 3-bromo-5-chloro-pyridine (2.5 g, 13.0 mmol) in anhydrous THF (30 mL) The solution was stirred at −78° C. for 30 min, then a solution of ethyl formate (10.46 mL, 130 mmol) in anhydrous THF (30 mL) was added dropwise. The resulting solution was stirred at −78° C. for 1.5 h and then treated with saturated NaHCO$_3$ with vigorous stirring. The quenched mixture was extracted with EA (2×25 mL) and the combined organic extracts were washed with saturated NaHCO$_3$ (15 mL) and dried over Na$_2$SO$_4$. The residue was purified by flash chromatography on silica gel with EA/hexane to provide 3-bromo-5-chloro-pyridine-4-carbaldehyde as a yellow solid. Reduction of the aldehyde according to the synthesis of (3,5-dichloro-pyridin-4-yl)-methanol yielded the title compound. MS (m/z): 224.0 [M+H$^+$].

B. 8-(3-Bromo-5-chloro-pyridin-4-ylmethoxy)-2-methyl-4-(1-methyl-1H-imidazol-2-yl)-quinoline Conversion of (3-bromo-5-chloro-pyridin-4-yl)-methanol into the corresponding chloride 3-bromo-5-chloro-4-chloromethyl-pyridine according to the synthesis of 3,5-dichloro-4-chloromethyl-pyridine, and subsequent reaction with 2-methyl-4-(1-methyl-1H-imidazol-2-yl)-quinolin-8-ol according to the synthesis of 8-(3,5-dichloro-pyridin-4-yl-methoxy)-4-imidazol-1-yl-2-methyl-quinoline yielded the title compound as the TFA salt. MS (m/z): 445.3 [M+H$^+$].

C. 3-{5-Chloro-4-[2-methyl-4-(1-methyl-1H-imidazol-2-yl)-quinolin-8-yloxymethyl]-pyridin-3-yl}-acrylic acid methyl ester To a solution of 8-(3-bromo-5-chloro-pyridin-4-ylmethoxy)-2-methyl-4-(1-methyl-1H-imidazol-2-yl)-quinoline (80 mg, 0.18 mmol) and acrylic acid methyl ester (0.30 g, 3.5 mmol) in DMF (3 mL) Pd(OAc)$_2$ (42 mg, 0.18 mmol) and tri-p-tolyl-phosphane (110 mg, 0.36 mmol) was added. Stirring of the solution at 90° C. for 10 h and subsequent HPLC purification yielded the title compound as the TFA salt. MS (m/z): 449.3 [M+H$^+$].

D. 3-{5-Chloro-4-[2-methyl-4-(1-methyl-1H-imidazol-2-yl)-quinolin-8-yloxymethyl]-pyridin-3-yl}-propionic acid methyl ester To a solution of 3-{5-chloro-4-[2-methyl-4-(1-methyl-1H-imidazol-2-yl)-quinolin-8-yloxymethyl]-pyridin-3-yl}- acrylic acid methyl ester (8.8 mg, 0.02 mmol) in MeOH (1 mL) NaBH₄ (7 mg, 0.08 mmol) was added. Stirring of the solution for 1 h at 30° C. and subsequent HPLC purification yielded the title compound as the TFA salt. MS (m/z): 451.3 [M+H⁺].

Example 87

Synthesis of 1-{5-chloro-4-[2-methyl-4-(1-methyl-1H-imidazol-2-yl)-quinolin-8-yloxymethyl]-pyridin-3-yl}-2-methoxy-ethanone A. 3-Bromo-5-chloro-4-(tetrahydro-pyran-2-yloxymethyl)-pyridine To (3-bromo-5-chloro-pyridin-4-yl)-methanol (2.8 g, 12.7 mmol) dissolved in anhydrous DCM (80 mL) 3,4-dihydro-2H-pyran (1.7 mL, 19.1 mmol) and p-TsOH monohydrate (2.9 g, 15.2 mmol) were added and the solution was stirred overnight at RT. The mixture was washed with saturated NaHCO₃ and the organic layer was separated and the aqueous solution extracted with DCM. The combined organic extracts were dried over Na₂SO₄ and concentrated. The residue was purified by flash chromatography on silica gel with EA/hexane to provide the title compound as a yellow oil. MS (m/z): 308.5 [M+H⁺].

B. 1-[5-Chloro-4-(tetrahydro-pyran-2-yloxymethyl)-pyridin-3-yl]-2-methoxy-ethanone 3-Bromo-5-chloro-4-(tetrahydro-pyran-2-yloxymethyl)-pyridine (0.30 g, 0.98 mmol) was dissolved in anhydrous THF (15 mL) under Ar and the solution was cooled to −78° C. n-BuLi (0.62 mL, 1.6 M in hexanes, 0.98 mmol) was added dropwise and the reaction mixture was stirred at −78° C. for 0.5 h. Then methoxy-acetic acid methyl ester (0.97 mL, 9.8 mmol) dissolved in anhydrous THF (10 mL) was added dropwise and stirring was continued at −78° C. for 2 h. At completion of the reaction, monitored by TLC, saturated NaHCO₃ was added with vigorous stirring. The quenched mixture was extracted with EA (2×20 mL) and the combined organic extracts were washed with saturated NaHCO₃ (20 mL) and dried over Na₂SO₄. The residue was purified by flash chromatography on silica gel with EA/hexane to provide the title compound as a colorless oil. MS (m/z): 300.5 [M+H⁺].

C. 1-(5-Chloro-4-hydroxymethyl-pyridin-3-yl)-2-methoxy-ethanone

To a solution of 1-[5-chloro-4-(tetrahydro-pyran-2-yloxymethyl)-pyridin-3-yl]-2-methoxy-ethanone (0.14 g, 0.46 mmol) in ethanol (15 mL) p-TsOH monohydrate was added. After stirring overnight at RT, solvent was evaporated and the residue was purified by flash chromatography on silica gel with EA/hexane to provide the title compound as a colourless oil. MS (m/z): 216.0 [M+H⁺].

D. 1-{5-Chloro-4-[2-methyl-4-(1-methyl-1H-imidazol-2-yl)-quinolin-8-yloxymethyl]-pyridin-3-yl}-2-methoxy-ethanone Conversion of 1-(5-chloro-4-hydroxymethyl-pyridin-3-yl)-2-methoxy-ethanone into the corresponding chloride 1-(5-chloro-4-chloromethyl-pyridin-3-yl)-2-methoxy-ethanone according to the synthesis of 3,5-dichloro-4-chloromethyl-pyridine, and subsequent reaction with 2-methyl-4-(1-methyl-1H-imidazol-2-yl)-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 437.2 [M+H⁺].

Example 91

Synthesis of 8-(3,5-Dichloro-pyridin-4-ylmethoxy)-2-fluoromethyl-4-(2-methyl-2H-pyrazol-3-yl)-quinoline A. 4-Bromo-2-fluoromethyl-quinolin-8-ol A solution of lithium diisopropylamide (1.8 M in THF, 0.70 mL, 1.3 mmol) in anhydrous THF (1.0 mL) was added dropwise to a stirred solution of 4-bromo-2-methyl-quinolin-8-ol (100 mg, 0.420 mmol) in anhydrous THF (1.0 mL) at −80° C. After stirring for 1 h at −80° C., a solution of N-fluorobenzenesulfonimide (331 mg, 1.05 mmol) in anhydrous THF (1 mL) was added dropwise at −100° C. The reaction mixture was allowed to warm to −20° C. and was then quenched by the addition of concentrated aqueous NH₄Cl (0.4 mL). The mixture was partitioned between DCM (30 mL) and water (5 mL). The aqueous layer was extracted with DCM (2×10 mL) and the combined organic layers were dried over Na₂SO₄, filtered, and concentrated in vacuo. The residue was purified by flash chromatography on silica gel (elution with DCM) to give the title compound. MS (m/z): 258.1 [M+H⁺].

B. 8-(3,5-Dichloro-pyridin-4-ylmethoxy)-2-fluoromethyl-4-(2-methyl-2H-pyrazol-3-yl)-quinoline Coupling of 1-methyl-1H-pyrazole (27 mg, 0.33 mmol) with 4-bromo-2-fluoromethyl-quinolin-8-ol (21 mg, 0.082 mmol) according to the synthesis of 2-methyl-4-(1-methyl-1H-imidazol-2-yl)-quinolin-8-ol, and subsequent alkylation according to the synthesis of 8-(3,5-dichloro-pyridin-4-ylmethoxy)-4-imidazol-1-yl-2-methyl-quinoline yielded the title compound as the TFA salt. MS (m/z): 417.4 [M+H⁺].

Example 94

Synthesis of 8-(3,5-dichloro-pyridin-4-ylmethoxy)-4-(2-fluoromethyl-2H-pyrazol-3-yl)-2-methyl-quinoline A. 1-Fluoromethyl-1H-pyrazole Diethylaminosulfur trifluoride (4.5 mL, 34 mmol) was added dropwise to a stirred solution of pyrazol-1-yl-methanol (3.34 g, 34.1 mmol) in anhydrous THF (67 mL) at −80° C. The reaction mixture was allowed to warm to room temperature and was then concentrated in vacuo. The residue was partitioned between DCM (100 mL) and water (30 mL). The pH of the aqueous layer was adjusted to 8 by the addition of solid NHCO₃. The organic layer was dried over Na₂SO₄, filtered, and concentrated in vacuo to give the title compound. MS (m/z): 101.0 [M+H⁺].

B. 8-(3,5-Dichloro-pyridin-4-ylmethoxy)-4-(2-fluoromethyl-2H-pyrazol-3-yl)-2-methyl-quinoline Coupling of 1-fluoromethyl-1H-pyrazole (79 mg, 0.79 mmol) with 4-bromo-2-fluoromethyl-quinolin-8-ol (75 mg, 0.32 mmol) according to the synthesis of 2-methyl-4-(1-methyl-1H-imidazol-2-yl)-quinolin-8-ol using lithium diisopropylamide (1.8 M in THF, 0.74 mL, 1.3 mmol) as the base, and subsequent alkylation according to the synthesis of 8-(3,5-dichloro-pyridin-4-ylmethoxy)-4-imidazol-1-yl-2-methyl-quinoline yielded the title compound as the TFA salt. MS (m/z): 417.0 [M+H$^+$].

Example 110

Synthesis of 8-[3-(1-butyl-1H-imidazol-2-ylsulfanyl)-5-chloro-pyridin-4-ylmethoxy]-2-methyl-4-(2-methyl-2H-pyrazol-3-yl)-quinoline A. 3-Chloro-5-(1H-imidazol-2-ylsulfanyl)-pyridine-4-carbaldehyde A mixture of 3,5-dichloro-pyridine-4-carbaldehyde (600 mg, 3.41 mmol), 1H-imidazole-2-thiol (341 mg, 3.41 mmol) and Cs$_2$CO$_3$ (1.33 g, 4.09 mmol) in THF (10 mL) was stirred at RT for 8.5 h. The solvent was removed in vacuo and the residue was partitioned between EA (30 mL) and brine (30 mL). After extraction of the aqueous layer with EA (2×30 mL) the combined organic layers were dried over Na$_2$SO$_4$, filtered, and concentrated in vacuo. The resulting title compound was used for the next reaction without purification. MS (m/z): 240.0 [M+H$^+$].

B. [3-Chloro-5-(1H-imidazol-2-ylsulfanyl)-pyridin-4-yl]-methanol

NaBH$_4$ (30.8 mg, 0.82 mmol) was added to a stirred solution of 3-chloro-5-(1H-imidazol-2-ylsulfanyl)-pyridine-4-carbaldehyde (130 mg, 0.54 mmol) in ethanol (4 mL). After stirring for 30 min at room temperature, the reaction mixture was concentrated in vacuo and the residue was purified by reversed phase HPLC using a gradient of acetonitrile in water with 0.1% TFA to give the title compound as the TFA salt. MS (m/z): 242.0 [M+H$^+$].

C. [3-(1-Butyl-1H-imidazol-2-ylsulfanyl)-5-chloro-pyridin-4-yl]-methanol

Under argon atmosphere sulfuric acid dibutyl ester (37.3 μL, 0.189 mmol) was added to a stirred solution of [3-chloro-5-(1H-imidazol-2-ylsulfanyl)-pyridin-4-yl]-methanol (65 mg, 0.270 mmol) and 1,8-diazabicyclo[5.4.0]undec-7-ene (DBU, 40.5 μL, 0.270 mmol) in DCM (6 mL) and DMF (1 mL). After stirring for 2.5 h at room temperature, the reaction mixture was concentrated in vacuo and the residue was purified by reversed phase HPLC using a gradient of acetonitrile in water with 0.1% TFA to give the title compound as the TFA salt. MS (m/z): 298.2 [M+H$^+$].

D. 3-(1-Butyl-1H-imidazol-2-ylsulfanyl)-5-chloro-4-chloromethyl-pyridine

SOCl$_2$ (27 μL, 0.37 mmol) was added dropwise to a stirred solution of [3-(1-butyl-1H-imidazol-2-ylsulfanyl)-5-chloro-pyridin-4-yl]-methanol (22 mg, 0.74 mmol) in DCM (4 mL). After stirring for 1 h at room temperature, saturated aqueous Na$_2$CO$_3$ solution (5 mL) and DCM (5 mL) was added to the reaction mixture. The organic layer was dried over Na$_2$SO$_4$, filtered, and concentrated in vacuo. The resulting title compound was used for the next reaction without purification. MS (m/z): 316.1 [M+H$^+$].

E. 8-[3-(1-Butyl-1H-imidazol-2-ylsulfanyl)-5-chloro-pyridin-4-ylmethoxy]-2-methyl-4-(2-methyl-2H-pyrazol-3-yl)-quinoline Cs$_2$CO$_3$ (26.5 mg, 0.081 mmol) was added to a vigorously stirred solution of 3-(1-butyl-1H-imidazol-2-ylsulfanyl)-5-chloro-4-chloromethyl-pyridine (21.5 mg, 0.068 mmol) and 2-methyl-4-(2-methyl-2H-pyrazol-3-yl)-quinolin-8-ol (17.6 mg, 0.074 mmol) in DMF (1 mL). After stirring for 1 h at room temperature the solvent was removed in vacuo. The residue was purified by reversed phase HPLC using a gradient of acetonitrile in water with 0.1% TFA to give the title compound as the TFA salt. MS (m/z): 519.1 [M+H$^+$].

Example 122

Synthesis of 3-[5-chloro-4-(4-imidazol-1-yl-2-methyl-quinolin-8-yloxymethyl)-pyridin-3-yl]-N,N-dimethyl-propionamide A. 8-(3-Bromo-5-chloro-pyridin-4-ylmethoxy)-4-imidazol-1-yl-2-methyl-quinoline Reaction of 3-bromo-5-chloro-4-chloromethyl-pyridine with 4-imidazol-1-yl-2-methyl-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 431.3 [M+H$^+$].

B. 3-[5-Chloro-4-(4-imidazol-1-yl-2-methyl-quinolin-8-yloxymethyl)-pyridin-3-yl]-N,N-dimethyl-acrylamide Reaction of 8-(3-bromo-5-chloro-pyridin-4-ylmethoxy)-4-imidazol-1-yl-2-methyl-quinoline (10 mg, 0.023 mmol) with N,N-dimethyl-acrylamide (46 mg, 0.46 mmol) according to the synthesis of (3-{5-chloro-4-[2-methyl-4-(1-methyl-1H-imidazol-2-yl)-quinolin-8-yloxymethyl]-pyridin-3-yl}-acrylic acid methyl ester yielded the title compound as the TFA salt. MS (m/z): 448.6 [M+H$^+$].

C. 3-[5-Chloro-4-(4-imidazol-1-yl-2-methyl-quinolin-8-yloxymethyl)-pyridin-3-yl]-N,N-dimethyl-propionamide Reduction of the vinyl group in 3-[5-chloro-4-(4-imidazol-1-yl-2-methyl-quinolin-8-yloxymethyl)-pyridin-3-yl]-N,N-dimethyl-acrylamide (7.4 mg, 0.017 mmol) with NaBH$_4$ (2 spatula amounts) according to the synthesis of 3-{5-chloro-4-[2-methyl-4-(1-methyl-1H-imidazol-2-yl)-quinolin-8-yloxymethyl]-pyridin-3-yl}-propionic acid methyl ester yielded the title compound as the TFA salt. MS (m/z): 450.4 [M+H$^+$].

Example 126

Synthesis of 8-[3-chloro-5-(2-methanesulfonyl-ethyl)-pyridin-4-ylmethoxy]-2-methyl-4-(2-methyl-2H-pyrazol-3-yl)-quinoline A. 8-(3-Bromo-5-chloro-pyridin-4-ylmethoxy)-2-methyl-4-(2-methyl-2H-pyrazol-3-yl)-quinoline Reaction of 3-bromo-5-chloro-4-chloromethyl-pyridine with 2-methyl-4-(2-methyl-2H-pyrazol-3-yl)-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 445.2 [M+H$^+$].

B. 8-[3-Chloro-5-(2-methanesulfonyl-vinyl)-pyridin-4-ylmethoxy]-2-methyl-4-(2-methyl-2H-pyrazol-3-yl)-quinoline Reaction of 8-(3-bromo-5-chloro-pyridin-4-ylmethoxy)-2-methyl-4-(2-methyl-2H-pyrazol-3-yl)-quinoline (15 mg, 0.034 mmol) with methanesulfonyl-ethene (59.2 mL, 0.68 mmol) according to the synthesis of (3-{5-chloro-4-[2-methyl-4-(1-methyl-1H-imidazol-2-yl)-quinolin-8-yloxymethyl]-pyridin-3-yl}-acrylic acid methyl ester yielded the title compound as the TFA salt. MS (m/z): 469.2 [M+H$^+$].

C. 8-[3-Chloro-5-(2-methanesulfonyl-ethyl)-pyridin-4-ylmethoxy]-2-methyl-4-(2-methyl-2H-pyrazol-3-yl)-quinoline Reduction of the vinyl group in 8-[3-chloro-5-(2-methanesulfonyl-vinyl)-pyridin-4-ylmethoxy]-2-methyl-4-(2-methyl-2H-pyrazol-3-yl)-quinoline (6.6 mg, 0.014 mmol NaBH$_4$ (5.3 mg, 0.14 mmol) according to the synthesis of 3-{5-chloro-4-[2-methyl-4-(1-methyl-1H-imidazol-2-yl)-quinolin-8-yloxymethyl]-pyridin-3-yl}-propionic acid methyl ester yielded the title compound as the TFA salt. MS (m/z): 471.3 [M+H$^+$].

Example 138

Synthesis of 8-(3-chloro-5-methoxymethyl-pyridin-4-ylmethoxy)-4-imidazol-1-yl-2-methyl-quinoline A. 5-Chloro-4-(tetrahydro-pyran-2-yloxymethyl)-pyridine-3-carbaldehyde Reaction of 3-bromo-5-chloro-4-(tetrahydro-pyran-2-yloxymethyl)-pyridine (0.36 g, 1.0 mmol) with formic acid ethyl ester (1.6 mL, 20 mmol) according to the synthesis of 1-[5-chloro-4-(tetrahydro-pyran-2-yloxymethyl)-pyridin-3-yl]-2-methoxy-ethanone yielded the title compound. MS (m/z): 256.0 [M+H$^+$].

B. [5-Chloro-4-(tetrahydro-pyran-2-yloxymethyl)-pyridin-3-yl]-methanol

Reduction of the aldehyde group in 5-chloro-4-(tetrahydro-pyran-2-yloxymethyl)-pyridine-3-carbaldehyde according to the synthesis of (3,5-dichloro-pyridin-4-yl)-methanol yielded the title compound. MS (m/z): 258.2 [M+H$^+$].

C. (3-Chloro-5-methoxymethyl-pyridin-4-yl)-methanol

To a solution of [5-chloro-4-(tetrahydro-pyran-2-yloxymethyl)-pyridin-3-yl]-methanol (39 mg, 0.15 mmol) in DMF (1.5 mL) NaH (7 mg, 0.16 mmol) and iodomethane (14.2 µL, 0.22 mmol) were added at 0° C. and stirring was continued overnight at RT. HPLC purification and subsequent deprotection of the tetrahydropyranyl group by stirring 3-chloro-5-methoxymethyl-4-(tetrahydro-pyran-2-yloxymethyl)-pyridine for 3 h in the ACN/H$_2$O solution coming from HPLC yielded the title compound as TFA salt. MS (m/z): 188.3 [M+H$^+$].

D. 8-(3-Chloro-5-methoxymethyl-pyridin-4-ylmethoxy)-4-imidazol-1-yl-2-methyl-quinoline Conversion of (3-chloro-5-methoxymethyl-pyridin-4-yl)-methanol into the corresponding chloride 3-chloro-4-chloromethyl-5-methoxymethyl-pyridine according to the synthesis of 3,5-dichloro-4-chloromethyl-pyridine, and subsequent reaction with 4-imidazol-1-yl-2-methyl-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 395.2 [M+H$^+$].

Example 165

Synthesis of 2-{5-chloro-4-[2-methyl-4-(2-methyl-2H-pyrazol-3-yl)-quinolin-8-yloxymethyl]-1-oxy-pyridine-3-sulfinyl}-N,N-dimethyl-acetamide A. (3-Chloro-5-mercapto-pyridin-4-yl)-methanol Under argon atmosphere a mixture of 3,5-dichloro-pyridine-4-carbaldehyde (3.00 g, 17.05 mmol) and sodium hydrosulfide hydrate (flakes 70%, 1.37 g, 17.05 mmol) in DMF (20 mL) was stirred at 0° C. for 15 min. NaBH$_4$ (8.52 g, 17.05 mmol) was added. After 30 min at 0° C. the solution was filtered and the solvent was removed in vacuo. The resulting title compound was used for the next reaction without purification. MS (m/z): 176.0 [M+H$^+$].

B. 2-(5-Chloro-4-hydroxymethyl-pyridin-3-ylsulfanyl)-N,N-dimethyl-acetamide

NaHCO$_3$ (944 mg, 1.71 mmol) was added to a stirred solution of (3-chloro-5-mercapto-pyridin-4-yl)-methanol (300 mg, 1.71 mmol) and 2-chloro-N,N-dimethyl-acetamide (176 µL, 1.71 mmol) in DMF (5 mL). After stirring for 15 min at room temperature the solvent was removed in vacuo. The residue was purified by reversed phase HPLC using a gradient of acetonitrile in water with 0.1% TFA to give the title compound as the TFA salt. MS (m/z): 260.9 [M+H$^+$].

C. 2-(5-Chloro-4-chloromethyl-pyridin-3-ylsulfanyl)-N,N-dimethyl-acetamide 2-(5-Chloro-4-hydroxymethyl-pyridin-3-ylsulfanyl)-N,N-dimethyl-acetamide (188 mg, 0.72 mmol) was chlorinated with SOCl$_2$ according to the synthesis of 3,5-dichloro-4-chloromethyl-pyridine and purified by reversed phase HPLC using a gradient of acetonitrile in water with 0.1% TFA to give the title compound as the TFA salt. MS (m/z): 279.3 [M+H$^+$].

D. 2-(5-Chloro-4-chloromethyl-1-oxy-pyridine-3-sulfinyl)-N,N-dimethyl-acetamide

H$_2$O$_2$ (30% solution, 576 mg, 5.64 mmol) was added to a stirred solution of 2-(5-chloro-4-chloromethyl-pyridin-3-yl-sulfanyl)-N,N-dimethyl-acetamide (56 mg, 0.201 mmol) in HOAc (10 mL). After stirring for 1 d at 50° C. the solvent was removed in vacuo. The residue was purified by reversed phase HPLC using a gradient of acetonitrile in water with 0.1% TFA to give the title compound as the TFA salt. MS (m/z): 310.9 [M+H$^+$].

E. 2-{5-Chloro-4-[2-methyl-4-(2-methyl-2H-pyrazol-3-yl)-quinolin-8-yloxymethyl]-1-oxy-pyridine-3-sulfinyl}-N,N-dimethyl-acetamide 2-(5-Chloro-4-chloromethyl-1-oxy-pyridine-3-sulfinyl)-N,N-dimethyl-acetamide (6.2 mg, 0.020 mmol) was alkylated with 2-methyl-4-(2-methyl-2H-pyrazol-3-yl)-quinolin-8-ol (6.2 mg, 0.026 mmol) according to the synthesis of 8-(3,5-dichloro-pyridin-4-ylmethoxy)-4-imidazol-1-yl-2-methyl-quinoline to give the title compound as the TFA salt. MS (m/z): 514.0 [M+H$^+$].

Example 166

Synthesis of 8-[3-chloro-5-(thiazol-2-ylsulfanyl)-pyridin-4-ylmethoxy]-4-isopropyl-2-methyl-quinoline

A. 4-Isopropyl-2-methyl-quinolin-8-ol

A solution of $ZnCl_2$ (0.29 g, 2.1 mmol) in anhydrous THF (2.1 mL) was added dropwise to a stirred solution of isopropyllithium (0.7 M in pentane, 1.6 mL, 1.1 mmol) at −92° C. The reaction mixture was allowed to reach room temperature and was than transferred to a suspension of dichloro(1,2-bis (diphenylphosphino)ethane)palladium (II) (36 mg, 0.063 mmol) and 4-bromo-2-methyl-quinolin-8-ol (75 mg, 0.32 mmol) in anhydrous dioxane (1.1 mL). After stirring for 2 h at 80° C., the reaction mixture was cooled to room temperature, MeOH (5 mL) was added and the solvent was removed in vacuo. The residue was purified by flash chromatography on silica gel (elution with DCM/MeOH 20:1) to give the title compound. MS (m/z): 202.2 [M+H$^+$].

B. 8-[3-Chloro-5-(thiazol-2-ylsulfanyl)-pyridin-4-ylmethoxy]-4-isopropyl-2-methyl-quinoline 4-Isopropyl-2-methyl-quinolin-8-ol (25 mg, 0.12 mmol) was alkylated with 3-chloro-4-chloromethyl-5-(thiazol-2-ylsulfanyl)-pyridine (24 mg, 0.087 mmol) according to the synthesis of 8-(3,5-dichloro-pyridin-4-ylmethoxy)-4-imidazol-1-yl-2-methyl-quinoline to give the title compound as the TFA salt. MS (m/z): 442.1 [M+H$^+$].

Example 167

Synthesis of 8-[2-chloro-4-(thiazol-2-ylsulfanyl)-pyridin-3-ylmethoxy]-4-imidazol-1-yl-2-methyl-quinoline

A. 2-Chloro-4-(thiazol-2-ylsulfanyl)-pyridine-3-carbaldehyde

Introduction of the formyl group in 2,4-dichloro-pyridine according to the synthesis of 3-bromo-5-chloro-pyridine-4-carbaldehyde and subsequent reaction with thiazole-2-thiol according to the synthesis of 3-chloro-5-(thiazol-2-ylsulfanyl)-pyridine-4-carbaldehyde yielded the title compound. MS (m/z): 257.2 [H+H$^+$].

B. [2-Chloro-4-(thiazol-2-ylsulfanyl)-pyridin-3-yl]-methanol

The aldehyde group in 2-chloro-4-(thiazol-2-ylsulfanyl)-pyridine-3-carbaldehyde was reduced as described for the synthesis of (3,5-dichloro-pyridin-4-yl)-methanol to give the title compound which was used in the following step without further purification. MS (m/z): 259.2 [M+H$^+$].

C. 8-[2-Chloro-4-(thiazol-2-ylsulfanyl)-pyridin-3-ylmethoxy]-4-imidazol-1-yl-2-methyl-quinoline Conversion of [2-chloro-4-(thiazol-2-ylsulfanyl)-pyridin-3-yl]-methanol into the corresponding chloride 2-chloro-3-chloromethyl-4-(thiazol-2-ylsulfanyl)-pyridine according to the synthesis of 3,5-dichloro-4-chloromethyl-pyridine and subsequent reaction with 4-imidazol-1-yl-2-methyl-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 466.0 [M+H$^+$].

Example 171

Synthesis of 2-{5-chloro-4-[2-methyl-4-(2-methyl-2H-pyrazol-3-yl)-quinolin-8-yloxymethyl]-pyridin-3-ylsulfanyl}-N-isopropyl-N-methyl-acetamide

A. Bromo-acetic acid 2,4-dinitro-phenyl ester

Under argon atmosphere bromo-acetyl bromide (2.67 mL, 30.66 mmol) dissolved in DCM (15 mL) was added within 15 min to a mixture of 2,4-dinitro-phenol (5.13 g, 27.88 mmol) and pyridine (2.92 mL, 36.24 mmol) in DCM (40 mL) at 0° C. After 1 h at RT, aqueous citric acid solution (10%, 30 mL) was added to the reaction mixture. The organic layer was dried over $Na_2SO_4$, filtered, and concentrated in vacuo. The resulting residue recrystallized from diethyl ether (75 mL) to afford the title compound.

B. 2-Bromo-N-isopropyl-N-methyl-acetamide

Isopropyl-methyl-amine (154 µL, 1.48 mmol) was added to a stirred solution of bromo-acetic acid 2,4-dinitro-phenyl ester (450 mg, 1.48 mmol) in DCM (4 mL). After stirring for 3 h at room temperature the organic layer was extracted twice with 0.1 M NaOH solution (30 mL). The organic layer was dried over $Na_2SO_4$, filtered, and concentrated in vacuo. The resulting title compound was used for the next reaction without purification. MS (m/z): 194.0 [M+H$^+$].

C. 2-(5-Chloro-4-hydroxymethyl-pyridin-3-ylsulfanyl)-N-isopropyl-N-methyl-acetamide (3-Chloro-5-mercapto-pyridin-4-yl)-methanol (145 mg, 0.83 mmol) was alkylated by 2-bromo-N-isopropyl-N-methyl-acetamide (160 mg, 0.83 mmol) according to the synthesis of 2-(5-chloro-4-hydroxymethyl-pyridin-3-ylsulfanyl)-N,N-dimethyl-acetamide to give the title compound as the TFA salt. MS (m/z): 289.0 [M+H$^+$].

D. 2-(5-Chloro-4-chloromethyl-pyridin-3-ylsulfanyl)-N-isopropyl-N-methyl-acetamide 2-(5-Chloro-4-hydroxymethyl-pyridin-3-ylsulfanyl)-N-isopropyl-N-methyl-acetamide (7.5 mg, 0.026 mmol) was chlorinated with $SOCl_2$ according to the synthesis of 3,5-dichloro-4-chloromethyl-pyridine to give the title compound. MS (m/z): 307.0 [M+H$^+$].

E. 2-{5-Chloro-4-[2-methyl-4-(2-methyl-2H-pyrazol-3-yl)-quinolin-8-yloxymethyl]-pyridin-3-ylsulfanyl}-N-isopropyl-N-methyl-acetamide 2-Methyl-4-(2-methyl-2H-pyrazol-3-yl)-quinolin-8-ol (5.86 mg, 0.025 mmol) was alkylated with 2-(5-chloro-4-chloromethyl-pyridin-3-ylsulfanyl)-N-isopropyl-N-methyl-acetamide (7.5 mg, 0.024 mmol) according to the synthesis of 8-(3,5-dichloro-pyridin-4-ylmethoxy)-4-imidazol-1-yl-2-methyl-quinoline to give the title compound as the TFA salt. MS (m/z): 510.2 [M+H$^+$].

Example 193

Synthesis of N-{5-chloro-4-[2-methyl-4-(2-methyl-2H-pyrazol-3-yl)-quinolin-8-yloxymethyl]-pyridin-3-ylmethyl}-isobutyramide

A. 3-Azidomethyl-5-chloro-4-(tetrahydro-pyran-2-yloxymethyl)-pyridine

A solution of [5-chloro-4-(tetrahydro-pyran-2-yloxymethyl)-pyridin-3-yl]-methanol (1.3 g, 4.9 mmol), phosphorazidic acid diphenyl ester (1.4 mL, 6.4 mmol) and 2,3,4,6,7,8,9,10-octahydro-pyrimido[1,2-a]azepine (0.96 mL, 6.4 mmol) in toluene (0.15 mL) was stirred at RT overnight. Solvents were concentrated in vacuo and the residue was partitioned between DCM (10 mL) and saturated NaCl solution (10 mL). After extraction of the aqueous layer with DCM (2×10 mL) the combined organic layers were dried over $Na_2SO_4$, filtered, and concentrated in vacuo. The residue was purified by flash chromatography on silica gel (elution with hexanes/EA 3:1) to give the title compound. MS (m/z): 282.9 $[M+H^+]$.

B. C-[5-Chloro-4-(tetrahydro-pyran-2-yloxymethyl)-pyridin-3-yl]-methylamine

A solution of 3-azidomethyl-5-chloro-4-(tetrahydro-pyran-2-yloxymethyl)-pyridine (0.46 g, 1.6 mmol) and triphenylphosphine (0.43 g, 1.6 mmol) in THF (15 mL) and $H_2O$ (0.15 mL) was stirred at RT overnight. Solvents were concentrated in vacuo and the residue was partitioned between DCM (10 mL) and saturated $NaHCO_3$ solution (10 mL). After extraction of the aqueous layer with DCM (2×10 mL) the combined organic layers were dried over $Na_2SO_4$, filtered, and concentrated in vacuo. The resulting title compound was used for the next reaction without purification. MS (m/z): 256.8 $[M+H^+]$.

C. N-[5-Chloro-4-(tetrahydro-pyran-2-yloxymethyl)-pyridin-3-ylmethyl]-isobutyramide To a solution of C-[5-chloro-4-(tetrahydro-pyran-2-yloxymethyl)-pyridin-3-yl]-methylamine (0.37 g, 1.4 mmol) in DCM (20 mL) DIPEA (0.41 mL, 2.2 mmol) and isobutyryl chloride (0.18 mL, 1.6 mmol) were added. Stirring was continued overnight at RT. The solvent was evaporated and the residue was used in the following step without further purification. MS (m/z): 326.9 $[M+H^+]$.

D. N-(5-Chloro-4-hydroxymethyl-pyridin-3-ylmethyl)-isobutyramide

Deprotection of the tetrahydropyranyl group in N-[5-chloro-4-(tetrahydro-pyran-2-yloxymethyl)-pyridin-3-ylmethyl]-isobutyramide according to the synthesis of 1-(5-chloro-4-hydroxymethyl-pyridin-3-yl)-2-methoxy-ethanone yielded the title compound. MS (m/z): 243.0 $[M+H^+]$.

E. N-{5-Chloro-4-[2-methyl-4-(2-methyl-2H-pyrazol-3-yl)-quinolin-8-yloxymethyl]-pyridin-3-ylmethyl}-isobutyramide Conversion of N-(5-chloro-4-hydroxymethyl-pyridin-3-ylmethyl)-isobutyramide into the corresponding chloride N-(5-chloro-4-chloromethyl-pyridin-3-ylmethyl)-isobutyramide according to the synthesis of 3,5-dichloro-4-chloromethyl-pyridine and subsequent reaction with 2-methyl-4-(2-methyl-2H-pyrazol-3-yl)-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 464.1 $[M+H^+]$.

Example 179

Synthesis of 3-{5-chloro-4-[2-methyl-4-(2-methyl-2H-pyrazol-3-yl)-quinolin-8-yloxymethyl]-pyridin-3-ylmethyl}-1,1-dimethyl-urea

A. C-{5-Chloro-4-[2-methyl-4-(2-methyl-2H-pyrazol-3-yl)-quinolin-8-yloxymethyl]-pyridin-3-yl}-methylamine Conversion of {5-chloro-4-[2-methyl-4-(2-methyl-2H-pyrazol-3-yl)-quinolin-8-yloxymethyl]-pyridin-3-yl}-methanol into the corresponding chloride according to the synthesis of 3,5-dichloro-4-chloromethyl-pyridine yielded the benzylchloride which was used in the following step without further purification. A solution of 8-(3-chloro-5-chloromethyl-pyridin-4-ylmethoxy)-2-methyl-4-(2-methyl-2H-pyrazol-3-yl)-quinoline (6.2 mg, 0.015 mmol) in a 2 M $NH_3$ in ethanol (0.3 mL) was stirred at 45° C. for 2 h. Solvents were evaporated to dryness and the residue was used in the following step without further purification. MS (m/z): 394.1 $[M+H^+]$.

B. 3-{5-chloro-4-[2-methyl-4-(2-methyl-2H-pyrazol-3-yl)-quinolin-8-yloxymethyl]-pyridin-3-ylmethyl}-1,1-dimethyl-urea To a solution of C-{5-chloro-4-[2-methyl-4-(2-methyl-2H-pyrazol-3-yl)-quinolin-8-yloxymethyl]-pyridin-3-yl}-methylamine (11 mg, 0.028 mmol) and DIPEA (9.4 µL, 0.056 mmol) in DCM (0.5 mL) dimethylcarbamyl chloride (5.1 µL, 0.056 mmol) was added and stirring was continued at RT for 2 h. Evaporation of the solvents and HPLC purification yielded the title compound as the TFA salt. MS (m/z): 465.0 $[M+H^+]$.

Example 181

Synthesis of N-{5-chloro-4-[2-methyl-4-(2-methyl-2H-pyrazol-3-yl)-quinolin-8-yloxymethyl]-pyridin-3-ylmethyl}-N-methyl-acetamide

A. (3-Chloro-5-methylaminomethyl-pyridin-4-yl)-methanol

A solution of 5-chloro-4-(tetrahydro-pyran-2-yloxymethyl)-pyridine-3-carbaldehyde (25 mg, 0.098 mmol) and methylamine (0.49 mL, 0.98 mmol) in methanol (1.5 mL) and acetic acid (0.25 mL) was stirred overnight at RT. $NaBH_3CN$ (6.8 mg, 0.1 mmol) was added and stirring was continued for 6 h. Solvents were evaporated and the residue was purified via HPLC. Subsequent deprotection of the tetrahydropyranyl group by stirring [5-chloro-4-(tetrahydro-pyran-2-yloxymethyl)-pyridin-3-ylmethyl]-methyl-amine for 3 h in the ACN/$H_2O$ solution coming from HPLC yielded the title compound as TFA salt. MS (m/z): 187.0 $[M+H^+]$.

B. N-(5-Chloro-4-hydroxymethyl-pyridin-3-ylmethyl)-N-methyl-acetamide

To a solution of (3-chloro-5-methylaminomethyl-pyridin-4-yl)-methanol (15 mg, 0.049 mmol) in methanol (0.5 mL)

acetic acid anhydride (46 mL, 0.49 mmol) was added and stirring was continued at RT for 5 h. Solvents were evaporated and the residue was used in the following step without further purification. MS (m/z): 228.9 [M+H$^+$].

C. N-{5-Chloro-4-[2-methyl-4-(2-methyl-2H-pyrazol-3-yl)-quinolin-8-yloxymethyl]-pyridin-3-ylmethyl}-N-methyl-acetamide Conversion of N-(5-chloro-4-hydroxymethyl-pyridin-3-ylmethyl)-N-methyl-acetamide into the corresponding chloride N-(5-chloro-4-chloromethyl-pyridin-3-ylmethyl)-N-methyl-acetamide according to the synthesis of 3,5-dichloro-4-chloromethyl-pyridine and subsequent reaction with 2-methyl-4-(2-methyl-2H-pyrazol-3-yl)-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 450.1 [M+H$^+$].

Example 183

Synthesis of dimethyl-carbamic acid 5-chloro-4-[2-methyl-4-(2-methyl-2H-pyrazol-3-yl)-quinolin-8-yloxymethyl]-pyridin-3-ylmethyl ester

A. Dimethyl-carbamic acid 5-chloro-4-(tetrahydro-pyran-2-yloxymethyl)-pyridin-3-ylmethyl ester To a solution of [5-chloro-4-(tetrahydro-pyran-2-yloxymethyl)-pyridin-3-yl]-methanol (0.11 g, 0.43 mmol) and NaH (17 mg, 0.86 mmol) in DMF (3 mL) dimethylcarbamyl chloride (0.39 µL, 2.15 mmol) was added and stirring was continued at RT overnight. Solvents were concentrated in vacuo and the residue was partitioned between EA (10 mL) and saturated NaCl solution (10 mL). After extraction of the aqueous layer with EA (2×10 mL) the combined organic layers were dried over Na$_2$SO$_4$, filtered, and concentrated in vacuo. The resulting title compound was used for the next reaction without purification. MS (m/z): 328.9 [M+H$^+$].

B. Dimethyl-carbamic acid 5-chloro-4-[2-methyl-4-(2-methyl-2H-pyrazol-3-yl)-quinolin-8-yloxymethyl]-pyridin-3-ylmethyl ester Simultaneous deprotection of the tetrahydropyranyl group and conversion of dimethyl-carbamic acid 5-chloro-4-hydroxymethyl-pyridin-3-ylmethyl ester into the corresponding chloride dimethyl-carbamic acid 5-chloro-4-chloromethyl-pyridin-3-ylmethyl ester according to the synthesis of 3,5-dichloro-4-chloromethyl-pyridine and subsequent reaction with 2-methyl-4-(2-methyl-2H-pyrazol-3-yl)-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 466.0 [M+H$^+$].

Example 192

Synthesis of acetic acid 1-{5-chloro-4-[2-methyl-4-(2-methyl-2H-pyrazol-3-yl)-quinolin-8-yloxymethyl]-pyridin-3-yl}-ethyl ester

A. 1-{5-Chloro-4-[2-methyl-4-(2-methyl-2H-pyrazol-3-yl)-quinolin-8-yloxymethyl]-pyridin-3-yl}-ethanone Reaction of 8-(3-bromo-5-chloro-pyridin-4-ylmethoxy)-2-methyl-4-(2-methyl-2H-pyrazol-3-yl)-quinoline (0.1 g, 0.22 mmol) with ethylvinylether (0.32 g, 4.5 mmol), according to the synthesis of {5-chloro-4-[2-methyl-4-(2-methyl-2H-pyrazol-3-yl)-quinolin-8-yloxymethyl]-pyridin-3-yl}-acetaldehyde yielded the title compound as the TFA salt. MS (m/z): 407.2 [M+H$^+$].

B. 1-{5-Chloro-4-[2-methyl-4-(2-methyl-2H-pyrazol-3-yl)-quinolin-8-yloxymethyl]-pyridin-3-yl}-ethanol Reduction of the ketone in 1-{5-chloro-4-[2-methyl-4-(2-methyl-2H-pyrazol-3-yl)-quinolin-8-yloxymethyl]-pyridin-3-yl}-ethanone according to the synthesis of (3,5-dichloro-pyridin-4-yl)-methanol yielded the title compound. MS (m/z): 409.0 [M+H$^+$].

C. Acetic acid 1-{5-chloro-4-[2-methyl-4-(2-methyl-2H-pyrazol-3-yl)-quinolin-8-yloxymethyl]-pyridin-3-yl}-ethyl ester Reaction of 1-{5-chloro-4-[2-methyl-4-(2-methyl-2H-pyrazol-3-yl)-quinolin-8-yloxymethyl]-pyridin-3-yl}-ethanol (5.8 mg, 0.014 mmol) with acetic acid anhydride (6.7 µL, 0.07 mmol) according to the synthesis of 5-chloro-4-(tetrahydro-pyran-2-yloxymethyl)-pyridin-3-ylmethyl ester and HPLC purification yielded the title compound as the TFA salt. MS (m/z): 451.0 [M+H$^+$].

Example 195

Synthesis of 8-[3-chloro-5-(pyridin-2-yloxy)-pyridin-4-ylmethoxy]-2-methyl-4-(2-methyl-2H-pyrazol-3-yl)-quinoline

A. 3-Chloro-5-(pyridin-2-yloxy)-pyridine

A mixture of 5-chloro-pyridin-3-ol (1000 mg, 7.72 mmol), potassium tert-butylate (866 mg, 7.72 mmol) and 2-chloro-pyridine (730 g, 7.72 mmol) in DMF (6 mL) was stirred at 130° C. for 3 h. The solvent was removed in vacuo and the residue was partitioned between DCM (50 mL) and 2 N NaOH solution (50 mL). After extraction of the aqueous layer with DCM (6×50 mL) the combined organic layers were dried over MgSO$_4$, filtered, and concentrated in vacuo. The residue was purified by flash chromatography on silica gel (elution with mixtures of hexane and EA) to give the title compound. MS (m/z): 207.2 [M+H$^+$].

B. 3-Chloro-5-(pyridin-2-yloxy)-pyridine-4-carbaldehyde

Under argon atmosphere 3-chloro-5-(pyridin-2-yloxy)-pyridine (169 mg, 0.82 mmol) in THF (5 mL) was added over 4 min to a stirred solution of lithium diisopropylamide (500 µL of 2 M solution in THF/heptane/ethylbenzene, 0.90 mmol) in THF (10 mL) at −90° C. After stirring for 30 min at −90° C. ethylformate (657 µL, 8.18 mmol) dissolved in THF (5 mL) was added at once. The reaction was stirred for 1.6 h at −90° C. and poured into an ice cold sat. solution of NaHCO$_3$ in water (100 mL). EA (100 mL) was added, the aqueous layer was extracted with EA (2×50 mL) and the combined organic layers were extracted with a sat. solution of NaHCO$_3$ in water (2×50 mL) and brine (3×50 mL). The organic layer was dried over MgSO$_4$, filtered, and concentrated in vacuo. The residue was purified by reversed phase HPLC using a gradient of acetonitrile in water with 0.1% TFA to give the title compound as the TFA salt. MS (m/z): 235.2 [M+H⁺].

C. [3-Chloro-5-(pyridin-2-yloxy)-pyridin-4-yl]-methanol

A mixture of 3-chloro-5-(pyridin-2-yloxy)-pyridine-4-carbaldehyde (83 mg, 0.36 mmol) and polymer bound sodium borohydride (184 mg, 2.0 mmol/g, 0.57 mmol) in DMF (1 mL) was stirred at RT for 30 min. The reaction was filtered and the solvent was removed in vacuo. The residue was purified by reversed phase HPLC using a gradient of acetonitrile in water with 0.1% TFA to give the title compound as the TFA salt. MS (m/z): 237.0 [M+H⁺].

D. 3-Chloro-4-chloromethyl-5-(pyridin-2-yloxy)-pyridine

[3-Chloro-5-(pyridin-2-yloxy)-pyridin-4-yl]-methanol (4.24 mg, 0.018 mmol) was chlorinated with SOCl₂ according to the synthesis of 3-(1-butyl-1H-imidazol-2-ylsulfanyl)-5-chloro-4-chloromethyl-pyridine to give the title compound. MS (m/z): 255.0 [M+H⁺].

E. 8-[3-Chloro-5-(pyridin-2-yloxy)-pyridin-4-ylmethoxy]-2-methyl-4-(2-methyl-2H-pyrazol-3-yl)-quinoline 2-Methyl-4-(2-methyl-2H-pyrazol-3-yl)-quinolin-8-ol (10.7 mg, 0.045 mmol) was alkylated with 3-chloro-4-chloromethyl-5-(pyridin-2-yloxy)-pyridine according to the synthesis of 8-[3-(1-butyl-1H-imidazol-2-ylsulfanyl)-5-chloro-pyridin-4-ylmethoxy]-2-methyl-4-(2-methyl-2H-pyrazol-3-yl)-quinoline to give the title compound as the TFA salt. MS (m/z): 458.0 [M+H⁺].

Example 196

Synthesis of 2-{5-chloro-4-[2-methyl-4-(2-methyl-2H-pyrazol-3-yl)-quinolin-8-yloxymethyl]-pyridin-3-yloxy}-N,N-dimethyl-acetamide

A. 3,5-Dichloro-4-(tetrahydro-pyran-2-yloxymethyl)-pyridine

Dihydropyrane (3.01 mL, 33.2 mmol) and p-toluenesulfonic acid monohydrate (5.06 g, 26.6 mmol) were added to a stirred solution of (3,5-dichloro-pyridin-4-yl)-methanol (1.97 g, 11.06 mmol) in DCM (40 mL). After stirring for 1 d at 40° C. the solvent was removed in vacuo and the residue was partitioned between DCM (50 mL) and saturated NaHCO₃ solution (50 mL). After extraction of the aqueous layer with DCM (2×50 mL) the combined organic layers were dried over Na₂SO₄, filtered, and concentrated in vacuo. The residue was purified by flash chromatography on silica gel (elution with mixtures of hexane and EA) to give the title compound. MS (m/z): 261.9 [M+H⁺].

B. 5-Chloro-4-(tetrahydro-pyran-2-yloxymethyl)-pyridin-3-ol

Potassium tert-butylate (1.77 g, 15.80 mmol) was added to a stirred solution of 3,5-dichloro-4-(tetrahydro-pyran-2-yloxymethyl)-pyridine (825 mg, 3.16 mmol) in dioxane. After stirring for 3 d at 100° C. the solvent was removed in vacuo. The resulting title compound was used for the next reaction without purification. MS (m/z): 243.8 [M+H⁺].

C. 2-(5-Chloro-4-hydroxymethyl-pyridin-3-yloxy)-N,N-dimethyl-acetamide

2-Chloro-N,N-dimethyl-acetamide (85 μL, 0.827 mmol) was added to a stirred solution of 5-chloro-4-(tetrahydro-pyran-2-yloxymethyl)-pyridin-3-ol (67 mg, 0.276 mmol) and Cs₂CO₃ (134.7 mg, 0.414 mmol) in THF (5 mL). After stirring for 1 d at 50° C. the solution was filtered and the solvent was removed in vacuo. The residue was purified by reversed phase HPLC using a gradient of acetonitrile in water with 0.1% TFA. Upon storage of the HPLC fractions for 3 h at RT the THP ether was cleaved to give the title compound as the TFA salt. MS (m/z): 243.8 [M+H⁺].

D. 2-(5-Chloro-4-chloromethyl-pyridin-3-yloxy)-N,N-dimethyl-acetamide 2-(5-Chloro-4-hydroxymethyl-pyridin-3-yloxy)-N,N-dimethyl-acetamide (4 mg, 0.016 mmol) was chlorinated with SOCl₂ according to the synthesis of 3,5-dichloro-4-chloromethyl-pyridine and purified by reversed phase HPLC using a gradient of acetonitrile in water with 0.1% TFA to give the title compound as the TFA salt. MS (m/z): 263.0 [M+H⁺].

E. 2-{5-Chloro-4-[2-methyl-4-(2-methyl-2H-pyrazol-3-yl)-quinolin-8-yloxymethyl]-pyridin-3-yloxy}-N,N-dimethyl-acetamide 4-Imidazol-1-yl-2-methyl-quinolin-8-ol (3.6 mg, 0.015 mmol) was alkylated with 2-(5-chloro-4-chloromethyl-pyridin-3-yloxy)-N,N-dimethyl-acetamide (3 mg, 0.011 mmol) according to the synthesis of 8-(3,5-dichloro-pyridin-4-ylmethoxy)-4-imidazol-1-yl-2-methyl-quinoline to give the title compound as the TFA salt. MS (m/z): 466.1 [M+H⁺].

Example 198

Synthesis of 8-[3-chloro-5-(tetrahydro-pyran-2-ylmethoxy)-pyridin-4-ylmethoxy]-2-methyl-4-(2-methyl-2H-pyrazol-3-yl)-quinoline

A. [3-Chloro-5-(tetrahydro-pyran-2-ylmethoxy)-pyridin-4-yl]-methanol

2-Bromomethyl-tetrahydro-pyran (98.1 μL, 0.766 mmol) was added to a stirred solution of 5-chloro-4-(tetrahydro-pyran-2-yloxymethyl)-pyridin-3-ol (23.3 mg, 0.096 mmol) and Cs₂CO₃ (249 mg, 0.764 mmol) in THF (5 mL). After stirring for 1 d at 120° C. the solution was filtered and the solvent was removed in vacuo. The residue was purified by reversed phase HPLC using a gradient of acetonitrile in water with 0.1% TFA. Upon storage of the HPLC fractions for 3 h at RT the THP ether was cleaved to give the title compound as the TFA salt. MS (m/z): 258.1 [M+H⁺].

B. 3-Chloro-4-chloromethyl-5-(tetrahydro-pyran-2-ylmethoxy)-pyridine

[3-Chloro-5-(tetrahydro-pyran-2-ylmethoxy)-pyridin-4-yl]-methanol (10 mg, 0.039 mmol) was chlorinated with SOCl₂ according to the synthesis of 3-(1-butyl-1H-imidazol-2-ylsulfanyl)-5-chloro-4-chloromethyl-pyridine. The result-

C. 8-[3-Chloro-5-(tetrahydro-pyran-2-ylmethoxy)-pyridin-4-ylmethoxy]-2-methyl-4-(2-methyl-2H-pyrazol-3-yl)-quinoline 4-Imidazol-1-yl-2-methyl-quinolin-8-ol (4 mg, 0.016 mmol) was alkylated with 3-chloro-4-chloromethyl-5-(tetrahydro-pyran-2-ylmethoxy)-pyridine (4 mg, 0.015 mmol) according to the synthesis of 8-[3-(1-butyl-1H-imidazol-2-ylsulfanyl)-5-chloro-pyridin-4-ylmethoxy]-2-methyl-4-(2-methyl-2H-pyrazol-3-yl)-quinoline (40° C. for 2 h). Purification by reversed phase HPLC using a gradient of acetonitrile in water with 0.1% TFA to give the title compound as the TFA salt. MS (m/z): 479.2 [M+H$^+$].

Example 205

Synthesis of 2-{5-Chloro-4-[2-methyl-4-(2-methyl-2H-pyrazol-3-yl)-quinolin-8-yloxymethyl]-pyridin-3-yl}-N,N-dimethyl-acetamide

A. {5-Chloro-4-[2-methyl-4-(2-methyl-2H-pyrazol-3-yl)-quinolin-8-yloxymethyl]-pyridin-3-yl}-acetaldehyde A solution of 8-(3-bromo-5-chloro-pyridin-4-ylmethoxy)-2-methyl-4-(2-methyl-2H-pyrazol-3-yl)-quinoline (0.1 g, 0.22 mmol), ethylvinylether (0.32 g, 4.5 mmol), palladium (II) acetate (15 mg, 0.067 mmol), tri-p-tolyl-phosphane (0.14 g, 0.45 mmol) and DIPEA (76 µL, 0.45 mmol) in DMF (3 mL) was stirred at 120° C. for 2 h. HPLC purification yielded the title compound as the TFA salt. MS (m/z): 407.2 [M+H$^+$].

B. {5-Chloro-4-[2-methyl-4-(2-methyl-2H-pyrazol-3-yl)-quinolin-8-yloxymethyl]-pyridin-3-yl}-acetic acid To a solution of {5-chloro-4-[2-methyl-4-(2-methyl-2H-pyrazol-3-yl)-quinolin-8-yloxymethyl]-pyridin-3-yl}-acetaldehyde (3.3 mg, 0.0081 mmol), 2,3 dimethyl-2-butene (3.4 mg, 0.040 mmol) and KH$_2$PO$_4$ (5.5 mg, 0.040 mmol) in t-butyl alcohol (2.5 mL) and H$_2$O (0.5 mL) NaClO$_2$ (3.6 mg, 0.040 mmol)) was added at 0° C. and stirring was continued at this temperature for 30 min. Evaporation of solvents and HPLC purification of the residue yielded the title compound as the TFA salt. MS (m/z): 423.1 [M+H$^+$].

C. 2-{5-Chloro-4-[2-methyl-4-(2-methyl-2H-pyrazol-3-yl)-quinolin-8-yloxymethyl]-pyridin-3-yl}-N,N-dimethyl-acetamide N,N'-diisopropylcarbodiimide (0.98 mg, 0.0078 mmol) was added to a solution of {5-chloro-4-[2-methyl-4-(2-methyl-2H-pyrazol-3-yl)-quinolin-8-yloxymethyl]-pyridin-3-yl}-acetic acid (2.2 mg, 0.0052 mmol), N-hydroxybenzotriazole (1.0 mg, 0.0078 mmol) and DIPEA (3.5 mg, 0.026 mmol) and stirring was continued at RT for 2 h. Evaporation of solvents and HPLC purification of the residue yielded the title compound as the TFA salt. MS (m/z): 450.0 [M+H$^+$].

Example 216

Synthesis of 2-chloro-8-(3,5-dichloro-pyridin-4-ylmethoxy)-4-(2-methyl-imidazol-1-yl)-quinoline

A. 2-Chloro-8-methoxy-4-(2-methyl-imidazol-1-yl)-quinoline

A mixture of 2,4-dichloro-8-methoxy-quinoline (0.20 g, 0.88 mmol) and 2-methyl-1H-imidazole (0.11 g, 1.3 mmol) in NMP (0.20 mL) was heated to 140° C. for 20 h. The solvent was removed in vacuo and the residue was purified by reversed phase HPLC using a gradient of acetonitrile in water with 0.1% TFA to give the title compound as the TFA salt. MS (m/z): 419.0 [M+H$^+$].

B. 2-Chloro-8-(3,5-dichloro-pyridin-4-ylmethoxy)-4-(2-methyl-imidazol-1-yl)-quinoline 2-Chloro-8-methoxy-4-(2-methyl-imidazol-1-yl)-quinoline TFA salt (50 mg) was demethylated according to the synthesis of 4-chloro-5-fluoro-2-methyl-quinolin-8-ol and subsequently alkylated according to the synthesis of of 8-(3,5-dichloro-pyridin-4-ylmethoxy)-4-imidazol-1-yl-2-methyl-quinoline to give the title compound as the TFA salt. MS (m/z): 403.6 [M+H$^+$].

Example 230

Synthesis of propane-2-sulfonic acid {5-chloro-4-[2-methyl-4-(2-methyl-2H-pyrazol-3-yl)-quinolin-8-yloxymethyl]-pyridin-3-ylmethyl}-methyl-amide

A. Propane-2-sulfonic acid (5-chloro-4-hydroxymethyl-pyridin-3-ylmethyl)-methyl-amide To a solution of [5-chloro-4-(tetrahydro-pyran-2-yloxymethyl)-pyridin-3-ylmethyl]-methyl-amine (57 mg, 0.21 mmol) in DCM (0.8 mL) and pyridine (0.4 mL) isopropylsulfonyl chloride (60 mg, 0.42 mmol) was added and stirring was continued at 50° C. overnight. Evaporation of the solvents, HPLC purification and subsequent deprotection of the tetrahydropyranyl group by stirring propane-2-sulfonic acid [5-chloro-4-(tetrahydro-pyran-2-yloxymethyl)-pyridin-3-ylmethyl]-methyl-amide for 3 h in the ACN/H$_2$O solution coming from HPLC yielded the title compound as TFA salt. MS (m/z): 292.9 [M+H$^+$].

B. Propane-2-sulfonic acid {5-chloro-4-[2-methyl-4-(2-methyl-2H-pyrazol-3-yl)-quinolin-8-yloxymethyl]-pyridin-3-ylmethyl}-methyl-amide Conversion of propane-2-sulfonic acid (5-chloro-4-hydroxymethyl-pyridin-3-ylmethyl)-methyl-amide into the corresponding chloride propane-2-sulfonic acid (5-chloro-4-chloromethyl-pyridin-3-ylmethyl)-methyl-amide according to the synthesis of 3,5-dichloro-4-chloromethyl-pyridine and subsequent reaction with 2-methyl-4-(2-methyl-2H-pyrazol-3-yl)-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 514.1 [M+H$^+$].

Example 240

Synthesis of {5-chloro-4-[2-methyl-4-(2-methyl-2H-pyrazol-3-yl)-quinolin-8-yloxymethyl]-pyridin-3-ylmethyl}-methyl-carbamic acid isopropyl ester

A. (5-Chloro-4-hydroxymethyl-pyridin-3-ylmethyl)-methyl-carbamic acid isopropyl ester To a solution of [5-chloro-4-(tetrahydro-pyran-2-yloxymethyl)-pyridin-3-ylmethyl]-methyl-amine (52 mg, 0.19 mmol) and DIPEA (65 µL, 0.38 mmol) in DCM (0.5 mL) a 1 M solution of isopropyl chloroformiate in toluene (0.19 mL) was added and stirring was continued at RT for 1 h. Evaporation of the solvents, HPLC purification and subsequent deprotection of the tetrahydropyranyl group by stirring [5-chloro-4-(tetrahydro-pyran-2-yloxymethyl)-pyridin-3-yl-methyl]-methyl-carbamic acid isopropyl ester for 3 h in the ACN/H$_2$O solution coming from HPLC yielded the title compound as TFA salt. MS (m/z): 272.9 [M+H$^+$].

B. {5-Chloro-4-[2-methyl-4-(2-methyl-2H-pyrazol-3-yl)-quinolin-8-yloxymethyl]-pyridin-3-ylmethyl}-methyl-carbamic acid isopropyl ester Conversion of (5-chloro-4-hydroxymethyl-pyridin-3-ylmethyl)-methyl-carbamic acid isopropyl ester into the corresponding chloride (5-chloro-4-chloromethyl-pyridin-3-ylmethyl)-methyl-carbamic acid isopropyl ester according to the synthesis of 3,5-dichloro-4-chloromethyl-pyridine and subsequent reaction with 2-methyl-4-(2-methyl-2H-pyrazol-3-yl)-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 494.1 [M+H$^+$].

Example 246

Synthesis of 3,5-dichloro-4-[2-methyl-4-(2-methyl-2H-pyrazol-3-yl)-quinolin-8-yloxymethyl]-pyridin-2-ylamine A. 3,5-Dichloro-4-(tetrahydro-pyran-2-yloxymethyl)-pyridine 1-oxide 3-Chloroperoxybenzoic acid (mCPBA, 1.32 g, 7.66 mmol) was added to a stirred solution of 3,5-Dichloro-4-(tetrahydro-pyran-2-yloxymethyl)-pyridine (200 mg, 0.766 mmol) in DCM (5 mL). After stirring for 3 h at RT the solvent was removed in vacuo and the residue was partitioned between DCM (50 mL) and 2 N NaOH solution (50 mL). After extraction of the organic layer with water (50 mL) the organic layer was dried over Na$_2$SO$_4$, filtered, and concentrated in vacuo. The resulting title compound was used for the next reaction without purification. MS (m/z): 278.0 [M+H$^+$].

B. (2-Amino-3,5-dichloro-pyridin-4-yl)-methanol

A mixture of 3,5-Dichloro-4-(tetrahydro-pyran-2-yloxymethyl)-pyridine 1-oxide (133 mg, 0.48 mmol) and p-toluenesulfonyl chloride (238 mg, 1.25 mmol) in pyridine (10 mL) was heated to 40° C. for 1 d. p-toluenesulfonyl chloride (92 mg, 0.48 mmol) was added and the solution was heated to 56° C. for 5 h. The solvent was removed in vacuo and the residue was dissolved in 2-amino-ethanol (5 mL). After stirring for 3 d at 40° C. the solvent was removed in vacuo and the residue was partitioned between DCM (20 mL) and a sat. solution of NaHCO$_3$ in water (20 mL). After extraction of the aqueous layer with DCM (2×20 mL) the organic layer was dried over Na$_2$SO$_4$, filtered, and concentrated in vacuo. The residue was purified by reversed phase HPLC using a gradient of acetonitrile in water with 0.1% TFA. Upon storage of the HPLC fractions for 3 h at RT the THP ether was cleaved to give the title compound as the TFA salt. MS (m/z): 193.1 [M+H$^+$].

C. 3,5-Dichloro-4-chloromethyl-pyridin-2-ylamine (2-Amino-3,5-dichloro-pyridin-4-yl)-methanol (7 mg, 0.036 mmol) was chlorinated with SOCl$_2$ according to the synthesis of 3,5-dichloro-4-chloromethyl-pyridine. The resulting title compound was used for the next reaction without purification. MS (m/z): 211.0 [M+H$^+$].

D. 3,5-Dichloro-4-[2-methyl-4-(2-methyl-2H-pyrazol-3-yl)-quinolin-8-yloxymethyl]-pyridin-2-ylamine 4-Imidazol-1-yl-2-methyl-quinolin-8-ol (8.7 mg, 0.036 mmol) was alkylated with 3,5-dichloro-4-chloromethyl-pyridin-2-ylamine (7.7 mg, 0.036 mmol) according to the synthesis of 8-(3,5-dichloro-pyridin-4-ylmethoxy)-4-imidazol-1-yl-2-methyl-quinoline at 50° C. for 1 d. Purification by reversed phase HPLC using a gradient of acetonitrile in water with 0.1% TFA yielded the title compound as the TFA salt. MS (m/z): 414.0 [M+H$^+$].

Example 247 and 248

Synthesis of dimethyl-carbamic acid 6-amino-5-chloro-4-[2-methyl-4-(2-methyl-2H-pyrazol-3-yl)-quinolin-8-yloxymethyl]-pyridin-3-ylmethyl ester and dimethyl-carbamic acid 2-amino-5-chloro-4-[2-methyl-4-(2-methyl-2H-pyrazol-3-yl)-quinolin-8-yloxymethyl]-pyridin-3-ylmethyl ester A. Dimethyl-carbamic acid 6-amino-5-chloro-4-(tetrahydro-pyran-2-yloxymethyl)-pyridin-3-ylmethyl ester and dimethyl-carbamic acid 2-amino-5-chloro-4-(tetrahydro-pyran-2-yloxymethyl)-pyridin-3-ylmethyl ester Dimethyl-carbamic acid 5-chloro-4-(tetrahydro-pyran-2-yloxymethyl)-pyridin-3-ylmethyl ester was converted to the N-oxide according to the synthesis of 3,5-dichloro-4-(tetrahydro-pyran-2-yloxymethyl)-pyridine 1-oxide. The resulting residue was reacted with p-toluenesulfonyl chloride and 2-amino-ethanol according to the synthesis of (2-amino-3,5-dichloro-pyridin-4-yl)-methanol with the exception that the reaction in 2-amino-ethanol was done at 40° C. for 2.5 h. The residue was purified by reversed phase HPLC using a gradient of acetonitrile in water with 0.1% TFA. Upon storage of the HPLC fractions for 3 h at RT the THP ether was cleaved. This gave the two title compounds as pure compounds in form of their TFA salts. MS (m/z): 259.9 [M+H$^+$] and MS (m/z): 259.9 [M+H$^+$].

B. Dimethyl-carbamic acid 6-amino-5-chloro-4-chloromethyl-pyridin-3-ylmethyl ester Dimethyl-carbamic acid 6-amino-5-chloro-4-hydroxymethyl-pyridin-3-ylmethyl ester (18.5 mg, 0.071 mmol) was chlorinated with SOCl$_2$ according to the synthesis of 3,5-dichloro-4-chloromethyl-pyridine. The resulting title compound was used for the next reaction without purification. MS (m/z): 278.0 [M+H$^+$].

C. Dimethyl-carbamic acid 2-amino-5-chloro-4-chloromethyl-pyridin-3-ylmethyl ester Dimethyl-carbamic acid 6-amino-5-chloro-4-hydroxymethyl-pyridin-3-ylmethyl ester (4 mg, 0.015 mmol) was chlorinated with SOCl$_2$ according to the synthesis of 3,5-dichloro-4-chloromethyl-pyridine. The resulting title compound was used for the next reaction without purification. MS (m/z): 277.9 [M+H$^+$].

D. Dimethyl-carbamic acid 6-amino-5-chloro-4-[2-methyl-4-(2-methyl-2H-pyrazol-3-yl)-quinolin-8-yloxymethyl]-pyridin-3-ylmethyl ester 4-Imidazol-1-yl-2-methyl-quinolin-8-ol (17.1 mg, 0.071 mmol) was alkylated with dimethyl-carbamic acid 6-amino-5-chloro-4-chloromethyl-pyridin-3-ylmethyl ester (19.7 mg, 0.071 mmol) according to the synthesis of 8-(3,5-dichloro-pyridin-4-ylmethoxy)-4-imidazol-1-yl-2-methyl-quinoline. Purification by reversed phase HPLC using a gradient of acetonitrile in water with 0.1% TFA to give the title compound as the TFA salt. MS (m/z): 480.9 [M+H$^+$].

E. Dimethyl-carbamic acid 2-amino-5-chloro-4-[2-methyl-4-(2-methyl-2H-pyrazol-3-yl)-quinolin-8-yloxymethyl]-pyridin-3-ylmethyl ester 4-Imidazol-1-yl-2-methyl-quinolin-8-ol (3.7 mg, 0.015 mmol) was alkylated with dimethyl-carbamic acid 2-amino-5-chloro-4-chloromethyl-pyridin-3-ylmethyl ester (4.2 mg, 0.015 mmol) according to the synthesis of 8-(3,5-dichloro-pyridin-4-ylmethoxy)-4-imidazol-1-yl-2-methyl-quinoline. Purification by reversed phase HPLC using a gradient of acetonitrile in water with 0.1% TFA to give the title compound as the TFA salt. MS (m/z): 480.9 [M+H$^+$].

Example 250

Synthesis of 8-(3,5-dichloro-pyridin-4-ylmethoxy)-4-(2-methoxy-thiazol-4-yl)-2-methyl-quinoline Under argon atmosphere a mixture of 4-bromo-8-(3,5-dichloro-pyridin-4-ylmethoxy)-2-methyl-quinoline (15 mg, 0.038 mmol), 2-methoxy-4-tributylstannanyl-thiazole (18.4 mg, 0.046 mmol) bis(tri-t-butylphosphine)palladium (0) (1 mg, 0.002 mmol) and CsF (12.7 mg, 0.083 mmol) in dioxane (2 mL) was heated to 100° C. for 1 d. The solvent was removed in vacuo and the residue was purified by reversed phase HPLC using a gradient of acetonitrile in water with 0.1% TFA to give the title compound as the TFA salt. MS (m/z): 431.9 [M+H$^+$].

Example 262

Synthesis of 1-{5-chloro-4-[2-methyl-4-(2-methyl-2H-pyrazol-3-yl)-quinolin-8-yloxymethyl]-pyridin-3-ylmethyl}-3-methyl-pyrrolidine-2,5-dione

A. N-(5-Chloro-4-hydroxymethyl-pyridin-3-ylmethyl)-3-methyl-succinamic acid methyl ester A mixture of C-[5-chloro-4-(tetrahydro-pyran-2-yloxymethyl)-pyridin-3-yl]-methylamine (15.3 mg, 0.060 mmol), HBTU (33.9 mg, 0.089 mmol), (R)-(+)-methylsuccinic acid 4-methyl ester (13.1 mg, 0.089 mg) and DIPEA (30.4 µL, 0.179 mmol) in DMF (0.50 mL) was stirred at RT for 1 d. The solvent was removed in vacuo and the residue was partitioned between DCM (2 mL) and an aqueous phosphate buffer solution (pH 7, 2 mL). After extraction of the aqueous layer with DCM (4×2 mL) the organic layer was dried over Na$_2$SO$_4$, filtered, and concentrated in vacuo. The residue was purified by reversed phase HPLC using a gradient of acetonitrile in water with 0.1% TFA. Upon storage of the HPLC fractions for 3 h at RT the THP ether was cleaved to give the title compound as the TFA salt. MS (m/z): 300.9 [M+H$^+$].

B. N-(5-Chloro-4-chloromethyl-pyridin-3-ylmethyl)-3-methyl-succinamic acid methyl ester N-(5-Chloro-4-hydroxymethyl-pyridin-3-ylmethyl)-3-methyl-succinamic acid methyl ester (1.39 mg, 0.0046 mmol) was chlorinated with SOCl$_2$ according to the synthesis of 3,5-dichloro-4-chloromethyl-pyridine. The resulting title compound was used for the next reaction without purification. MS (m/z): 318.9 [M+H$^+$].

C. 1-{5-Chloro-4-[2-methyl-4-(2-methyl-2H-pyrazol-3-yl)-quinolin-8-yloxymethyl]-pyridin-3-ylmethyl}-3-methyl-pyrrolidine-2,5-dione 4-Imidazol-1-yl-2-methyl-quinolin-8-ol (3.0 mg, 0.0125 mmol) was alkylated with N-(5-chloro-4-chloromethyl-pyridin-3-ylmethyl)-3-methyl-succinamic acid methyl ester (1.47 mg, 0.0046 mmol) according to the synthesis of 8-(3,5-dichloro-pyridin-4-ylmethoxy)-4-imidazol-1-yl-2-methyl-quinoline. After 1 d at RT purification by reversed phase HPLC using a gradient of acetonitrile in water with 0.1% TFA gave the title compound as the TFA salt. MS (m/z): 490.0 [M+H$^+$].

Example 278

Synthesis of 8-(3,5-dichloro-pyridin-4-ylmethoxy)-2-methyl-4-(5-trifluoromethyl-pyrazol-1-yl)-quinoline

A. 4-Hydrazino-2-methyl-quinolin-8-ol

A mixture of 4-chloro-2-methyl-quinolin-8-ol (0.10 g, 0.51 mmol) and hydrazine monohydrate (0.75 mL, 15 mmol) in dioxane (10 mL) was heated to reflux for 4 d. The solvent was removed in vacuo and the residue was purified by flash chromatography on silica gel (elution with DCM/methanol/conc. aqueous NH$_3$ 5:1:0.033) to give the title compound. MS (m/z): 190.1 [M+H$^+$].

B. 2-Methyl-4-(5-trifluoromethyl-pyrazol-1-yl)-quinolin-8-ol

A mixture of 4-hydrazino-2-methyl-quinolin-8-ol (21 mg, 0.11 mmol) and 4-ethoxy-1,1,1-trifluoro-but-3-en-2-one (16 µL, 0.11 mmol) in ethanol (0.5 mL) was heated to 75° C. for 30 min. The solvent was than removed in vacuo and the residue was redissolved in acetic acid (0.5 mL). After the addition of concentrated H$_2$SO$_4$ (20 µL) and stirring for 1 h at 100° C., the reaction mixture was cooled to room temperature and a mixture of Na$_2$CO$_3$ (0.40 mg, 3.8 mmol) in water (1 mL) was added. The reaction mixture was then concentrated in vacuo and the residue was partitioned between DCM (10 mL) and water (5 mL). The pH of the aqueous layer was adjusted to 10 by the addition of saturated aqueous NH$_3$ solution and the aqueous layer was extracted with DCM (1×320 mL). The combined organic layers were dried over Na$_2$SO$_4$, filtered, and concentrated in vacuo to give the title compound. MS (m/z): 294.2 [M+H$^+$].

C. 8-(3,5-dichloro-pyridin-4-ylmethoxy)-2-methyl-4-(5-trifluoromethyl-pyrazol-1-yl)-quinoline The 2-methyl-4-(5-trifluoromethyl-pyrazol-1-yl)-quinolin-8-ol (7.4 mg, 25 µmol) was alkylated according to the synthesis of 8-(3,5-dichloro-pyridin-4-ylmethoxy)-4-imidazol-1-yl-2-methyl-quinoline to give the title compound as the TFA salt. MS (m/z): 453.0 [M+H$^+$].

Example 281

Synthesis of N-{5-chloro-4-[2-methyl-4-(2-methyl-2H-pyrazol-3-yl)-quinolin-8-yloxymethyl]-pyridin-3-ylmethyl}-N-(2,3-dihydroxy-propyl)-isobutyramide A. [5-Chloro-4-(tetrahydro-pyran-2-yloxymethyl)-pyridin-3-ylmethyl]-(2,2-dimethyl-[1,3]dioxolan-4-ylmethyl)-amine Acetic acid (133 µL) and NaBH$_3$CN (14.8 mg, 0.235 mmol) were added to a stirred solution of 5-chloro-4-(tetrahydro-pyran-2-yloxymethyl)-pyridine-3-carbaldehyde (40 mg, 0.157 mmol) and 2,2-dimethyl-1,3-dioxolane-4-methanamine (203 µL, 1.57 mmol) in MeOH (1 mL). After stirring for 2 h at room temperature the solvent was removed in vacuo and the residue was partitioned between DCM (10 mL) and saturated NaHCO$_3$ solution (10 mL). After extraction of the aqueous layer with DCM (2×10 mL) the combined organic layers were dried over Na$_2$SO$_4$, filtered, and concentrated in vacuo. The resulting title compound was used for the next reaction without purification. MS (m/z): 370.9 [M+H$^+$].

B. N-(5-Chloro-4-hydroxymethyl-pyridin-3-ylmethyl)-N-(2,2-dimethyl-[1,3]dioxolan-4-ylmethyl)-isobutyramide and N-(5-chloro-4-hydroxymethyl-pyridin-3-ylmethyl)-N-(2,3-dihydroxy-propyl)-isobutyramide DIPEA (49.5 µL, 0.291 mmol) and isobutyryl chloride (21.4 µL, 0.204 mmol) were added to a stirred solution of [5-chloro-4-(tetrahydro-pyran-2-yloxymethyl)-pyridin-3-ylmethyl]-(2,2-dimethyl-[1,3]dioxolan-4-ylmethyl)-amine (54 mg, 0.146 mmol) in THF (3 mL). After stirring for 1 h at room temperature the solvent was removed in vacuo and the residue was purified by reversed phase HPLC using a gradient of acetonitrile in water with 0.1% TFA. Upon storage of the HPLC fractions for 3 h at RT the THP ether was cleaved and the dioxolane was partially cleaved. This gave a mixture of the two title compounds as their TFA salts. MS (m/z): 357.0 [M+H$^+$] and MS (m/z): 317.0 [M+H$^+$].

C. N-(5-Chloro-4-chloromethyl-pyridin-3-ylmethyl)-N-(2,2-dimethyl-[1,3]dioxolan-4-ylmethyl)-isobutyramide and N-(5-chloro-4-chloromethyl-pyridin-3-ylmethyl)-N-(2,3-dihydroxy-propyl)-isobutyramide A mixture of N-(5-chloro-4-hydroxymethyl-pyridin-3-ylmethyl)-N-(2,2-dimethyl-[1,3]dioxolan-4-ylmethyl)-isobutyramide and N-(5-chloro-4-hydroxymethyl-pyridin-3-ylmethyl)-N-(2,3-dihydroxy-propyl)-isobutyramide (39 mg, 0.110 mmol) was chlorinated with SOCl$_2$ according to the synthesis of 3,5-dichloro-4-chloromethyl-pyridine with SOCl$_2$ (16 µL, 0.219 mmol) The resulting mixture of the two title compounds was used for the next reaction without purification. MS (m/z): 374.9 [M+H$^+$] and MS (m/z): 335.0 [M+H$^+$].

D. N-{5-Chloro-4-[2-methyl-4-(2-methyl-2H-pyrazol-3-yl)-quinolin-8-yloxymethyl]-pyridin-3-ylmethyl}-N-(2,3-dihydroxy-propyl)-isobutyramide 4-Imidazol-1-yl-2-methyl-quinolin-8-ol (12 mg, 0.050 mmol) was alkylated with a mixture of N-(5-chloro-4-chloromethyl-pyridin-3-ylmethyl)-N-(2,2-dimethyl-[1,3]dioxolan-4-ylmethyl)-isobutyramide and N-(5-chloro-4-chloromethyl-pyridin-3-ylmethyl)-N-(2,3-dihydroxy-propyl)-isobutyramide (17 mg, 0.045 mmol) according to the synthesis of 8-(3,5-dichloro-pyridin-4-ylmethoxy)-4-imidazol-1-yl-2-methyl-quinoline. After 1 d at RT the solvent was removed in vacuo and the residue was purified by reversed phase HPLC using a gradient of acetonitrile in water with 0.1% TFA. This gave the title compound as the TFA salt. MS (m/z): 538.1 [M+H$^+$].

Example 292

Synthesis of N-{4-methyl-3-[2-methyl-4-(2-methyl-2H-pyrazol-3-yl)-quinolin-8-yloxymethyl]-pyridin-2-ylmethyl}-isobutyramide A. 4-Bromo-2-chloro-nicotinic acid methyl ester A solution of 4-bromo-2-chloro-pyridine (4.5 mL, 41 mmol) in anhydrous THF (60 mL) was added dropwise to a stirred solution of lithium diisopropylamide (1.8 M in THF, 25 mL, 45 mmol) in anhydrous THF (60 mL) at −85° C. After stirring for 30 min at −80° C., the reaction mixture was added dropwise via cannula to a stirred solution of methylchloroformate (31 mL, 400 mmol) in anhydrous THF at −80° C. After stirring for 50 min at −80° C., the reaction was quenched by the addition of concentrated aqueous NaHCO$_3$ (90 mL), and subsequently diluted with EA (250 mL). The organic layer was dried over Na$_2$SO$_4$, filtered, and concentrated in vacuo. The residue was purified by flash chromatography on silica gel (elution with hexane/EA 4:1) to give the title compound. MS (m/z): 252.0.1 [M+H$^+$].

B. 2-Chloro-4-methyl-nicotinic acid methyl ester

ZnMe$_2$ (2.0 M in toluene, 15.5 mL, 25 mmol) was added to a stirred mixture of 4-bromo-2-chloro-nicotinic acid methyl ester (9.6 g, 38 mmol) and Pd(dppf)Cl$_2$ (0.50 g, 0.61 mmol) in anhydrous dioxane (180 mL). After stirring for 8 h at 70° C., the reaction mixture was cooled to room temperature, MeOH (15 mL) was added and the solvent was removed in vacuo. The residue was partitioned between EA (300 mL) and water (50 mL). Concentrated aqueous HCl was then added until the emulsion became homogeneous. The organic layers were dried over Na$_2$SO$_4$, filtered, and concentrated in vacuo. The residue was purified by flash chromatography on silica gel (elution with hexane/EA 2:1) to give the title compound. MS (m/z): 186.0 [M+H$^+$].

C. 2-Cyano-4-methyl-nicotinic acid methyl ester

A suspension of 2-chloro-4-methyl-nicotinic acid methyl ester (2.64 g, 14.3 mmol) and CuCN (6.4 g, 71 mmol) in NMP (5.3 mL) was heated to 180° C. for 30 min. The reaction mixture was then cooled to room temperature and diluted with water (80 mL). After vigorous stirring for 16 h, the suspension was centrifuged and the precipitate suspended in a solution of FeCl$_3$.6H$_2$O (5.8 g, 21 mmol) in aqueous HCl (4 M, 80 mL). After vigorous stirring for 1 h, the suspension was extracted with DCM (3×70 mL). The organic layer was dried over Na$_2$SO$_4$/Na$_2$CO$_3$, filtered, and concentrated in vacuo. The residue was purified by flash chromatography on silica gel (elution with EA/DCM 1:10) to give the title compound. MS (m/z): 177.0 [M+H$^+$].

D. (2-Aminomethyl-4-methyl-pyridin-3-yl)-methanol

A solution of AlCl₃ (0.15 g, 1.1 mmol) in anhydrous THF (1.1 mL) was added dropwise to a stirred solution of 2-cyano-4-methyl-nicotinic acid methyl ester (0.10 g, 0.57 mmol) at −35° C. DIBAL (1.5 M in toluene, 3.0 mL, 4.5 mmol) was then added at −95° C. The reaction mixture was allowed to warm to 4° C. over 5 h and was then quenched by the addition of water (0.20 mL) at −20° C. ACN (17 mL) and concentrated aqueous NH₃ (1.4 mL) was added to the mixture. After vigorous stirring for 30 min, the suspension was centrifuged and the precipitate suspended in a solution of ACN (5 mL) and concentrated aqueous NH₃ (0.5 mL). After vigorous stirring for 30 min the suspension was centrifuged. The combined supernatants were concentrated in vacuo to give the title compound. MS (m/z): 153.0 [M+H⁺].

E. N-(3-Hydroxymethyl-4-methyl-pyridin-2-ylmethyl)-isobutyramide

A solution of isobutyryl chloride (29 µL, 0.276 mmol) in DCM (0.20 mL) was added to a vigorously stirred mixture of (2-aminomethyl-4-methyl-pyridin-3-yl)-methanol (30 mg, 0.20 mmol) in DCM (1.0 mL) and aqueous Na₂CO₃ (1 M, 1 mL) at 0° C. After stirring for 30 min at 0° C., DCM (10 mL) and water (1 mL) was added, and the aqueous layer was extracted with DCM (1×10 mL). The combined organic layers were dried over Na₂SO₄, filtered, and concentrated in vacuo. The residue was purified by flash chromatography on silica gel (elution with MeOH/DCM 1:20) to give the title compound. MS (m/z): 223.0 [M+H⁺].

F. N-{4-Methyl-3-[2-methyl-4-(2-methyl-2H-pyrazol-3-yl)-quinolin-8-yloxymethyl]-pyridin-2-ylmethyl}-isobutyramide Conversion of N-(3-hydroxymethyl-4-methyl-pyridin-2-ylmethyl)-isobutyramide (29 mg, 0.13 mmol) into the corresponding chloride according to the synthesis of 3,5-dichloro-4-chloromethyl-pyridine and subsequent reaction with 2-methyl-4-(2-methyl-2H-pyrazol-3-yl)-quinolin-8-ol according to the synthesis of 8-(3,5-dichloro-pyridin-4-ylmethoxy)-4-imidazol-1-yl-2-methyl-quinoline yielded the title compound as the TFA salt. MS (m/z): 444.1 [M+H⁺].

Example 303

Synthesis of 8-(3,5-dichloro-pyridin-4-ylmethoxy)-2-methyl-4-(5-methyl-[1,3,4]thiadiazol-2-ylsulfanyl)-quinoline

A. 2-Methyl-4-(5-methyl-[1,3,4]thiadiazol-2-ylsulfanyl)-quinolin-8-ol

A mixture of 4-chloro-2-methyl-quinolin-8-ol (10 mg, 52 µmol) and 5-methyl-[1,3,4]thiadiazole-2-thiol (6.9 mg, 52 µmol) in MeOH (0.3 mL) was heated to 80° C. for 1.5 h. The solvent was removed in vacuo to give title compound. MS (m/z): 289.9 [M+H⁺].

B. 8-(3,5-Dichloro-pyridin-4-ylmethoxy)-2-methyl-4-(5-methyl-[1,3,4]thiadiazol-2-ylsulfanyl)-quinoline 2-Methyl-4-(5-methyl-[1,3,4]thiadiazol-2-ylsulfanyl)-quinolin-8-ol (15 mg, 52 µmol) was alkylated according to the synthesis of 8-(3,5-dichloro-pyridin-4-ylmethoxy)-4-imidazol-1-yl-2-methyl-quinoline to give the title compound as the TFA salt. MS (m/z): 448.9 [M+H⁺].

Example 319

Synthesis of 4-(5-chloro-thiazol-4-yl)-8-(3,5-dichloro-pyridin-4-ylmethoxy)-2-methyl-quinoline

A. (4-Bromo-5-chloro-thiazol-2-yl)-carbamic acid tert-butyl ester

Lithium diisopropylamide (1.8 M in THF, 19.8 mL, 35.6 mmol) was added dropwise to a stirred solution of (5-bromo-thiazol-2-yl)-carbamic acid tert-butyl ester (Kuo, Gee-Hong; et al. *J. Med. Chem.* 2005; 6; 1886-1900) (3.00 g, 10.8 mmol) in anhydrous THF (75 mL) at 0° C. After stirring for 30 min at 0° C., a solution of 1,1,1,2,2,2-hexachloro-ethane (8.43 g, 35.6 mmol) in anhydrous THF (45 mL) was added dropwise at −90° C. The reaction mixture was allowed to warm to −10° C. and was then quenched by the addition of concentrated aqueous NH₄Cl (15 mL). The mixture was concentrated in vacuo and the residue was partitioned between DCM (100 mL) and water (30 mL). The aqueous layer was extracted with DCM (2×50 mL) and the combined organic layers were dried over Na₂SO₄, filtered, and concentrated in vacuo. The residue was purified by flash chromatography on silica gel (elution with DCM/hexane 2:1) to give the title compound. MS (m/z): 314.6 [M+H⁺].

B. 4-Bromo-5-chloro-thiazole (4-Bromo-5-chloro-thiazol-2-yl)-carbamic acid tert-butyl ester (1.28 g, 4.06 mmol) was dissolved in a 1:1 mixture of TFA and DCM (10 mL). After stirring for 1 h at room temperature, the reaction mixture was concentrated in vacuo and the residue was partitioned between DCM (50 mL) and aqueous concentrated NaHCO₃ (15 mL). The organic layer was dried over Na₂SO₄, filtered, and concentrated in vacuo. The residue was dissolved in anhydrous THF (15 mL) and 2-methyl-2-nitrosooxy-propane (0.73 mL, 6.1 mmol) was added dropwise. After stirring for 1 h at 60° C., the reaction mixture was concentrated in vacuo. The residue was purified by flash chromatography on silica gel (elution with DCM/hexane 1:2) to give the title compound.

C. 4-(5-chloro-thiazol-4-yl)-8-(3,5-dichloro-pyridin-4-ylmethoxy)-2-methyl-quinoline Coupling of 4-bromo-5-chloro-thiazole (10 mg, 50 µmol) with 8-((3,5-dichloropyridin-4-yl)methoxy)-2-methylquinolin-4-ylboronic acid TFA salt (15 mg) according to the synthesis of 8-(3,5-dichloro-pyridin-4-ylmethoxy)-2-methyl-4-(4-methyl-thiazol-5-yl)-quinoline yielded the title compound as the TFA salt. MS (m/z): 437.9 [M+H⁺].

Example 430

Synthesis of N-{4-chloro-3-[2-methyl-4-(2-methyl-2H-pyrazol-3-yl)-quinolin-8-yloxymethyl]-pyridin-2-ylmethyl}-isobutyramide

A. 2,4-Dichloro-3-(tetrahydro-pyran-2-yloxymethyl)-pyridine 2,4-Dichloro-pyridine-3-carbaldehyde (1.565 g. 8.89 mmol) was reduced to (2,4-dichloro-pyridin-3-yl)-methanol according to the procedure described for the preparation of (3,5-dichloro-pyridin-4-yl)-methanol and subsequently protected with the THP-group according to the procedure described for the preparation 3-bromo-5-chloro-4-(tetrahydro-pyran-2-yloxymethyl)-pyridine to provide the title compound.

B. 4-Chloro-3-(tetrahydro-pyran-2-yloxymethyl)-pyridine-2-carbonitrile 2,4-Dichloro-3-(tetrahydro-pyran-2-yloxymethyl)-pyridine (455 mg. 1.74 mmol) was dissolved in a mixture of DMF (3 mL) and water (30 µL). The following reagents were added subsequently: zinc cyanide (112 mg. 0.95 mmol), zinc dust (9.1 mg. 139 µmol), zinc acetate (25.5 mg. 139 µmol). 1,1'-bis(diphenylphosphino)ferrocene (58 mg. 104 µmol) and tris(dibenzylideneacetone)palladium (0). The reaction mixture was degassed two times and afterwards heated at 95° C. for 4 h. The solvents were removed in vacuo and the residue was pardoned between water (20 mL) and EtOAc (20 mL) and extracted with EtOAc (3×20 ml). The combined organic layers were washed with brine and dried over $Na_2SO_4$ filtered and concentrated in vacuo. The residue was purified by flash chromatography on silica gel (elution with hexane/EtOAc 10:1→5:1) to give the title compound. MS (m/z): 253.0 [M+H$^+$].

C. N-[4-Chloro-3-(tetrahydro-pyran-2-yloxymethyl)-pyridin-2-ylmethyl]-isobutyramide 4-Chloro-3-(tetrahydro-pyran-2-yloxymethyl)-pyridine-2-carbonitrile (30 mg. 0.12 mmol) was dissolved in a mixture of MeOH (0.75 mL) and THF (1 mL). $CoCl_2$ hexahydrate (56 mg. 0.24 mmol) and $NaBH_4$ (45 mg. 1.19 mmol dissolved in 1 mL MeOH) were added. After stirring for 8 min at RT sat. $NaHCO_3$ solution (1 mL) and isobutyryl chloride (125 µL. 1.19 mmol) were added. The solvents were removed in vacuo and the residue was partioned between sat. $NH_4Cl$ solution (10 mL) and DCM (10 mL) and extracted with DCM (3×10 ml). The combined organic layers were washed with brine and dried over $Na_2SO_4$ filtered and concentrated in vacuo. The residue was purified by flash chromatography on silica gel (elution with hexane/EtOAc 2:1→1:2) to give the title compound. MS (m/z): 326.8 [M+H$^+$]

D. N-{4-chloro-3-[2-methyl-4-(2-methyl-2H-pyrazol-3-yl)-quinolin-8-yloxymethyl]-pyridin-2-ylmethyl}-isobutyramide N-[4-Chloro-3-(tetrahydro-pyran-2-yloxymethyl)-pyridin-2-ylmethyl]-isobutyramide was chlorinated according to the procedure described for the synthesis of 1-(3-chloromethyl-4-methyl-pyridin-2-ylmethyl)-3-trifluoromethyl-1H-pyridin-2-one. The resulting N-(4-chloro-3-chloromethyl-pyridin-2-ylmethyl)-isobutyramide was coupled with 2-methyl-4-(2-methyl-2H-pyrazol-3-yl)-quinolin-8-ol according to the proecure described for the preparation of 8-(3,5-dichloro-pyridin-4-ylmethoxy)-4-imidazol-1-yl-2-methyl-quinoline to give the title compound as the TFA salt. MS (m/z): 464.1 [M+H$^+$].

Example 501

Synthesis of 1-{4-methyl-3-[2-methyl-4-(4-methyl-2H-pyrazol-3-yl)-quinolin-8-yloxymethyl]-pyridin-2-ylmethyl}-3-trifluoromethyl-1H-pyridin-2-one

A. 4-Methyl-1-(tetrahydro-pyran-2-yl)-1H-pyrazole was converted to 2-methyl-4-[4-methyl-1-(tetrahydro-pyran-2-yl)-1H-pyrazol-3-yl]-quinolin-8-ol according to the procedure described for the synthesis of 2-methyl-4-(1-methyl-1H-imidazol-2-yl)-quinolin-8-ol

B. 2-Chloro-4-methyl-3-(tetrahydro-pyran-2-yloxymethyl)-pyridine

2-Chloro-4-methyl-nicotinic acid methyl ester (1 g. 5.4 mmol) was dissolved in THF (10 mL) and cooled to −78° C. and DIBAL (1 M in toluene) was added via a syringe (14.4 mL. 21.6 mmol). The reaction mixture was allowed to warm to RT over a period of 4 h. Additional DIBAL (5 mL. 5 mmol) was added and the reaction was stirred at RT for 1 h before cooled to −20° C. Water (2 mL). sat. $Na_2CO_3$ solution (1.5 mL). aqueous $NH_3$ (3 mL) and ACN (70 mL) were added. After vigorous stirring for 30 min. the suspension was centrifuged and the precipitate suspended in a solution of ACN (100 mL) and concentrated aqueous $NH_3$ (5 mL). After vigorous stirring for 30 min the suspension was centrifuged. The combined supernatants were concentrated in vacuo to yield crude (2-chloro-4-methyl-pyridin-3-yl)-methanol which was converted into the title compound according to the procedure described for the preparation of 3-bromo-5-chloro-4-(tetrahydro-pyran-2-yloxymethyl)-pyridine. MS (m/z): 158.0 [M+H$^+$].

C. 4-Methyl-3-(tetrahydro-pyran-2-yloxymethyl)-2-vinyl-pyridine

2-Chloro-4-methyl-3-(tetrahydro-pyran-2-yloxymethyl)-pyridine (500 mg. 2.07 mmol) was dissolved in a mixture of 1,2-dimethoxyethane (16.5 mL) and water (7 mL). $K_2CO_3$ (286 mg. 2.07 mmol) and 2,4,6-trivinyl-cyclotriboroxane pyridine complex (498 mg. 2.07 mmol) were added and the reaction mixture was degassed two times before the addition of $Pd((PPh_3)_4$ (120 mg. 0.10 mmol). The reaction mixture was stirred at 100° C. for 18 h. The solvents were removed in vacuo and the residue was purified by flash chromatography on silica gel (elution with hexane/EtOAc 6:1) to give the title compound. MS (m/z): 234.1 [M+H$^+$]

D. [4-Methyl-3-(tetrahydro-pyran-2-yloxymethyl)-pyridin-2-yl]-methanol

4-Methyl-3-(tetrahydro-pyran-2-yloxymethyl)-2-vinyl-pyridine (300 mg. 1.29 mmol) was dissolved in DCM (36 mL) and cooled to −50° C. A gentle flow of ozone was bubbled through the reaction mixture until the colour of the solution changed to slight blue. $NaBH_4$ (486 mg. 12.9 mmol) dissolved in MeOH (15 mL) was added and the reaction was allowed to warm to RT over a period of 1 h. The solvents were removed in vacuo and the residue pardoned between water (20 mL) and EtOAc (20 mL) extracted with EtOAc (3×20 mL). The combined organic fractions were washed with brine and dried over $Na_2SO_4$ filtered and concentrated in vacuo. The residue was purified by flash chromatography on silica gel (elution with DCM/MeOH 40:1→20:1) to give the title compound. MS (m/z): 238.0 [M+H$^+$].

E. 1-[4-Methyl-3-(tetrahydro-pyran-2-yloxymethyl)-pyridin-2-ylmethyl]-3-trifluoromethyl-1H-pyridin-2-one

[4-Methyl-3-(tetrahydro-pyran-2-yloxymethyl)-pyridin-2-yl]-methanol (138 mg. 0.58 mmol) was dissolved in DCM (5 mL) and cooled to 0° C. NEt$_3$ (324 µL. 2.33 mmol) and methanesulfonyl chloride (90 µL. 1.16 mmol) were added and the reaction mixture was stirred for 1 h at 0° C. After removal of the solvents in vacuo the residue was dissolved in DMF (10 mL) and CsCO$_3$ (570 mg. 1.75 mmol) and 3-trifluoromethyl-pyridin-2-ol (142 mg. 0.87 mmol) were added. After stirring for 2 h at RT the solvent was removed in vacuo and the residue was partioned between water (20 mL) and DCM (20 mL) extracted with DCM (3×20 mL) and the combined organic fractions were dried over Na$_2$SO$_4$ filtered and concentrated in vacuo. The residue was purified by flash chromatography on silica gel (elution with hexane/EtOAc 2:1→1:1) to give the title compound. MS (m/z): 382.9 [M+H$^+$].

F. 1-(3-Chloromethyl-4-methyl-pyridin-2-ylmethyl)-3-trifluoromethyl-1H-pyridin-2-one 1-[4-Methyl-3-(tetrahydro-pyran-2-yloxymethyl)-pyridin-2-ylmethyl]-3-trifluoromethyl-1H-pyridin-2-one (100 mg. 0.26 mmol) was dissolved in DCM (5 mL). SOCl$_2$ (97 µL. 1.31 mmol) and water (25 µL) were added and the reaction mixture was stirred for 1 h at RT. After removal of the solvents in vacuo the resulting title compound was used for the next reaction without purification. MS (m/z): 317.0 [M+H$^+$].

G. 1-(4-Methyl-3-{2-methyl-4-[4-methyl-1-(tetrahydro-pyran-2-yl)-1H-pyrazol-3-yl]-quinolin-8-yloxymethyl}-pyridin-2-ylmethyl)-3-trifluoromethyl-1H-pyridin-2-one 2-Methyl-4-[4-methyl-1-(tetrahydro-pyran-2-yl)-1H-pyrazol-3-yl]-quinolin-8-ol and 1-(3-chloromethyl-4-methyl-pyridin-2-ylmethyl)-3-trifluoromethyl-1H-pyridin-2-one were coupled according to the procedure described for the synthesis of 8-(3,5-dichloro-pyridin-4-ylmethoxy)-4-imidazol-1-yl-2-methyl-quinoline to give the title compound which was used in the next step without purification.

H. 1-{4-Methyl-3-[2-methyl-4-(4-methyl-1H-pyrazol-3-yl)-quinolin-8-yloxymethyl]-pyridin-2-ylmethyl}-3-trifluoromethyl-1H-pyridin-2-one 1-(4-Methyl-3-{2-methyl-4-[4-methyl-1-(tetrahydro-pyran-2-yl)-1H-pyrazol-3-yl]-quinolin-8-yloxymethyl}-pyridin-2-ylmethyl)-3-trifluoromethyl-1H-pyridin-2-one (2.02 g. 3.34 mmol) was dissolved in MeOH (25 mL) and concentrated aqueous HCl (2.5 mL) was added. After stirring for 30 min the solvents were removed in vacuo and the residue was purified by reversed phase HPLC using a gradient of acetonitrile in water with 0.1% TFA to give the title compound as the TFA salt. MS (m/z): 520.1 [M+H$^+$].

Example 597

Synthesis of 4-methyl-5-[2-methyl-4-(4-methyl-1H-pyrazol-3-yl)-quinolin-8-yloxymethyl]-6-(2-oxo-3-trifluoromethyl-2H-pyridin-1-ylmethyl)-1H-pyridin-2-one

A. 1-[4-Methyl-1-oxy-3-(tetrahydro-pyran-2-yloxymethyl)-pyridin-2-ylmethyl]-3-trifluoromethyl-1H-pyridin-2-one 3-Chloroperoxybenzoic acid (27.1 mg. 0.157 mmol) was added to a stirred solution of 1-[4-methyl-3-(tetrahydro-pyran-2-yloxymethyl)-pyridin-2-ylmethyl]-3-trifluoromethyl-1H-pyridin-2-one (20 mg. 0.052 mmol) in DCM (2 mL). After stirring for 3 h at room temperature the organic layer was extracted with sat. NaHCO$_3$ solution (3 mL) and the aqueous solution extracted three times with DCM (3 mL). The combined organic layers was dried over Na$_2$SO$_4$ filtered and concentrated in vacuo. The resulting title compound was used for the next reaction without purification. MS (m/z): 398.8 [M+H$^+$]

B. 5-Chloromethyl-4-methyl-6-(2-oxo-3-trifluoromethyl-2H-pyridin-1-ylmethyl)-1H-pyridin-2-one POCl$_3$ (68.6 µL. 0.735 mmol) was added to a stirred solution of 1-[4-methyl-1-oxy-3-(tetrahydro-pyran-2-yloxymethyl)-pyridin-2-ylmethyl]-3-trifluoromethyl-1H-pyridin-2-one (29.3 mg. 0.074 mmol) in dichloroethane (5 mL). After stirring for 90 min at 100° C. the organic layer was extracted with sat. NaHCO$_3$ solution (10 mL) and the aqueous solution extracted three times with DCM (10 mL). The combined organic layers were extracted with brine (10 mL) dried over Na$_2$SO$_4$ filtered and concentrated in vacuo. HPLC purification yielded the resulting title compound. MS (m/z): 332.9 [M+H$^+$].

C. 4-Methyl-5-[2-methyl-4-(4-methyl-1H-pyrazol-3-yl)-quinolin-8-yloxymethyl]-6-(2-oxo-3-trifluoromethyl-2H-pyridin-1-ylmethyl)-1H-pyridin-2-one Reaction of 5-chloromethyl-4-methyl-6-(2-oxo-3-trifluoromethyl-2H-pyridin-1-ylmethyl)-1H-pyridin-2-one (10.53 mg. 0.030 mmol) with 2-methyl-4-[4-methyl-1-(tetrahydro-pyran-2-yl)-1H-pyrazol-3-yl]-quinolin-8-ol (9.7 mg. 0.030 mmol) according to the synthesis of 8-(3,5-dichloro-pyridin-4-ylmethoxy)-4-imidazol-1-yl-2-methyl-quinoline and subsequent deprotection and purification according to the synthesis of 1-{4-methyl-3-[2-methyl-4-(4-methyl-1H-pyrazol-3-yl)-quinolin-8-yloxymethyl]-pyridin-2-ylmethyl}-3-trifluoromethyl-1H-pyridin-2-one yielded the title compound as the TFA salt. MS (m/z): 536.1 [M+H$^+$].

Example 654

Synthesis of 2-{8-[4-chloro-6-methyl-2-(2-oxo-3-trifluoromethyl-2-H-pyridin-1-ylmethyl)-pyridin-3-ylmethoxy]-2-methyl-quinolin-4-yl}-3-methyl 4-carbonitrile

A. 2-(8-Hydroxy-2-methyl-quinolin-4-yl)-3-methyl-3H-imidazole-4-carbonitrile Coupling of 4-bromo-2-methyl-quinolin-8-ol (400 mg. 1.68 mmol) with 3-methyl-3H-imidazole-4-carbonitrile (450 mg. 4.20 mmol) according to the synthesis of 2-methyl-4-(1- methyl-1H-imidazol-2-yl)-quinolin-8-ol yielded the title compound. MS (m/z): 265.2 [M+H⁺].

B. 2-{8-[4-Chloro-6-methyl-2-(2-oxo-3-trifluoromethyl-2H-pyridin-1-ylmethyl)-pyridin-3-ylmethoxy]-2-methyl-quinolin-4-yl}-3-methyl-3H-imidazole-4-carbonitrile Reduction of the 2,4-dichloro-6-methyl-nicotinic acid ethyl ester (550 mg. 2.35 mmol) to the alcohol according to the synthesis of (2-chloro-4-methyl-pyridin-3-yl)-methanol subsequent THP protection according to the synthesis of 3-bromo-5-chloro-4-(tetrahydro-pyran-2-yloxymethyl)-pyridine subsequent Pd catalyzed vinylation according to the synthesis of 4-methyl-3-(tetrahydro-pyran-2-yloxymethyl)-2-vinyl-pyridine subsequent ozonolysis and reduction according to the synthesis of [4-methyl-3-(tetrahydro-pyran-2-yloxymethyl)-pyridin-2-yl]-methanol subsequent mesylation and alkylation according to the synthesis of 1-[4-methyl-3-(tetrahydro-pyran-2-yloxymethyl)-pyridin-2-ylmethyl]-3-trifluoromethyl-1H-pyridin-2-one conversion to the chloride according to the synthesis of 1-(3-chloromethyl-4-methyl-pyridin-2-ylmethyl)-3-trifluoromethyl-1H-pyridin-2-one and subsequent coupling with 2-(8-hydroxy-2-methyl-quinolin-4-yl)-3-methyl-3H-imidazole-4-carbonitrile according to the synthesis of 8-(3,5-dichloro-pyridin-4-ylmethoxy)-4-imidazol-1-yl-2-methyl-quinoline yielded the title compound as the TFA salt. MS (m/z): 579.0 [M+H⁺].

Example 682

Synthesis of 1-{5-chloro-2-hydroxy-4-[2-methyl-4-(4-methyl-2H-pyrazol-3-yl)-quinolin-8-yloxymethyl]-pyridin-3-ylmethyl}-3-trifluoromethyl-1H-pyridin-2-one A. 2-Benzyloxy-3-bromo-5-chloro-pyridine In a microwave tube NaH (60% in paraffin. 56 mg. 1.4 mmol) was washed with hexane and 3-bromo-2,5-dichloro-pyridine (245 mg. 1.08 mmol) in dry DMF (2 mL) were added. To this suspension BnOH (123 µL. 1.23 mmol) in dry DMF (1 mL) was dropped carefully. The reaction mixture was stirred 15 min until the formation of hydrogen has ceased. The tube was sealed and stirred at 100° C. in a microwave reactor for 30 min. After removal of the solvent in vacuo the residue was partioned between water (10 mL) and DCM (10 mL) and extracted with DCM (3×10 mL). The combined organic fractions were washed with brine dried over Na₂SO₄ filtered and concentrated in vacuo. The resulting title compound was used for the next reaction without purification. GC-MS (m/z): 297 [M⁺].

B. 1-{5-Chloro-2-hydroxy-4-[2-methyl-4-(4-methyl-2H-pyrazol-3-yl)-quinolin-8-yloxymethyl]-pyridin-3-ylmethyl}-3-trifluoromethyl-1H-pyridin-2-one one 2-Benzyloxy-3-bromo-5-chloro-pyridine (207 mg. 0.69 mmol) was formulated according to the procedure described for the synthesis of 3-bromo-5-chloro-pyridine-4-carbaldehyde subsequently reduced according to the procedure described for the synthesis of (3,5-dichloro-pyridin-4-yl)-methanol and protected with the THP group according to the procedure described for the synthesis of 3-bromo-5-chloro-4-(tetrahydro-pyran-2-yloxymethyl)-pyridine. The resulting 2-benzyloxy-3-bromo-5-chloro-4-(tetrahydro-pyran-2-yloxymethyl)-pyridine was vinylated according to the procedure described for the synthesis of 4-chloro-6-methyl-3-(tetrahydro-pyran-2-yloxymethyl)-2-vinyl-pyridine and subsequently transformed to the alcohol according to the procedure described for the preparation of [4-methyl-3-(tetrahydro-pyran-2-yloxymethyl)-pyridin-2-yl]-methanol. The resulting [2-benzyloxy-5-chloro-4-(tetrahydro-pyran-2-yloxymethyl)-pyridin-3-yl]-methanol was transformed according to the procedure described for the synthesis of 1-[4-methyl-3-(tetrahydro-pyran-2-yloxymethyl)-pyridin-2-ylmethyl]-3-trifluoromethyl-1H-pyridin-2-one and subsequently transformed into 1-(2-benzyloxy-5-chloro-4-chloromethyl-pyridin-3-ylmethyl)-3-trifluoromethyl-1H-pyridin-2-one according to the procedure described for the preparation of 1-(3-chloromethyl-4-methyl-pyridin-2-ylmethyl)-3-trifluoromethyl-1H-pyridin-2-one. Final coupling of this chloride with 2-methyl-4-[4-methyl-2-(tetrahydro-pyran-2-yl)-2H-pyrazol-3-yl]-quinolin-8-ol according to the procedure described for the synthesis of 8-(3,5-Dichloro-pyridin-4-ylmethoxy)-4-imidazol-1-yl-2-methyl-quinoline and subsequent deprotection of both the THP group and the benzyl ether according to the procedure described for the preparation 1-{4-methyl-3-[2-methyl-4-(4-methyl-1H-pyrazol-3-yl)-quinolin-8-yloxymethyl]-pyridin-2-ylmethyl}-3-trifluoromethyl-1H-pyridin-2-one yielded after purification by reversed phase HPLC using a gradient of acetonitrile in water with 0.1% TFA the title compound as the TFA salt. MS (m/z): 556.0 [M+H⁺].

Example 711

Synthesis of 1-{3-[4-(5-cyano-1-methyl-1H-pyrrol-2-yl)-2-methyl-quinolin-8-yloxymethyl]-4-methoxy-pyridin-2-ylmethyl}-2-oxo-1,2-dihydro-pyridine-3-carbonitrile A. 2-Chloro-4-methoxy-3-(tetrahydro-pyran-2-yloxymethyl)-pyridine To a stirred solution of 2-chloro-4-fluoro-3-(tetrahydro-pyran-2-yloxymethyl)-pyridine (0.20 g. 0.81 mmol) which was prepared according to the synthesis of 3-bromo-5-chloro-4-(tetrahydro-pyran-2-yloxymethyl)-pyridine in anhydrous MeOH (4 mL) was added Cs₂CO₃ (0.54 g. 1.6 mmol). After vigorous stirring for 20 h at room temperature acedic acid (92 µL. 1.6 mmol) was added the solvent was removed in vacuo and the residue was partitioned between DCM (20 mL) and water (4 mL). The organic layer was dried over Na₂SO₄ filtered and concentrated in vacuo. The resulting title compound was used for the next reaction without purification. MS (m/z): 257.9 [M+H⁺].

B. 5-(8-Hydroxy-2-methyl-quinolin-4-yl)-1-methyl-1H-pyrrole-2-carbonitrile

Coupling of 4-bromo-2-methyl-quinolin-8-ol (75 mg. 0.32 mmol) with 1-methyl-1H-pyrrole-2-carbonitrile (84 mg. 0.79 mmol) according to the synthesis of of 2-methyl-4-(1-methyl-1H-imidazol-2-yl)-quinolin-8-ol using LDA as the base (1.8 M in Heptan/THF/Ethylbenzol. 0.44 mL. 0.79 mmol) yielded the title compound. MS (m/z): 264.2 [M+H⁺].

C. 1-{3-[4-(5-Cyano-1-methyl-1H-pyrrol-2-yl)-2-methyl-quinolin-8-yloxymethyl]-4-methoxy-pyridin-2-ylmethyl}-2-oxo-1,2-dihydro-pyridine-3-carbonitrile Pd catalyzed vinylation of 2-chloro-4-methoxy-3-(tetrahydro-pyran-2-yloxymethyl)-pyridine (0.20 g. 0.79 mmol)

according to the synthesis of 4-methyl-3-(tetrahydro-pyran-2-yloxymethyl)-2-vinyl-pyridine ozonolysis and reduction according to the synthesis of [4-methyl-3-(tetrahydro-pyran-2-yloxymethyl)-pyridin-2-yl]-methanol mesylation and alkylation with 2-hydroxy-nicotinonitrile according to the synthesis of 1-[4-methyl-3-(tetrahydro-pyran-2-yloxymethyl)-pyridin-2-ylmethyl]-3-trifluoromethyl-1H-pyridin-2-one conversion to the chloride according to the synthesis of 1-(3-chloromethyl-4-methyl-pyridin-2-ylmethyl)-3-trifluoromethyl-1H-pyridin-2-one and subsequent coupling with 5-(8-hydroxy-2-methyl-quinolin-4-yl)-1-methyl-1H-pyrrole-2-carbonitrile according to the synthesis of 8-(3,5-dichloro-pyridin-4-ylmethoxy)-4-imidazol-1-yl-2-methyl-quinoline and purification by reversed phase HPLC using a gradient of acetonitrile in water with 0.1% TFA yielded the title compound as the TFA salt. MS (m/z): 516.5 [M+H$^+$].

Example 733

Synthesis of 1-(1-{4-chloro-3-[4-(4-hydroxy-1H-pyrazol-3-yl)-2-methyl-quinolin-8-yloxymethyl]-pyridin-2-yl}-ethyl)-2-oxo-1,2-dihydro-pyridine-3-carbonitrile A. 1H-pyrazol-4-ol At 0° C. Hydrogen peroxide (30% in H$_2$O. 379 µL. 3.71 mmol) and NaOH (2M in H$_2$O. 1.86 mL. 3.71 mmol) were added to a stirred solution of 4-(4,4,5,5-tetramethyl-[1.3.2]dioxaborolan-2-yl)-1H-pyrazole in THF (5 mL). After stirring for 3 min at 0° C. the reaction was warmed to room temperature and stirred for further 50 min. The reaction was diluted with H$_2$O (20 mL) acidified with HCl (2 N) and extracted four times with DCM (50 mL) and four times with DCM/isopropanol (4:1. 50 mL). The combined organic layers were dried over Na$_2$SO$_4$ filtered and concentrated in vacuo. The resulting title compound was used for the next reaction without purification. MS (m/z): 85.0 [M+H$^+$].

B. 2-Methyl-4-[1-(tetrahydro-pyran-2-yl)-4-(tetrahydro-pyran-2-yloxy)-1H-pyrazol-3-yl]-quinolin-8-ol THP protection of 1H-Pyrazol-4-ol (420 mg. 2.06 mmol) according to the synthesis of 3-bromo-5-chloro-4-(tetrahydro-pyran-2-yloxymethyl)-pyridine subsequent coupling with 4-bromo-2-methyl-quinolin-8-ol according to the synthesis of 2-methyl-4-(1-methyl-1H-imidazol-2-yl)-quinolin-8-ol and flash chromatographic purification yielded the title compound. MS (m/z): 410.0 [M+H$^+$].

C. [4-Chloro-3-(tetrahydro-pyran-2-yloxymethyl)-pyridin-2-yl]-methanol

Pd catalyzed vinylation of 2,4-dichloro-3-(tetrahydro-pyran-2-yloxymethyl)-pyridine (1.71 g. 6.52 mmol) according to the synthesis of 4-methyl-3-(tetrahydro-pyran-2-yloxymethyl)-2-vinyl-pyridine subsequent ozonolysis and reduction according to the synthesis of [4-methyl-3-(tetrahydro-pyran-2-yloxymethyl)-pyridin-2-yl]-methanol and flash chromatographic purification yielded the title compound. MS (m/z): 257.8 [M+H$^+$].

D. 4-Chloro-3-(tetrahydro-pyran-2-yloxymethyl)-pyridine-2-carbaldehyde

Dess-Martin periodinane (370 mg. 0.873 mmol) was added to a stirred solution of [4-chloro-3-(tetrahydro-pyran-2-yloxymethyl)-pyridin-2-yl]-methanol (150 mg. 0.582 mmol) in THF (5 mL). After stirring for 2 h at room temperature the reaction was concentrated. Sat. NaHCO$_3$ solution (20 mL) was added and extracted three times with DCM (50 mL). The combined organic layers were dried over Na$_2$SO$_4$ filtered and concentrated in vacuo. The resulting title compound was used for the next reaction without purification. MS (m/z): 255.7 [M+H$^+$].

E. 1-[4-Chloro-3-(tetrahydro-pyran-2-yloxymethyl)-pyridin-2-yl]-ethanol

MeMgBr (3.0 M in Diethylether. 582 µL. 1.75 mmol) was added to a stirred solution of 4-Chloro-3-(tetrahydro-pyran-2-yloxymethyl)-pyridine-2-carbaldehyde (149 mg. 0.58 mmol) in THF (6 mL). After stirring for 10 min at room temperature sat. NaHCO$_3$ solution (30 mL) was added and extracted three times with DCM (50 mL). The combined organic layers were dried over Na$_2$SO$_4$ filtered and concentrated in vacuo. The residue was purified by flash chromatography on silica gel (elution with a gradient of ethyl acetate and MeOH) to give the title compound. MS (m/z): 271.8 [M+H$^+$].

F. 1-(1-{4-Chloro-3-[4-(4-hydroxy-1H-pyrazol-3-yl)-2-methyl-quinolin-8-yloxymethyl]-pyridin-2-yl}-ethyl)-2-oxo-1,2-dihydro-pyridine-3-carbonitrile Mesylation and alkylation of 1-[4-chloro-3-(tetrahydro-pyran-2-yloxymethyl)-pyridin-2-yl]-ethanol (120 mg. 0.44 mmol) with 2-hydroxy-nicotinonitrile (79.3 mg. 0.66 mmol) according to the synthesis of 1-[4-methyl-3-(tetrahydro-pyran-2-yloxymethyl)-pyridin-2-ylmethyl]-3-trifluoromethyl-1H-pyridin-2-one. HPLC purification conversion to the chloride according to the synthesis of 1-(3-chloromethyl-4-methyl-pyridin-2-ylmethyl)-3-trifluoromethyl-1H-pyridin-2-one subsequent coupling with 2-methyl-4-[1-(tetrahydro-pyran-2-yl)-4-(tetrahydro-pyran-2-yloxy)-1H-pyrazol-3-yl]-quinolin-8-ol according to the synthesis of 8-(3,5-dichloro-pyridin-4-ylmethoxy)-4-imidazol-1-yl-2-methyl-quinoline and subsequent deprotection and purification according to the synthesis of 1-{4-methyl-3-[2-methyl-4-(4-methyl-1H-pyrazol-3-yl)-quinolin-8-yloxymethyl]-pyridin-2-ylmethyl}-3-trifluoromethyl-1H-pyridin-2-one yielded the title compound as the TFA salt. MS (m/z): 513.0 [M+H$^+$].

Example 754

Radioligand Binding Assay

The following assay is defined herein as a standard in vitro B2 receptor binding assay.

The pharmaceutical utility of compounds of this invention is indicated by detection of activity in the following assay for BK B2 receptor activity. The B2 receptor binding assay is performed using the following experimental settings.

Incubation buffer:

Consists of: 40 mM PIPES, 109 mM NaCl, 5 mM KCl, 0.1% glucose, 0.05% BSA, 2 mM CaCl$_2$, 1 mM MgCl$_2$, pH 7.4; with following inhibitors: 2 mM bacitracin, 0.8 mM 1,10-phenanthrolin, 100 µM captopril. Before starting the experiment, [$^3$H]BK is added to obtain a final concentration of 2 nM.

Addition of Test Compounds to Incubation Buffer and Preparation of Serial Dilutions:

10 µL of a 10 mM stock solution of the individual test compounds in DMSO was diluted in 90 µL DMSO, resulting in a compound concentration of 1 mM in 100% DMSO. 7.5

μL of this (1 mM) compound solution was then added to 242.5 μL of incubation buffer (contains 2 nM [³H]BK, see above), resulting in a test compound concentration of 30 μM. A 10 μM compound solution was prepared by addition of 2.5 μL of the 1 mM compound solution to 247.5 μL incubation buffer. Based on these 30 μM and 10 μM compound solutions in incubation buffer, further dilutions were prepared by serial 1:10 dilution with incubation buffer (containing 2 nM [³H]BK, see above) steps resulting in 3, 1, 0.3, 0.1, 0.03, 0.01, 0.003 and 0.001 μM compound solutions. For determination of non-specific binding 1.25 μL of a 10 mM BK solution was added to 248.8 μL incubation buffer (contains 2 nM [³H]BK). For determination of total binding, incubation buffer with [³H]BK but without compound was used. Beside of compounds to be tested, appropriate controls were prepared in the same way.

Procedure:

Coating with Cells:

96-well cell culture-trays were treated with 0.01% poly-D-lysin hydrobromide in PBS for at least 1 hour. Afterwards, HEK293 cells that stably express recombinant human B2R (10 pmol/mg protein) were added and cultivated for 1-3 days until at least 90% confluence was reached.

Wash Steps:

Then, multiwell-trays were stored on ice and the culture medium was removed using a 12-channel rack of an ELISA-wash device. Afterwards, ice-cold PBS (10×-stock solution, 1:10 diluted, pH adjusted to 7.4) was added starting at the front of the plate (until wells are half-filled) and this wash procedure is repeated 3 times.

Incubation with Compound and Read-Out:

100 μL each of the incubation buffer containing [³H]BK and serial dilutions of test/control compounds/controls or 50 μM BK, respectively, were added to the rinsed cells on ice. After 90 minutes incubation on ice, the incubation medium was removed and the cells were washed 4 times with ice-cold PBS. In order to dissociate surface-bound [³H]BK, 200 μL 0.2 M acetic acid/0.5 M NaCl, pH 2.7 were added subsequently, followed by a further incubation step on ice for 10 minutes. Afterwards, the supernatants were transferred into 6 mL scintillation vials; 0.9 mL scintillation fluid were added each and the amount of [³H]BK was determined by analysis in a beta-counter (cpm, counting time 1 min). For analysis of results, the cpm determined for non-specific binding were subtracted from the total counts and the cpm values for each compound dilution were used for curve fit and IC$_{50}$ calculation.

The compounds shown in Examples 1-465 have been tested in this assay and found to exhibit IC$_{50}$ values of less than or equal to 5 micromolar. Most preferred compounds of formula (I) exhibited IC$_{50}$ values of less than 50 nanomolar.

Example 755

Calcium Mobilization Assay

Inhibitory effects of test compounds on BK-mediated calcium mobilization were tested on HF-15 primary human fibroblasts.

Preparation of Cell-Coated Plates and Loading of the Cells with Calcium Dye:

50.000 HF-15 cells (passage 12) were added per well of a black, clear bottom 96 well plate. After incubation overnight, cells were washed with HBSS (37° C.) and 100 μL of HBSS were left per well. Then, 100 μL of a freshly prepared calcium dye (Ca3, Molecular Devices) solution containing 2.5 mM probenicide were added per well. Cells then were incubated for 60 minutes at 37° C.

Preparation of Serial Dilutions and Incubation with Test Compounds:

Based on 5 mM stock solutions in 100% DMSO (and pre-dilutions in 100% DMSO if necessary), serial 1:3 dilutions of test compounds and controls are prepared in 100% DMSO. Concentration range to be used was chosen to be between 2 mM and 1 nM, dependent on the optimal concentration range for each compound. 2.5 μL of the compound/control dilutions then were added per well of the cell-coated assay plate, already containing 200 μL HBSS/dye solution. Subsequently, cells were pre-incubated with compounds/controls for 25 minutes at 25° C.

Calcium Mobilization and Analysis of Results:

After pre-incubation with compounds/controls for 25 minutes, calcium mobilization was tested in a Flexstation device (Molecular Devices). 20 seconds after start of the continous recording of fluorescence signals, 50 μL of a 25 nM BK solution in HBSS were added per well by the liquid-handling system of the device. Height of the resulting peak over baseline (relative fluorescence units [RFU] max-min) was used for calculation of inhibitory effects of test compounds on BK-mediated calcium mobilization. Percent inhibition was calculated by comparison of the obtained RFU max-min values for the blanks (only BK, no antagonist) with the values obtained for the antagonist-treated cells. Percent inhibition values each referring to a certain concentration of antagonist were used for curve fit and IC$_{50}$ calculation.

Most preferred compounds of formula (I) exhibited IC$_{50}$ values of less than 50 nanomolar in this assay.

The features of the present invention disclosed in the specification, the claims and/or the drawings may both separately and in any combination thereof be material for realizing the invention in various forms thereof.

The invention claimed is:

1. A Compound of the formula (I):

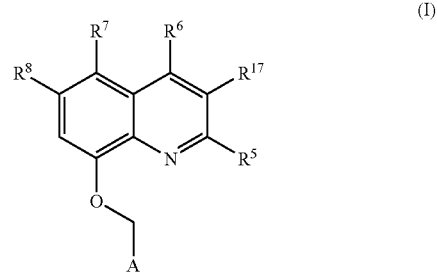

or a pharmacologically acceptable salt, wherein

A is a 6-membered heteroaryl having from 1 to 3 heteroatoms each independently selected from N or O, wherein said 6-membered heteroaryl is substituted with from 2 to 4 substituents each independently selected from halogen atom, oxygen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl;

R5 is halogen atom, hydroxy, cyano, nitro, mercapto, alkyl, alkenyl, alkynyl, or heteroalkyl;

R6 is optionally substituted alkyl; optionally substituted alkenyl; 5-membered heterocycloalkyl having from 1 to 3 heteroatoms each independently selected from N, O or S, or cycloalkyl, wherein said 5-membered heterocycloalkyl or cycloalkyl is substituted with from 0 to 3 substituents each independently selected from halogen atom, oxygen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl; 5-membered heteroaryl having from 1 to 4 heteroatoms each independently selected from N, O or S, wherein said 5-membered heteroaryl is substituted with from 0 to 3 substituents each independently selected from halogen atom, oxygen atom, hydroxy, cyano, amino, nitro, mercapto, alkyl, alkenyl, alkynyl, heteroalkyl, optionally substituted aryl or optionally substituted heteroaryl; or —S—$R^{10}$;

$R^{10}$ is 5-membered heterocycloalkyl having from 1 to 3 heteroatoms each independently selected from N, O or S, or cycloalkyl, wherein said 5-membered heterocycloalkyl or cycloalkyl is substituted with from 0 to 4 substituents each independently selected from halogen atom, oxygen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl;

or 5-membered heteroaryl having from 1 to 4 heteroatoms each independently selected from N, O or S, wherein said 5-membered heteroaryl is substituted with from 0 to 4 substituents each independently selected from halogen atom, oxygen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl;

$R^7$ is hydrogen atom, halogen atom, hydroxy, cyano, amino, nitro, alkyl, or heteroalkyl;

$R^8$ is hydrogen atom or halogen atom; and $R^{17}$ is hydrogen atom or halogen atom.

2. The compound according to claim 1, wherein heteroaryl A comprises 1 to 3 nitrogen atoms.

3. The compound according to claim 1 or 2, wherein A is

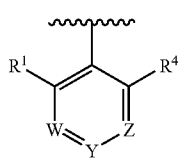

wherein

W is N, NO or $CR^9$;
Y is N, NO or $CR^2$;
Z is N, NO or $CR^3$;
with the proviso that at least one of W, Y or Z is N or NO;
$R^1$ is halogen atom, hydroxy, cyano, amino, nitro, mercapto, alkyl, alkenyl, alkynyl, heteroalkyl, or heteroalkylcycloalkyl;
$R^2$ is hydrogen atom, hydroxyl, halogen atom, cyano, nitro, mercapto, alkyl, alkenyl, alkynyl, or heteroalkyl;
$R^3$ is hydrogen atom, halogen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl;
$R^4$ is halogen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl; and
$R^9$ is hydrogen atom, halogen atom, or $C_1$-$C_6$alkyl.

4. The compound according to any of claims 1 to 3, wherein $R^6$ is

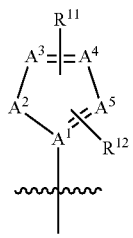

wherein $A^1$, $A^2$, $A^3$, $A^4$, and $A^5$ are each independently selected from O, S, N, N—H, NO, C, or C—H; and $R^{11}$ and $R^{12}$ are each independently selected from hydrogen atom, halogen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl.

5. The compound according to any of claims 1 to 3, wherein $R^6$ is

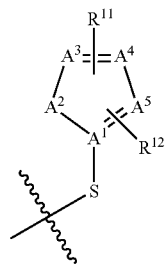

wherein $A^1$, $A^2$, $A^3$, $A^4$, and $A^5$ are each independently selected from O, S, N,N—H, NO, C, or C—H; and $R^{11}$ and $R^{12}$ are each independently selected from hydrogen atom, halogen atom, hydroxy, cyano, amino, nitro, mercapto, alkyl, alkenyl, alkynyl, heteroalkyl, cycloalkyl, heterocycloalkyl, alkylcycloalkyl, heteroalkylcycloalkyl, aryl, heteroaryl, aralkyl, or heteroaralkyl.

6. The compound according to any of claims 3 to 5, wherein $R^4$ is selected from heteroalkyl, heterocycloalkyl, heteroalkylcykloalkyl, aralkyl or heteroaralkyl;
W is $CR^9$; Y is N, NO or $CR^2$;
Z is N, NO or $CR^3$;
with the proviso that at least one of Y or Z is N or NO;
$R^1$ is halogen atom, hydroxy, cyano, —O—$C_1$-$C_6$alkyl or $C_1$-$C_6$alkyl;
$R^2$ is hydrogen atom, halogen atom, hydroxy, cyano, —O—$C_1$-$C_6$alkyl or $C_1$-$C_6$alkyl; and
$R^3$ is hydrogen atom, halogen atom, hydroxy, cyano, amino, nitro, O-alkyl or alkyl.

7. The compound according to any of claims 3 to 6, wherein $R^4$ is selected from the groups —S—$Y^a$-L, —S—$Y^a$—CO—NR$^a$R$^b$, —$Y^a$—NR$^c$—CO—NR$^a$R$^b$, —$Y^a$—NR$^c$—CO—O'R$^e$, —$Y^a$—NR$^c$—CO—R$^e$, —$Y^{a'}$O—CO—NR$^a$R$^b$, —$Y^a$—CO—NR$^a$R$^b$, —$Y^a$—CO—NR$^c$L, —O—$Y^a$—CO—NR$^a$R$^b$, —$Y^a$—NR$^c$—CO-L, —Y$^a$-L, —Y$^a$—O—CO—O—R$^c$, —Y$^a$—O—CO—R$^c$, —Y$^a$—NR$^c$—SO$_2$—NR$^a$R$^b$, —Y$^a$—SO$_2$—NR$^a$R$^b$, or —Y$^a$—NR$^c$—SO$_2$—R$^e$, wherein Y$^a$ is a bond, a C$_1$-C$_6$alkylene, a C$_2$-C$_6$alkenylene or a C$_2$-C$_6$alkynylene;

R$^a$ is hydrogen atom, C$_1$-C$_6$alkyl, C$_2$-C$_6$alkenyl, C$_2$-C$_6$alkynyl or is joined to R$^b$ to form a 4- to 10-membered cycloalkyl or heterocycloalkyl;

R$^b$ is hydrogen atom, C$_1$-C$_6$alkyl, C$_2$-C$_6$alkenyl, C$_2$-C$_6$alkynyl, or taken together with R$^a$ to form a 4- to 10-membered cycloalkyl or heterocycloalkyl;

R$^c$ and R$^e$ are each independently selected from hydrogen atom, an optionally substituted C$_1$-C$_6$alkyl, an optionally substituted C$_2$-C$_6$alkenyl, or an optionally substituted C$_2$-C$_6$alkynyl; and L is a cycloalkyl, heterocycloalkyl, alkylcycloalkyl, heteroalkylcycloalkyl, aryl, optionally substituted heteroaryl, aralkyl, or heteroaralkyl.

8. The compound according to any of claims 3 to 7, wherein R$^4$ is

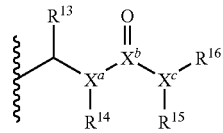

X$^a$ is N, O or CH;

X$^b$ is C, S or S=O;

X$^c$ is N, O or CH;

R$^{13}$, if present, is C$_1$-C$_6$alkyl;

R$^{14}$, if present, is C$_1$-C$_6$alkyl, C$_2$-C$_6$alkenyl or joined to R$^{15}$ to form
  (i) a 5- to 10-membered cycloalkyl;
  (ii) a 5- to 10-membered heterocycloalkyl;
  (iii) a 5- to 10-membered heteroaryl; or
  (iv) a 6- to 10-membered aryl;

R$^{15}$ is alkyl, alkenyl, or joined to R$^{14}$ to form
  (i) a 5- to 10-membered cycloalkyl;
  (ii) a 5- to 10-membered heterocycloalkyl;
  (iii) a 5- to 10-membered heteroaryl; or
  (iv) a 6- to 10-membered aryl; and/or if R$^{15}$ is taken together with R$^{16}$ to form
  (i) a 4- to 10-membered cycloalkyl;
  (ii) a 4- to 10-membered heterocycloalkyl;
  (iii) a 5- to 10-membered heteroaryl; or
  (iv) a 6- to 10-membered aryl; and R$^{16}$ is hydrogen, alkyl, alkenyl, aryl, heteroaryl or taken together with R$^{15}$ to form
  (i) a 4- to 10-membered cycloalkyl;
  (ii) a 4- to 10-membered heterocycloalkyl;
  (iii) a 5- to 10-membered heteroaryl; or
  (iv) a 6- to 10-membered aryl.

9. The compound according to any of claims 3 to 8, wherein R$^4$ is

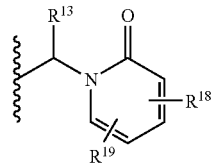

wherein

R$^{13}$ is hydrogen atom or C$_1$-C$_6$alkyl;

R$^{18}$ and R$^{19}$ are each independently selected from hydrogen atom, halogen atom, hydroxy, cyano, amino, nitro, C$_1$-C$_6$alkyl, —O—C$_1$-C$_6$alkyl, —CO—NR$^a$R$^b$, or —SO$_2$—NR$^a$R$^b$, wherein R$^a$ and R$^b$ are each independently selected from hydrogen atom, or C$_1$-C$_6$alkyl.

10. The compound according to any of claims 1 to 9, wherein R$^5$ is halogen atom, cyano, or C$_1$-C$_6$alkyl.

11. The compound according to any of claims 1 to 10, wherein R$^7$, R$^8$, and R$^{17}$ are each independently selected from H or F.

12. The compound according to any of claims 1 to 11, wherein R$^5$ is methyl or ethyl.

13. The compound according to any of claims 1 to 12, wherein R$^6$ is selected from the groups:

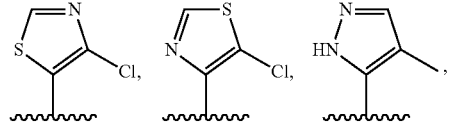

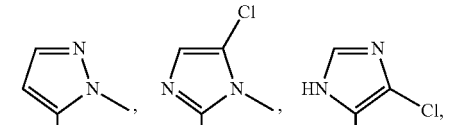

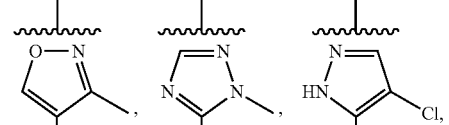

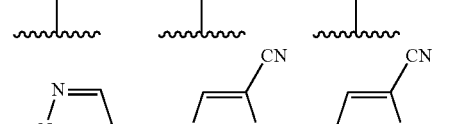

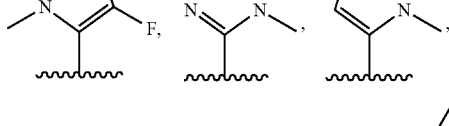

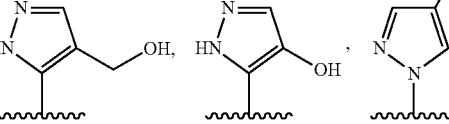

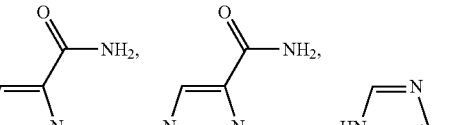

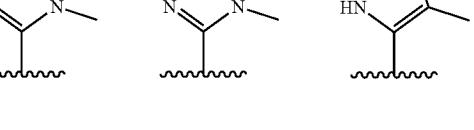

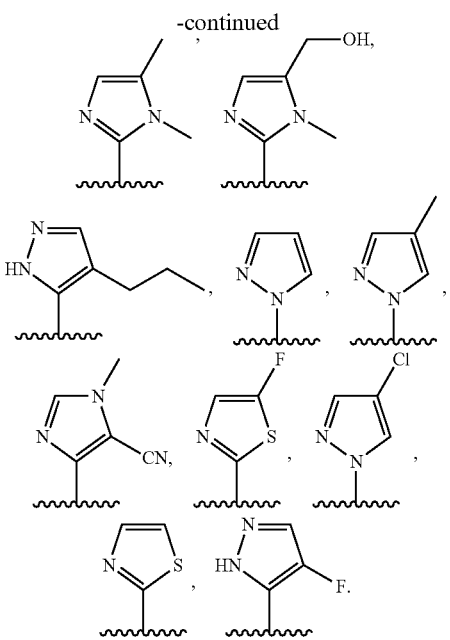

14. The compound according to any of claims 3 to 13, wherein
R$^1$ is methyl, Cl, F, CN, or O—CH$_3$;
W is CH;
Y is N, NO, CH, C—CH$_3$, C—OH, or C—OCH$_3$;
Z is N, NO, CH, C—CH$_3$, C—OH, or C—OCH$_3$; and
with the proviso that at least one of Y or Z is N or NO.

15. The compound according to any of claims 3 to 14, wherein R$^4$ is

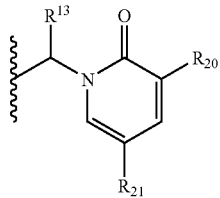

wherein
R$^{13}$ is hydrogen atom or methyl;
R$^{20}$ is Cl, F, cyano, or CF$_3$; and
R$^{21}$ is hydrogen atom or F.

16. The compound according to any of claims 1 to 15, wherein R$^7$, R$^8$ and R$^{17}$ are H.

17. A compound according to any one of claims 1 to 16 or a salt thereof, wherein the compound exhibits an IC$_{50}$ of 500 nM or less in a standard in vitro BK 82 receptor-mediated assay.

18. A compound, preferably a compound according to any of claims 1 to 17, which is: 1-{3-[4-(5-Chloro-thiazol-4-yl)-2-methyl-quinolin-8-yloxymethyl]-4-methyl-pyridin-2-ylmethyl}-3-trifluoromethyl-1H-pyridin-2-one,
  1-{4-Chloro-3-[4-(5-chloro-thiazol-4-yl)-2-methyl-quinolin-8-yloxymethyl]-6-methyl-pyridin-2-ylmethyl}-3-trifluoromethyl-1H-pyridin-2-one,
  1-{4-Chloro-3-[4-(5-chloro-thiazol-4-yl)-2-methyl-quinolin-8-yloxymethyl]-6-methyl-pyridin-2-ylmethyl}-2-oxo-1,2-dihydro-pyridine-3-carbonitrile,
  1-{4-Methyl-3-[2-methyl-4-(4-methyl-2H-pyrazol-3-yl)-quinolin-8-yloxymethyl]-pyridin-2-ylmethyl}-3-trifluoromethyl-1H-pyridin-2-one,
  1-{4-Chloro-3-[4-(5-chloro-1-methyl-1H-imidazol-2-yl)-2-methyl-quinolin-8-yloxymethyl]-pyridin-2-ylmethyl}-3-trifluoromethyl-1H-pyridin-2-one,
  1-{5-Chloro-2-methoxy-4-[2-methyl-4-(2-methyl-2H-[1,2,4]triazol-3-yl)-quinolin-8-yloxymethyl]-pyridin-3-ylmethyl}-3-trifluoromethyl-1H-pyridin-2-one,
  1-(3-{4-[4-(2-Amino-ethoxy)-1H-pyrazol-3-yl]-2-methyl-quinolin-8-yloxymethyl}-4-methyl-pyridin-2-ylmethyl)-3-trifluoromethyl-1H-pyridin-2-one,
  1-{4-Chloro-3-[4-(1,5-dimethyl-1H-imidazol-2-yl)-2-methyl-quinolin-8-yloxymethyl]-pyridin-2-ylmethyl}-3-trifluoromethyl-1H-pyridin-2-one,
  1-{3-[4-(4-Hydroxymethyl-2H-pyrazol-3-yl)-2-methyl-quinolin-8-yloxymethyl]-4-methyl-pyridin-2-ylmethyl}-3-trifluoromethyl-1H-pyridin-2-one,
  N-(3-{2-Me %1-8-[4-methyl-2-(2-oxo-3-trifluoromethyl-2H-pyridin-1-ylmethyl)-pyridin-3-ylmethoxy]-quinolin-4-yl}-1H-pyrazol-4-ylmethyl)-acetamide,
  1-{3-[4-(4-Aminomethyl-1H-pyrazol-3-yl)-2-methyl-quinolin-8-yloxymethyl]-4-methyl-pyridin-2-ylmethyl}-3-trifluoromethyl-1H-pyridin-2-one,
  N-(5-{8-[4-Chloro-2-(2-oxo-3-trifluoromethyl-2H-pyridin-1-ylmethyl)-pyridin-3-ylmethoxy]-2-methyl-quinolin-4-yl}-1H-pyrazol-4-ylmethyl)-acetamide,
  2-{8-[4-Chloro-6-methyl-2-(2-oxo-3-trifluoromethyl-2H-pyridin-1-yhnethyl)-pyridin-3-ylmethoxy]-2-methyl-quinolin-4-yl}-3-methyl-3H-imidazole-4-carbonitrile,
  1-{4-Chloro-6-methyl-3-[2-methyl-4-(4-methyl-2H-pyrazol-3-yl)-quinolin-8-yloxymethyl]-pyridin-2-ylmethyl}-2-oxo-1,2-dihydro-pyridine-3-carbonitrile,
  1-{4-Chloro-6-methyl-3-[2-methyl-4-(4-methyl-1H-pyrazol-3-yl)-quinolin-8-yloxymethyl]-pyridin-2-ylmethyl}-3-trifluoromethyl-1H-pyridin-2-one,
  5-{8-[4-Chloro-2-(2-oxo-3-trifluoromethyl-2H-pyridin-1-ylmethyl)-pyridin-3-ylmethoxy]-2-methyl-quinolin-4-yl}-3-methyl-3H-imidazole-4-carbonitrile,
  1-{4-Chloro-3-[4-(4-chloro-thiazol-5-yl)-2-methyl-quinolin-8-yloxymethyl]-6-methyl-pyridin-2-ylmethyl}-2-oxo-1,2-dihydro-pyridine-3-carbonitrile,
  1-{4-Chloro-3-[4-(5-cyano-1-methyl-1H-pyrrol-2-yl)-2-methyl-quinolin-8-yloxymethyl]-6-methyl-pyridin-2-ylmethyl}-2-oxo-1,2-dihydro-pyridine-3-carbonitrile,
  1-{3-[4-(5-Chloro-thiazol-4-yl)-2-methyl-quinolin-8-yloxymethyl]-4-methoxy-pyridin-2-ylmethyl}-3-trifluoromethyl-1H-pyridin-2-one,
  1-{4-Chloro-3-[4-(5-cyano-1-methyl-1H-pyrrol-2-yl)-2-methyl-quinolin-8-yloxymethyl]-pyridin-2-ylmethyl}-2-oxo-1,2-dihydro-pyridine-3-carbonitrile,
  5-{8-[4-Chloro-6-methyl-2-(2-oxo-3-trifluoromethyl-2H-pyridin-1-ylmethyl)-pyridin-3-ylmethoxy]-2-methyl-quinolin-4-yl}-1-methyl-1H-pyrrole-2-carboxylic acid amide,
  5-{8-[4-Chloro-2-(3-cyano-2-oxo-2H-pyridin-1-ylmethyl)-6-methyl-pyridin-3-ylmethoxy]-2-methyl-quinolin-4-yl}-1-methyl-1H-pyrrole-2-carboxylic acid amide,
  1-{4-Chloro-3-[4-(4-hydroxymethyl-2H-pyrazol-3-yl)-2-methyl-quinolin-8-yloxymethyl]-pyridin-2-ylmethyl}-3-trifluoromethyl-1H-pyridin-2-one,
  1-{4-Chloro-3-[4-(4-hydroxy-1H-pyrazol-3-yl)-2-methyl-quinolin-8-yloxymethyl]-6-methyl-pyridin-2-ylmethyl}-2-oxo-1,2-dihydro-pyridine-3-carbonitrile,
  1-{4-Chloro-3-[4-(4-hydroxy-1H-pyrazol-3-yl)-2-methyl-quinolin-8-yloxymethyl]-6-methyl-pyridin-2-ylmethyl}-3-trifluoromethyl-1H-pyridin-2-one, 1-{4-Chloro-3-[4-(4-fluoro-pyrazol-1-yl)-2-methyl-quinolin-8-yloxymethyl]-6-methyl-pyridin-2-ylmethyl}-2-oxo-1,2-dihydro-pyridine-3-carbonitrile, 1-{3-[4-(5-Chloro-thiazol-4-yl)-2-methyl-quinolin-8-yloxymethyl]-4-methoxy-pyridin-2-ylmethyl}-2-oxo-1,2-dihydro-pyridine-3-carbonitrile, 2-{8-[5-Fluoro-2-methoxy-3-(2-oxo-3-trifluoromethyl-2H-pyridin-1-ylmethyl)-pyridin-4-ylmethoxy]-2-methyl-quinolin-4-yl}-3-methyl-3H-imidazole-4-carbonitrile, 1-{4-Chloro-6-methyl-3-[2-methyl-4-(5-methyl-1H-imidazol-4-yl)-quinolin-8-yloxymethyl]-pyridin-2-ylmethyl}-2-oxo-1,2-dihydro-pyridine-3-carbonitrile, 1-(1-{4-Chloro-3-[2-methyl-4-(4-methyl-1H-pyrazol-3-yl)-quinolin-8-yloxymethyl]-pyridin-2-yl}-ethyl)-2-oxo-1,2-dihydro-pyridine-3-carbonitrile, 1-(1-{4-Chloro-3-[4-(4-hydroxy-1H-pyrazol-3-yl)-2-methyl-quinolin-8-yloxymethyl]-pyridin-2-yl}-ethyl)-2-oxo-1,2-dihydro-pyridine-3-carbonitrile, 5-{8-[4-Chloro-2-(3-cyano-2-oxo-2H-pyridin-1-ylmethyl)-pyridin-3-ylmethoxy]-2-methyl-quinolin-4-yl}-1-methyl-1H-pyrrole-2-carboxylic acid amide, 1-{4-Chloro-3-[4-(4-fluoro-pyrazol-1-yl)-2-methyl-quinolin-8-yloxymethyl]-pyridin-2-ylmethyl}-2-oxo-1,2-dihydro-pyridine-3-carbonitrile, 1-(1-{4-Chloro-3-[4-(4-hydroxy-1H-pyrazol-3-yl)-2-methyl-quinolin-8-yloxymethyl]-6-methyl-pyridin-2-yl}-ethyl)-2-oxo-1,2-dihydro-pyridine-3-carbonitrile, 1-{4-Chloro-6-methyl-3-[2-methyl-4-(3-methyl-isoxazol-4-yl)-quinolin-8-yloxymethyl]-pyridin-2-ylmethyl}-2-oxo-1,2-dihydro-pyridine-3-carbonitrile, 1-{5-Chloro-4-[4-(5-cyano-1-methyl-1H-pyrrol-2-yl)-2-methyl-quinolin-8-yloxymethyl]-2-hydroxy-pyridin-3-ylmethyl}-2-oxo-1,2-dihydro-pyridine-3-carbonitrile, 1-{4-Methoxy-6-methyl-3-[2-methyl-4-(4-methyl-1H-pyrazol-3-yl)-quinolin-8-yloxymethyl]-pyridin-2-ylmethyl}-3-trifluoromethyl-1H-pyridin-2-one, 1-{4-Chloro-3-[4-(4-hydroxymethyl-1H-pyrazol-3-yl)-2-methyl-quinolin-8-yloxymethyl]-6-methyl-pyridin-2-ylmethyl}-2-oxo-1,2-dihydro-pyridine-3-carbonitrile, 1-{4-Chloro-3-[4-(5-fluoro-thiazol-2-yl)-2-methyl-quinolin-8-yloxymethyl]-6-methyl-pyridin-2-yhn-ethyl}-2-oxo-1,2-dihydro-pyridine-3-carbonitrile.

19. A pharmaceutical composition that comprises one or more compounds according to any one of claims 1 to 18 and, optionally, at least one carrier substance, excipient and/or adjuvant.

20. The pharmaceutical composition according to claim 19, wherein the pharmaceutical composition is formulated as an aerosol, a cream, a gel, a pill, a capsule, a syrup, a solution, a transdermal patch or a pharmaceutical delivery device.

21. A method of inhibiting binding of bradykinin to a bradykinin B2 receptor in vitro, the method comprising contacting the bradykinin B2 receptor with at least one compound according to claim 1, under conditions and in an amount sufficient to detectably inhibit binding of bradykinin to the bradykinin B2 receptor.

22. A method for the treatment of an inflammatory disease in a subject in need of such treatment, comprising administering a therapeutically effective amount of a compound according to claim 1 to the subject.

23. The method according to claim 22, wherein the inflammatory disease is hereditary angioedema.

24. A compound of the formula (II):

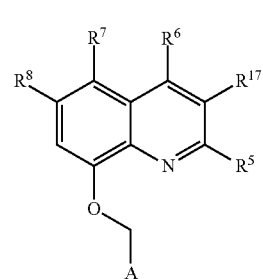

or a pharmacologically acceptable salt thereof, wherein
A is a 6-membered heteroaryl having 1 heteroatom, wherein said heteroatom is N, and wherein said 6-membered heteroaryl is substituted with 3 substituents each independently selected from halogen atom, alkyl and heteroalkylcycloalkyl;
$R^5$ is alkyl;
$R^6$ is a 5-membered heterocycloalkyl having 2 heteroatoms, wherein each heteroatom is N, and wherein said 5-membered heterocycloalkyl is substituted with 1 substituent, wherein said substituent is a halogen atom; and
$R^7$, $R^8$ and $R^{17}$ are hydrogen atom.

25. The compound according to claim 24, wherein A is

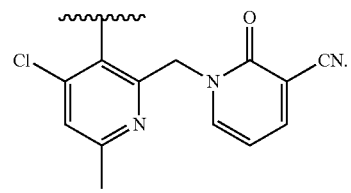 [SMILES: *c1c(Cl)cc(C)nc1Cn1cccc(C#N)c1=O]

26. The compound according to claim 24, wherein $R^5$ is methyl.

27. The compound according to claim 24, wherein $R^6$ is

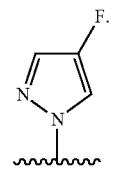

28. The compound according to claim 24 wherein said compound is 1-{4-Chloro-3-[4-(4-fluoro-pyrazol-1-yl)-2-methyl-quinolin-8-yloxymethyl]-6-methylpyridin-2-ylmethyl}-2-oxo-1,2-dihydro-pyridine-3-carbonitrile.

29. A pharmaceutical composition that comprises one or more compounds according to any one of claims 24 to 28 and, optionally, at least one carrier substance, excipient and/or adjuvant.

30. The pharmaceutical composition according to claim 29, wherein the pharmaceutical composition is formulated as an aerosol, a cream, a gel, a pill, a capsule, a syrup, a solution, a transdermal patch or a pharmaceutical delivery device.

31. A method for the treatment of hereditary angioedema in a subject in need of such treatment, comprising administering a therapeutically effective amount of a compound according to claim 24 to the subject.

32. The compound of formula (III):

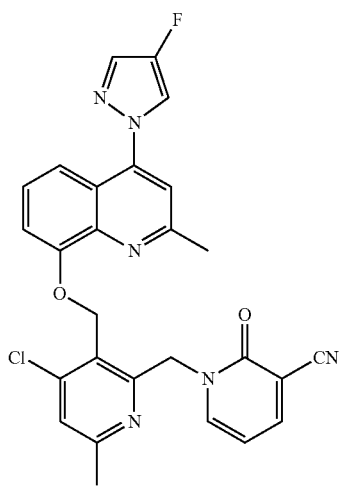

(III)

or a pharmacologically acceptable salt thereof.

33. A pharmaceutical composition that comprises one or more compounds according to claims 32 and, optionally, at least one carrier substance, excipient and/or adjuvant.

34. The pharmaceutical composition according to claim 33, wherein the pharmaceutical composition is formulated as an aerosol, a cream, a gel, a pill, a capsule, a syrup, a solution, a transdermal patch or a pharmaceutical delivery device.

35. A method for the treatment of hereditary angioedema in a subject in need of such treatment, comprising administering a therapeutically effective amount of a compound according to claim 32 to the subject.

36. A method of inhibiting binding of bradykinin to a bradykinin B2 receptor, the method comprising contacting the bradykinin B2 receptor with at least one compound according to claim 1 in an amount sufficient to inhibit binding of bradykinin to a bradykinin B2 receptor.

* * * * *

UNITED STATES PATENT AND TRADEMARK OFFICE
CERTIFICATE OF CORRECTION

| | | |
|---|---|---|
| PATENT NO. | : 8,410,134 B2 | Page 1 of 1 |
| APPLICATION NO. | : 12/532703 | |
| DATED | : April 2, 2013 | |
| INVENTOR(S) | : Gibson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 732 days.

Signed and Sealed this
Seventh Day of October, 2014

Michelle K. Lee
*Deputy Director of the United States Patent and Trademark Office*